(12) United States Patent
Venkatesan et al.

(10) Patent No.: US 7,691,842 B2
(45) Date of Patent: Apr. 6, 2010

(54) TRICYCLIC 6-ALKYLIDENE-PENEMS AS β-LACTAMASE INHIBITORS

(75) Inventors: Aranapakam Mudumbai Venkatesan, Rego Park, NY (US); Tarek Suhayl Mansour, New City, NY (US); Takao Abe, Saitama (JP); Ado Mihira, Saitama (JP); Atul Agarwal, Hamden, CT (US); Hideki Ushirogochi, Saitama (JP); Yansong Gu, Pearl River, NY (US); Satoshi Tamai, Kanagawa (JP); Fuk-Wah Sum, Pomona, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/187,707

(22) Filed: Aug. 7, 2008

(65) Prior Publication Data
US 2008/0318921 A1 Dec. 25, 2008

Related U.S. Application Data

(60) Continuation of application No. 11/283,288, filed on Nov. 18, 2005, now abandoned, which is a division of application No. 10/427,427, filed on May 1, 2003, now Pat. No. 7,018,997.

(60) Provisional application No. 60/377,051, filed on May 1, 2002.

(51) Int. Cl.
| C07D 503/10 | (2006.01) |
| C07D 519/06 | (2006.01) |
| A61P 31/04 | (2006.01) |
| A61K 31/424 | (2006.01) |
| A61K 31/43 | (2006.01) |
| A61K 31/431 | (2006.01) |
| C07D 499/881 | (2006.01) |

(52) U.S. Cl. .................. 514/210.06; 540/347
(58) Field of Classification Search .......... 540/347; 514/210.06
See application file for complete search history.

(56) References Cited

U.S. PATENT DOCUMENTS

| 4,206,067 A | 6/1980 | MacKinnon | |
| 4,485,110 A | 11/1984 | Osborne | |
| 4,891,369 A | 1/1990 | Torii et al. | |
| 5,096,899 A * | 3/1992 | Pfaendler et al. ....... | 514/210.06 |
| 5,911,985 A | 6/1999 | Coleman et al. ............ | 514/193 |
| 6,268,393 B1 | 7/2001 | Xu et al. | |
| 7,018,997 B2 | 3/2006 | Venkatesan et al. | |
| 7,112,582 B2 | 9/2006 | Venkatesan et al. | |
| 2003/0080312 A1 | 5/2003 | Seddon et al. | |
| 2004/0043978 A1 | 3/2004 | Venkatesan et al. | |
| 2004/0043980 A1* | 3/2004 | Pfaendler .............. | 514/210.06 |
| 2004/0053913 A1 | 3/2004 | Abe et al. ................... | 540/310 |
| 2004/0077622 A1 | 4/2004 | Venkatesan et al. ........ | 514/195 |
| 2004/0132708 A1 | 7/2004 | Abe et al. ................... | 540/310 |
| 2004/0176349 A1* | 9/2004 | Simpson et al. ........ | 514/210.06 |
| 2005/0101654 A1 | 5/2005 | Weiberth et al. | |
| 2006/0276445 A1* | 12/2006 | Mansour et al. ............. | 514/195 |
| 2006/0276446 A1* | 12/2006 | Mansour et al. ............. | 514/195 |
| 2007/0027130 A1 | 2/2007 | Mansour et al. ............. | 514/193 |
| 2007/0129344 A1* | 6/2007 | Mansour et al. ............. | 514/193 |

FOREIGN PATENT DOCUMENTS

| EP | 0 041 768 B1 | 12/1981 |
| EP | 0 120 613 A1 | 10/1984 |
| EP | 0 150 781 A1 | 8/1985 |
| EP | 0 150 984 B1 | 8/1985 |
| EP | 0 154 132 B1 | 9/1985 |
| EP | 0167050 | 1/1986 |
| EP | 0 210 065 A1 | 1/1987 |
| EP | 0 210 814 A1 | 2/1987 |
| EP | 0 313 458 | 4/1989 |
| EP | 0 321 187 B1 | 6/1989 |
| EP | 0 321 186 B1 | 6/1994 |
| EP | 0232966 B1 | 8/1997 |
| WO | WO 87/00525 A1 | 1/1987 |
| WO | WO-91/12815 | 9/1991 |
| WO | WO 93/03042 A1 | 2/1993 |
| WO | WO 94/10178 A1 | 5/1994 |
| WO | WO 95/17184 A1 | 6/1995 |
| WO | WO 95/28935 A1 | 11/1995 |
| WO | WO-03/093277 | 11/2003 |
| WO | WO-03/093279 | 11/2003 |
| WO | WO-03/093280 | 11/2003 |

OTHER PUBLICATIONS

Bush, K., Antimicrob. Agents Chemother. 1993, 37, 851.
Yang, Y.; Janota, K.; Tabei, K.; Huang, N.; Seigal, M.M.; Lin, Y.I. Rasmussen, B.A. and Shlaes D.M., J. Biol. Chem. 2000, 35, 26674-26682.

(Continued)

*Primary Examiner*—Mark L Berch
(74) *Attorney, Agent, or Firm*—Michael J. Herman; A. David Joran

(57) ABSTRACT

The present invention provides a compound of formula I, pharmaceutical compositions and the use thereof for the treatment of bacterial infection or disease in a patient in need thereof,

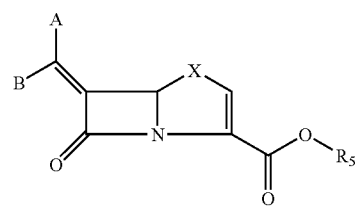

wherein one of A and B denotes hydrogen and the other an optionally substituted fused tricyclic heteroaryl group; and X is O.

36 Claims, No Drawings

OTHER PUBLICATIONS

Abiko, et al., "Concerning the Boron Mediated Aldol Reaction of Carboxytic Esters", J. Org. Chem., 61:2590-2591 (1996).

Bennett, et al., "6-(Substituted Methylene)Penems, Potent Broad Spectrum Inhibitors of Bacterial β-Lactamase: III. Structure-Activity Relationships of the 5-Membered Heterocyclic Derivatives", Journal of Antibiotics, 44(3):331-337 (1991).

Bouffard, et al., "A New Approach to the Diastereoselective Synthesis of Aldols: Introduction of the 6α-(1R-Hydroxyethyl) Side Chain of the Carbapenem and Penem Antiobiotics", Tetrahedron Letters, 26(51):6285-6288 (1985).

Bouffard, et al., "Thienamycin Total Synthesis. 1. Synthesis of Azetidinone Percursors of (±)-Thienamycin and Its Stereoisomers", J. Org. Chem., 45:1130-1135 (1980).

Dininno, et al., "Aldol Condensations of Regiospecific Penicillanate and Cephalosporanate Enolates, Hydroxyethylation at C-6 and C-7", J. Org. Chem., 42(18):2960-2965 (1977).

Innis, "Human Milk and Formula Fatty Acids", Journal of Pediatrics, 120(4,Pt. 2):S56-S59 (1992).

Mansour, "Hunig's Base-Magnesium Chloride Mediated Carbon Alkylation and Oxygen Acylation of Benzoylacetonitrile", Tetrahedron Letters, 29(28):3437-3440 (1988).

Mansour, et al., "N-Protected α-Aminomethylketone Analogues of C-Terminal p-Nitrobenzyl-3-Ketoesters of N-Protected Amino Acids", Synthetic Communications, 19(3&4):667-672 (1989).

Office Action that issued from the European Patent Office on Jun. 20, 2006 in EP 03 733 911.6-1211.

Osborne, et al., "A Novel and Stereocontrolled Synthesis of (5R)-(Z)-6-(1Methyl-1,2,3-triazol-4-ylmethylene)penem-3-carboxylic Acid, a Potent Broad Spectrum β-Lactamase Inhibitor", J. Chem. Soc., Chem. Commun., pp. 371-373 (1989).

Osborne, et al., "Synthesis of (5R)-(Z)-6-(1-Methyl-1,2,3-triazol-4-ylmethylene-penem-3-carboxylic Acid, a Potent Broad Spectrum β-Lactamase Inhibitor, from 6-Aminopenicillanic Acid", J. Chem. Soc. Perkin Trans., pp. 179-188 (1994).

Rathke, et al., "Procedures for the Acylationof Diethyl Malonate and Ethyl Acetoacetate with Acid Chlorides Using Tertiary Amine Bases and Magnesium Chloride", J. Org. Chem., 50:2622-2624 (1985).

International Search Report and the Written Opinion of the International Searching Authority issued for PCT/US2006/032781, dated May 8, 2007.

Cignarella, et al., "6-Chloro- and 6-Bromopenicillanic Acids", J. Org. Chem., 27:2668-2669 (1962).

Grant and Hackh's Chemical Dictionary, Fifth Edition, p. 412 (1987).

Haslam, "Protection of Carboxyl Groups", *Protective Groups in Organic Chemistry*, Chapter 5, McOmie, ed., Plenum Press, p. 183-215 (1973).

Osborne, et al., "A Novel and Stereocontrolled Synthesis of (5R)-(Z)-6-(1-Methyl-1,2,3-Triazol-4-Ylmethylene)Penem-3-Carboxylic Acid, A Potent Broad Spectrum β-Lactamase Inhibitor", Journal of The Chemical Society, Letchworth, Great Britain, 6:371-373 1989.

Weiss, et al., "In Vitro and In Vivo Activities of Novel 6-Methylidene Penems as Bets-Lactamase Inhibitors", Antimicrobial Agents and Chemotherapy, 48(12):4589-4596 (2004).

Bush, "β-Lactamases of Increasing Clinical Importance", Cur. Pharm. Design, 5:839-845 (1999).

Bush, et al., "Kinetic Interactions of Tazobactam with β-Lactamases from All Major Structural Classes", Antimicrobial Agents and Chemotherapy, 37(4):851-858(1993).

Coleman, "Anti-Infectives: An Update on β-Lactamases and β-Lactamase Inhibitors", Expert Opin. Invest. Drugs, 4(8):693-704 (1995).

Jones, "Resistance Patterns Among Nosocomial Pathogens: Trends Over the Past Few Years", Chest, 119:397S-404S (2001).

Payne, et al., "β-Lactamase Epidemiology and the Utility of Established and Novel β-Lactamase Inhibitors", Exp. Opin. Invest. Drugs 9(2):247-261 (2000).

Rietscha, et al., "Collaborative Clinical Pharmacokinetics Service in a Community Hospital", Am. J. Hosp. Pharm., 41:463-477 (1984).

Sanders, "Cefepime: The Next Generation?", Clin. Infect. Dis., 17:369-379 (1993).

Sutherland, "β-Lactam/β-Lactamase Inhibitor Combinations: Development, Antibacterial Activity and Clinical Applications", Infection, 23(4):191-200 (1995).

* cited by examiner

TRICYCLIC 6-ALKYLIDENE-PENEMS AS β-LACTAMASE INHIBITORS

This application claims priority from copending divisional application Ser. No. 11/283,288, filed Nov. 18, 2005, which claims priority from non-provisional application Ser. No. 10/427,427, filed May 1, 2003, which claims priority from provisional application 60/377,051, filed May 1, 2002, the entire disclosures of which are hereby incorporated by reference.

FIELD OF INVENTION

This invention relates to certain tricyclic 6-alkylidene penems which act as a broad spectrum β-lactamase inhibitors. β-Lactamases hydrolyze β-lactam antibiotics, and as such serve as the primary cause of bacterial resistance. The compounds of the present invention when combined with β-lactam antibiotics will provide an effective treatment against life threatening bacterial infections.

BACKGROUND OF THE INVENTION

Penicillins and cephalosporins are the most frequently and widely used β-lactam antibiotics in the clinic. However, the development of resistance to β-lactam antibiotics by different pathogens has had a damaging effect on maintaining the effective treatment of bacterial infections. (Coleman, K. *Expert Opin. Invest. Drugs* 1995, 4, 693; Sutherland, R. *Infection* 1995, 23 (4) 191; Bush, K, *Cur Pharm. Design* 1999, 5, 839-845). The most significant known mechanism related to the development of bacterial resistance to the β-lactam antibiotics is the production of class-A, class-B and class-C serine β-lactamases. These enzymes degrade the β-lactam antibiotics, resulting in the loss of antibacterial activity. Class-A enzymes preferentially hydrolyze penicillins where as Class-C lactamases have a substrate profile favoring cephalosporin hydrolysis. (Bush, K.; Jacoby, G. A.; Medeiros, A. A. *Antimicrob. Agents Chemother.* 1995, 39, 1211). To date over 250 different β-lactamases have been reported (Payne, D. J.: Du, W and Bateson, J. H. *Exp. Opin. Invest. Drugs* 2000, 247) and there is a need for a new generation of broad spectrum β-lactamase inhibitors. Bacterial resistance to these antibiotics could be greatly reduced by administering the β-lactam antibiotic in combination with a compound which inhibits these enzymes.

The commercially available β-lactamase inhibitors such as clavulanic acid, sulbactam and tazobactam are all effective against class-A producing pathogens. Clavulanic acid is clinically used in combination with amoxicillin and ticarcillin; similarly sulbactam with ampicillin and tazobactam with piperacillin. However, these compounds are ineffective against class C producing organisms. The mechanism of inactivation of class-A β-lactamases (such as PCI and TEM-1) has been elucidated. (Bush, K.; *Antimicrob. Agents Chemother.* 1993, 37, 851; Yang, Y.; Janota, K.; Tabei, K.; Huang, N.; Seigal, M. M.; Lin, Y. I.; Rasmussen, B. A. and Shlaes, D. M. *J. Biol. Chem.* 2000, 35, 26674-26682).

In 1981, the Beecham group disclosed 6-alkylidine penems of general structure 1 as inhibitors of β-lactamases. [N. F. Osborne, U.S. Pat. No. 4,485,110 (1984); N. F. Osborne, *Eur. Pat. Appl.* 81 301683.9.]

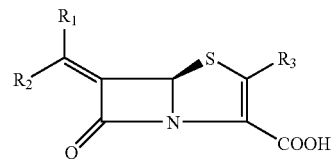

1

$R_1$ and $R_2$ are independently hydrogen or a $C_{1-10}$ hydrocarbon group or mono heterocyclic, and $R_3$ represents a hydrogen or an organic group. Subsequently, the same group disclosed compounds of the general formula 1, wherein $R_1$ comprises a 1,2,3-triazole moiety. [N. F. Osborne, *Eur. Pat. Appl.* 84301255.0]. The following year, the same group filed three patent applications of the structure 1, wherein $R_1$ is an optionally substituted six membered or five membered mono aromatic ring system. [N. F. Osborne, *Eur. Pat. Appl.* 85100520.7; *Eur. Pat. Appl.* 85100521.5 and *Eur. Pat. Appl.* 85300456.2]. European patent application No. 86305585.1 discloses the synthesis and the utility of (Z)-6-(1-methyl-1,2, 3-triazol-4-ylmethylene)-penem-3-carboxylate 2 as a class-A and class-C β-lactamase inhibitor.

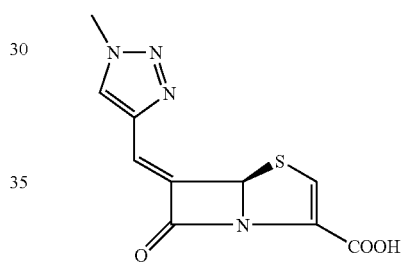

2

Eur. Pat. Appl. 86305584.4 disclosed the preparation of compounds of general formula 1, wherein $R_1$=non-aromatic heterocyclic group and a PCT application [N. J. Broom; P. D. Edwards, N. F. Osborne and S. Coulton PCT WO 87/00525] disclosing $R_1$=fused bicyclic hetero-aromatic group was published. Similarly patent applications [N. J. Broom; G. Brooks; S. Coulton, Eur. Pat. Appl. 88311786.3; N. J. Broom; G. Brooks; B. P. Clarke, Eur. Pat. Appl. 88311787.1) disclosed the preparation and use of compounds of general structure 1, wherein $R_1$ is a substituted five membered hetero-aromatic ring. A process for the preparation of compounds of general formula 1 has been disclosed by Coulton, et al. [S. Coulton; J. B. Harbridge; N. F. Osborne and G. Walker Eur. Pat. Appl. No 87300193.7]

In the year 1993, Beecham disclosed [A. V. Stachulski and R. walker, PCT WO 93/03042] the preparation and the use of compounds of general formula 1, in which $R_1$=($C_{1-6}$) alkyl and $R_2$=CH$_2$X or COY wherein X=halogen or CONR$_2$.

During the last decade three patents have been filed by Beecham describing compounds of general formula 3. [N. J. Broom; F. P. Harrington, PCT WO 94/10178; K. Coleman; J. E. Neale PCT WO 95/28935; K. Coleman; J. E. Neale PCT WO 95/17184] wherein $R_a$=hydrogen or an organic group, and $R_d$ and $R_e$ may be both hydrogen or one or more substituents replacing hydrogen atoms in the ring system shown below.

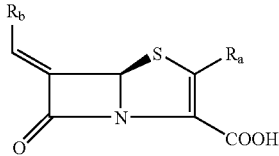

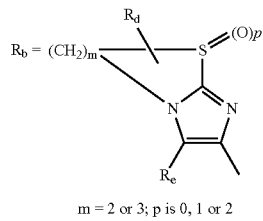

m = 2 or 3; p is 0, 1 or 2

BRIEF SUMMARY OF THE INVENTION

The present invention relates to novel, low molecular weight broad spectrum β-lactam compounds and in particular to a class of tricyclic heteroaryl substituted 6-alkylidene penems which have β-lactamase inhibitory and antibacterial properties. The compounds are therefore useful in the treatment of antibacterial infections in humans or animals, either alone or in combination with other antibiotics.

In accordance with the present invention there are provided compounds of general formula I or a pharmaceutically acceptable salt or in vivo hydrolysable ester thereof:

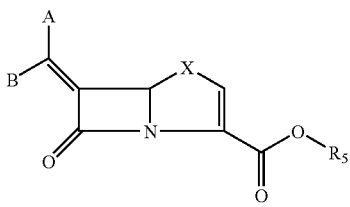

I wherein:

One of A and B denotes hydrogen and the other an optionally substituted fused tricyclic heteroaryl group;

X is S or O, preferably S;

$R_5$ is H, an in vivo hydrolyzable ester such as C1-C6 alkyl, C5-C6 cycloalkyl, $CHR_3OCOC1$-C6 or salts such as Na, K, Ca; and $R_3$ is hydrogen, C1-C6 alkyl, C3-C6 cycloalkyl, optionally substituted aryl, optionally substituted heteroaryl.

DETAILED DESCRIPTION OF THE INVENTION

In accordance with the present invention there are provided compounds of general formula I or a pharmaceutically acceptable salt or in vivo hydrolysable ester thereof:

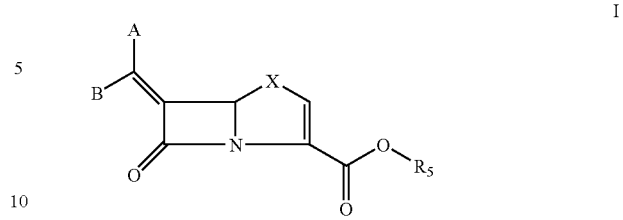

I wherein:

One of A and B denotes hydrogen and the other an optionally substituted fused tricyclic heteroaryl group;

X is S or O, preferably S;

$R_5$ is H, an in vivo hydrolyzable ester such as C1-C6 alkyl, C5-C6 cycloalkyl, $CHR_3OCOC1$-C6 or salts such as Na, K, Ca; preferable $R_5$ groups are H or salts.

The expression "Fused tricyclic heteroaryl group" is used in the specification and claims to mean:

a group comprising three fused rings in which at least one ring has aromatic character (i.e meets Huckel's rule (4n+2)). The fused tricyclic heteroaryl group contains 1-6 heteroatoms selected from the group consisting of O, S, N and N—$R_1$. The fused tricyclic heteroaryl must be bonded through a carbon preferably in one of the at least one aromatic rings to the remainder of the formula I molecule. The fused tricyclic heteroaryl group may contain 1-3 aromatic rings and 0-2 non-aromatic rings. Each aromatic ring(s) in the fused tricyclic heteroaryl group may contain 5 to 7 ring atoms (including the bridgehead atoms) selected from $CR_2$, O, S, N, and N—$R_1$. Each of the aromatic ring(s) of the fused tricyclic heteroaryl group may contain 0 to 3 heteroatoms selected from O, S, N or N—$R_1$. The non-aromatic ring(s), if any, of the fused tricyclic heteroaryl group may contain 5-8 ring atoms (including bridgehead atoms) and contain 0-4 heteroatoms selected from N, N—$R_1$, O or $S(O)_n$, wherein n is 0-2. In each non-aromatic ring of the fused tricyclic heteroaryl group, one or two of the non-bridgehead carbon atoms may each be optionally substituted with one or two $R_4$, and each $R_4$ may be independently the same or different. Examples of fused tricyclic heteroaryl are optionally substituted ring systems such as imidazo[2,1-b][1,3]benzothiazole optionally substituted e.g., by for example C1-C6alkyl, C1-C6alkoxy or halo (such as chlorine or fluorine); imidazo[1,2-a]quinoline; 6,7-dihydro-5H-cyclopenta[d]imidazo[2,1-b][1,3]thiazole; imidazo[1,2-a]quinoxaline; 5,6,7,8-tetrahydro-[1,2,4]triazolo[1,5-a]pyridine dibenzo[b,f][1,4]-oxazepin-11(10H)-one optionally substituted e.g., by arylalkyl such as benzyl; 7,8-dihydro-6H-3,4,8b-triaza-as-indacene optionally substituted by C1-C6 alkoxy; 4H,10H-pyrazolo[5,1-c][1,4]benzoxazepine optionally substituted e.g., by C1-C6 alkoxy; 5H-Imidazo[2,1-a]isoindole; 5,8-dihydro-6H-imidazo[2,1-b]pyrano[4,3-d][1,3]thiazole; imidazo[2,1-b]benzothiazole; [1,3]thiazolo[3,2-a]benzimidazole; 7,8-dihydro-6H-cyclopenta[3,4]pyrazolo[5,1-b][1,3]thiazole; 5,6,7,8-tetrahydroimidazo[2,1-b][1,3]-benzothiazole; 9H-imidazo[1,2-a]benzimidazole optionally substituted e.g., by C1-C6alkyl; 4H-thieno[2', 3':4,5]thiopyrano[2,3-b]pyridine; 7,8-dihydro-6H-cyclopenta[e][1,2,4]-triazolo[1,5-a]pyrimidine optionally substituted e.g., by C1-C6alkyl; 6,7,8,9-tetrahydropyrido[3,4-e][1,2,4]triazolo[1,5-a]pyrimidine optionally substituted e.g., by C2-C7alkoxycarbonyl; 8',9'-dihydro-6'H-spiro[1,3-dioxolane-2,7'-[1,2,4]triazolo[1,5-a]-quinazoline;

6,7,8,9-tetrahydro[1,2,4]triazolo[1,5-a]quinazoline optionally substituted e.g., by C1-C6alkyl; 7,8-dihydro-6H-cyclopenta[e]imidazo[1,2-a]pyrimidine optionally substituted e.g., by C1-C6alkoxy; 7,8-dihydro-6H-cyclopenta[e]imidazo[1,2-a]pyrimidinyl optionally substituted e.g., by arylalkyloxyalkyloxy; 3-dihydro[1,3]thiazolo[3,2-a]-benzimidazole; 2,3-dihydro[1,3]thiazolo[3,2-a]benzimidazole; 4-dihydro-2H-[1,3]thiazino[3,2-a]-benzimidazole; [1,3]thiazolo[3,2-a]benzimidazole; 7,8-dihydro-5H-pyrano[4,3-d]pyrazolo[5,1-b][1,3]-oxazole; 5,6,7,8-tetrahydropyrazolo[5,1-b][1,3]benzoxazole; and 5,6,7,8-tetrahydropyrazolo[5',1':2,3][1,3]oxazolo[5,4-c]pyridine optionally substituted e.g., by C2-C7alkoxycarbonyl.

$R_1$ is H, optionally substituted —C1-C6 alkyl, optionally substituted -aryl, optionally substituted -heteroaryl or mono or bicyclic saturated heterocycles, optionally substituted —C3-C7 cycloalkyl, optionally substituted —C3-C6 alkenyl, optionally substituted —C3-C6 alkynyl with the proviso that both the double bond and the triple bond should not be present at the carbon atom which is directly linked to N; optionally substituted —C1-C6 per fluoro alkyl, —$S(O)_p$ optionally substituted alkyl or aryl where p is 2, optionally substituted —C=Oheteroaryl, optionally substituted —C=Oaryl, optionally substituted —C=O(C1-C6) alkyl, optionally substituted —C=O(C3-C6)cycloalkyl, optionally substituted —C=O mono or bicyclic saturated heterocycles, optionally substituted C1-C6 alkyl aryl, optionally substituted C1-C6 alkyl heteroaryl, optionally substituted aryl-C1-C6 alkyl, optionally substituted heteroaryl-C1-C6 alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkyl aryloxyaryl, optionally substituted C1-C6 alkyl aryloxyheteroaryl, optionally substituted alkyl aryloxy alkylamines, optionally substituted alkoxy carbonyl, optionally substituted aryloxy carbonyl, optionally substituted heteroaryloxy carbonyl. Preferred $R_1$ groups are H, optionally substituted alkyl, optionally substituted aryl, —C=O(C1-C6)alkyl, C3-C6alkenyl, C3-C6alkynyl, optionally substituted cycloalkyl, $SO_2$alkyl, $SO_2$aryl, optionally substituted heterocycles, —$CONR_6R_7$, and optionally substituted heteroaryl.

$R_2$ is hydrogen, optionally substituted C1-C6 alkyl, optionally substituted C2-C6 alkenyl having 1 to 2 double bonds, optionally substituted C2-C6 alkynyl having 1 to 2 triple bonds, halogen, cyano, N—$R_6R_7$, optionally substituted C1-C6 alkoxy, hydroxy; optionally substituted aryl, optionally substituted heteroaryl, $COOR_6$, optionally substituted alkyl aryloxy alkylamines, optionally substituted aryloxy, optionally substituted heteroaryfoxy, optionally substituted C3-C6 alkenyloxy, optionally substituted C3-C6 alkynyloxy, C1-C6 alkylamino-C1-C6 alkoxy, alkylene dioxy, optionally substituted aryloxy-C1-C6 alkyl amine, C1-C6 perfluoro alkyl, $S(O)_q$-optionally substituted C1-C6 alkyl, $S(O)_q$— optionally substituted aryl where q is 0, 1 or 2, $CONR_6R_7$, guanidino or cyclic guanidino, optionally substituted C1-C6 alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, optionally substituted alkylaryloxyalkylamines, optionally substituted C3-C7 cycloalkyl, optionally substituted C3-C7 saturated or partially saturated heterocycle. Preferred $R_2$ groups are H, optionally substituted alkyl, optionally substituted alkoxy, optionally substituted heteroaryl, halogen, CN, hydroxy, optionally substituted heterocycle, —$CONR_6R_7$, $COOR_6$, optionally substituted aryl, $S(O)_q$-alkyl, and $S(O)_q$-aryl.

$R_3$ is hydrogen, C1-C6 alkyl, C3-C6 cycloalkyl, optionally substituted aryl, optionally substituted heteroaryl. Preferred $R_3$ groups are H or C1-C6 alkyl.

$R_4$ is H, optionally substituted C1-C6 alkyl, one of $R_4$ is OH, C1-C6 alkoxy, —S—C1-C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S=(O)n (where n=0 to 2), N—$R_1$; preferred $R_4$ groups are H, C1-C6 alkyl, $NR_6R_7$, or $R_4R_4$ together with the carbon to which they are attached forming a spiro system of five to eight members.

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, $R_6$ and $R_7$ can together with the nitrogen to which they are attached form a 3-7 membered saturated ring system optionally having one or two heteroatoms such as N—$R_1$, O, S=(O)$_n$ n=0-2. Preferred $R_6$ and $R_7$ groups are H, C1-C6 alkyl, arylalkyl, heteroarylalkyl, or $R_6$ and $R_7$ together with the nitrogen to which they are attached forming a 3-7 membered saturated ring system.

Chemical Definitions

The term alkyl means both straight and branched chain alkyl moieties of 1-12 carbons, preferably of 1-6 carbon atoms.

The term alkenyl means both straight and branched alkenyl moieties of 2-8 carbon atoms containing at least one double bond, and no triple bond, preferably the alkenyl moiety has 1 or two double bonds. Such alkenyl moieties may exist in the E or Z conformations; the compounds of this invention include both conformations. In the case of alkenyl, hetero atoms such as O, S or N—$R_1$ should not be present on the carbon that is bonded to a double bond;

The term alkynyl includes both straight chain and branched alkynyl moieties containing 2-6 carbon atoms containing at least one triple bond, preferably the 2 alkynyl moiety has one or two triple bonds. In the case of alkynyl, hetero atoms such as O, S or N—$R_1$ should not be present on the carbon that is bonded to a double or triple bond;

The term cycloalkyl refers to a alicyclic hydrocarbon group having 3-7 carbon atoms. The term perfluoroalkyl is used herein to refer to both straight- and branched-chain saturated aliphatic hydrocarbon groups having at least one carbon atom and two or more fluorine atoms. Examples include $CF_3$, $CH_2CF_3$, $CF_2CF_3$ and $CH(CF_3)_2$. The term halogen is defined as Cl, Br, F, and I.

If alkyl, alkenyl, alkynyl, or cycloalkyl is "optionally substituted", one or two of the following are possible substituents: nitro, -aryl, -heteroaryl, alkoxycarbonyl-, -alkoxy, -alkoxy-alkyl, alkyl-O—C2-C4alkyl-O—, -cyano, -halogen, -hydroxy, —N—$R_6R_7$, -trifluoromethyl, -trifluoromethoxy, arylalkyl, alkylaryl, $R_6R_7$N-alkyl-, HO—C1-C6-alkyl-, alkoxyalkyl-, alkyl-S—, —$SO_2$N—$R_6R_7$, —$SO_2$NHR$_6$— $CO_2$H, CONR$_6$R$_7$, aryl-O—, heteroaryl-O—, —S(O)$_s$-aryl (where s=0-2), -alkyl-O-alkyl-NR$_6$R$_7$, -alkyl-aryl-O-alkylN— R$_6$R$_7$, C1-C6alkyl, alkenyl, alkynyl, cycloalkyl, alkoxyalkyl-O—, R$_6$R$_7$N-alkyl-, and —S(O)$_s$-heteroaryl (where s=0-2); Preferred substituents for alkyl, alkenyl, alkynyl, and cycloalkyl include: halogen, nitro, aryl, heteroaryl, alkoxycarbonyl-, alkoxy, -alkoxy-alkyl, -cyano, hydroxy, and —N—R$_6$R$_7$.

Aryl is defined as an aromatic hydrocarbon moiety selected from the group: phenyl, α-naphthyl, β-naphthyl, biphenyl, anthryl, tetrahydronaphthyl, fluorenyl, indanyl, biphenylenyl, acenaphthenyl, groups.

Heteroaryl is defined as a aromatic heterocyclic ring system (monocyclic or bicyclic) where the heteroaryl moieties are selected from: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline; (2) a bicyclic aromatic heterocycle where a phenyl, pyridine, pyrimidine or pyridizine ring is: (a) fused to a 6-membered aromatic (unsaturated) heterocyclic ring having one nitrogen atom; (b) fused to a 5 or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S.

If aryl or heteroaryl is 'optionally substituted', one or two of the following are possible substituents: nitro, -aryl, -heteroaryl, alkoxycarbonyl-, -alkoxy, -alkoxy-alkyl, alkyl-O— C2-C4alkyl-O—, -cyano, -halogen, -hydroxy, —N—R$_6$R$_7$, -trifluoromethyl, -trifluoromethoxy, arylalkyl, alkylaryl, R$_6$R$_7$N-alkyl-, HO—C1-C6-alkyl-, alkoxyalkyl-, alkyl-S—, —SO$_2$N—R$_6$R$_7$, —SO$_2$NHR$_6$—CO$_2$H, CONR$_6$R$_7$, aryl-O—, heteroaryl-O—, —S(O)$_s$-aryl (where s=0-2), -alkyl-O-alkyl-NR$_6$R$_7$, -alkyl-aryl-O-alkylN-R$_6$R$_7$, C1-C6alkyl, alkenyl, alkynyl, cycloalkyl, alkoxy-alkyl-O—, R$_6$R$_7$N-alkyl-, and —S(O)$_s$-heteroaryl (where s=0-2); Preferred substituents for aryl and heteroaryl include: alkyl, halogen, —N—R$_6$R$_7$, trifluoromethyl, -trifluoromethoxy, arylalkyl, and alkylaryl.

Arylalkyl is defined as Aryl-C1-C6alkyl-; Arylalkyl moieties include benzyl, 1-phenylethyl, 2-phenylethyl, 3-phenylpropyl, 2-phenylpropyl and the like. The term 'optionally substituted' refers to unsubstituted or substituted with 1 or 2 substituents on the alkyl or aryl moiety as defined above.

Alkylaryl is defined as C1-C6alkyl-aryl-. The term 'optionally substituted' refers to unsubstituted or substituted with 1 or 2 substituents on the aryl or alkyl moiety as defined above.

Heteroaryl-C1-C6-alkyl is defined as a heteroaryl substituted alkyl moiety wherein the alkyl chain is 1-6 carbon atoms (straight or branched). Alkyl heteroaryl moieties include Heteroaryl-(CH$_2$)$_{1-6}$— and the like. The term 'optionally substituted' refers to unsubstituted or substituted with 1 or 2 substituents on the alkyl or heteroaryl moiety as defined above;

C1-C6 alkylheteroaryl is defined an alkyl chain of 1-6 carbon atoms (straight or branched) attached to a heteroaryl moiety, which is bonded to the rest of the molecule. Ex. C1-C6-alkyl-Heteroaryl-. The term 'optionally substituted' refers to unsubstituted or substituted with 1 or 2 substituents on the alkyl or heteroaryl moiety as defined above;

Saturated or partially saturated heterocycles groups are defined as heterocyclic rings selected from the moieties; aziridinyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl C1-C6 alkyl mono or bicyclic saturated or partially saturated heterocycles is defined as an alkyl group (straight or branched) of C1-C6 attached to a heterocycles (which is defined before) through a carbon atom or a nitrogen atom and the other end of the alkyl chain attached to the rest of the molecule. The terms 'optionally substituted' refers to unsubstituted or substituted with 1 or 2 substituents present on the alkyl or heterocyclic portion of the molecule, as defined before;

Arylalkyloxyalkyl is defined as Aryl-C1-C6alkyl-O—C1-C6alkyl-. The term 'optionally substituted' refers to unsubstituted or substituted with 1 or 2 substituents present on the alkyl and/or aryl portions as defined before;

Alkyloxyalkyl is defined as C1-C6 alkyl-O—C1-C6alkyl-. The term 'optionally substituted' refers to unsubstituted or substituted with 1 or 2 substituents present at the alkyl moiety as defined before;

Aryloxyalkyl is defined as Aryl-O—C1-C6 alkyl-. The term 'optionally substituted' refers to unsubstituted or substituted with 1 or 2 substituents present at the alkyl or aryl moiety as defined before;

Heteroarylalkyloxyalkyl is defined as Heteroaryl-C1-C6alkyl-O—C1-C6alkyl-. The term 'optionally substituted' refers to unsubstituted or substituted with 1 or 2 substituents present on the alkyl or heteroaryl moiety as defined before;

Aryloxyaryl is defined as Aryl-O-Aryl-. The term 'optionally substituted' refers to unsubstituted or substituted with 1 or 2 substituents present on the aryl moiety as defined before;

Aryloxyheteroaryl is defined as Aryl-O-Heteroaryl- or -Aryl-O-Heteroaryl; In this definition either the aryl moiety or the heteroaryl moiety can be attached to the remaining portion of the molecule; The term 'optionally substituted' refers to unsubstituted or substituted with 1 or 2 substituents present on the aryl moiety or on the heteroaryl moiety as defined before;

Alkyl aryloxyaryl is defined as Aryl-O-Aryl-C1-C6alkyl-; The term 'optionally substituted' refers to unsubstituted or substituted with 1 or 2 substituents present at the aryl moiety as defined before;

Alkylaryloxyheteroaryl is defined as Heteroaryl-O-Aryl-C1-C6alkyl-; The term 'optionally substituted' refers to unsubstituted or substituted with 1 or 2 substituents present on the aryl moiety or on the heteroaryl moiety as defined before;

Alkylaryloxyalkylamine is defined as R$_6$R$_7$N—C1-C6alkyl-O-Aryl-C1-C6alkyl-; The terms 'optionally substituted' refers to unsubstituted or substituted with 1 or 2 substituents present on the alkyl or aryl moiety as defined before; R$_6$ and R$_7$ as defined before;

Alkoxycarbonyl is defined as C1-C6alkyl-O—C═O—; The term 'optionally substituted' refers to unsubstituted or substituted with 1 or 2 substituents present on the alkyl portion of the alkoy moiety as defined before;

Aryloxycarbonyl is defined as Aryl-O—C═O—; The term 'optionally substituted' refers to unsubstituted or substituted with 1 or 2 substituents present at the aryl moiety as defined before;

Heteroaryloxy carbonyl is defined as Heteroaryl-O—C═O—; The term 'optionally substituted' refers to unsubstituted or substituted with 1 or 2 substituents present at the heteroaryl moiety as defined before;

Alkoxy is defined as C1-C6alkyl-O—; The terms 'optionally substituted' refers to unsubstituted or substituted with 1 or 2 substituents present at the alkyl moiety as defined before;

Aryloxy is defined as Aryl-O—; The term 'optionally substituted' refers to unsubstituted or substituted with 1 or 2 substituents present at the aryl moiety as defined before;

Heteroaryloxy is defined as Heteroaryl-O—; The term 'optionally substituted' refers to unsubstituted or substituted with 1 or 2 substituents present at the heteroaryl moiety as defined before;

Alkenyloxy is defined as C3-C6 alkene-O—; Example allyl-O—, but-2-ene-O or like moieties; The term 'optionally substituted' refers to unsubstituted or substituted with 1 or 2 substituents present at the alkene moiety as defined before, with the proviso that no hetero atom such as O, S or N—$R_1$ is present on the carbon atom, which is attached to a double bond;

Alkynyloxy is defined as C3-C6alkyne-O—; Example CH triple bond C—$CH_2$—O—, or like moieties; The term 'optionally substituted' refers to unsubstituted or substituted with 1 or 2 substituents present at the alkyne moiety as defined before, with the proviso that no hetero atom such as O, S or N—$R_1$ is present on a carbon atom which is attached to a double or triple bond;

Alkylaminoalkoxy is defined as $R_6R_7$N—C1-C6-alkyl-O—C1-C6-alkyl-, where the terminal alkyl group attached to the oxygen is connected to the rest of the molecule; The terms $R_6$ and $R_7$ are defined above; The term 'optionally substituted' refers to unsubstituted or substituted with 1 or 2 substituents present at the alkyl moiety as defined before;

Alkylenedioxy is defined as —O—$(CH_2)_2$—O—;

Aryloxyalkylamine is defined as $R_6R_7$N—C1-C6-alkyl-O-Aryl-, where the aryl is attached to the rest of the molecule; The term 'optionally substituted' refers to unsubstituted or substituted with 1 or 2 substituents present at the alkyl or aryl moiety as defined before;

Arylalkenyl is defined as Aryl-C2-C8alkene—, with the proviso that no hetero atom such as O, S or N—$R_1$ is present on the carbon atom, which is attached to a double bond; The term 'optionally substituted' refers to unsubstituted or substituted with 1 or 2 substituents present on the alkene or aryl moiety as defined before;

Heteroaryloxyalkyl is defined as Heteroaryl-O—C1-C6alkyl-; The term 'optionally substituted' refers to unsubstituted or substituted with 1 or 2 substituents present at the heteroaryl moiety as defined before;

Heteroaryloxyaryl is defined as Heteroaryl-O-aryl-, where the aryl moiety is attached to the rest of the molecule; The term 'optionally substituted' refers to unsubstituted or substituted with 1 or 2 substituents present at the heteroaryl moiety or the aryl moiety as defined before;

Alkoxy, alkoxyalkyl, alkoxyalkyloxy and alkylthioalkyloxy are moieties wherein the alkyl chain is 1-6 carbon atoms (straight or branched). Aryloxy, heteroaryloxy, arylthio and heteroarylthio are moieties wherein the aryl and heteroaryl groups are as herein before defined. Arylalkyloxy, heteroarylalkyloxy, arylalkylthio and heteroarylalkylthio are moieties wherein the aryl and heteroaryl groups are as herein before defined and wherein the alkyl chain is 1-6 carbons (straight or branched). Aryloxyalkyl, heteroaryloxyalkyl, aryloxyalkyloxy and heteroaryloxyalkyloxy are substituents wherein the alkyl radical is 1-6 carbon atoms. The terms monoalkylamino and dialkylamino refer to moieties with one or two alkyl groups wherein the alkyl chain is 1-6 carbons and the groups may be the same or different. The terms monoalkylaminoalkyl and dialkylaminoalkyl refer to monoalkylamino and dialkylamino moieties with one or two alkyl groups (the same or different) bonded to the nitrogen atom which is attached to an alkyl group of 1-3 carbon atoms.

Pharmaceutically acceptable salts are those salts which may be administered or provided to a warm blooded animal, preferably sodium, potassium or calcium alkaline earth metal salts.

Preferably the formula I compound has the following stereochemistry:

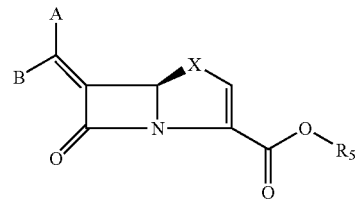

Examples of Tricyclic Heteroarylgroup A and B:

Ring Size and Arrangements: (5-5-5)

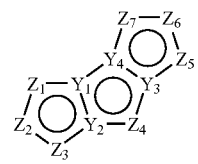

1-A

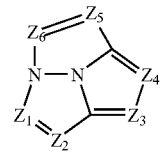

1-B

In both formula 1-A and 1-B $Z_1$, $Z_2$, $Z_3$, $Z_4$, $Z_5$, $Z_6$ and $Z_7$ are independently selected from $CR_2$, N, O, S or N—$R_1$ and as mentioned above one of $Z_1$-$Z_7$ is a carbon atom to which the remainder of the molecule is attached. $Y_1$, $Y_2$, $Y_3$ and $Y_4$ may independently be C or N.

Ring Size and Arrangement: (5-5-6)

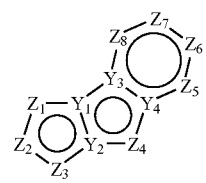

2-A

-continued

2-B
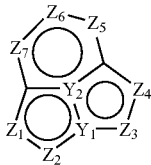

In both formula 2-A and 2-B $Z_1, Z_2, Z_3, Z_4, Z_5, Z_6, Z_7$ and $Z_8$ are independently selected from $CR_2$, N, O, S or N—$R_1$ and as mentioned above one of the $Z_1$-$Z_8$ is a carbon atom to which the remainder of the molecule is attached. $Y_1, Y_2, Y_3$ and $Y_4$ may be independently be C or N.

Ring Size and Arrangement: (5-6-5)

3-A
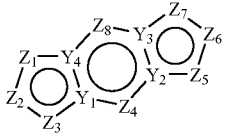

3-B
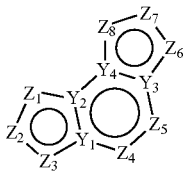

In both formula 3-A and 3-B $Z_1, Z_2, Z_3, Z_4, Z_5, Z_6, Z_7$ and $Z_8$ are independently selected from $CR_2$, N, O, S or N—$R_1$ and as mentioned above one of $Z_1$-$Z_8$ is a carbon atom to which the remainder of the molecule is attached. $Y_1, Y_2, Y_3$ and $Y_4$ may be C or N.

Ring Size and Arrangements: (5-6-6)

4-A
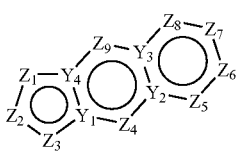

4-B
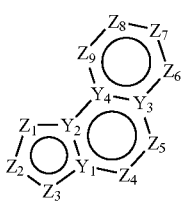

4-C
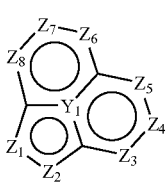

In formula 4-A 4-B and 4-C $Z_1, Z_2, Z_3, Z_4, Z_5, Z_6, Z_7$ and $Z_8$ are independently selected from $CR_2$, N, O, S or N—$R_1$ and as mentioned above one of the $Z_1$-$Z_8$ is a carbon atom to which the remainder of the molecule is attached. $Y_1, Y_2, Y_3$ and $Y_4$ are independently C or N.

Ring Size and Arrangements: [5-5-(Non-Aromatic)]

5-A
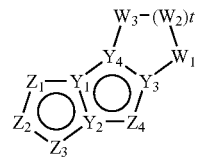

5-B
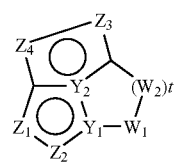

In both formula 5-A and 5-B $Z_1, Z_2, Z_3$ and 4 are independently selected from $CR_2$, N, O, S or N—$R_1$ and as mentioned above one of the $Z_1$-$Z_4$ is a carbon atom to which the remainder of the molecule is attached; $Y_1, Y_2, Y_3$ and $Y_4$ are independently C or N. $W_1, W_2$ and $W_3$ are independently selected from $CR_4R_4$, S(O)r (r=0-2), O, N—$R_1$ with the proviso that no S—S, S—O or O—O bond formation can occur to form a saturated ring; and t=1 to 3.

Ring Size and Arrangement: [5-6-(Non-Aromatic)]

6-A
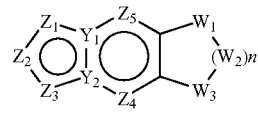

6-B
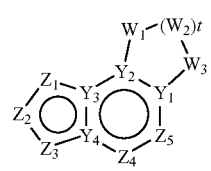

6-C
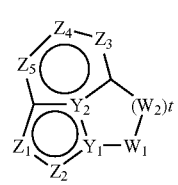

In formulae 6-A, 6-B and 6-C $Z_1, Z_2, Z_3, Z_4$ and $Z_5$ are independently selected from $CR_2$, N, O, S or N—$R_1$ and as mentioned above one of the $Z_1$-$Z_5$ is a carbon atom to which the remainder of the molecule is attached. $Y_1$, and $Y_2$ are independently C or N. $W_1, W_2$ and $W_3$ are independently $CR_4R_4$, S(O)r (r=0-2), O, or N—$R_1$ with the proviso that no S—S, S—O or O—O bond formation can occur to form a saturated ring; and t=1 to 3.

Ring Size and Arrangement: [5-(Non-Aromatic)-5]

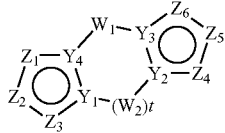
7-A

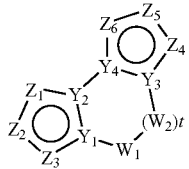
7-B

In formulae 7-A and 7-B $Z_1$, $Z_2$, $Z_3$, $Z_4$, $Z_5$ and $Z_6$ are independently selected from $CR_2$, N, O, S, and N—$R_1$; one of $Z_1$-$Z_6$ is a carbon atom to which the remainder of the molecule is attached. $Y_1$, $Y_2$, $Y_3$ and $Y_4$ are independently C or N. $W_1$ and $W_2$ are independently selected from $CR_4R_4$, S(O)r (r=0-2), O, N—$R_1$ with the proviso that no S—S, S—O or O—O bond formation can occur to form a saturated ring; and t=1 to 3.

Ring Size and Arrangement: [5-(Non-Aromatic)-6]

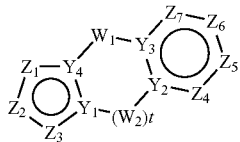
8-A

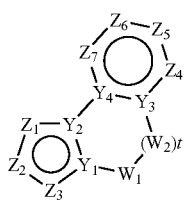
8-B

In formulae 8-A and 8-B $Z_1$, $Z_2$, $Z_3$, $Z_4$, $Z_5$, $Z_6$ and $Z_7$ are independently selected from $CR_2$, N, O, S and N—$R_1$ and as mentioned above one of the $Z_1$-$Z_7$ is a carbon atom to which the remainder of the molecule is attached. $Y_1$, $Y_2$, $Y_3$ and $Y_4$ are independently C or N. $W_1$ and $W_2$ are independently $CR_4R_4$, S(O)r (r=0-2), O, or N—$R_1$ with the proviso that no S—S, S—O or O—O bond formation can occur to form a saturated ring; and t=0-3.

Ring Size and Arrangement [5-(Non-Aromatic)-(Non-Aromatic)]

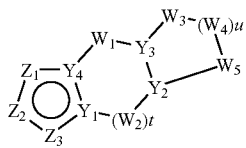
9-A

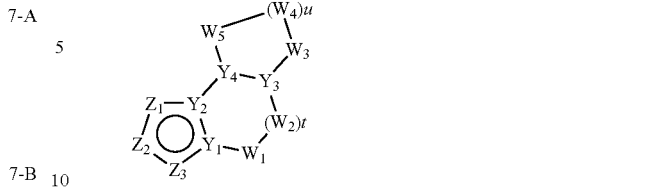
9-B

In formulae 9-A and 9-B $Z_1$, $Z_2$ and $Z_3$ are independently selected from $CR_2$ N, O, S or N—$R_1$; one of $Z_1$-$Z_3$ is a carbon atom to which the remainder of the molecule is attached. $Y_1$ and $Y_4$ are independently C or N; $Y_2$ and $Y_3$ are independently CH or N; $W_1$, $W_2$, $W_3$, $W_4$ and $W_5$ are independently $CR_4R_4$, S(O)r (r=0-2), O, or N—$R_1$ with the proviso that no S—S, S—O or O—O bond formation can occur to form a saturated ring; t=0 to 2 and u=1 to 3.

Ring Size and Arrangement (6-5-6)

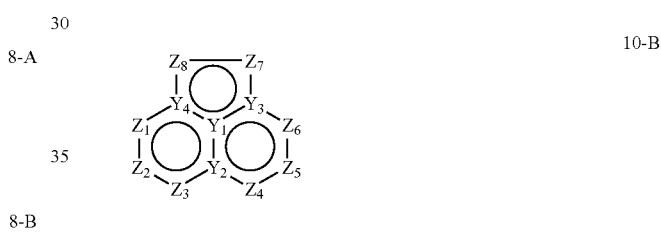

In formula 10-A and 10-B $Z_1$, $Z_2$, $Z_3$, $Z_4$, $Z_5$, $Z_6$, $Z_7$, $Z_8$ and $Z_9$ are independently selected from $CR_2$, N, O, S or N—$R_1$ and as mentioned above one of the $Z_1$-$Z_9$ is a carbon atom to which the remainder of the molecule is attached. $Y_1$, $Y_2$, $Y_3$ and $Y_4$ are independently C or N.

Ring Size and Arrangement (6-6-6)

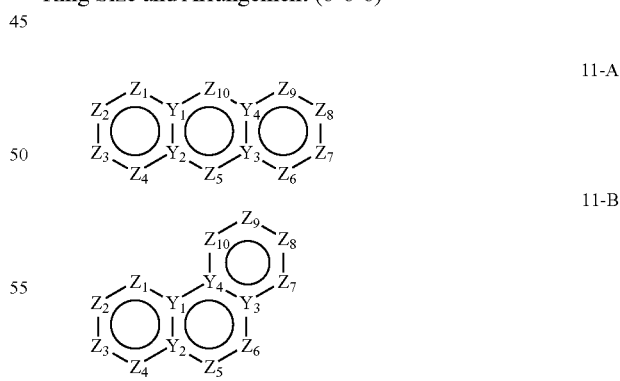

In formula 11-A, 11-B and 11-C $Z_1$, $Z_2$, $Z_3$, $Z_4$, $Z_5$, $Z_6$, $Z_7$, $Z_8$, $Z_9$ and $Z_{10}$ are independently $CR_2$, N, O, S or N—$R_1$; one of the $Z_1$-$Z_{10}$ is a carbon atom to which the remainder of the molecule is attached. $Y_1$, $Y_2$, $Y_3$ and $Y_4$ are independently C or N.

Ring Size and Arrangement [6-5-(Non-Aromatic)]

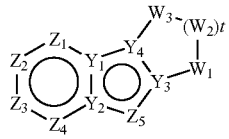
12-A

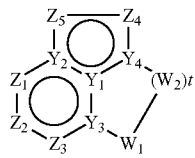
12-B

In formula 12-A and 12-B $Z_1$, $Z_2$, $Z_3$, $Z_4$ and $Z_5$ are independently $CR_2$, N, O, S or N—$R_1$ with the proviso that one of $Z_1$-$Z_5$ is a carbon atom to which the remainder of the molecule is attached. $Y_1$, $Y_2$, $Y_3$ and $Y_4$ are independently C or N; $W_1$, $W_2$, $W_3$ are independently $CR_4R_4O$, N—$R_1$, or S=(O)$_r$ (r=0-2) with the proviso that no S—S, S—O or O—O bond formation can occur to form a saturated ring; and t=1-4.

Ring Size and Arrangement [6-6-(Non-Aromatic)]

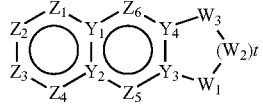
13-A

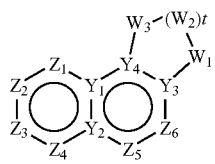
13-B

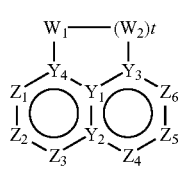
13-C

In formula 13-A, 13-B and 13-C $Z_1$, $Z_2$, $Z_3$, $Z_4$, $Z_5$ and $Z_6$ are independently $CR_2$, N, O, S or N—$R_1$; one of $Z_1$-$Z_6$ is a carbon atom to which the remainder of the molecule is attached. $Y_1$, $Y_2$, $Y_3$ and $Y_4$ are independently C or N; $W_1$, $W_2$ and $W_3$ are independently $CR_4R_4$, S(O)r (r=0-2), O, or N—$R_1$ with the proviso that no S—S, S—O or O—O bond formation can occur to form a saturated ring; and t=1 to 3.

Ring Size and Arrangement [6-(Non-Aromatic)-6]

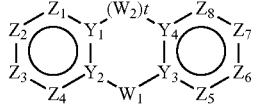
14-A

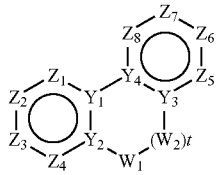
14-B

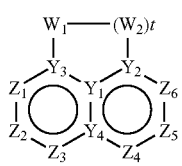
14-C

In formula 14-A, 14-B and 14-C $Z_1$, $Z_2$, $Z_3$, $Z_4$, $Z_5$, $Z_6$, $Z_7$ and $Z_8$ are independently $CR_2$, N, O, S or N—$R_1$; one of $Z_1$-$Z_8$ is a carbon atom to which the remainder of the molecule is attached. $Y_1$, $Y_2$, $Y_3$ and $Y_4$ are independently C or N; $W_1$, and $W_2$ are independently $CR_4R_4$, S(O)r (r=0-2), O, or N—$R_1$ with the proviso that no S—S, S—O or O—O bond formation can occur to form a saturated ring; and t=1 to 2.

Ring Size and Arrangement [6-(Non-Aromatic)-(Non-Aromatic)]

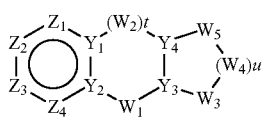
15-A

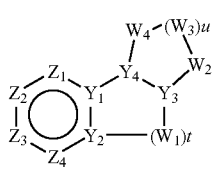
15-B

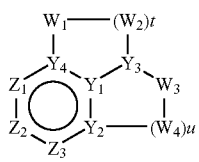
15-C

In formula 15-A, 15-B and 15-C $Z_1$, $Z_2$, $Z_3$ and $Z_4$ are independently $CR_2$, N, O, S or N—$R_1$; one of $Z_1$-$Z_4$ is a carbon atom to which the remainder of the molecule is attached. $Y_1$, $Y_2$, $Y_3$ and $Y_4$ are independently C or N; $W_1$, $W_2$, $W_3$, $W_4$ and $W_5$ are independently $CR_4R_4$, S(O)r (r=0-2), O, or N—$R_1$ with the proviso that no S—S, S—O or O—O bond formation can occur to form a saturated ring; t=1 to 3 and u=1 to 3.

The preferred embodiments of formula 1-A are:
1. $Z_1$ is O, S, or N—$R_1$; $Z_2$, $Z_3$, $Z_4$, $Z_5$, $Z_6$ and $Z_7$ are independently $CR_2$, or N; $Y_1$, $Y_2$, $Y_3$, $Y_4$ are C; any one of $Z_2$, $Z_3$, $Z_4$, $Z_5$, $Z_6$, $Z_7$ is a carbon to which the remainder of the molecule is attached.

2. $Z_1$ is O, S, or N—$R_1$; $Z_2, Z_3, Z_4, Z_5, Z_6$ and $Z_7$ are independently $CR_2$; $Y_1, Y_2, Y_3$, and $Y_4$ are C; one of $Z_2, Z_3, Z_4, Z_5, Z_6, Z_7$ is a carbon to which the remainder of the molecule is attached.
3. $Z_2$ is O, S, or N—$R_1$; $Z_1, Z_3, Z_4, Z_5, Z_6$ and $Z_7$ are independently $CR_2$, or N; $Y_1, Y_2, Y_3, Y_4$ are C; one of $Z_1, Z_3, Z_4, Z_5, Z_6, Z_7$ is a carbon to which the remainder of the molecule is attached.
4. $Z_2$ is O, S, or N—$R_1$; $Z_1, Z_3, Z_4, Z_5, Z_6$ and $Z_7$ are independently $CR_2$; $Y_1, Y_2, Y_3, Y_4$ are C; one of $Z_1, Z_3, Z_4, Z_5, Z_6, Z_7$ is a carbon to which the remainder of the molecule is attached.
5. $Z_3$ is O, S, or N—$R_1$; $Z_1, Z_2, Z_4, Z_5, Z_6, Z_7$ are independently $CR_2$, or N; $Y_1, Y_2, Y_3, Y_4$ are C; one of $Z_1, Z_2, Z_4, Z_5, Z_6, Z_7$ is a carbon to which the remainder of the molecule is attached.
6. $Z_3$ is O, S, or N—$R_1$; $Z_1, Z_2, Z_4, Z_5, Z_6, Z_7$ are independently $CR_2$; $Y_1, Y_2, Y_3, Y_4$ are C; one of $Z_1, Z_3, Z_4, Z_5, Z_6$, or $Z_7$ is a carbon to which the remainder of the molecule is attached.
7. $Z_7$ is O, S, or N—$R_1$; $Z_1, Z_2, Z_3, Z_4, Z_5$ and $Z_6$ are independently $CR_2$ or N; $Y_1, Y_2, Y_3, Y_4$ are C; one of $Z_1, Z_2, Z_3, Z_4, Z_5$ and $Z_6$ is a carbon to which the remainder of the molecule is attached.
8. $Z_7$ is O, S, or N—$R_1$; $Z_1, Z_2, Z_3, Z_4, Z_5$ and $Z_6$ are independently $CR_2$; $Y_1, Y_2, Y_3, Y_4$ are C; any of $Z_1, Z_2, Z_3, Z_4, Z_5$ and $Z_6$ is a carbon to which the remainder of the molecule is attached.
9. $Z_1, Z_4$, and $Z_6$ are independently O, S, or N—$R_1$; $Z_2, Z_3, Z_5, Z_7$ are independently $CR_2$, or N; $Y_1, Y_2, Y_3, Y_4$ are C; any one of $Z_2, Z_3, Z_5$, or $Z_7$ is a carbon to which the remainder of the molecule is attached.
10. $Z_1, Z_4$, and $Z_6$ are independently O, S, or N—$R_1$; $Z_2, Z_3, Z_5, Z_7$ are independently $CR_2$; $Y_1, Y_2, Y_3, Y_4$ are C; any one of $Z_2, Z_3, Z_5$, or $Z_7$ is a carbon to which the remainder of the molecule is attached.
11. $Z_3, Z_4$, and $Z_6$ are independently O, S, or N—$R_1$; $Z_1, Z_2, Z_5, Z_7$ are independently $CR_2$, or N; $Y_1, Y_2, Y_3, Y_4$ are C; any one of $Z_1, Z_2, Z_5$, or $Z_7$ is a carbon to which the remainder of the molecule is attached.
12. $Z_3, Z_4$, and $Z_6$ are independently O, S, or N—$R_1$; $Z_2, Z_3, Z_5, Z_7$ are independently $CR_2$; $Y_1, Y_2, Y_3, Y_4$ are C; any one of $Z_1, Z_2, Z_5$, or $Z_7$ is a carbon to which the remainder of the molecule is attached.
13. $Z_1$ is O, S, or N—$R_1$; $Z_2, Z_3, Z_4, Z_5, Z_6$ and $Z_7$ are independently $CR_2$, or N; $Y_2$ is N; $Y_1, Y_3, Y_4$ are C; any one of $Z_2, Z_3, Z_4, Z_5, Z_6$, or $Z_7$ is a carbon to which the remainder of the molecule is attached.
14. $Z_1$ is O, S, or N—$R_1$; $Z_2, Z_3, Z_4, Z_5, Z_6$ and $Z_7$ are independently $CR_2$; $Y_2$ is N; $Y_1, Y_3, Y_4$ are C; one of $Z_2, Z_3, Z_4, Z_5, Z_6$, or $Z_7$ is a carbon to which the remainder of the molecule is attached.
15. $Z_2$ and $Z_4$ are independently O, S, or N—$R_1$; $Z_1, Z_3, Z_5, Z_6, Z_7$ are independently $CR_2$, N; $Y_1$ is N; $Y_2, Y_3, Y_4$ are C; any one of $Z_1, Z_3, Z_5, Z_6$, or $Z_7$ is a carbon to which the remainder of the molecule is attached.
16. $Z_2$ and $Z_4$ are independently O, S, or N—$R_1$; $Z_1, Z_3, Z_5, Z_6, Z_7$ are independently $CR_2$; $Y_1$ is N; $Y_2, Y_3, Y_4$ are C; any one of $Z_1, Z_3, Z_5, Z_6$, or $Z_7$ is a carbon to which the remainder of the molecule is attached
17. $Z_3$ and $Z_5$ are independently O, S, or N—$R_1$; $Z_1, Z_2, Z_4, Z_6, Z_7$ are independently $CR_2$, or N; $Y_1$ is N; $Y_2, Y_3, Y_4$ are C; any one of $Z_1, Z_2, Z_4, Z_6$, or $Z_7$ is a carbon to which the remainder of the molecule is attached.
18. $Z_3$ and $Z_5$ are independently O, S, or N—$R_1$; $Z_1, Z_2, Z_4, Z_6, Z_7$ are independently $CR_2$; $Y_1$ is N; $Y_2, Y_3, Y_4$ are C; any one of $Z_1, Z_3, Z_5, Z_6$, or $Z_7$ is a carbon to which the remainder of the molecule is attached.
19. $Z_1$ and $Z_5$ are independently O, S, or N—$R_1$; $Z_2, Z_3, Z_4, Z_6, Z_7$ are independently N, or $CR_2$; $Y_1$ is N; $Y_2, Y_3, Y_4$ are C; any one of $Z_2, Z_3, Z_4, Z_6, Z_7$ is a carbon to which the remainder of the molecule is attached.
20. $Z_1$ and $Z_5$ are independently O, S, or N—$R_1$; $Z_2, Z_3, Z_4, Z_6, Z_7$ are independently $CR_2$; $Y_1$ is N; $Y_2, Y_3, Y_4$ are C; any one of $Z_2, Z_3, Z_4, Z_6$, or $Z_7$ is a carbon to which the remainder of the molecule is attached.
21. $Z_3$ and $Z_7$ are independently O, S, or N—$R_1$; $Z_1, Z_2, Z_4, Z_5, Z_6$ are independently N, or $CR_2$; $Y_1$ is N; $Y_2, Y_3, Y_4$ are C; any one of $Z_1, Z_2, Z_4, Z_5$, or $Z_6$ is a carbon to which the remainder of the molecule is attached.
22. $Z_3$ and $Z_7$ are independently O, S, N—$R_1$; $Z_1, Z_2, Z_4, Z_5, Z_6$ are independently $CR_2$; $Y_1$ is N; $Y_2, Y_3, Y_4$ are C; Any one of $Z_1, Z_2, Z_4, Z_5$, or $Z_6$ is a carbon to which the remainder of the molecule is attached.
23. $Z_3$ and $Z_7$ are independently O, S, N—$R_1$; $Z_1, Z_2, Z_4, Z_5, Z_6$ are independently N, or $CR_2$; $Y_2$ is N; $Y_1, Y_3, Y_4$ are C; any one of $Z_1, Z_2, Z_4, Z_5$, or $Z_6$ is a carbon to which the remainder of the molecule is attached.
24. $Z_3$ and $Z_7$ are independently O, S, or N—$R_1$; $Z_1, Z_2, Z_4, Z_5, Z_6$ are independently $CR_2$; $Y_2$ is N; $Y_1, Y_3, Y_4$ are C; any one of $Z_1, Z_2, Z_4, Z_5$, or $Z_6$ is a carbon to which the remainder of the molecule is attached.
25. $Z_3$ and $Z_5$ are independently O, S, N—$R_1$; $Z_1, Z_2, Z_4, Z_6, Z_7$ are independently N, or $CR_2$; $Y_2$ is N; $Y_1, Y_3, Y_4$ are C; any one of $Z_1, Z_2, Z_4, Z_6$, or $Z_7$ is a carbon to which the remainder of the molecule is attached.
26. $Z_3$ and $Z_5$ are independently O, S, or N—$R_1$; $Z_1, Z_2, Z_4, Z_6, Z_7$ are independently $CR_2$; $Y_2$ is N; $Y_1, Y_3, Y_4$ are C; any one of $Z_1, Z_2, Z_4, Z_6$, or $Z_7$ is a carbon to which the remainder of the molecule is attached.

The preferred embodiment of formula 1-B is:

27. $Z_1, Z_2, Z_3, Z_4, Z_5, Z_6$ and $Z_7$ are independently $CR_2$.

The preferred embodiments of formula 2-A are:

28. $Z_1$ is $CR_2$; $Z_2$ is the carbon to which the remainder of the molecule is attached; $Z_3$ is N or $CR_2$; $Z_4$ is O, S, $CR_2$ or N—$R_1$; $Z_5, Z_6, Z_7, Z_8$ are independently $CR_2$ or N; $Y_1$ is N; $Y_2, Y_3$ and $Y_4$ are C.
29. $Z_2$ is $CR_2$; $Z_1$ is carbon to which the remainder of the molecule is attached; $Z_3$ is N or $CR_2$; $Z_4$ is O, S, $CR_2$ or N—$R_1$; $Z_5, Z_6, Z_7, Z_8$ are independently $CR_2$ or N; $Y_1$ is N; $Y_2, Y_3$ and $Y_4$ are C.
30. $Z_1$ is N, $Z_2$ is carbon to which the remainder of the molecule is attached; $Z_3$ is N or $CR_2$; $Z_4$O, S, $CR_2$ or N—$R_1$; $Z_5, Z_6, Z_7, Z_8$ are independently $CR_2$ or N; $Y_1$ is N; $Y_2, Y_3$ and $Y_4$ are C.
31. $Z_1, Z_2, Z_3$ are independently $CR_2$ or N; $Z_4$ is O, S, $CR_2$ or N—$R_1$; $Z_5, Z_6, Z_7, Z_8$ are independently $CR_2$ or N and one of $Z_5, Z_6, Z_7$, or $Z_8$ is a carbon to which the remainder of the molecule is attached; $Y_1$ is N; $Y_2, Y_3$ and $Y_4$ is C.
32. $Z_1$ is $CR_2$ or N; $Z_2$ is $CR_2$; $Z_3$ is O, S or N—$R_1$; $Z_4$ is N or $CR_2$; $Z_5, Z_6, Z_7, Z_8$ are independently $CR_2$; $Y_1$ is N, or C; $Y_2, Y_3$ and $Y_4$ are C.
33. $Z_1, Z_2, Z_3, Z_4, Z_5, Z_6, Z_7, Z_8$ are independently N or $CR_2$; $Y_1, Y_2, Y_3, Y_4$ are C.
34. $Z_1, Z_2, Z_5, Z_6, Z_7, Z_8$ are independently N or $CR_2$; $Z_3$ and $Z_4$ are independently O, S, or N—$R_1$; $Y_1, Y_2, Y_3$, and $Y_4$ are C.
35. $Z_1, Z_2$, and $Z_3$ are independently $CR_2$ or N; 4 is O, S, $CR_2$ or N—$R_1$; $Z_5, Z_6, Z_7$, and $Z_8$ are independently $CR_2$ or N; $Y_1$ is N; $Y_2, Y_3$ and $Y_4$ are C.

36. $Z_1$ is N; $Z_2$ is $CR_2$; $Z_3$ is the carbon atom to which remainder of the molecule is attached; $Z_4$ is N; $Z_4$, $Z_6$, $Z_7$, $Z_8$ are independently N or $CR_2$; $Y_1$, $Y_2$, $Y_3$, $Y_4$ are independently N or C.

The preferred embodiment of formula 2-B is:

37. $Z_1$ and $Z_4$ are independently $CR_2$ or N; $Z_2$ and $Z_3$ are $CR_2$; $Z_5$, $Z_6$, $Z_7$ are independently $CR_2$ or N; $Y_1$ is C and $Y_2$ is N.

38. $Z_1$ is O, S, or N—$R_1$; $Z_2$ is $CR_2$; $Z_3$ is $CR_2$, or N; $Z_4$ is O, S, N—$R_1$, or $CR_2$; $Z_5$, $Z_6$, $Z_7$, $Z_8$ are independently N or $CR_2$; $Y_1$, $Y_2$, $Y_3$, and $Y_4$ are C; one of $Z_2$, $Z_3$, $Z_5$, $Z_6$, $Z_7$, or $Z_8$ is a carbon atom to which the remainder of the molecule is attached.

The preferred embodiments of formula 3-A are:

39. $Z_1$ is O, S, or N—$R_1$; $Z_2$ is N, or $CR_2$; $Z_3$ is $CR_2$; $Z_5$, $Z_6$, and $Z_7$ are independently N or $CR_2$; $Z_4$ and $Z_8$ are independently O, S, or N—$R_1$; $Y_1$, $Y_2$, $Y_3$, and $Y_4$ are C and one of $Z_2$, $Z_5$, $Z_6$, or $Z_7$ is a carbon atom to which the remainder of the molecule is attached.

40. $Z_3$ is O, S, or N—$R_1$; $Z_2$ is N, $CR_2$; $Z_1$ is $CR_2$; $Z_5$, $Z_6$, and $Z_7$ are independently N or $CR_2$; $Z_4$ and $Z_8$ are independently O, S, or N—$R_1$; $Y_1$, $Y_2$, $Y_3$, and $Y_4$ are C and one of $Z_2$, $Z_5$, $Z_6$, or $Z_7$ is a carbon atom to which the remainder of the molecule is attached.

The preferred embodiments of formula 3-B are:

41. $Z_1$ is O, S, or N—$R_1$; $Z_2$ is N or $CR_2$; $Z_3$ is $CR_2$; $Z_4$, $Z_5$, $Z_6$, $Z_7$, and $Z_8$ are independently N or $CR_2$; $Y_1$, $Y_2$, $Y_3$, and $Y_4$ are C; and one of $Z_2$, $Z_5$, $Z_6$, $Z_7$ is a carbon atom to which the remainder of the molecule is attached.

42. $Z_1$ is N or $CR_2$; $Z_2$ is $CR_2$; $Z_3$ is O, S, N—$R_1$ or $CR_2$; $Z_7$ is $CR_2$ or N; $Z_6$, and $Z_8$ are independently N or $CR_2$; $Z_4$ and $Z_5$ are $CR_2$ or N; $Y_1$, $Y_2$, and $Y_3$ are C; $Y_4$ is N and one of $Z_2$, $Z_4$, $Z_5$, $Z_6$ is a carbon atom to which the remainder of the molecule is attached.

43. $Z_1$ is N, or $CR_2$; $Z_2$ is $CR_2$; $Z_3$ is O, S, N—$R_1$ or $CR_2$; $Z_6$ is $CR_2$ or N; $Z_7$, and $Z_8$ are independently N or $CR_2$; $Z_4$ and $Z_5$ are independently $CR_2$ or N; $Y_1$, $Y_2$, $Y_3$ are C; $Y_4$ is N and one of $Z_2$, $Z_4$, $Z_5$, $Z_6$ is a carbon atom to which the remainder of the molecule is attached.

44. $Z_1$ is O, S, or N—$R_1$; $Z_2$ is N, or $CR_2$; $Z_3$ is $CR_2$; $Z_6$, $Z_7$, and $Z_8$ are N; $Z_4$ and $Z_5$ are independently $CR_2$ or N; $Y_1$, $Y_2$, $Y_4$ are C; $Y_3$ is N and one of $Z_2$, or $Z_3$ is a carbon atom to which the remainder of the molecule is attached.

45. $Z_1$ is N or $CR_2$; $Z_2$ is $CR_2$; $Z_3$ is O, S, N—$R_1$ or $CR_2$; $Z_6$, $Z_7$, and $Z_8$ are N; $Z_4$, and $Z_5$ are independently $CR_2$ or N; $Y_1$, $Y_2$, $Y_4$ are C; $Y_3$ is N and one of $Z_1$, $Z_2$ is a carbon atom to which the remainder of the molecule is attached.

46. $Z_1$ is N or $CR_2$; $Z_2$ is $CR_2$; $Z_3$ is O, S, N—$R_1$ or $CR_2$; $Z_6$, $Z_7$, and $Z_8$ are N; $Z_4$ and $Z_4$ are independently $CR_2$ or N; $Y_1$, $Y_2$, $Y_4$ are C; $Y_3$ is N and one of $Z_4$, $Z_2$, is a carbon atom to which the remainder of the molecule is attached.

47. $Z_1$ is N; $Z_2$, $Z_3$, $Z_4$ and $Z_5$ are independently $CR_2$; $Z_6$, $Z_7$, and $Z_8$ are independently O, S, N, N—$R_1$ or $CR_2$; $Y_2$, $Y_3$, and $Y_4$ are C; $Y_1$ is N; one of $Z_2$, $Z_3$, $Z_6$, $Z_6$, $Z_7$, $Z_8$ is a carbon atom to which the remainder of the molecule is attached.

48. $Z_3$ is N; $Z_2$ and $Z_1$ are independently $CR_2$; $Z_4$, and $Z_5$ are independently $CR_2$; $Z_6$, $Z_7$, $Z_8$ are independently O, S, N, N—$R_1$ or $CR_2$; $Y_2$, $Y_3$, and $Y_1$ are C; $Y_4$ is N; one of $Z_2$, $Z_1$, $Z_6$, $Z_6$, $Z_7$, $Z_8$ is a carbon atom to which the remainder of the molecule is attached.

49. $Z_1$ is N, or $CR_2$; $Z_2$ is $CR_2$; $Z_3$ is O, S, or N—$R_1$; $Z_4$ and $Z_5$ are independently $CR_2$; $Z_6$, $Z_7$, $Z_8$ are independently O, S, N, N—$R_1$ or $CR_2$; $Y_1$, $Y_2$, $Y_3$, and $Y_4$ are C; one of $Z_1$, $Z_2$, $Z_3$, $Z_6$, $Z_7$, $Z_8$ is a carbon atom to which the remainder of the molecule is attached.

The Preferred embodiments of formula 4-A

50. $Z_1$ and $Z_3$ are independently O, S, N—$R_1$, N, or $CR_2$; $Z_2$ is $CR_2$; $Z_4$, $Z_5$, $Z_6$, $Z_7$, $Z_8$, $Z_9$, are independently $CR_2$; $Y_1$, $Y_2$, $Y_3$, $Y_4$, are C.

51. $Z_1$ and $Z_3$ are independently O, S, N—$R_1$, N, or $CR_2$; $Z_2$ is $CR_2$; $Z_4$, and $Z_9$ are independently $CR_2$, or N; $Z_5$, $Z_6$, $Z_7$, $Z_8$ are independently $CR_2$; $Y_1$, $Y_2$, $Y_3$, $Y_4$, are C; One of $Z_1$, $Z_2$, $Z_3$, $Z_5$, $Z_6$, $Z_7$, $Z_8$ is a carbon atom to which the remainder of the molecule is attached.

52. $Z_1$ is S, O, or N—$R_1$; $Z_2$, $Z_3$, $Z_4$, $Z_5$, $Z_6$, $Z_7$, $Z_8$ are independently $CR_2$; $Z_9$ is N; $Y_1$, $Y_2$, $Y_3$, $Y_4$, are C.

53. $Z_1$, and $Z_3$ are independently O, S, N—$R_1$, N, or $CR_2$; 4, and $Z_9$, are independently N or $CR_2$; $Z_5$, $Z_6$, $Z_7$, $Z_8$ are independently $CR_2$ or N; $Y_1$, $Y_2$, $Y_3$, $Y_4$, are C; $Z_2$ is the carbon to which the remainder of the molecule is attached.

54. $Z_1$ is N; $Z_2$, $Z_3$, and $Z_4$ are independently $CR_2$; $Z_5$, $Z_6$, $Z_7$, $Z_8$ are independently N or $CR_2$; $Z_9$ is $CR_2$ or N; $Y_1$ is N; $Y_2$, $Y_3$, and $Y_4$, are C; $Z_2$ or $Z_3$ is the carbon to which the remainder of the molecule is attached.

55. $Z_3$ is N; $Z_1$, $Z_2$, and $Z_4$ are independently $CR_2$; $Z_5$, $Z_6$, $Z_7$, and $Z_8$ are independently $CR_2$, or N; $Z_9$ is $CR_2$, or N; $Y_4$ is N; $Y_1$, $Y_2$, and $Y_3$ are C.

The Preferred embodiments of formula 4-B

56. $Z_1$ is N; $Z_2$, $Z_3$, $Z_4$, $Z_5$, $Z_6$, $Z_7$, $Z_8$, and $Z_9$ are independently $CR_2$; $Y_1$ is N; $Y_2$, $Y_3$, and $Y_4$ are C; one of $Z_2$, $Z_3$, $Z_6$, $Z_7$, $Z_8$, $Z_9$ is the carbon atom to which the remainder of the molecule is attached.

57. $Z_3$ is N; $Z_1$, $Z_2$, and $Z_4$ are independently $CR_2$; $Z_5$, $Z_6$, $Z_7$, $Z_8$, and $Z_9$ are independently $CR_2$ or N; $Y_1$, $Y_3$, $Y_4$ are C; $Y_2$ is N.

58. $Z_1$ is O, S, or N—$R_1$; $Z_2$, $Z_3$, and $Z_4$ are independently $CR_2$; $Z_5$ is $CR_2$ or N; $Z_6$, $Z_7$, $Z_8$, and $Z_9$ are independently $CR_2$, or N; one of $Z_6$, $Z_7$, $Z_8$, $Z_9$ is a carbon atom to which the remainder of the molecule is attached.

59. $Z_1$ and $Z_3$ are independently O, S, N—$R_1$, N, or $CR_2$; $Z_4$ is $CR_2$ or N; $Z_5$ is $CR_2$; $Z_6$, $Z_7$, $Z_8$, and $Z_9$ are independently $CR_2$, or N; $Y_1$, and $Y_2$ are independently C or N; $Y_3$ and $Y_4$ are C.

The Preferred embodiments of formula 4-C

60. $Z_1$ and $Z_2$ are independently N or $CR_2$; $Z_3$, $Z_4$, $Z_5$, $Z_6$, $Z_7$, and $Z_8$ are independently $CR_2$; $Y_1$ is C.

61. $Z_1$ and $Z_2$ are independently $CR_2$; $Z_3$, $Z_4$, $Z_5$, $Z_6$, $Z_7$, and $Z_8$ are independently N or $CR_2$; $Y_1$ is C.

62. $Z_1$, $Z_2$, $Z_3$, $Z_4$, $Z_5$, $Z_6$, $Z_7$, and $Z_8$ are independently N or $CR_2$; $Y_1$ is C.

The Preferred embodiments of formula 5-A

63. $Z_1$ is O, S, or N—$R_1$; $Z_2$, and $Z_3$ are independently $CR_2$; $Z_4$ is O, S, N—$R_1$, or $CR_2$; $Y_1$, and $Y_2$ are C; $Y_4$, and $Y_3$ are independently C, or N; $W_1$, $W_2$, $W_3$ are independently $CR_4R_4$; t=1 or 2.

64. $Z_1$ is O, S, or N—$R_1$; $Z_2$ and $Z_3$ are independently $CR_2$; $Z_4$ is O, S, N—$R_1$, or $CR_2$; $Y_1$, and $Y_2$ are C; $Y_4$, and $Y_3$ are independently C, or N; $W_1$, and $W_3$ are independently $CR_4R_4$; t=1 to 2; $W_2$ is O, S(O)r (r=0-2), N—$R_1$ or $CR_4R_4$.

65. $Z_3$ is N; $Z_2$ is $CR_2$; $Z_7$ is $CR_2$, or N; $Z_4$ is O, S, N—$R_1$, $W_1$, $W_2$, and $W_3$ are independently $CR_4R_4$; t=1 to 3; $Y_1$, $Y_3$, and $Y_4$ are C; $Y_2$ is N; one of $Z_1$, $Z_2$ or $Z_4$ is the carbon atom to which the remainder of the molecule is attached.

66. $Z_1$ is N; $Z_2$ is $CR_2$; $Z_7$ is $CR_2$, or N; $Z_4$ is O, S, or N—$R_1$; $W_1$, $W_2$, and $W_3$ are independently $CR_4R_4$; t=1 to 3; $Y_2$, $Y_3$, and $Y_4$ are C; $Y_1$ is N; one of $Z_2$, $Z_3$, $Z_4$ is the carbon atom to which the remainder of the molecule is attached.

67. $Z_3$ is N; $Z_2$ is $CR_2$; $Z_1$ is $CR_2$, or N; $Z_4$ is O, S, or N—$R_1$; $Y_1$, $Y_3$, and $Y_4$ are C; $Y_2$ is N; $W_1$, $W_2$, and $W_3$ are independently $CR_4R_4$, O, S(O)r (r=0-2), or N—$R_1$ with the proviso that no S—S, S—O or O—O bond formation can occur to form a saturated ring; t=1 to 3; one of $Z_1$, $Z_2$ or $Z_4$ is the carbon atom to which the remainder of the molecule is attached.

68. $Z_1$ is N; $Z_2$ is $CR_2$; $Z_3$ is $CR_2$, or N; $Z_4$ is O, S, or N—$R_1$; $Y_2$, $Y_3$, and $Y_4$ are C; $Y_1$ is N; $W_1$, $W_2$, and $W_3$ are independently $CR_4R_4$, O, S=(O)r (r=0-2); or N—$R_1$, with the proviso that no S—S, S=O or O—O bond formation can occur to form a saturated ring; t=1-3; one of $Z_2$, $Z_3$, $Z_4$ is a carbon atom to which the remainder of the molecule is attached.

69. $Z_1$ is $CR_2$; $Z_2$ is the carbon atom to which the remainder of the molecule is attached; $Z_3$ is N; $Z_4$ is O, S, or N—$R_1$; $Y_1$ is C; $Y_2$ is N; $Y_3$, and $Y_4$ are C; $W_1$, $W_2$, and $W_3$ are independently $CR_4R_4$, O, S=(O)$_r$ (r=0-2), or N—$R_1$ with the proviso that no S—S, S=O or O—O bond formation can occur to form a saturated ring; t=1 to 3.

70. $Z_1$ is the carbon atom to which the remainder of the molecule is attached; $Z_2$ is $CR_2$; $Z_3$ is N; $Z_4$ is O, S, N—$R_1$; $Y_1$ is C; $Y_2$ is N; $Y_3$, and $Y_4$ are C; $W_1$, $W_2$, and $W_3$ are independently $CR_4R_4$, O, S=(O)$_r$ (r=0-2), or N—$R_1$ with the proviso that no S—S, S=O or O—O bond formation can occur to form a saturated ring; t=1-3.

71. $Z_1$, $Z_2$, and $Z_3$ are independently $CR_2$, or N; $Z_4$ is $CR_2$; $Y_1$, $Y_2$ are C; $Y_3$, $Y_4$ are N; $W_1$, $W_2$, and $W_3$ are independently $CR_4R_4$, O, S=(O)r (r=0-2), or N—$R_1$ with the proviso that no S—S, S=O or O—O bond formation can occur to form a saturated ring; t=1-3.

The Preferred embodiments of formula 5-B

72. $Z_1$, $Z_2$, $Z_3$, $Z_4$ are independently $CR_2$; $Y_1$, $Y_2$ are N; $W_1$, $W_2$ are independently O, S, N—$R_1$ or $CR_4R_4$; t=1-2.

73. $Z_1$, $Z_2$ are independently N, or $CR_2$; $Z_3$ is $CR_2$; $Z_4$ is O, S, or N—$R_1$; $W_1$, and $W_2$ are independently O, S, N—$R_1$, $CR_4R_4$; t=1-2.

The preferred embodiments of formula 6-A are:

74. $Z_1$ is O, S, N—$R_1$; $Z_2$, $Z_3$, $Z_4$, $Z_5$ are independently $CR_2$; $W_1$, $W_2$, $W_3$ are independently N—$R_1$, O, S=(O)$_r$ (r=0-2), or $CR_4R_4$; $Y_1$, $Y_2$ are C; t=1-3; one of $Z_2$, $Z_3$ is the carbon atom to which the remainder of the molecule is attached.

75. $Z_1$ is O, S, or N—$R_1$; $Z_3$ is N, O, or S; $Z_2$, $Z_4$, $Z_5$ are independently $CR_2$; $W_1$, $W_2$, $W_3$ are independently N—$R_1$, O, S=(O)$_r$ (r=0-2), or $CR_4R_4$; $Y_1$, and $Y_2$ are C; t=1-3; $Z_2$ is the carbon atom to which the remainder of the molecule is attached.

76. $Z_1$ is $CR_2$; $Z_3$ is N; $Z_2$, $Z_4$, and $Z_5$ are independently $CR_2$; $W_1$, $W_2$, and $W_3$ are 1° independently N—$R_1$, O, S=(O)$_r$ (r=0-2), or $CR_4R_4$; $Y_1$ is N; $Y_2$ is C; t=1-3; $Z_1$, or $Z_2$ is the carbon atom to which the remainder of the molecule is attached.

77. $Z_1$ is N; $Z_2$, $Z_3$, $Z_4$, $Z_5$ are independently $CR_2$; $W_1$, $W_2$, $W_3$ are independently N—$R_1$, O, S=(O)$_r$ (r=0-2), or $CR_4R_4$; $Y_1$ is C; $Y_2$ is N; t=1-3; $Z_2$, or $Z_3$ is the 1 carbon atom to which the remainder of the molecule is attached.

78. $Z_1$ is O, S, or N—$R_1$; $Z_2$ is N, O, or S; $Z_3$, $Z_4$, and $Z_5$ are independently $CR_2$; $W_1$, $W_2$, and $W_3$ are independently N—$R_1$, O, S=(O)$_r$ (r=0-2), or $CR_4R_4$; $Y_1$, and $Y_2$ are C; t=1-3; one of $Z_3$ is a carbon atom to which the remainder of the molecule is attached.

79. $Z_1$ is O, S, or N—$R_1$; $Z_2$, and $Z_3$ are independently $CR_2$; $Z_4$, and $Z_5$ are independently $CR_2$, or N; $W_1$, $W_2$, and $W_3$ are independently N—$R_1$, O, S=(O)$_r$ (r=0-2), or $CR_4R_4$; $Y_1$, $Y_2$ are C; t=1-3; $Z_2$ or $Z_3$ is the carbon atom to which the remainder of the molecule is attached.

80. $Z_1$ is O, S, or N—$R_1$; $Z_1$ is N, O, or S; $Z_2$ is $CR_2$; $Z_4$, $Z_5$ are independently $CR_2$, or N; $W_1$, $W_2$, $W_3$ are independently N—$R_1$, O, S=(O)$_r$ (r=0-2), or $CR_4R_4$; $Y_1$, $Y_2$ are C; t=1-3; $Z_2$ is the carbon atom to which the remainder of the molecule is attached.

81. $Z_1$ is $CR_2$; $Z_1$ is N; $Z_2$ is $CR_2$; $Z_4$, $Z_5$ are independently N, or $CR_2$; $W_1$, $W_2$, $W_3$ are independently N—$R_1$, O, S=(O)$_r$ (r=0-2), or $CR_4R_4$; $Y_1$ is N; $Y_2$ is C; t=1-3; $Z_1$ or $Z_2$ is the carbon atom to which the remainder of the molecule is attached.

82. $Z_1$ is N; $Z_2$, and $Z_3$ are independently $CR_2$; $Z_4$, $Z_5$ are independently N or $CR_2$; $W_1$, $W_2$, $W_3$ are independently N—$R_1$, O, S=(O)$_r$ (r=0-2), or $CR_4R_4$; $Y_1$ is C; $Y_2$ is N; t=1-3; $Z_2$ or $Z_3$ is the carbon atom to which the remainder of the molecule is attached.

83. $Z_1$ is O, S, or N—$R_1$; $Z_2$ is N, O, or S; $Z_3$ is $CR_2$; $Z_4$, and $Z_5$ are independently N, or $CR_2$; $W_1$, $W_2$, $W_3$ are independently N—$R_1$, O, S=(O)$_r$ (r=0-2), or $CR_4R_4$; $Y_1$, $Y_2$ are C; t=1-3; $Z_3$ is the carbon atom to which the remainder of the molecule is attached.

The preferred embodiments of formula 6-B are:

84. $Z_1$ is O, S, or N—$R_1$; $Z_2$, $Z_3$, $Z_4$, and $Z_5$ are independently $CR_2$; $W_1$, $W_2$, $W_3$ are independently N—$R_1$, O, S=(O)$_r$ (r=0-2), or $CR_4R_4$; $Y_1$, $Y_2$, $Y_3$, and $Y_4$ are C; t=1-3; $Z_2$ or $Z_3$ is the carbon atom to which the remainder of the molecule is attached.

85. $Z_1$ is O, S, or N—$R_1$; $Z_3$ is N, O, or S; $Z_2$, $Z_4$, $Z_5$ are independently $CR_2$; $W_1$, $W_2$, $W_3$ are independently N—$R_1$, O, S=(O)$_r$ (r=0-2), or $CR_4R_4$; $Y_1$, $Y_2$, $Y_3$, $Y_4$ are C; t=1-3; $Z_2$ is the carbon atom to which the remainder of the molecule is attached.

86. $Z_1$ is $CR_2$; $Z_3$ is N; $Z_2$, $Z_4$, and $Z_5$ are independently $CR_2$; $W_1$, $W_2$, $W_3$ are independently N—$R_1$, O, S=(O)$_r$ (r=0-2), or $CR_4R_4$; $Y_3$ is N; $Y_1$, $Y_2$, $Y_4$ are C; t=1-3; $Z_1$, or $Z_2$ is the carbon atom to which the remainder of the molecule is attached.

87. $Z_1$ is N; $Z_2$, $Z_3$, $Z_4$, $Z_5$ are independently $CR_2$; $W_1$, $W_2$, $W_3$ are independently N—$R_1$, O, S=(O)$_r$ (r=0-2), or $CR_4R_4$; $Y_1$, $Y_2$, $Y_3$ are C; $Y_4$ is N; t=1-3; $Z_2$ or $Z_3$ is the carbon atom to which the remainder of the molecule is attached.

88. $Z_1$ is O, S, or N—$R_1$; $Z_2$ is N, O, or S; $Z_3$, $Z_4$, and $Z_5$ are independently $CR_2$; $W_1$, $W_2$, $W_3$ are independently N—$R_1$, O, S=(O)$_r$ (r=0-2), or $CR_4R_4$; $Y_1$, $Y_2$, $Y_3$, and $Y_4$ are C; t=1-3; $Z_3$ is the carbon atom to which the remainder of the molecule is attached.

89. $Z_1$ is O, S, or N—$R_1$; $Z_2$, and $Z_3$ are independently $CR_2$; $Z_4$, and $Z_5$ are independently $CR_2$, or N; $W_1$, $W_2$, $W_3$ are independently N—$R_1$, O, S=(O)$_r$ (r=0-2), or $CR_4R_4$; $Y_1$, $Y_2$, $Y_3$, $Y_4$ are C; t=1-3; $Z_2$ or $Z_3$ is the carbon atom to which the remainder of the molecule is attached.

90. $Z_1$ is O, S, or N—$R_1$; $Z_3$ is N, O, or S; $Z_2$ is $CR_2$; $Z_4$, and $Z_5$ are independently $CR_2$ or N; $W_1$, $W_2$, $W_3$ are independently N—$R_1$, O, S=(O)$_r$ (r=0-2), or $CR_4R_4$; $Y_1$, $Y_2$, $Y_3$, $Y_4$ are C; t=1-3; $Z_2$ is the carbon atom to which the remainder of the molecule is attached.

91. $Z_1$ is $CR_2$; $Z_3$ is N; $Z_2$ is $CR_2$; $Z_4$, and $Z_5$ are independently N, $CR_2$; $W_1$, $W_2$, $W_3$ are independently N—$R_1$, O, S=(O)$_r$ (r=0-2), or $CR_4R_4$; $Y_3$ is N; $Y_1$, $Y_2$, $Y_4$ are C; t=1-3; $Z_1$ or $Z_2$ is the carbon atom to which the remainder of the molecule is attached.

92. $Z_1$ is N; $Z_2$, $Z_3$ are independently $CR_2$; $Z_4$, $Z_5$ are independently N, or $CR_2$; $W_1$, $W_2$, $W_3$ are independently N—$R_1$, O, S=(O)$_r$ (r=0-2), or $CR_4R_4$; $Y_1$, $Y_2$, $Y_3$ are C; $Y_4$ is N; t=1-3; $Z_2$, or $Z_3$ is the carbon atom to which the remainder of the molecule is attached.

93. $Z_1$ is O, S, or N—$R_1$; $Z_2$ is N, O, or S; $Z_3$ is $CR_2$; $Z_4$, $Z_5$ are independently N, or $CR_2$; $W_1$, $W_2$, $W_3$ are independently N—$R_1$, O, S=(O)$_r$ (r=0-2), or $CR_4R_4$; $Y_1$, $Y_2$, $Y_3$, $Y_4$ are C; t=1-3; $Z_3$ is the carbon atom to which the remainder of the molecule is attached.

The preferred embodiments of formula 6-C are:

94. $Z_1, Z_3, Z_4$, and $Z_5$ are independently N or $CR_2$; $Z_2$ is O, S, or N—$R_1$; $Y_1, Y_2$ are C; $W_1, W_2$ are independently N—$R_1$, O, S=(O)$_r$ (r=0-2), $CR_4R_4$; t=1-2.

95. $Z_1, Z_3, Z_4, Z_5$ are independently $CR_2$; $Z_2$ is O, S, or N—$R_1$; $Y_1, Y_2$ are C; $W_1, W_2$ are independently N—$R_1$, O, S=(O)$_r$ (r=0-2), or $CR_4R_4$; t=1-2.

96. $Z_1, Z_3, Z_5$ are independently $CR_2$; $Z_2$ is O, S, N—$R_1$; $Z_4$ is N; $Y_1, Y_2$ are C; $W_1, W_2$ are independently N—$R_1$, O, S=(O)$_r$ (r=0-2), or $CR_4R_4$; t=1-2.

97. $Z_1, Z_2, Z_3, Z_4$, and $Z_5$ are independently $CR_2$; $Y_1$ is C; $Y_2$ is N; $W_1, W_2$ are independently N—$R_1$, O, S=(O)$_r$ (r=0-2), or $CR_4R_4$; t=1-2.

98. $Z_1, Z_2, Z_3, Z_5$ are independently $CR_2$; $Z_4$ is N; $Y_1$ is C; $Y_2$ is N; $W_1, W_2$ are independently N—$R_1$, O, S=(O)$_r$ (r=0-2), or $CR_4R_4$; t=1-2.

The preferred embodiments of formula 7-A are:

99. $Z_3, Z_6$ are independently O, S, or N—$R_1$; $Z_1, Z_2, Z_4, Z_5$ are independently $CR_2$; $W_1, W_2$ are independently N—$R_1$, O, S=(O)$_r$ (r=0-2), or $CR_4R_4$; t=1-2.

100. $Z_3, Z_6$ are independently O, S, or N—$R_1$; $Z_1, Z_4$ are N; $Z_2, Z_5$ are independently $CR_2$; $W_1, W_2$ are independently N—$R_1$, O, S=(O)$_r$ (r=0-2), or $CR_4R_4$; t=1-2; $Z_2$ or $Z_5$ is the carbon atom to which the remainder of the molecule is attached.

101. $Z_1, Z_4$ are independently O, S, or N—$R_1$; $Z_2, Z_3, Z_5, Z_6$ are independently $CR_2$; $W_1, W_2$ are independently N—$R_1$, O, S=(O)$_r$ (r=0-2), or $CR_4R_4$; t=1-2.

102. $Z_1, Z_4$ are independently O, S, or N—$R_1$; $Z_3, Z_6$ are N; $Z_2, Z_5$ are independently $CR_2$; $W_1, W_2$ are independently N—$R_1$, O, S=(O)$_r$ (r=0-2), or $CR_4R_4$; t=1-2; $Z_2$ or $Z_5$ is the carbon atom to which the remainder of the molecule is attached.

103. $Z_2, Z_5$ are independently O, S, or N—$R_1$; $Z_1, Z_3, Z_4, Z_6$ are independently $CR_2$; $W_1, W_2$ are independently N—$R_1$, O, S=(O)$_r$ (r=0-2), or $CR_4R_4$; t=1-2.

104. $Z_2, Z_5$ are independently O, S, N—$R_1$; $Z_1, Z_3, Z_4, Z_6$ are independently $CR_2$, N, S; $W_1, W_2$ are independently N—$R_1$, O, S=(O)$_r$ (r=0-2), $CR_4R_4$; t=1-2; One of $Z_1, Z_3, Z_4, Z_6$ is the carbon atom to which the remainder of the molecule is attached.

105. $Z_1$ is $CR_2$, N; $Z_2$ is $CR_2$; $Z_3$ is N; $Z_4, Z_5$ are independently $CR_2$; $Z_6$ is N; $Y_1, Y_3$ are independently $CR_2$; $Y_2, Y_4$ are N; $W_1, W_2$ are independently N—$R_1$, O, S=(O)$_r$ (r=0-2), or $CR_4R_4$; t=1-2; One of $Z_1, Z_2, Z_4, Z_5$ is the carbon atom to which the remainder of the molecule is attached.

106. $Z_1$ is $CR_2$, or N; $Z_2$ is $CR_2$; $Z_7$ is O, S, N—$R_1$; $Z_4, Z_5$ are independently $CR_2$; $Z_6$ is N; $Y_1, Y_4, Y_3$ are independently $CR_2$; $Y_2$ is N; $W_1, W_2$ are independently N—$R_1$, O, S=(O)$_r$ (r=0-2), $CR_4R_4$; t=1-2; One of $Z_1, Z_2, Z_4, Z_5$ is the carbon atom to which the remainder of the molecule is attached.

107. $Z_1$ is $CR_2$, or N; $Z_2$ is $CR_2$; $Z_3$ is N; $Z_4, Z_5, Z_6$ are independently N, or $CR_2$; $Y_1$ and $Y_3$ are N; $Y_2, Y_4$ are independently $CR_2$; $W_1, W_2$ are independently N—$R_1$, O, S=(O)$_r$ (r=0-2), or $CR_4R_4$; t=1-2; One of $Z_1, Z_2, Z_4, Z_5, Z_6$ is the carbon atom to which the remainder of the molecule is attached.

The preferred embodiments of formula 7-B are:

108. $Z_1, Z_2, Z_4, Z_5, Z_6$ are independently $CR_2$; $Z_3$ is O, S, or N—$R_1$; $Y_1, Y_2, Y_4$ are C; $Y_3$ is N; $W_1, W_2$ are independently N—$R_1$, O, S=(O)$_r$ (r=0-2), or $CR_4R_4$; t=1-2.

109. $Z_1, Z_2, Z_4, Z_5, Z_3$ are independently $CR_2$ or N; $Z_3$ is O, S, or N—$R_1$; $Y_1, Y_2, Y_4$ are C; $Y_3$ is N; $W_1, W_2$ are independently N—$R_1$, O, S=(O)$_r$ (r=0-2), or $CR_4R_4$; t=1-2; One of $Z_1, Z_2, Z_4, Z_5, Z_6$ is the carbon atom to which the remainder of the molecule is attached.

110. $Z_1, Z_2, Z_3, Z_5, Z_6$ are independently $CR_2$; $Z_4$ is O, S, or N—$R_1$; $Y_1, Y_2, Y_3$ are C; $Y_4$ is N; $W_1, W_2$ are independently N—$R_1$, O, S=(O)$_r$ (r=0-2), or $CR_4R_4$; t=1-2; One of $Z_1, Z_2, Z_3, Z_5, Z_6$ is the carbon atom to which the remainder of the molecule is attached.

111. $Z_1, Z_2, Z_3, Z_5, Z_6$ are independently $CR_2$ or N; $Z_4$ is O, S, or N—$R_1$; $Y_1, Y_2, Y_3$ are C; $Y_4$ is N; $W_1, W_2$ are independently N—$R_1$, O, S=(O)$_r$ (r=0-2), or $CR_4R_4$; t=1-2; One of $Z_1, Z_2, Z_3, Z_5, Z_6$ is the carbon atom to which the remainder of the molecule is attached.

112. $Z_1, Z_2, Z_3, Z_4, Z_5, Z_6$ are independently $CR_2$; $Y_1, Y_3$ are N; $Y_2, Y_4$ are C; $W_1, W_2$ are independently N—$R_1$, O, S=(O)$_r$ (r=0-2), or $CR_4R_4$; t=1-2; One of $Z_1, Z_2, Z_3, Z_4, Z_5, Z_6$ is the carbon atom to which the remainder of the molecule is attached.

113. $Z_1, Z_2, Z_3, Z_4, Z_5, Z_6$ are independently $CR_2$ or N; $Y_1, Y_3$ are N; $Y_2, Y_4$ are C; $W_1, W_2$ are independently N—$R_1$, O, S=(O)$_r$ (r=0-2), or $CR_4R_4$; t=1-2; One of $Z_1, Z_2, Z_3, Z_4, Z_5, Z_6$ is the carbon atom to which the remainder of the molecule is attached.

114. $Z_1, Z_3, Z_4, Z_5, Z_6$ are independently $CR_2$; $Z_2$ is O, S, or N—$R_1$; $Y_1, Y_2, Y_4$ is C; $Y_3$ is N; $W_1, W_2$ are independently N—$R_1$, O, S=(O)$_r$ (r=0-2), or $CR_4R_4$; t=1-2; One of $Z_1, Z_3, Z_4, Z_5, Z_6$ is the carbon atom to which the remainder of the molecule is attached.

115. $Z_1, Z_3, Z_4, Z_5, Z_6$ are independently $CR_2$, or N; $Z_2$ is O, S, or N—$R_1$; $Y_1, Y_2, Y_4$ are C; $Y_3$=N; $W_1, W_2$ are independently N—$R_1$, O, S=(O)$_r$ (r=0-2), or $CR_4R_4$; t=1-2; One of $Z_1, Z_3, Z_4, Z_5, Z_6$ is the carbon atom to which the remainder of the molecule is attached.

116. $Z_1, Z_2, Z_4, Z_6$ are independently $CR_2$; $Z_3, Z_5$ are independently O, S, or N—$R_1$; $Y_1, Y_2, Y_3, Y_4$ are C; $W_1, W_2$ are independently N—$R_1$, O, S=(O)$_r$ (r=0-2), or $CR_4R_4$; t=1-2; One of $Z_1, Z_2, Z_4, Z_6$ is the carbon atom to which the remainder of the molecule is attached.

117. $Z_1, Z_2, Z_4, Z_6$ are independently $CR_2$, or N; $Z_3, Z_5$ are independently O, S, or N—$R_1$; $Y_1, Y_2, Y_3, Y_4$ are C; $W_1, W_2$ are independently N—$R_1$, O, S=(O)$_r$ (r=0-2), or $CR_4R_4$; t=1-2; One of $Z_1, Z_2, Z_4, Z_6$ is the carbon atom to which the remainder of the molecule is attached.

118. $Z_1, Z_2, Z_4, Z_5$ are independently $CR_2$; $Z_3, Z_6$ are independently O, S, or N—$R_1$; $Y_1, Y_2, Y_3, Y_4$ are C; $W_1, W_2$ are independently N—$R_1$, O, S=(O)$_r$ (r=0-2), or $CR_4R_4$; t=1-2; One of $Z_1, Z_2, Z_4, Z_5$ is the carbon atom to which the remainder of the molecule is attached.

119. $Z_1, Z_2, Z_4, Z_5$ are independently $CR_2$, or N; $Z_3, Z_6$ are independently O, S, or N—$R_1$; $Y_1, Y_2, Y_3, Y_4$ are C; $W_1, W_2$ are independently N—$R_1$, O, S=(O)$_r$ (r=0-2), or $CR_4R_4$; t=1-2; One of $Z_1, Z_2, Z_4, Z_5$ is the carbon atom to which the remainder of the molecule is attached.

120. $Z_1, Z_2, Z_5, Z_6$ are independently $CR_2$; $Z_3, Z_4$ are independently O, S, or N—$R_1$; $Y_1, Y_2, Y_3, Y_4$ are C; $W_1, W_2$ are independently N—$R_1$, O, S=(O)$_r$ (r=0-2), or $CR_4R_4$; t=1-2; One of $Z_1, Z_2, Z_5, Z_6$ is the carbon atom to which the remainder of the molecule is attached.

121. $Z_1, Z_2, Z_5, Z_6$ are independently $CR_2$ or N; $Z_3, Z_4$ are independently O, S, or N—$R_1$; $Y_1, Y_2, Y_3, Y_4$ are C; $W_1, W_2$ are independently N—$R_1$, O, S=(O)$_r$ (r=0-2), or $CR_4R_4$; t=1-2; One of $Z_1, Z_2, Z_5, Z_6$ is the carbon atom to which the remainder of the molecule is attached.

122. $Z_1, Z_2, Z_4, Z_5$ are independently $CR_2$; $Z_3, Z_6$ are independently O, S, or N—$R_1$; $Y_1, Y_2, Y_3, Y_4$ are C; $W_1, W_2$ are independently N—$R_1$, O, S=(O)$_r$ (r=0-2), or $CR_4R_4$; t=1-2; One of $Z_1, Z_2, Z_5, Z_6$ is the carbon atom to which the remainder of the molecule is attached.

123. $Z_1, Z_2, Z_4, Z_5$ are independently $CR_2$, or N; $Z_3, Z_6$ are independently O, S, or N—$R_1$; $Y_1, Y_2, Y_3, Y_4$ are C; $W_1, W_2$ are independently $N-R_1$, O, $S=(O)_r$ (r=0-2), or $CR_4R_4$; t=1-2; One of $Z_1$, $Z_2$, $Z_5$, $Z_6$ is the carbon atom to which the remainder of the molecule is attached.

124. $Z_1$, $Z_2$, $Z_3$, $Z_4$, $Z_6$ are independently $CR_2$; $Z_5$ is O, S, or $N-R_1$; $Y_1$ is N; $Y_2$, $Y_3$, $Y_4$ are C; $W_1$, $W_2$ are independently $N-R_1$, O, $S=(O)_r$ (r=0-2), or $CR_4R_4$; t=1-2; One of $Z_1$, $Z_2$, $Z_3$, $Z_4$, $Z_6$ is the carbon atom to which the remainder of the molecule is attached.

125. $Z_1$, $Z_2$, $Z_3$, $Z_4$, $Z_6$ are independently $CR_2$, or N; $Z_5$ is O, S, or $N-R_1$; $Y_1$ is N; $Y_2$, $Y_3$, $Y_4$ are C; $W_1$, $W_2$ are independently $N-R_1$, O, $S=(O)_r$ (r=0-2), or $CR_4R_4$; t=1-2; One of $Z_1$, $Z_2$, $Z_3$, $Z_4$, $Z_6$ is the carbon atom to which the remainder of the molecule is attached.

126. $Z_1$, $Z_3$, $Z_4$, $Z_6$ are independently $CR_2$; $Z_2$, $Z_5$ are independently O, S, or $N-R_1$; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_1$, $Z_3$, $Z_4$, $Z_6$ is the carbon atom to which the remainder of the molecule is attached.

127. $Z_1$, $Z_3$, $Z_4$, $Z_6$ are independently $CR_2$ or N; $Z_2$, $Z_5$ are independently O, S, or $N-R_1$; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_1$, $Z_3$, $Z_4$, $Z_6$ is the carbon atom to which the remainder of the molecule is attached.

The preferred embodiments of formula 8-A are:

128. $Z_1$ is O, S, or $N-R_1$; $Z_2$, $Z_4$, $Z_5$, $Z_6$, $Z_7$ are independently $CR_2$; $Z_3$ is $CR_2$, or N; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_2$, $Z_3$, $Z_4$, $Z_6$ is the carbon atom to which the remainder of the molecule is attached.

129. $Z_1$ is O, S, or $N-R_1$; $Z_2$, $Z_4$, $Z_5$, $Z_6$, $Z_7$ are independently $CR_2$; $Z_3$ is $CR_2$; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_2$, $Z_3$, $Z_4$, $Z_5$, $Z_6$, $Z_7$ is the carbon atom to which the remainder of the molecule is attached.

130. $Z_1$ is O, S, or $N-R_1$; $Z_2$, $Z_4$, $Z_5$, $Z_6$, $Z_7$ are independently $CR_2$; $Z_3$ is N; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_2$, $Z_4$, $Z_5$, $Z_6$, $Z_7$ is the carbon atom to which the remainder of the molecule is attached.

131. $Z_1$ is O, S, or $N-R_1$; $Z_3$, $Z_4$, $Z_5$, $Z_6$, $Z_7$ are independently $CR_2$; $Z_2$ is $CR_2$, or N; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_2$, $Z_3$, $Z_4$, $Z_5$, $Z_6$, $Z_7$ is the carbon atom to which the remainder of the molecule is attached.

132. $Z_1$ is O, S, or $N-R_1$; $Z_3$, $Z_4$, $Z_5$, $Z_6$, $Z_7$ are independently $CR_2$; $Z_2$ is N; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_3$, $Z_4$, $Z_5$, $Z_6$, $Z_7$ is the carbon atom to which the remainder of the molecule is attached.

133. $Z_1$ is O, S, or $N-R_1$; $Z_3$, $Z_4$, $Z_5$, $Z_6$, $Z_7$ are independently $CR_2$; $Z_2$ is $CR_2$; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_2$, $Z_3$, $Z_4$, $Z_5$, $Z_6$, $Z_7$ is the carbon atom to which the remainder of the molecule is attached.

134. $Z_1$ is O, S, or $N-R_1$; $Z_2$, $Z_3$, $Z_4$, $Z_5$, $Z_6$, $Z_7$ are independently N or $CR_2$; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_2$, $Z_3$, $Z_4$, $Z_5$, $Z_6$, $Z_7$ is the carbon atom to which the remainder of the molecule is attached.

135. $Z_1$ is O, S, or $N-R_1$; $Z_2$ is $CR_2$; $Z_4$, $Z_5$, $Z_6$, $Z_7$ are independently N or $CR_2$; $Z_3$ is $CR_2$; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_2$, $Z_3$, $Z_4$, $Z_5$, $Z_6$, $Z_7$ is the carbon atom to which the remainder of the molecule is attached.

136. $Z_1$ is O, S, or $N-R_1$; $Z_2$ is $CR_2$; $Z_4$, $Z_5$, $Z_6$, and $Z_7$ are independently N or $CR_2$; $Z_3$ is N; $Y_1$, $Y_2$, $Y_3$, $Y_4$ are C; $W_1$ and $W_2$ are independently $N-R_1$, O, $S=(O)_r$ (r=0-2), or $CR_4R_4$; t=1-2; One of $Z_2$, $Z_4$, $Z_5$, $Z_6$, $Z_7$ is the carbon atom to which the remainder of the molecule is attached.

137. $Z_1$ is O, S, or $N-R_1$; $Z_4$, $Z_5$, $Z_6$, and $Z_7$ are independently N or $CR_2$; $Z_2$ and $Z_3$ are independently $CR_2$ or N; $Y_1$, $Y_2$, $Y_3$, $Y_4$ are C; $W_1$ and $W_2$ are independently $N-R_1$, O, $S=(O)_r$ (r=0-2), or $CR_4R_4$; t=1-2; One of $Z_2$, $Z_3$, $Z_4$, $Z_5$, $Z_6$, $Z_7$ is the carbon atom to which the remainder of the molecule is attached.

138. $Z_1$ is O, S, or $N-R_1$; $Z_3$ is $CR_2$; $Z_4$, $Z_5$, $Z_6$, and $Z_7$ are independently N or $CR_2$; $Z_2$ is N; $Y_1$, $Y_2$, $Y_3$, and $Y_4$ are C; $W_1$ and $W_2$ are independently $N-R_1$, O, $S=(O)_r$ (r=0-2), or $CR_4R_4$; t=1-2; One of $Z_3$, $Z_4$, $Z_5$, $Z_6$, $Z_7$ is the carbon atom to which the remainder of the molecule is attached.

139. $Z_1$ is O, S, $N-R_1$; $Z_4$, $Z_5$, $Z_6$, and $Z_7$ are independently N or $CR_2$; $Z_2$ and $Z_3$ are independently $CR_2$; $Y_1$, $Y_2$, $Y_3$, $Y_4$ are C; $W_1$ and $W_2$ are independently $N-R_1$, O, $S=(O)_r$ (r=0-2), or $CR_4R_4$; t=1-2; One of $Z_2$, $Z_3$, $Z_4$, $Z_5$, $Z_6$, $Z_7$ is the carbon atom to which the remainder of the molecule is attached.

140. $Z_3$ is O, S, or $N-R_1$; $Z_2$, $Z_4$, $Z_5$, $Z_6$, and $Z_7$ are independently $CR_2$; $Z_1$ is $CR_2$ or N; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_1$, $Z_2$, $Z_4$, $Z_5$, $Z_6$, $Z_7$ is the carbon atom to which the remainder of the molecule is attached.

141. $Z_3$ is O, S, or $N-R_1$; $Z_1$, $Z_2$, $Z_4$, $Z_5$, $Z_6$, $Z_7$ are independently $CR_2$; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_1$, $Z_2$, $Z_4$, $Z_5$, $Z_6$, $Z_7$ is the carbon atom to which the remainder of the molecule is attached.

142. $Z_3$ is O, S, or $N-R_1$; $Z_2$, $Z_4$, $Z_5$, $Z_6$, and $Z_7$ are independently $CR_2$; $Z_1$ is N; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_1$, $Z_2$, $Z_4$, $Z_5$, $Z_6$, $Z_7$ is the carbon atom to which the remainder of the molecule is attached.

143. $Z_3$ is O, S, or $N-R_1$; $Z_1$, $Z_4$, $Z_5$, $Z_6$, $Z_7$ are independently $CR_2$; $Z_2$ is $CR_2$ or N; $Y_1$, $Y_2$, $Y_3$, $Y_4$ are C; $W_1$, $W_2$ are independently $N-R_1$, O, $S=(O)_r$ (r=0-2), or $CR_4R_4$; t=1-2; One of $Z_1$, $Z_2$, $Z_4$, $Z_5$, $Z_6$, $Z_7$ is the carbon atom to which the remainder of the molecule is attached.

144. $Z_3$ is O, S, or $N-R_1$; $Z_1$, $Z_4$, $Z_5$, $Z_6$, $Z_7$ are independently $CR_2$; $Z_2$ is N; $Y_1$, $Y_2$, $Y_3$, $Y_4$ are C; $W_1$ and $W_2$ are independently $N-R_1$, O, $S=(O)_r$ (r=0-2), or $CR_4R_4$; t=1-2; One of $Z_1$, $Z_4$, $Z_5$, $Z_6$, $Z_7$ is the carbon atom to which the remainder of the molecule is attached.

145. $Z_3$ is O, S, or $N-R_1$; $Z_1$, $Z_2$, $Z_4$, $Z_5$, $Z_6$, $Z_7$ are independently $CR_2$; $Y_1$, $Y_2$, $Y_3$, $Y_4$ are C; $W_1$ and $W_2$ are independently $N-R_1$, O, $S=(O)_r$ (r=0-2), or $CR_4R_4$; t=1-2; One of $Z_1$, $Z_2$, $Z_4$, $Z_5$, $Z_6$, $Z_7$ is the carbon atom to which the remainder of the molecule is attached.

146. $Z_3$ is O, S, or $N-R_1$; $Z_2$, $Z_4$, $Z_5$, $Z_6$, $Z_7$ are independently N or $CR_2$; $Z_1$ is $CR_2$, or N; $Y_1$, $Y_2$, $Y_3$, $Y_4$ are C; $W_1$, $W_2$ are independently $N-R_1$, O, $S=(O)_r$ (r=0-2), $CR_4R_4$; t=1-2; One of $Z_1$, $Z_2$, $Z_4$, $Z_5$, $Z_6$, $Z_7$ is the carbon atom to which the remainder of the molecule is attached.

147. $Z_3$ is O, S, or $N-R_1$; $Z_2$ is $CR_2$; $Z_4$, $Z_5$, $Z_6$, $Z_7$ are independently N or $CR_2$; $Z_1$ is $CR_2$; $Y_1$, $Y_2$, $Y_3$, $Y_4$ are C; $W_1$ and $W_2$ are independently $N-R_1$, O, $S=(O)_r$ (r=0-2), or $CR_4R_4$; t=1-2; One of $Z_1$, $Z_2$, $Z_4$, $Z_5$, $Z_6$, $Z_7$ is the carbon atom to which the remainder of the molecule is attached.

148. $Z_3$ is O, S, or $N-R_1$; $Z_2$ is $CR_2$; $Z_4$, $Z_5$, $Z_6$, and $Z_7$ are independently N or $CR_2$; $Z_1$ is N; $Y_1$, $Y_2$, $Y_3$, $Y_4$ are C; $W_1$ and $W_2$ are independently $N-R_1$, O, $S=(O)_r$ (r=0-2), or $CR_4R_4$; t=1-2; One of $Z_2$, $Z_4$, $Z_5$, $Z_6$, $Z_7$ is the carbon atom to which the remainder of the molecule is attached.

149. $Z_3$ is O, S, or $N-R_1$; $Z_4$, $Z_5$, $Z_6$, and $Z_7$ are independently N or $CR_2$; $Z_2$ and $Z_1$ are independently $CR_2$ or N; $Y_1$, $Y_2$, $Y_3$, $Y_4$ are C; $W_1$ and $W_2$ are independently $N-R_1$, O, S=(O)$_r$ (r=0-2), or CR$_4$R$_4$; t=1-2; One of Z$_1$, Z$_2$, Z$_4$, Z$_5$, Z$_6$, Z$_7$ is the carbon atom to which the remainder of the molecule is attached.

150. Z$_3$ is O, S, N—R$_1$; Z$_1$ is CR$_2$; Z$_4$, Z$_5$, Z$_6$, Z$_7$ are independently N or CR$_2$; Z$_2$ is N; Y$_1$, Y$_2$, Y$_3$, Y$_4$ are C; W$_1$, W$_2$ are independently N—R$_1$, O, S=(O)$_r$ (r=0-2), CR$_4$R$_4$; t=1-2; One of Z$_1$, Z$_4$, Z$_5$, Z$_6$, and Z$_7$ is the carbon atom to which the remainder of the molecule is attached.

151. Z$_3$ is O, S, N—R$_1$; Z$_4$, Z$_5$, Z$_6$, and Z$_7$ are independently N or CR$_2$; Z$_1$ and Z$_2$ are independently CR$_2$; Y$_1$, Y$_2$, Y$_3$, Y$_4$ are C; W$_1$ and W$_2$ are independently N—R$_1$, O, S=(O)$_r$ (r=0-2), or CR$_4$R$_4$; t=1-2; One of Z$_1$, Z$_2$, Z$_4$, Z$_5$, Z$_6$, and Z$_7$ is the carbon atom to which the remainder of the molecule is attached.

152. Z$_1$, Z$_2$, Z$_3$, Z$_4$, Z$_5$, Z$_6$, and Z$_7$ are independently CR$_2$; Y$_4$ is N; Y$_1$, Y$_2$, Y$_3$ are C; W$_1$, W$_2$ are independently N—R$_1$, O, S=(O)$_r$ (r=0-2), or CR$_4$R$_4$; t=1-2; One of Z$_1$, Z$_2$, Z$_3$, Z$_4$, Z$_5$, Z$_6$, Z$_7$ is the carbon atom to which the remainder of the molecule is attached.

153. Z$_1$ is N; Z$_2$, Z$_3$, Z$_4$, Z$_5$, Z$_6$, and Z$_7$ are independently CR$_2$; Y$_4$ is N; Y$_1$, Y$_2$, Y$_3$ are C; W$_1$ and W$_2$ are independently N—R$_1$, O, S=(O)$_r$ (r=0-2), or CR$_4$R$_4$; t=1-2; One of Z$_2$, Z$_3$, Z$_4$, Z$_5$, Z$_6$, and Z$_7$ is the carbon atom to which the remainder of the molecule is attached.

154. Z$_2$ is N; Z$_1$, Z$_3$, Z$_4$, Z$_5$, Z$_6$, Z$_7$ are independently CR$_2$; Y$_4$ is N; Y$_1$, Y$_2$, Y$_3$ are C; W$_1$ and W$_2$ are independently N—R$_1$, O, S=(O)$_r$ (r=0-2), CR$_4$R$_4$; t=1-2; One of Z$_1$, Z$_3$, Z$_4$, Z$_5$, Z$_6$, and Z$_7$ is the carbon atom to which the remainder of the molecule is attached.

155. Z$_3$ is N; Z$_1$, Z$_2$, Z$_4$, Z$_5$, Z$_6$, and Z$_7$ are independently CR$_2$; Y$_4$ is N; Y$_1$, Y$_2$, Y$_3$ are C; W$_1$, W$_2$ are independently N—R$_1$, O, S=(O)$_r$ (r=0-2), or CR$_4$R$_4$; t=1-2; One of Z$_1$, Z$_2$, Z$_4$, Z$_5$, Z$_6$, and Z$_7$ is the carbon atom to which the remainder of the molecule is attached.

156. Z$_1$ and Z$_2$ are N; Z$_3$, Z$_4$, Z$_5$, Z$_6$, Z$_7$ are independently CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_3$, Z$_4$, Z$_5$, Z$_6$, Z$_7$ is the carbon atom to which the remainder of the molecule is attached.

157. Z$_1$, Z$_3$ are N; Z$_2$, Z$_4$, Z$_5$, Z$_6$, Z$_7$ are independently CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_1$, Z$_2$, Z$_3$, Z$_4$, Z$_5$, Z$_6$, Z$_7$ is the carbon atom to which the remainder of the molecule is attached.

158. Z$_1$, Z$_2$, Z$_3$ are N; Z$_4$, Z$_5$, Z$_6$, Z$_7$ are independently CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_4$, Z$_5$, Z$_6$, Z$_7$ is the carbon atom to which the remainder of the molecule is attached.

159. Z$_1$, Z$_2$, Z$_3$ are independently CR$_2$; Z$_4$, Z$_5$, Z$_6$, Z$_7$ are independently N, CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_1$, Z$_2$, Z$_3$, Z$_4$, Z$_5$, Z$_6$, Z$_7$ is the carbon atom to which the remainder of the molecule is attached.

160. Z$_1$ is N; Z$_2$, Z$_3$ are independently CR$_2$; Z$_4$, Z$_5$, Z$_6$, Z$_7$ are independently N, CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_2$, Z$_3$, Z$_4$, Z$_5$, Z$_6$, Z$_7$ is the carbon atom to which the remainder of the molecule is attached.

161. Z$_2$ is N; Z$_1$, Z$_3$ are independently CR$_2$; Z$_4$, Z$_5$, Z$_6$, Z$_7$ are independently N, CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_1$, Z$_3$, Z$_4$, Z$_5$, Z$_6$, Z$_7$ is the carbon atom to which the remainder of the molecule is attached.

162. Z$_3$ is N; Z$_1$, Z$_2$ are independently CR$_2$; Z$_4$, Z$_5$, Z$_6$, Z$_7$ are independently N, CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_1$, Z$_2$, Z$_4$, Z$_5$, Z$_6$, Z$_7$ is the carbon atom to which the remainder of the molecule is attached.

163. Z$_1$, Z$_2$ are N; Z$_3$ are independently CR$_2$; Z$_4$, Z$_5$, Z$_6$, Z$_7$ are independently N, CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_3$, Z$_4$, Z$_5$, Z$_6$, Z$_7$ is the carbon atom to which the remainder of the molecule is attached.

164. Z$_1$, Z$_3$ are N; Z$_2$ are independently CR$_2$; Z$_4$, Z$_5$, Z$_6$, Z$_7$ are independently N, CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_1$, Z$_2$, Z$_3$, Z$_4$, Z$_5$, Z$_6$, Z$_7$ is the carbon atom to which the remainder of the molecule is attached.

165. Z$_1$, Z$_2$, Z$_3$ are N; Z$_4$, Z$_5$, Z$_6$, Z$_7$ are independently N, CR$_2$; Y$_4$ is N; Y$_1$, Y$_2$, Y$_3$ are C; W$_1$, W$_2$ are independently N—R$_1$, O, S=(O)$_r$ (r=0-2), CR$_4$R$_4$; t=1-2; One of Z$_4$, Z$_5$, Z$_6$, Z$_7$ is the carbon atom to which the remainder of the molecule is attached.

The preferred embodiments of formula 8-B are:

166. Z$_1$ is O, S, N—R$_1$; Z$_2$, Z$_3$, Z$_4$, Z$_5$, Z$_6$, Z$_7$ are independently N, CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_2$, Z$_3$, Z$_4$, Z$_5$, Z$_6$, Z$_7$ is the carbon atom to which the remainder of the molecule is attached.

167. Z$_1$ is O, S, N—R$_1$; Z$_2$, Z$_3$, Z$_4$, Z$_5$, Z$_6$, Z$_7$ are CH$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_2$, Z$_3$, Z$_4$, Z$_5$, Z$_6$, Z$_7$ is the carbon atom to which the remainder of the molecule is attached.

168. Z$_1$ is O, S, N—R$_1$; Z$_2$ is N; Z$_3$, Z$_4$, Z$_5$, Z$_6$, Z$_7$ are independently N, CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_3$, Z$_4$, Z$_5$, Z$_6$, Z$_7$ is the carbon atom to which the remainder of the molecule is attached.

169. Z$_1$ is O, S, N—R$_1$; Z$_2$, Z$_3$ are N; Z$_4$, Z$_5$, Z$_6$, Z$_7$ are independently N, CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_4$, Z$_5$, Z$_6$, Z$_7$ is the carbon atom to which the remainder of the molecule is attached.

170. Z$_1$ is O, S, N—R$_1$; Z$_2$, Z$_3$, Z$_4$, Z$_5$, Z$_6$, Z$_7$ are independently N, CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_3$ is N; Z$_2$, Z$_4$, Z$_5$, Z$_6$, Z$_7$ is the carbon atom to which the remainder of the molecule is attached.

171. Z$_2$ is O, S, N—R$_1$; Z$_1$, Z$_3$, Z$_4$, Z$_5$, Z$_6$, Z$_7$ are independently N, CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_1$, Z$_3$, Z$_4$, Z$_5$, Z$_6$, Z$_7$ is the carbon atom to which the remainder of the molecule is attached.

172. Z$_2$ is O, S, N—R$_1$; Z$_1$, Z$_3$, Z$_4$, Z$_5$, Z$_6$, Z$_7$ are independently CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_1$, Z$_3$, Z$_4$, Z$_5$, Z$_6$, Z$_7$ is the carbon atom to which the remainder of the molecule is attached.

173. Z$_2$ is O, S, N—R$_1$; Z$_1$ is N; Z$_3$ is CR$_2$; Z$_4$, Z$_5$, Z$_6$, Z$_7$ are independently N, CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_3$, Z$_4$, Z$_5$, Z$_6$, Z$_7$ is the carbon atom to which the remainder of the molecule is attached.

174. Z$_2$ is O, S, N—R$_1$; Z$_1$, Z$_3$ are N; Z$_4$, Z$_5$, Z$_6$, Z$_7$ are independently N, CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of Z$_4$, Z$_5$, Z$_6$, Z$_7$ is the carbon atom to which the remainder of the molecule is attached.

175. Z$_3$ is O, S, N—R$_1$; Z$_1$, Z$_2$, Z$_4$, Z$_5$, Z$_6$, Z$_7$ are independently N, CR$_2$; Y$_1$, Y$_2$, Y$_3$, Y$_4$ are C; W$_1$, W$_2$ are independently N—R$_1$, O, S=(O)$_r$ (r=0-2), CR$_4$R$_4$; t=0-2; One of $Z_1$, $Z_2$, $Z_4$, $Z_5$, $Z_6$, $Z_7$ is the carbon atom to which the remainder of the molecule is attached.

176. $Z_3$ is O, S, N—$R_1$; $Z_1$, $Z_2$, $Z_4$, $Z_5$, $Z_6$, $Z_7$ are independently $CR_2$; $Y_1$, $Y_2$, $Y_3$, $Y_4$ are C; $W_1$, $W_2$ are independently N—$R_1$, O, S=(O)$_r$ (r=0-2), $CR_4R_4$; t=0-2; One of $Z_1$, $Z_2$, $Z_4$, $Z_5$, $Z_6$, $Z_7$ is the carbon atom to which the remainder of the molecule is attached.

177. $Z_3$ is O, S, N—$R_1$; $Z_1$ is N; $Z_2$ is $CR_2$; $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0-2), $CR_4R_4$; t=0-2; One of $Z_2$, $Z_4$, $Z_5$, $Z_6$, $Z_7$ is the carbon atom to which the remainder of the molecule is attached.

178. $Z_3$ is O, S, N—$R_1$; $Z_1$, $Z_2$ is N; $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0-2), $CR_4R_4$; t=0-2; One of $Z_4$, $Z_5$, $Z_6$, $Z_7$ is the carbon atom to which the remainder of the molecule is attached.

179. $Z_1$, $Z_2$, $Z_3$, $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0-2), $CR_4R_4$; t=0-2; One of $Z_1$, $Z_2$, $Z_3$, $Z_4$, $Z_5$, $Z_6$, $Z_7$ is the carbon atom to which the remainder of the molecule is attached.

180. $Z_1$ is N; $Z_2$, $Z_3$ are independently $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0-2), $CR_4R_4$; t=0-2; One of $Z_2$, $Z_3$, $Z_4$, $Z_5$, $Z_6$, $Z_7$ is the carbon atom to which the remainder of the molecule is attached.

181. $Z_1$, $Z_2$ are N; $Z_3$ is $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0-2), $CR_4R_4$; t=0-2; One of $Z_3$, $Z_4$, $Z_5$, $Z_6$, $Z_7$ is the carbon atom to which the remainder of the molecule is attached.

182. $Z_1$, $Z_2$, $Z_3$ are N; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0-2), $CR_4R_4$; t=0-2; One of $Z_4$, $Z_5$, $Z_6$, $Z_7$ is the carbon atom to which the remainder of the molecule is attached.

183. $Z_2$ is N; $Z_1$, $Z_3$ are independently $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0-2), $CR_4R_4$; t=0-2; One of $Z_1$, $Z_3$, $Z_4$, $Z_5$, $Z_6$, $Z_7$ is the carbon atom to which the remainder of the molecule is attached.

184. $Z_2$, $Z_3$ are N; $Z_1$ is $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0-2), $CR_4R_4$; t=0-2; One of $Z_1$, $Z_4$, $Z_5$, $Z_6$, $Z_7$ is the carbon atom to which the remainder of the molecule is attached.

185. $Z_3$ is N; $Z_1$, $Z_2$ are independently $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0-2), $CR_4R_4$; t=0-2; One of $Z_1$, $Z_2$, $Z_4$, $Z_5$, $Z_6$, $Z_7$ is the carbon atom to which the remainder of the molecule is attached.

186. $Z_1$, $Z_2$, $Z_3$, $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0-2), $CR_4R_4$; t=0-2; One of $Z_1$, $Z_2$, $Z_3$, $Z_4$, $Z_5$, $Z_6$, $Z_7$ is the carbon atom to which the remainder of the molecule is attached.

187. $Z_1$ is N; $Z_2$, $Z_3$ are independently $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0-2), $CR_4R_4$; t=0-2; One of $Z_2$, $Z_3$, $Z_4$, $Z_5$, $Z_6$, $Z_7$ is the carbon atom to which the remainder of the molecule is attached.

188. $Z_1$, $Z_2$ are N; $Z_3$ is $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0-2), $CR_4R_4$; t=2; One of $Z_3$, $Z_4$, $Z_5$, $Z_6$, $Z_7$ is the carbon atom to which the remainder of the molecule is attached.

189. $Z_1$, $Z_2$, $Z_3$ are N; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0-2), $CR_4R_4$; t=0-2; One of $Z_4$, $Z_5$, $Z_6$, $Z_7$ is the carbon atom to which the remainder of the molecule is attached.

190. $Z_2$ is N; $Z_1$, $Z_3$ are independently $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0-2), $CR_4R_4$; t 0-2; One of $Z_1$, $Z_3$, $Z_4$, $Z_5$, $Z_6$, $Z_7$ is the carbon atom to which the remainder of the molecule is attached.

191. $Z_2$, $Z_3$ are N; $Z_1$ is $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0-2), $CR_4R_4$; t=0-2; One of $Z_1$, $Z_4$, $Z_5$, $Z_6$, $Z_7$ is the carbon atom to which the remainder of the molecule is attached.

192. $Z_3$ is N; $Z_1$, $Z_2$ are independently $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0-2), $CR_4R_4$; t=0-2; One of $Z_1$, $Z_2$, $Z_4$, $Z_5$, $Z_6$, $Z_7$ is the carbon atom to which the remainder of the molecule is attached.

The preferred embodiments of formula 9-A are:

193. $Z_1$ is O, S, N—$R_1$; $Z_2$, $Z_3$ are independently $CR_2$; $Y_1$, $Y_4$ are C; $Y_2$, $Y_3$ are independently N, C, CH (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_2$, $Z_3$ is the carbon atom to which the remainder of the molecule is attached.

194. $Z_1$ is O, S, N—$R_1$; $Z_2$ is N; $Z_3$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_3$ is the carbon atom to which the remainder of the molecule is attached.

195. $Z_1$ is O, S, N—$R_1$; $Z_3$ is N $Z_2$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_2$ is the carbon atom to which the remainder of the molecule is attached.

196. $Z_2$ is O, S, N—$R_1$; $Z_1$, $Z_3$ are independently $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_2$, $Z_3$ is the carbon atom to which the remainder of the molecule is attached.

197. $Z_2$ is O, S, N—$R_1$; $Z_1$ is N; $Z_3$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_3$ is the carbon atom to which the remainder of the molecule is attached.

198. $Z_2$ is O, S, N—$R_1$; $Z_3$ is N $Z_1$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_1$ is the carbon atom to which the remainder of the molecule is attached.

199. $Z_3$ is O, S, N—$R_1$; $Z_1$, $Z_2$ are independently $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_1$, $Z_2$ is the carbon atom to which the remainder of the molecule is attached.

200. $Z_3$ is O, S, N—$R_1$; $Z_1$ is N; $Z_2$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_2$ is the carbon atom to which the remainder of the molecule is attached.

201. $Z_3$ is O, S, N—$R_1$; $Z_1$ is $CH_2$; $Z_2$ is N; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_1$ is the carbon atom to which the remainder of the molecule is attached.

202. $Z_1$, $Z_2$, $Z_3$ are independently $CR_2$; $Y_1$ is N; $Y_4$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_1$, $Z_2$, $Z_3$ is the carbon atom to which the remainder of the molecule is attached.

203. $Z_1$ is N; $Z_2$, $Z_3$ are independently $CR_2$; $Y_1$ is N; $Y_4$ is C; $Y_2$, $Y_3$ are independently C, CH. N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_2$, $Z_3$ is the carbon atom to which the remainder of the molecule is attached.

204. $Z_1$, $Z_2$ is N; $Z_3$ is $CR_2$; $Y_1$ is N; $Y_4$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_3$ is the carbon atom to which the remainder of the molecule is attached.

205. $Z_1$, $Z_3$ are N; $Z_2$ is $CR_2$; $Y_1$ is N; $Y_4$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_2$ is the carbon atom to which the remainder of the molecule is attached.

206. $Z_1$, $Z_2$, $Z_3$ are independently $CR_2$; $Y_4$ is N; $Y_1$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_1$, $Z_2$, $Z_3$ is the carbon atom to which the remainder of the molecule is attached.

207. $Z_1$ is N; $Z_2$, $Z_3$ are independently $CR_2$; $Y_4$ is N; $Y_1$ is C; $Y_2$, $Y_3$ are independently C, CH. N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_2$, $Z_3$ is the carbon atom to which the remainder of the molecule is attached.

208. $Z_1$, $Z_2$ are N; $Z_3$ is $CR_2$; $Y_4$ is N; $Y_1$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_3$ is the carbon atom to which the remainder of the molecule is attached.

209. $Z_1$, $Z_3$ are N; $Z_2$ is $CR_2$; $Y_4$ is N; $Y_1$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_2$ is the carbon atom to which the remainder of the molecule is attached.

The preferred embodiments of formula 9-B:

210. $Z_1$ is O, S, N—$R_1$; $Z_2$, $Z_3$ are independently $CR_2$; $Y_1$, $Y_2$ are C; $Y_3$, $Y_4$ are independently N, C, CH (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_2$, $Z_3$ is the carbon atom to which the remainder of the molecule is attached.

211. $Z_1$ is O, S, N—$R_1$; $Z_2$ is N; $Z_3$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_3$ is the carbon atom to which the remainder of the molecule is attached.

212. $Z_1$ is O, S, N—$R_1$; $Z_3$ is N $Z_2$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_2$ is the carbon atom to which the remainder of the molecule is attached.

213. $Z_2$ is O, S, N—$R_1$; $Z_1$, $Z_3$ are independently $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_2$, $Z_3$ is the carbon atom to which the remainder of the molecule is attached.

214. $Z_2$ is O, S, N—$R_1$; $Z_1$ is N; $Z_3$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_3$ is the carbon atom to which the remainder of the molecule is attached.

215. $Z_2$ is O, S, N—$R_1$; $Z_3$ is N $Z_1$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_1$ is the carbon atom to which the remainder of the molecule is attached.

216. $Z_3$ is O, S, N—$R_1$; $Z_1$, $Z_2$ are independently $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_1$, $Z_2$ is the carbon atom to which the remainder of the molecule is attached.

217. $Z_3$ is O, S, N—$R_1$; $Z_1$ is N; $Z_2$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_2$ is the carbon atom to which the remainder of the molecule is attached.

218. $Z_3$ is O, S, N—$R_1$; $Z_1$ is $CH_2$; $Z_2$ is N; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_1$ is the carbon atom to which the remainder of the molecule is attached.

219. $Z_1$, $Z_2$, $Z_3$ are independently $CR_2$; $Y_1$ is N; $Y_2$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_1$, $Z_2$, $Z_3$ is the carbon atom to which the remainder of the molecule is attached.

220. $Z_1$ is N; $Z_2$, $Z_3$ are $CR_2$; $Y_1$ is N; $Y_2$ is C; $Y_3$, $Y_4$ are independently C, CH. N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_2$, $Z_3$ is the carbon atom to which the remainder of the molecule is attached.

221. $Z_1$, $Z_2$ are N; $Z_3$ is $CR_2$; $Y_1$ is N; $Y_2$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_3$ is the carbon atom to which the remainder of the molecule is attached.

222. $Z_1$, $Z_3$ are N; $Z_2$ is $CR_2$; $Y_1$ is N; $Y_2$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_2$ is the carbon atom to which the remainder of the molecule is attached.

223. $Z_1$, $Z_2$, $Z_3$ are independently $CR_2$; $Y_2$ is N; $Y_1$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_1$, $Z_2$, $Z_3$ is the carbon atom to which the remainder of the molecule is attached.

224. $Z_1$ is N; $Z_2$, $Z_3$ are independently $CR_2$; $Y_2$ is N; $Y_1$ is C; $Y_3$, $Y_4$ are independently C, CH. N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; One of $Z_2$, $Z_3$ is the carbon atom to which the remainder of the molecule is attached.

225. $Z_1$, $Z_2$ are N; $Z_3$ is $CR_2$; $Y_2$ is N; $Y_1$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_3$ is the carbon atom to which the remainder of the molecule is attached.

226. $Z_1$, $Z_3$ are N; $Z_2$ is $CR_2$; $Y_2$ is N; $Y_1$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0-2), $CR_4R_4$; t=0-2; u=1-3; $Z_2$ is the carbon atom to which the remainder of the molecule is attached.

The preferred embodiments of formula 10-A:

227. $Z_1$, $Z_2$, $Z_3$, $Z_4$, $Z_6$, $Z_7$, $Z_8$, $Z_9$ are independently $CR_2$; $Z_1$ is O, S, N—$R_1$; $Y_1$, $Y_2$, $Y_3$, $Y_4$ are C; one of $Z_1$, $Z_2$, $Z_3$, $Z_4$, $Z_6$, $Z_7$, $Z_8$, $Z_9$ must be a carbon atom to which the remainder of the molecule is attached.

228. $Z_1$ is N; $Z_2$, $Z_3$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_2$, $Z_3$, $Z_4$, $Z_6$, $Z_7$, $Z_8$, $Z_9$ must be a carbon atom to which the remainder of the molecule is attached.

229. $Z_1$, $Z_2$ are N; $Z_3$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_3$, $Z_4$, $Z_6$, $Z_7$, $Z_8$, $Z_9$ must be a carbon atom to which the remainder of the molecule is attached.

230. $Z_1$, $Z_3$ are N; $Z_2$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_2$, $Z_4$, $Z_6$, $Z_7$, $Z_8$, $Z_9$ must be a carbon atom to which the remainder of the molecule is attached.

231. $Z_1$, $Z_4$ are N; $Z_3$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_3$, $Z_6$, $Z_7$, $Z_8$, $Z_9$ must be a carbon atom to which the remainder of the molecule is attached.

232. $Z_1$ is N; $Z_2$, $Z_3$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_2$, $Z_3$, $Z_4$, $Z_6$, $Z_7$, $Z_8$, $Z_9$ must be a carbon atom to which the remainder of the molecule is attached.

233. $Z_1$, $Z_2$ are N; $Z_3$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_3$, $Z_4$, $Z_6$, $Z_7$, $Z_8$, $Z_9$ must be a carbon atom to which the remainder of the molecule is attached.

234. $Z_1$, $Z_3$ are N; $Z_2$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_2$, $Z_4$, $Z_6$, $Z_7$, $Z_8$, $Z_9$ must be a carbon atom to which the remainder of the molecule is attached.

235. $Z_1$, $Z_4$ are N; $Z_2$, $Z_3$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_2$, $Z_3$, $Z_6$, $Z_7$, $Z_8$, $Z_9$ must be a carbon atom to which the remainder of the molecule is attached.

236. $Z_2$ is N; $Z_1$, $Z_3$, $Z_4$, $Z_6$, $Z_7$, $Z_8$, $Z_9$ are independently $CR_2$; $Z_7$ is O, S, N—$R_1$; $Y_1$, $Y_2$, $Y_3$, $Y_4$ are C; one of $Z_1$, $Z_3$, $Z_4$, $Z_6$, $Z_7$, $Z_8$, $Z_9$ must be a carbon atom to which the remainder of the molecule is attached.

237. $Z_2$, $Z_3$ are N; $Z_1$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_1$, $Z_4$, $Z_6$, $Z_7$, $Z_8$, $Z_9$ must be a carbon atom to which the remainder of the molecule is attached.

238. $Z_2$, $Z_4$ are N; $Z_1$, $Z_3$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_1$, $Z_3$, $Z_6$, $Z_7$, $Z_8$, $Z_9$ must be a carbon atom to which the remainder of the molecule is attached.

239. $Z_2$ is N; $Z_1$, $Z_3$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_1$, $Z_3$, $Z_4$, $Z_6$, $Z_7$, $Z_8$, $Z_9$ must be a carbon atom to which the remainder of the molecule is attached.

240. $Z_2$, $Z_7$ are N; $Z_1$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_1$, $Z_4$, $Z_6$, $Z_7$, $Z_8$, $Z_9$ must be a carbon atom to which the remainder of the molecule is attached.

241. $Z_2$, $Z_4$ are N; $Z_1$, $Z_3$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_1$, $Z_3$, $Z_6$, $Z_7$, $Z_8$, $Z_9$ must be a carbon atom to which the remainder of the molecule is attached.

The preferred embodiments of formula 11-A:

242. $Z_1$, $Z_2$, $Z_3$, $Z_4$, $Z_6$, $Z_7$, $Z_8$, $Z_9$ are independently $CR_2$; $Z_5$, $Z_{10}$ are independently O, S, N—$R_1$; $Y_1$, $Y_2$, $Y_3$, $Y_4$ are C; Any one of $Z_1$, $Z_2$, $Z_3$, $Z_4$, $Z_6$, $Z_7$, $Z_8$, $Z_9$ must be a carbon atom to which the remainder of the molecule is attached.

243. $Z_1$, $Z_2$, $Z_3$, $Z_4$, $Z_6$, $Z_7$, $Z_8$, $Z_9$ are independently N, $CR_2$; $Z_5$, $Z_{10}$ are independently O, S, N—$R_1$; $Y_1$, $Y_2$, $Y_3$, $Y_4$ are C; Any one of $Z_1$, $Z_2$, $Z_3$, $Z_4$, $Z_8$, $Z_7$, $Z_8$, $Z_9$ must be a carbon atom to which the remainder of the molecule is attached.

The preferred embodiments of formula 11-B:

244. $Z_1$, $Z_2$, $Z_3$, $Z_4$, $Z_7$, $Z_8$, $Z_9$, $Z_{10}$ are independently $CR_2$; $Z_5$, $Z_6$ are independently N, $CR_2$; $Y_1$, $Y_2$, $Y_3$, $Y_4$ are C; Any one of $Z_1$, $Z_2$, $Z_3$, $Z_4$, $Z_7$, $Z_8$, $Z_9$, $Z_{10}$ must be a carbon atom to which the remainder of the molecule is attached.

245. 163. $Z_1$, $Z_2$, $Z_3$, $Z_4$ are independently $CR_2$, N; $Z_5$, $Z_6$, $Z_7$, $Z_8$, $Z_9$, $Z_{10}$ are independently $CR_2$; $Y_1$, $Y_2$, $Y_3$, $Y_4$ are C; Any one of $Z_1$, $Z_2$, $Z_3$, $Z_4$, $Z_7$, $Z_8$, $Z_9$, $Z_{10}$ must be a carbon atom to which the remainder of the molecule is attached.

The preferred embodiments of formula 11-C:

246. $Z_1$, $Z_2$, $Z_3$, $Z_4$, $Z_6$, $Z_7$, $Z_8$, $Z_9$ are independently $CR_2$; $Y_1$ is N; $Y_2$ is C; Any one of $Z_1$, $Z_2$, $Z_3$, $Z_4$, $Z_6$, $Z_7$, $Z_8$, $Z_9$ must be a carbon atom to which the remainder of the molecule is attached.

247. $Z_1$, $Z_2$, $Z_3$, $Z_4$, $Z_7$, $Z_8$, $Z_9$ are independently $CR_2$; $Z_6$ is O, S, N—$R_1$; $Y_1$ is C; $Y_2$ is N; Any one of $Z_1$, $Z_2$, $Z_3$, $Z_4$, $Z_6$, $Z_7$, $Z_8$, $Z_9$ must be a carbon atom to which the remainder of the molecule is attached.

The preferred embodiments of formula 12-A:

248. $Z_1$, $Z_2$, $Z_3$, $Z_4$ are independently $CR_2$; $Z_5$ is O, S, N—$R_1$; $W_1$, $W_2$, $W_3$ are independently $CR_4R_4$, S(O)r (r=0-2), O, N—$R_1$ with the proviso that no S—S, S—O or O—O bond formation can occur to form a saturated ring. In the ring formed by $W_1$, $W_2$, $W_3$ one double bond might be present; t=1-4; $Y_1$, $Y_2$, $Y_3$, $Y_4$ are C; Any one of $Z_1$, $Z_2$, $Z_3$, $Z_4$ must be a carbon atom to which the remainder of the molecule is attached.

249. $Z_1$, $Z_2$, $Z_3$, $Z_4$ are independently $CR_2$; $Z_5$ is N, $CR_2$; $W_1$, $W_2$, $W_3$ are independently $CR_4R_4$, S(O)r (r=0-2), O, N—$R_1$ with the proviso that no S—S, S—O or O—O bond formation can occur to form a saturated ring; In the ring formed by $W_1$, $W_2$, $W_3$ one double bond might be present; t=1-4; $Y_1$, $Y_2$, $Y_3$ are C; $Y_4$ is N; Any one of $Z_1$, $Z_2$, $Z_3$, $Z_4$ must be a carbon atom to which the remainder of the molecule is attached.

250. $Z_1, Z_2, Z_3, Z_4$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_1, Z_2, Z_3, Z_4$ must be a carbon atom to which the remainder of the molecule is attached.

251. $Z_1$ is N; $Z_2, Z_3, Z_4$ are independently $CR_2$; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_2, Z_3, Z_4$ must be a carbon atom to which the 2 remainder of the molecule is attached.

252. $Z_1, Z_2$ are N; $Z_3, Z_4$ are independently $CR_2$; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_3, Z_4$ must be a carbon atom to which the remainder of the molecule is attached.

253. $Z_1, Z_3$ are N; $Z_2, Z_4$ are independently $CR_2$; $Z_5$ is O, S, N—$R_1$; $Z_1, Z_2$ are N; $Z_3, Z_4$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_2, Z_4$ must be a carbon atom to which the remainder of the molecule is attached.

254. $Z_1, Z_4$ are N; $Z_2, Z_3$ are independently $CR_2$; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_2, Z_3$ must be a carbon atom to which the remainder of the molecule is attached.

255. $Z_1$ is N; $Z_2, Z_3, Z_4$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_2, Z_3, Z_4$ must be a carbon atom to which the remainder of the molecule is attached.

256. $Z_1, Z_3$ are N; $Z_2, Z_4$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_2, Z_4$ must be a carbon atom to which the remainder of the molecule is attached.

257. $Z_1, Z_4$ are N; $Z_2, Z_3$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_2, Z_3$ must be a carbon atom to which the remainder of the molecule is attached.

258. $Z_1, Z_2$ are N; $Z_3, Z_4$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_3, Z_4$ must be a carbon atom to which the remainder of the molecule is attached.

259. $Z_1, Z_3$ are N; $Z_2, Z_4$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_2, Z_4$ must be a carbon atom to which the remainder of the molecule is attached.

260. $Z_1, Z_4$ are N; $Z_2, Z_3$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_2, Z_3$ must be a carbon atom to which the remainder of the molecule is attached.

261. $Z_2$ is N; $Z_1, Z_3, Z_4$ are independently $CR_2$; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_1, Z_3, Z_4$ must be a carbon atom to which the remainder of the molecule is attached.

262. $Z_2, Z_3$ are N; $Z_1, Z_4$ are independently $CR_2$; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_1, Z_4$ must be a carbon atom to which the 3 remainder of the molecule is attached.

263. $Z_2, Z_4$ are N; $Z_1, Z_3$ are independently $CR_2$; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_1, Z_3$ must be a carbon atom to which the remainder of the molecule is attached.

264. $Z_2$ is N; $Z_1, Z_3, Z_4$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_1, Z_3, Z_4$ must be a carbon atom to which the remainder of the molecule is attached.

265. $Z_2, Z_3$ are N; $Z_1, Z_4$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_1, Z_4$ must be a carbon atom to which the remainder of the molecule is attached.

266. $Z_2, Z_4$ are N; $Z_1, Z_3$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present;

267. $Z_2$ is N; $Z_1, Z_3, Z_4$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_1, Z_3, Z_4$ must be a carbon atom to which the remainder of the molecule is attached.

268. $Z_2, Z_3$ are N; $Z_1, Z_4$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_1, Z_4$ must be a carbon atom to which the remainder of the molecule is attached.

269. $Z_2, Z_4$ are N; $Z_1, Z_3$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_1, Z_3$ must be a carbon atom to which the remainder of the molecule is attached.

270. $Z_3$ is N; $Z_1, Z_2, Z_4$ are independently $CR_2$; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_1, Z_2, Z_4$ must be a carbon atom to which the remainder of the molecule is attached.

271. $Z_3, Z_4$ are N; $Z_1, Z_4$ are independently $CR_2$; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_1, Z_2$ must be a carbon atom to which the remainder of the molecule is attached.

272. $Z_3$ is N; $Z_1, Z_3, Z_4$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_1, Z_2, Z_4$ must be a carbon atom to which the remainder of the molecule is attached.

273. $Z_3, Z_4$ are N; $Z_1, Z_2$ are independently $CR_2$; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_1, Z_2$ must be a carbon atom to which the remainder of the molecule is attached.

274. $Z_3$ is N; $Z_1, Z_3, Z_4$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_1, Z_2, Z_4$ must be a carbon atom to which the remainder of the molecule is attached.

275. $Z_3, Z_4$ are N; $Z_1, Z_4$ are independently $CR_2$; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_1, Z_2$ must be a carbon atom to which the remainder of the molecule is attached.

276. $Z_1, Z_2, Z_3$ are independently $CR_2$; $Z_4$ is N; $Z_5$ is O, S, N—$R_1$; $W_1, W_2, W_3$ are independently $CR_4R_4$, $S(O)r$ (r=0-2), O, N—$R_1$ with the proviso that no S—S, S—O or O—O bond formation can occur to form a saturated ring. In the ring formed by $W_1, W_2, W_3$ one double bond might be present; t=1-4; $Y_1, Y_2, Y_3, Y_4$ are C; Any one of $Z_1, Z_2, Z_3$, must be a carbon atom to which the remainder of the molecule is attached.

277. $Z_1, Z_2, Z_3$ are independently $CR_2$; $Z_4$ is N; $Z_5$ is N, $CR_2$; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-4; $Y_1, Y_2, Y_3$ are C; $Y_4$ is N; Any one of $Z_1, Z_2, Z_3$ must be a carbon atom to which the remainder of the molecule is attached.

278. $Z_1, Z_2, Z_3$ are independently $CR_2$; $Z_4$ is N; $Z_5$ is O, S, N; $W_1, W_2, W_3$ are independently $CR_4R_4$, $S(O)r$ (r=0-2), O, N—$R_1$ with the proviso that no S—S, S—O or O—O bond formation can occur to form a saturated ring; In the ring formed by $W_1, W_2, W_3$ one double bond might be present; t=1-3; $Y_1, Y_2, Y_3$ are C; $Y_4$ is N; Any one of $Z_1, Z_2, Z_3, Z_4$ must be a carbon atom to which the remainder of the molecule is attached.

The preferred embodiments of formula 12-B:

279. $Z_1, Z_2, Z_3, Z_4$ are independently $CR_2$; $Z_5$ is O, S, N—$R_1$; $Y_1, Y_2, Y_3, Y_4$ are C; $W_1, W_2$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_2, Z_3, Z_4$ must be a carbon atom to which the remainder of the molecule is attached.

280. $Z_1$ is N; $Z_2, Z_3, Z_4$ are independently $CR_2$; $Z_5$ is O, S, N—$R_1$; $Y_1, Y_2, Y_3, Y_4$ are C; $W_1, W_2$ are independently $CR_4R_4$, $S(O)r$ (r=0-2), O, N—$R_1$ with the proviso that no S—S, S—O or O—O bond formation can occur to form a saturated ring; t=1-3. Any one of $Z_2, Z_3, Z_4$ must be a carbon atom to which the remainder of the molecule is attached.

281. $Z_1, Z_2$ are N; $Z_3, Z_4$ are independently $CR_2$; $Z_5$ is O, S, N—$R_1$; $Y_1, Y_2, Y_3, Y_4$ are C; $W_1, W_2$ are independently $CR_4R_4$, $S(O)r$ (r=0-2), O, N—$R_1$ with the proviso that no S—S, S—O or O—O bond formation can occur to form a saturated ring; t=1-3. Any one of $Z_3, Z_4$ must be a carbon atom to which the remainder of the molecule is attached.

282. $Z_1, Z_3$ are N; $Z_2, Z_4$ are independently $CR_2$; $Z_5$ is O, S, N—$R_1$; $Y_1, Y_2, Y_3, Y_4$ are C; $W_1, W_2$ are independently $CR_4R_4$, $S(O)r$ (r=0-2), O, N—$R_1$ with the proviso that no S—S, S—O or O—O bond formation can occur to form a saturated ring; t=1-3. Any one of $Z_2, Z_4$ must be a carbon atom to which the remainder of the molecule is attached.

283. $Z_2$ is N; $Z_1, Z_3, Z_4$ are independently $CR_2$; $Z_5$ is O, S, N—$R_1$; $Y_1, Y_2, Y_3, Y_4$ are C; $W_1, W_2$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_3, Z_4$ must be a carbon atom to which the remainder of the molecule is attached.

284. $Z_2, Z_3$ are N; $Z_1, Z_4$ are independently $CR_2$; $Z_5$ is O, S, N—$R_1$; $Y_1, Y_2, Y_3, Y_4$ are C; $W_1, W_2$ are independently 285. $Z_3$ is N; $Z_1$, $Z_2$, $Z_4$ are independently $CR_2$; $Z_5$ is O, S, N—$R_1$; $Y_1$, $Y_2$, $Y_3$, $Y_4$ are C; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_4$ must be a carbon atom to which the remainder of the molecule is attached.

286. $Z_1$, $Z_2$, $Z_3$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_5$ must be a carbon atom to which the remainder of the molecule is attached.

287. $Z_1$ is N; $Z_2$, $Z_3$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_3$, $Z_5$ must be a carbon atom to which the remainder of the molecule is attached.

288. $Z_1$, $Z_2$ are N; $Z_3$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_3$, $Z_5$ must be a carbon atom to which the remainder of the molecule is attached.

289. $Z_1$, $Z_3$ are N; $Z_2$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_5$ must be a carbon atom to which the remainder of the molecule is attached.

290. $Z_2$ is N; $Z_1$, $Z_3$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_3$, $Z_5$ must be a carbon atom to which the remainder of the molecule is attached.

291. $Z_2$, $Z_3$ are N; $Z_1$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_5$ must be a carbon atom to which the remainder of the molecule is attached.

292. $Z_3$ is N; $Z_1$, $Z_2$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_5$ must be a carbon atom to which the remainder of the molecule is attached.

293. $Z_1$, $Z_2$, $Z_4$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_4$ must be a carbon atom to which the remainder of the molecule is attached.

294. $Z_1$ is N; $Z_2$, $Z_3$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0-2), O, N—$R_1$ with the proviso that no S—S, S—O or O—O bond formation can occur to form a saturated ring; t=1-3.
Any one of $Z_2$, $Z_3$, $Z_4$ must be a carbon atom to which the remainder of the molecule is attached.

295. $Z_1$, $Z_2$ are N; $Z_3$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_3$, $Z_4$ must be a carbon atom to which the remainder of the molecule is attached.

296. $Z_1$, $Z_3$ are N; $Z_2$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_4$, $Z_5$ must be a carbon atom to which the remainder of the molecule is attached.

297. $Z_2$ is N; $Z_1$, $Z_3$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_3$, $Z_4$ must be a carbon atom to which the remainder of the molecule is attached.

298. $Z_2$, $Z_3$ are N; $Z_1$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_4$, $Z_5$ must be a carbon atom to which the remainder of the molecule is attached.

299. $Z_3$ is N; $Z_1$, $Z_2$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_4$, $Z_5$ must be a carbon atom to which the remainder of the molecule is attached.

The preferred embodiments of formula 13-A:

300. $Z_1$, $Z_2$, $Z_3$, $Z_4$, $Z_5$, $Z_6$ are independently N, $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_4$, $Z_5$, $Z_6$ must be a carbon atom to which the remainder of the molecule is attached.

301. $Z_1$ is N; $Z_2$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_3$, $Z_4$, $Z_5$, $Z_6$ must be a carbon atom to which the remainder of the molecule is attached.

302. $Z_1$, $Z_2$ are N; $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_3$, $Z_4$, $Z_5$, $Z_6$ must be a carbon atom to which the remainder of the molecule is attached.

303. $Z_1$, $Z_3$ are N; $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_4$, $Z_5$, $Z_6$ must be a carbon atom to which the remainder of the molecule is attached.

304. $Z_1$, $Z_4$ are N; $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_3$, $Z_5$, $Z_6$ must be a carbon atom to which the remainder of the molecule is attached.

305. $Z_1$, $Z_5$ are N; $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_3$, $Z_4$, $Z_6$ must be a carbon atom to which the remainder of the molecule is attached.

306. $Z_1$, $Z_6$ are N; $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_3$, $Z_4$, $Z_5$ must be a carbon atom to which the remainder of the molecule is attached.

307. $Z_2$ is N; $Z_1$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_3$, $Z_4$, $Z_5$, $Z_6$ must be a carbon atom to which the remainder of the molecule is attached.

308. $Z_2$, $Z_3$ are N; $Z_1$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_4$, $Z_5$, $Z_6$ must be a carbon atom to which the remainder of the molecule is attached.

309. $Z_2$, $Z_4$ are N; $Z_1$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_3$, $Z_5$, $Z_6$ must be a carbon atom to which the remainder of the molecule is attached.

310. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_3$, $Z_4$, $Z_6$ must be a carbon atom to which the remainder of the molecule is attached.

311. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_3$, $Z_4$, $Z_6$ must be a carbon atom to which the remainder of the molecule is attached.

312. $Z_2$, $Z_6$ are N; $Z_1$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_3$, $Z_4$, $Z_5$ must be a carbon atom to which the remainder of the molecule is attached.

313. $Z_3$ is N; $Z_1$, $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_4$, $Z_5$, $Z_6$ must be a carbon atom to which the remainder of the molecule is attached.

314. $Z_3$, $Z_4$ are N; $Z_1$, $Z_2$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_5$, $Z_6$ must be a carbon atom to which the remainder of the molecule is attached.

315. $Z_3$, $Z_5$ are N; $Z_1$, $Z_2$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_4$, $Z_6$ must be a carbon atom to which the remainder of the molecule is attached.

316. $Z_3$, $Z_6$ are N; $Z_1$, $Z_2$, $Z_4$, $Z_5$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_4$, $Z_5$ must be a carbon atom to which the remainder of the molecule is attached.

317. $Z_4$ is N; $Z_1$, $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_5$, $Z_6$ must be a carbon atom to which the remainder of the molecule is attached.

318. $Z_4$, $Z_5$ are N; $Z_1$, $Z_2$, $Z_3$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_5$, $Z_6$ must be a carbon atom to which the remainder of the molecule is attached.

319. $Z_5$ is N; $Z_1$, $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_4$, $Z_6$ must be a carbon atom to which the remainder of the molecule is attached.

320. $Z_5$, $Z_6$ are N; $Z_1$, $Z_2$, $Z_3$, $Z_4$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_4$ must be a carbon atom to which the remainder of the molecule is attached.

321. $Z_6$ is N; $Z_1$, $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_4$, $Z_5$ must be a carbon atom to which the remainder of the molecule is attached.

The preferred embodiments of formula 13-B:

322. $Z_1$, $Z_2$, $Z_3$, $Z_4$, $Z_5$, $Z_6$ are independently N, $CR_2$; $Y_1$, $Y_2$, $Y_3$, $Y_4$ are C; $W_1$, $W_2$ $W_3$ are independently $CR_4R_4$, S(O)r (r=0-2), O, N—$R_1$ with the proviso that no S—S, S—O or O—O bond formation can occur to form a saturated ring; t=1-3. Any one of $Z_1$, $Z_2$, $Z_3$, $Z_4$, $Z_5$, $Z_6$ must be a carbon atom to which the remainder of the molecule is attached.

323. $Z_1$ is N; $Z_2$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_3$, $Z_4$, $Z_5$, $Z_6$ must be a carbon atom to which the remainder of the molecule is attached.

324. $Z_1$, $Z_2$ are N; $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_3$, $Z_4$, $Z_5$, $Z_6$ must be a carbon atom to which the remainder of the molecule is attached.

325. $Z_1$, $Z_3$ are N; $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_4$, $Z_5$, $Z_6$ must be a carbon atom to which the remainder of the molecule is attached.

326. $Z_1$, $Z_4$ are N; $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, S—O or O—O bond formation can occur to form a saturated ring; t=1-3. Any one of $Z_2$, $Z_3$, $Z_5$, $Z_6$ must be a carbon atom to which the remainder of the molecule is attached.

327. $Z_1$, $Z_5$ are N; $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0-2), O, N—$R_1$ with the proviso that no S—S, 328. $Z_1$, $Z_6$ are N; $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_2$, $Z_3$, $Z_4$, $Z_5$ must be a carbon atom to which the remainder of the molecule is attached.

329. $Z_2$ is N; $Z_1$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_3$, $Z_4$, $Z_5$, $Z_6$ must be a carbon atom to which the remainder of the molecule is attached.

330. $Z_2$, $Z_3$ are N; $Z_1$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_4$, $Z_5$, $Z_6$ must be a carbon atom to which the remainder of the molecule is attached.

331. $Z_2$, $Z_4$ are N; $Z_1$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_3$, $Z_5$, $Z_6$ must be a carbon atom to which the remainder of the molecule is attached.

332. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_3$, $Z_4$, $Z_6$ must be a carbon atom to which the remainder of the molecule is attached.

333. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_3$, $Z_4$, $Z_6$ must be a carbon atom to which the remainder of the molecule is attached.

334. $Z_2$, $Z_6$ are N; $Z_1$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_3$, $Z_4$, $Z_5$ must be a carbon atom to which the remainder of the molecule is attached.

335. $Z_3$ is N; $Z_1$, $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_4$, $Z_5$, $Z_6$ must be a carbon atom to which the remainder of the molecule is attached.

336. $Z_3$, $Z_4$ are N; $Z_1$, $Z_2$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_5$, $Z_6$ must be a carbon atom to which the remainder of the molecule is attached.

337. $Z_3$, $Z_5$ are N; $Z_1$, $Z_2$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_4$, $Z_6$ must be a carbon atom to which the remainder of the molecule is attached.

338. $Z_3$, $Z_6$ are N; $Z_1$, $Z_2$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_4$, $Z_5$ must be a carbon atom to which the remainder of the molecule is attached.

339. $Z_4$ is N; $Z_1$, $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_3$, $Z_5$, $Z_6$ must be a carbon atom to which the remainder of the molecule is attached.

340. $Z_4$, $Z_5$ are N; $Z_1$, $Z_2$, $Z_3$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_3$, $Z_5$, $Z_6$ must be a carbon atom to which the remainder of the molecule is attached.

341. $Z_1$ is N; $Z_1$, $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_3$, $Z_4$, $Z_6$ must be a carbon atom to which the remainder of the molecule is attached.

342. $Z_5$, $Z_6$ are N; $Z_1$, $Z_2$, $Z_3$, $Z_4$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_3$, $Z_4$ must be a carbon atom to which the remainder of the molecule is attached.

343. $Z_6$ is N; $Z_1$, $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_3$, $Z_4$, $Z_5$ must be a carbon atom to which the remainder of the molecule is attached.

The preferred embodiments of formula 13-C:

344. $Z_1$, $Z_2$, $Z_3$, $Z_4$, $Z_5$, $Z_6$ are independently N, $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1$, $Z_2$, $Z_3$, $Z_4$, $Z_5$, $Z_6$ must be a carbon atom to which the remainder of the molecule is attached.

345. $Z_1$ is N; $Z_2$, $Z_3$, $Z_4$, $Z_5$, $Z_6$ are independently $CR_2$; $Y_1$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_2$, $Z_3$, $Z_4$, $Z_5$, $Z_6$ must be a carbon atom to which the remainder of the molecule is attached.

346. $Z_1$, $Z_2$ are N; $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_3$, $Z_4$, $Z_5$, $Z_6$ must be a carbon atom to which the remainder of the molecule is attached.

347. $Z_1$, $Z_3$ are N; $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_2$, $Z_4$, $Z_5$, $Z_6$ must be a carbon atom to which the remainder of the molecule is attached.

348. $Z_1$, $Z_4$ are N; $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_2$, $Z_3$, $Z_5$, $Z_6$ must be a carbon atom to which the remainder of the molecule is attached.

349. $Z_1$, $Z_5$ are N; $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_2, Z_3, Z_4, Z_6$ must be a carbon atom to which the remainder of the molecule is attached.

350. $Z_1, Z_6$ are N; $Z_2, Z_3, Z_4, Z_5$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_2, Z_3, Z_4, Z_5$ must be a carbon atom to which the remainder of the molecule is attached.

351. $Z_2$ is N; $Z_1, Z_3, Z_4, Z_5, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_3, Z_4, Z_5, Z_6$ must be a carbon atom to which the remainder of the molecule is attached.

352. $Z_2, Z_3$ are N; $Z_1, Z_4, Z_5, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_4, Z_5, Z_6$ must be a carbon atom to which the remainder of the molecule is attached.

353. $Z_2, Z_4$ are N; $Z_1, Z_3, Z_5, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_3, Z_5, Z_6$ must be a carbon atom to which the remainder of the molecule is attached.

354. $Z_2, Z_5$ are N; $Z_1, Z_3, Z_4, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_3, Z_4, Z_6$ must be a carbon atom to which the remainder of the molecule is attached.

355. $Z_2, Z_5$ are N; $Z_1, Z_3, Z_4, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_3, Z_4, Z_6$ must be a carbon atom to which the remainder of the molecule is attached.

356. $Z_2, Z_6$ are N; $Z_1, Z_3, Z_4, Z_5$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_3, Z_4, Z_5$ must be a carbon atom to which the remainder of the molecule is attached.

357. $Z_3$ is N; $Z_1, Z_2, Z_4, Z_5, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_4, Z_5, Z_6$ must be a carbon atom to which the remainder of the molecule is attached.

358. $Z_3, Z_4$ are N; $Z_1, Z_2, Z_5, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_5, Z_6$ must be a carbon atom to which the remainder of the molecule is attached.

359. $Z_3, Z_5$ are N; $Z_1, Z_2, Z_4, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_4, Z_6$ must be a carbon atom to which the remainder of the molecule is attached.

360. $Z_3, Z_6$ are N; $Z_1, Z_2, Z_4, Z_5$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_4, Z_5$ must be a carbon atom to which the remainder of the molecule is attached.

361. $Z_4$ is N; $Z_1, Z_2, Z_3, Z_5, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_3, Z_5, Z_6$ must be a carbon atom to which the remainder of the molecule is attached.

362. $Z_4, Z_5$ are N; $Z_1, Z_2, Z_3, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_3, Z_6$ must be a carbon atom to which the remainder of the molecule is attached.

363. $Z_5$ is N; $Z_1, Z_2, Z_3, Z_4, Z_6$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_3, Z_4, Z_6$ must be a carbon atom to which the remainder of the molecule is attached.

364. $Z_5, Z_6$ are N; $Z_1, Z_2, Z_3, Z_4$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_3, Z_4$ must be a carbon atom to which the remainder of the molecule is attached.

365. $Z_6$ is N; $Z_1, Z_2, Z_3, Z_4, Z_5$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_1, Z_2, Z_3, Z_4, Z_5$ must be a carbon atom to which the remainder of the molecule is attached.

The preferred embodiments of formula 14-A and 14-B:

366. $Z_1$ is N; $Z_2, Z_3, Z_4, Z_5, Z_6, Z_7, Z_8$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_2, Z_3, Z_4, Z_5, Z_6, Z_7, Z_8$ must be a carbon atom to which the remainder of the molecule is attached.

367. $Z_1, Z_2$ are N; $Z_3, Z_4, Z_5, Z_6, Z_7, Z_8$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_3, Z_4, Z_5, Z_6, Z_7, Z_8$ must be a carbon atom to which the remainder of the molecule is attached.

368. $Z_1, Z_3$ are N; $Z_2, Z_4, Z_5, Z_6, Z_7, Z_8$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_2, Z_4, Z_5, Z_6, Z_7, Z_8$ must be a carbon atom to which the remainder of the molecule is attached.

369. $Z_1, Z_4$ are N; $Z_2, Z_3, Z_5, Z_6, Z_7, Z_8$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_2, Z_3, Z_5, Z_6, Z_7, Z_8$ must be a carbon atom to which the remainder of the molecule is attached.

370. $Z_1, Z_2$ are N; $Z_3, Z_4, Z_5, Z_6, Z_7, Z_8$ are independently $CR_2$; $Y_1, Y_2, Y_3, Y_4$ are C; $W_1, W_2, W_3$ are independently $CR_4R_4$, S(O)r (r=0-2), O, N—$R_1$ with the proviso that no S—S, S—O or O—O bond formation can occur to form a saturated ring; t=1-3. Any one of $Z_3, Z_4, Z_5, Z_6, Z_7, Z_8$ must be a carbon atom to which the remainder of the molecule is attached.

371. $Z_1$ is N; $Z_2, Z_3, Z_4$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_2, Z_3, Z_4, Z_5, Z_6, Z_7, Z_8$ must be a carbon atom to which the remainder of the molecule is attached.

372. $Z_1, Z_2$ are N; $Z_3, Z_4$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_3, Z_4, Z_5, Z_6, Z_7, Z_8$ must be a carbon atom to which the remainder of the molecule is attached.

373. $Z_1, Z_3$ are N; $Z_2, Z_4$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_2, Z_4, Z_5, Z_6, Z_7, Z_8$ must be a carbon atom to which the remainder of the molecule is attached.

374. $Z_1, Z_4$ are N; $Z_2, Z_3$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_2, Z_3, Z_5, Z_6, Z_7, Z_8$ must be a carbon atom to which the remainder of the molecule is attached.

375. $Z_1, Z_2$ are N; $Z_3, Z_4$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_4, Z_5, Z_6, Z_7, Z_8$ must be a carbon atom to which the remainder of the molecule is attached.

376. $Z_2$ is N; $Z_1, Z_3, Z_4, Z_5, Z_6, Z_7, Z_8$ are independently $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_3, Z_4, Z_5, Z_6, Z_7, Z_8$ must be a carbon atom to which the remainder of the molecule is attached.

377. $Z_2, Z_3$ are N; $Z_1, Z_4, Z_5, Z_6, Z_7, Z_8$ are independently $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_4, Z_5, Z_6, Z_7, Z_8$ must be a carbon atom to which the remainder of the molecule is attached.

378. $Z_2, Z_4$ are N; $Z_1, Z_3, Z_5, Z_6, Z_7, Z_8$ are independently $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_3, Z_5, Z_6, Z_7, Z_8$ must be a carbon atom to which the remainder of the molecule is attached.

379. $Z_2$ is N; $Z_1, Z_3, Z_4$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_3, Z_4, Z_5, Z_6, Z_7, Z_8$ must be a carbon atom to which the remainder of the molecule is attached.

380. $Z_2, Z_3$ are N; $Z_1, Z_4$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_4, Z_5, Z_6, Z_7, Z_8$ must be a carbon atom to which the remainder of the molecule is attached.

381. $Z_2, Z_4$ are N; $Z_1, Z_3$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_3, Z_5, Z_6, Z_7, Z_8$ must be a carbon atom to which the remainder of the molecule is attached.

382. $Z_3$ is N; $Z_1, Z_2, Z_4, Z_5, Z_6, Z_7, Z_8$ are independently $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_2, Z_4, Z_5, Z_6, Z_7, Z_8$ must be a carbon atom to which the remainder of the molecule is attached.

383. $Z_3, Z_4$ are N; $Z_1, Z_2, Z_5, Z_6, Z_7, Z_8$ are independently $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_2, Z_5, Z_6, Z_7, Z_8$ must be a carbon atom to which the remainder of the molecule is attached.

384. $Z_4$ is N; $Z_1, Z_3, Z_4$ are independently $CR_2$; $Z_5, Z_6, Z_7, Z_8$ are independently N, $CR_2$; $Y_1, Y_2, Y_3, Y_4$ are C; $W_1, W_2, W_3$ are independently $CR_4R_4$, $S(O)r$ (r=0-2), O, N—$R_1$ with the proviso that no S—S, S—O or O—O bond formation can occur to form a saturated ring; t=1-3. Any one of $Z_1, Z_3, Z_4, Z_5, Z_6, Z_7, Z_8$ must be a carbon atom to which the remainder of the molecule is attached.

The preferred embodiments of formula 15-A:

385. $Z_1$ is N; $Z_2, Z_3, Z_4$ are independently $CR_2$; $Y_1, Y_2$ are C; $Y_3, Y_4$ are independently CH, N; $W_1$ is O, $S(O)r$ (r=0-2), $CR_4R_4$, N—$R_1$, a bond; $W_2$ is O, $S(O)r$ (r=0-2), $CR_4R_4$, N—$R_1$; t=0-2; $W_3, W_4, W_5$ are independently O, S (O)r (r=0-2), $CR_4R_4$, N—$R_1$ with the proviso that no S—S, S—O or O—O bond formation can occur to form a saturated ring; u=1-3; Any one of $Z_2, Z_3, Z_4$ must be a carbon atom to which the remainder of the molecule is attached.

386. $Z_1, Z_2$ are N; $Z_3, Z_4$ are independently $CR_2$; $Y_1, Y_2$ are C; $Y_3, Y_4$ are independently CH, N; $W_1$ is O, $S(O)r$ (r=0-2), $CR_4R_4$, N—$R_1$, a bond; $W_2$ is O, $S(O)r$ (r=0-2), $CR_4R_4$, N—$R_1$; t=0-2; $W_3, W_4, W_5$ are independently O, S (O)r (r=0-2), $CR_4R_4$, N—$R_1$ with the proviso that no S—S, S—O or O—O bond formation can occur to form a saturated ring; u=1-3; Any one of $Z_3, Z_4$ must be a carbon atom to which the remainder of the molecule is attached.

387. $Z_1, Z_3$ are N; $Z_2, Z_4$ are independently $CR_2$; $Y_1, Y_2$ are C; $Y_3, Y_4$ are independently CH, N; $W_1$ is O, $S(O)r$ (r=0-2), $CR_4R_4$, N—$R_1$, a bond; $W_2$ is O, $S(O)r$ (r=0-2), $CR_4R_4$, N—$R_1$; t=0-2; $W_3, W_4, W_5$ are independently O, S (O)r (r=0-2), $CR_4R_4$, N—$R_1$ with the proviso that no S—S, S—O or O—O bond formation can occur to form a saturated ring; u=1-3; Any one of $Z_2, Z_4$ must be a carbon atom to which the remainder of the molecule is attached.

388. $Z_1, Z_4$ are N; $Z_2, Z_3$ are independently $CR_2$; $Y_1, Y_2$ are C; $Y_3, Y_4$ are independently CH, N; $W_1$ is O, $S(O)r$ (r=0-2), $CR_4R_4$, N—$R_1$, a bond; $W_2$ is O, $S(O)r$ (r=0-2), $CR_4R_4$, N—$R_1$; t=0-2; $W_3, W_4, W_5$ are independently O, S (O)r (r=0-2), $CR_4R_4$, N—$R_1$ with the proviso that no S—S, S—O or O—O bond formation can occur to form a saturated ring; u=1-3; Any one of $Z_2$, $Z_3$ must be a carbon atom to which the remainder of the molecule is attached.

389. $Z_2$ is N; $Z_1$, $Z_3$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$, a bond; $W_2$ is O, S(O)r (r=0-2), $CR_4R_4$, N—$R_1$; t=0-2; $W_3$, $W_4$, $W_5$ are independently O, S (O)r (r=0-2), $CR_4R_4$, N—$R_1$ with the proviso that no S—S, S—O or O—O bond formation can occur to form a saturated ring; u=1-3; Any one of $Z_1$, $Z_3$, $Z_4$ must be a carbon atom to which the remainder of the molecule is attached.

390. $Z_2$, $Z_3$ are N; $Z_1$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$, a bond; $W_2$ is O, S(O)r (r=0-2), $CR_4R_4$, N—$R_1$; t=0-2; $W_3$, $W_4$, $W_5$ are independently O, S (O)r (r=0-2), $CR_4R_4$, N—$R_1$ with the proviso that no S—S, S—O or O—O bond formation can occur to form a saturated ring; u=1-3; Any one of $Z_1$, $Z_4$ must be a carbon atom to which the remainder of the molecule is attached.

391. $Z_2$, $Z_4$ are N; $Z_1$, $Z_3$ are independently $CR_2$; $Y_1$, $Y_2$ are C; $Y_3$, $Y_4$ are independently CH, N; $W_1$ is O, S(O)r (r=0-2), $CR_4R_4$, N—$R_1$, a bond; $W_2$ is O, S(O)r (r=0-2), $CR_4R_4$, N—$R_1$; t=0-2; $W_3$, $W_4$, $W_5$ are independently O, S (O)r (r=0-2), $CR_4R_4$, N—$R_1$ with the proviso that no S—S, S—O or O—O bond formation can occur to form a saturated ring; u=1-3; Any one of $Z_1$, $Z_3$ must be a carbon atom to which the remainder of the molecule is attached.

392. $Z_3$ is N; $Z_1$, $Z_2$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$, a bond; $W_2$ is O, S(O)r (r=0-2), $CR_4R_4$, N—$R_1$; t=0-2; $W_3$, $W_4$, $W_5$ are independently O, S (O)r (r=0-2), $CR_4R_4$, N—$R_1$ with the proviso that no S—S, S—O or O—O bond formation can occur to form a saturated ring; u=1-3; Any one of $Z_1$, $Z_2$, $Z_4$ must be a carbon atom to which the remainder of the molecule is attached, 393. $Z_3$, $Z_4$ are N; $Z_1$, $Z_2$ are independently $CR_2$; $Y_1$, $Y_2$ are C; $Y_3$, $Y_4$ are independently CH, N; $W_1$ is O, S(O)r (r=0-2), $CR_4R_4$, N—$R_1$, a bond; $W_2$ is O, S(O)r (r=0-2), $CR_4R_4$, N—$R_1$; t=0-2; $W_3$, $W_4$, $W_5$ are independently O, S (O)r (r=0-2), $CR_4R_4$, N—$R_1$ with the proviso that no S—S, S—O or O—O bond formation can occur to form a saturated ring; u=1-3; Any one of $Z_1$, $Z_2$ must be a carbon atom to which the remainder of the molecule is attached.

394. $Z_4$ is N; $Z_1$, $Z_2$, $Z_3$ are independently $CR_2$; $Y_1$, $Y_2$ are C; $Y_3$, $Y_4$ are independently CH, N; $W_1$ is O, S(O)r (r=0-2), $CR_4R_4$, N—$R_1$, a bond; $W_2$ is O, S(O)r (r=0-2), $CR_4R_4$, N—$R_1$; t=0-2; $W_3$, $W_4$, $W_5$ are independently O, S (O)r (r=0-2), $CR_4R_4$, N—$R_1$ with the proviso that no S—S, S—O or O—O bond formation can occur to form a saturated ring; u=1-3; Any one of $Z_1$, $Z_2$, $Z_3$ must be a carbon atom to which the remainder of the molecule is attached.

The preferred embodiments of formula 15-B

395. $Z_1$ is N; $Z_2$, $Z_3$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one of $Z_2$, $Z_3$, $Z_4$ must be a carbon atom to which the remainder of the molecule is attached.

396. $Z_1$, $Z_2$ are N; $Z_3$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one of $Z_3$, $Z_4$ must be a carbon atom to which the remainder of the molecule is attached.

397. $Z_1$, $Z_3$ are N; $Z_2$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one of $Z_2$, $Z_4$ must be a carbon atom to which the remainder of the molecule is attached.

398. $Z_1$, $Z_4$ are N; $Z_2$, $Z_3$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one of $Z_2$, $Z_3$ must be a carbon atom to which the remainder of the molecule is attached.

399. $Z_2$ is N; $Z_1$, $Z_3$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one of $Z_1$, $Z_3$, $Z_4$ must be a carbon atom to which the remainder of the molecule is attached.

400. $Z_2$, $Z_3$ are N; $Z_1$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one of $Z_1$, $Z_4$ must be a carbon atom to which the remainder of the molecule is attached.

401. $Z_2$, $Z_4$ are N; $Z_1$, $Z_3$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one of $Z_1$, $Z_3$ must be a carbon atom to which the remainder of the molecule is attached.

402. $Z_3$ is N; $Z_1$, $Z_2$, $Z_4$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one $Z_1$, $Z_2$, $Z_4$ of must be a carbon atom to which the remainder of the molecule is attached.

403. $Z_3$, $Z_4$ are N; $Z_1$, $Z_2$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one of $Z_1$, $Z_2$ must be a carbon atom to which the remainder of the molecule is attached.

404. $Z_4$ is N; $Z_1$, $Z_2$, $Z_3$ are independently $CR_2$; $Y_1$, $Y_2$ are C; $Y_3$, $Y_4$ are independently CH, N; $W_1$ is O, S(O)r (r=0-2), $CR_4R_4$, N—$R_1$; $W_2$, $W_3$, $W_4$ are independently O, S(O)r (r=0-2), $CR_4R_4$, N—$R_1$ with the proviso that no S—S, S—O or O—O bond formation can occur to form a saturated ring; t=1-2; u=1-3; Any one $Z_1$, $Z_2$, $Z_3$ of must be a carbon atom to which the remainder of the molecule is attached.

The preferred embodiments of formula 15-C:

405. $Z_1$, $Z_2$, $Z_3$ are independently $CR_2$; $Y_1$, $Y_2$, $Y_4$ are C; $Y_2$ is N; $W_1$, $W_2$, $W_4$ are independently O, S(O)r (r=0-2), CR$_4$R$_4$, N—R$_1$ with the proviso that no S—S, S—O or O—O bond formation can occur to form a saturated ring; t=1-2; u=1-2; Any one Z$_1$, Z$_2$, Z$_3$ of must be a carbon atom to which the remainder of the molecule is attached.

406. Z$_1$ is N; Z$_2$, Z$_3$ are independently CR$_2$; Y$_1$, Y$_2$, Y$_4$ are C; Y$_2$ is N; W$_1$, W$_2$, W$_4$ are independently O, S(O)r (r=0-2), CR$_4$R$_4$, N—R$_1$ with the proviso that no S—S, S—O or O—O bond formation can occur to form a saturated ring; t=1-2; u=1-2; Any one Z$_2$, Z$_3$ of must be a carbon atom to which the remainder of the molecule is attached.

407. Z$_1$, Z$_3$ are N; Z$_3$ is CR$_2$; Y$_1$, Y$_2$, Y$_4$ are C; Y$_2$ is N; W$_1$, W$_2$, W$_4$ are independently O, S(O)r (r=0-2), CR$_4$R$_4$, N—R$_1$ with the proviso that no S—S, S—O or O—O bond formation can occur to form a saturated ring; t=1-2; u=1-2; Z$_3$ is the carbon atom to which the remainder of the molecule is attached.

The preferred tricyclic heteroaryl group A and B are one of the following formulae: 1-A, 1-B, 2-A, 3-B, 4-B, 5-A, 5-B, 6-B, 6-C, 7-B, 8-B, 9-A, 10-A, 12-A, 12-B, 13-B, 14-A, 14-B, and 15-B.

More preferred compounds of the present invention are:
1. (5R,6Z)-6-(Imidazo[2,1-b][1,3]benzothiazol-2-ylmethylene)-7-oxo-4-thia-1-azabicyclo[3.2.0]hept-2-ene-2-carboxylic acid;
2. (5R,6Z)-6-[(7-methoxyimidazo[2,1-b][1,3]benzothiazol-2-ylmethylene)-7-oxo-4-thia-1-azabicyclo[3.2.0]hept-2-ene-2-carboxylic acid;
3. (5R,6Z)-6-[(7-chloroimidazo[2,1-b][1,3]benzothiazol-2-ylmethylene)-7-oxo-4-thia-1-azabicyclo[3.2.0]hept-2-ene-2-carboxylic acid;
4. (5R),(6Z)-6-Imidazo[1,2-a]quinolin-2-ylmethylene-7-oxo-4-thia-1-azabicyclo[3.2.0]hept-2-ene-2-carboxylic acid;
5. (5R), (6Z)-6-(6,7-dihydro-5H-cyclopenta[d]imidazo[2,1-b][1,3]thiazol-2-ylmethylene)-7-oxo-4-thia-1-azabicyclo[3.2.0]hept-2-ene-2-carboxylic acid;
6. (5R), (6Z)-6-(Imidazo[1.2-a]quinoxaline-2-ylmethylene)-7-oxo-4-thia-1-azabicyclo[3.2.0]hepto-2-ene-2-carboxylic acid, sodium salt;
7. (5R,6Z)-6-[(7-methylimidazo[2,1-b][1,3]benzothiazol-2-ylmethylene)-7-oxo-4-thia-1-azabicyclo[3.2.0]hept-2-ene-2-carboxylic acid;
8. (5R), (6Z)-6-(4,5,6,7-tetrahydro-1,3a,3b,8-tetraaza-cyclopenta[a]indene-2-ylmethylene)-7-oxo-4-thia-1-aza-bicyclo[3.2.0]hept-2-ene-2-carboxylic acid sodium salt;
9. (5R,6E)-6-[(10-benzyl-11-oxo-10,11-dihydrodibenzo[b,f][1,4]oxazepin-8-yl)methylene]-7-oxo-4-thia-1-azabicyclo[3.2.0]hept-2-ene-2-carboxylic acid;
10. 6-(5-ethoxy-7,8-dihydro-6H-3,4,8b-triaza-as-indacen-2-ylmethylene)-7-oxo-4-thia-1-aza-bicyclo[3.2.0]hept-2-ene-2-carboxylic acid;
11. (5R,6E&Z)-7-oxo-6-(4H,10H-pyrazolo[5,1-c][1,4]benzoxazepin-2-ylmethylene)-4-thia-1-azabicyclo[3.2.0]hept-2-ene-2-carboxylic acid, sodium salt;
12. (5R), (6Z)-6-(5H-Imidazo[2,1-a]isoindol-2-ylmethylene)-7-oxo-4-thia-1-aza-bicyclo[3.2.0]hept-2-ene-2-carboxylic acid sodium salt;
13. (5R,6Z)-6-[(5-methylimidazo[2,1-b][1,3]benzothiazol-2-ylmethylene)-7-oxo-4-thia-1-azabicyclo[3.2.0]hept-2-ene-2-carboxylic acid;
14. (5R,6Z)-6-[(7-fluoroimidazo[2,1-b][1,3]benzothiazol-2-ylmethylene)-7-oxo-4-thia-1-azabicyclo[3.2.0]hept-2-ene-2-carboxylic acid;
15. (5R), (6Z)-6-(5,8-dihydro-6H-imidazo[2,1-b]pyrano[4,3-d][1,3]thiazol-2-ylmethylene)-7-oxo-4-thia-1-azabicyclo[3.2.0]hept-2-ene-2-carboxylic acid;
16. (5R),(6Z)-6-(imidazo[2,1-b]bebzothiazol-7-ylmethylene)-7-oxo-4-thia-1-azabicyclo[3.2.0]hept-2-ene-2-carboxylic acid;
17. (5R), (6Z)-7-oxo-6-([1,3]thiazolo[3,2-a]benzimidazol-2-ylmethylene)-4-thia-1-azabicyclo[3.2.0]hept-2-ene-2-carboxylic acid;
18. (5R), (6Z)-6-(7,8-dihydro-6H-cyclopenta[3,4]pyrazolo[5,1-b][1,3]thiazol-2-ylmethylene)-7-oxo-6-4-thia-1-azabicyclo[3.2.0]hept-2-ene-2-carboxylic acid;
19. (5R), (6Z)-7-oxo-6-(5,6,7,8-tetrahydroimidazo[2,1-b][1,3]benzothiazol-2-ylmethylene)-4-thia-1-azabicyclo[3.2.0]hept-2-ene-2-carboxylic acid;
20. (5R), (6Z)-8-[(9-methyl-9H-imidazo[1,2-a]benzimidazol-2-yl)methylene]-7-oxo-4-thia-1-azabicyclo[3.2.0]hept-2-ene-2-carboxylic acid;
21. (5R,6Z)-7-oxo-6-(4H-thieno[2',3':4,5]thiopyrano[2,3-b]pyridin-2-ylmethylene)-4-thia-1-azabicyclo[3.2.0]hept-2-ene-2-carboxylic acid (Sodium salt);
22. (5R,6Z)-6-[(5-methyl-7,8-dihydro-6H-cyclopenta[e][1,2,4]triazolo[1,5-a]pyrimidin-2-yl)methylene]-7-oxo-4-thia-1-azabicyclo[3.2.0]hept-2-ene-2-carboxylic acid, sodium salt;
23. (5R,6Z)-6-{[7-(ethoxycarbonyl)-6,7,8,9-tetrahydropyrido[3,4-e][1,2,4]triazolo[1,5-a]pyrimidin-2-yl]methylene}-7-oxo-4-thia-1-azabicyclo[3.2.0]hept-2-ene-2-carboxylic acid, sodium salt;
24. (5R,6Z)-6-(8',9'-dihydro-6'H-spiro[1,3-dioxolane-2,7'-[1,2,4]triazolo[1,5-a]quinazolin]-2'-ylmethylene)-7-oxo-4-thia-1-azabicyclo[3.2.0]hept-2-ene-2-carboxylic acid, sodium salt;
25. (5R,6Z)-6-[(5-methyl-6,7,8,9-tetrahydro[1,2,4]triazolo[1,5-a]quinazolin-2-yl)methylene]-7-oxo-4-thia-1-azabicyclo[3.2.0]hept-2-ene-2-carboxylic acid, sodium salt;
26. (5R,6Z)-6-[(5-methoxy-7,8-dihydro-6H-cyclopenta[e]imidazo[1,2-a]pyrimidin-2-yl)methylene]-7-oxo-4-thia-1-azabicyclo[3.2.0]hept-2-ene-2-carboxylic acid, sodium salt;
27. (5R,6Z)-6-({5-[2-(benzyloxy)ethoxy]-7,8-dihydro-6H-cyclopenta[e]imidazo[1,2-a]pyrimidin-2-yl}methylene)-7-oxo-4-thia-1-azabicyclo[3.2.0]hept-2-ene-2-carboxylic acid, sodium salt;
28. (5R,6Z)-6-(2,3-dihydro[1,3]thiazolo[3,2-a]benzimidazol-6-ylmethylene)-7-oxo-4-thia-1-azabicyclo[3.2.0]hept-2-ene-2-carboxylic acid, sodium salt;
29. (5R,6Z)-6-(3,4-dihydro-2H-[1,3]thiazino[3,2-a]benzimidazol-7-ylmethylene)-7-oxo-4-thia-1-azabicyclo[3.2.0]hept-2-ene-2-carboxylic acid, sodium salt;
30. (5R,6Z)-7-oxo-6-([1,3]thiazolo[3,2-a]benzimidazol-6-ylmethylene)-4-thia-1-azabicyclo[3.2.0]hept-2-ene-2-carboxylic acid, sodium salt;
31. (5R,6Z)-6-(7,8-dihydro-5H-pyrano[4,3-d]pyrazolo[5,1-b][1,3]oxazol-2-ylmethylene)-7-oxo-4-thia-1-azabicyclo[3.2.0]hept-2-ene-2-carboxylic acid, sodium salt;
32. (5R,6Z)-7-oxo-6-(5,6,7,8-tetrahydropyrazolo[5,1-b][1,3]benzoxazol-2-ylmethylene)-4-thia-1-1-azabicyclo[3.2.0]hept-2-ene-2-carboxylic acid, sodium salt; and
33. (5R,6Z)-6-{[6-(ethoxycarbonyl)-5,6,7,8-tetrahydropyrazolo[5', 1':2,3][1,3]oxazolo[5,4-c]pyridin-2-yl]methylene}-7-oxo-4-thia-1-1-azabicyclo[3.2.0]hept-2-ene-2-carboxylic acid, sodium salt.

Especially preferred compounds of the present invention are:
(5R), (6Z)-6-(6,7-dihydro-5H-cyclopenta[d]imidazo[2,1-b][1,3]thiazol-2-ylmethylene)-7-oxo-4-thia-1-azabicyclo[3.2.0]hept-2-ene-2-carboxylic acid; and (5R), (6Z)-6-(5,8-dihydro-6H-imidazo[2,1-b]pyrano[4,3-d][1,3]thiazol-2-ylmethylene)-7-oxo-4-thia-1-azabicyclo[3.2.0]hept-2-ene-2-carboxylic acid.

A compound's structural formula includes any tautomers, any stereoisomers (except where stereochemistry is clearly noted) and any crystalline forms.

The compounds according to the present invention have β-lactamase inhibitory and antibacterial properties and are useful for the treatment of infections in humans and animals. It should be noted that the compounds of the present invention, when used in combination with β-lactam antibiotics will result in the increased antibacterial activity (synergistic effect) against class-A and class-C producing organisms. β-Lactam antibiotics include penicillin antibiotics such as piperacillin, amoxycillin, ticarcillin, benzylpenicillins, ampicillin, sulbenicillin, other known penicillins and cephalosporins such as cefatrizine, cephaloridine, cephalothin, cefazolin, cephalexin, cephradine, other known cephalosporins, aztreonam and latamoxef (Moxalactam). Most preferably compounds of this present invention are used with piperacillin, and Amoxicillin which has a broad spectrum of activity against Gram positive and Gram negative pathogens.

The administration of the compounds of the present invention may be provided in conjunction with prior, simultaneous or subsequent administration of a β-lactam antibiotic ("co-administration"). By "provided", it is intended to include direct administration as well as in vivo, e.g. pro-drugs. When the compounds of the present invention are co-administered with a β-lactam antibiotic, the ratio of the amount of the compound to the amount of the β-lactam antibiotic may vary in a wide range. The ratio of β-lactam antibiotic to β-lactamase inhibitor may vary from 1:1 to 100:1. Preferably the ratio of the β-lactam antibiotic to the β-lactamase inhibitor is less than 10:1. The composition of the present invention may be in a form suitable for oral (PO), intravenous (IV) or topical administration. The compositions of the invention may be in a form of tablets, capsules, creams, syrups, suspension, sterile solutions suitable for injection or infusion. Preferably, the compounds of the present invention are co-administered with piperacillin intravenously or Amoxicillin orally or intravenously.

$IC_{50}$ Determination for the Penem Inhibitor

β-Lactamase inhibitory activity of the penem inhibitors was determined spectrophotometrically as described by Bush et al., [Bush, K., Macalintal, C., Rasmussen, B. A., Lee, V. and Yang, Y. *Antimicrobial Agents and Chemotherapy* 1993, 37, 851]. Homogeneously purified class A β-lactamases TEM-1 from *E. Coli* and Imi-1 from *Enterobacter cloacae*, class B enzyme CcrA from *Bacteroides fragilis* and class C enzyme AmpC from *Enterobacter cloaca* were employed in the assay. The enzyme concentrations for TEM-1, Imi-1, CcrA and AmpC were 4.3, 7.1, 1.2 and 2.1 nM, respectively. A wide range of inhibitor concentrations were prepared in 50 mM $PO_4$, pH 7.0 to include the possible $IC_{50}$ values. The substrate used to initiate the enzyme reaction was nitrocefin at 50 μg/ml in the same buffer as the inhibitor. Initially the enzyme and inhibitor (20 μl each) were preincubated for 10 minutes at 25° C. prior to the addition of 160 μl volume of nitrocefin. Initial rates of hydrolysis were monitored for 5 minutes at 495 nm using a Molecular Devices Spectra Max 250 with kinetic protocol of SoftMax Program. Readings from the Spectra Max 250 were exported and transferred to Microsoft Excel. The percent of inhibition of each inhibitor concentration was calculated based on the control enzyme activity. The inhibitor concentration that caused a 50% reduction in the enzymatic activity ($IC_{50}$) was determined graphically.

TABLE 1

β-Lactamase Inhibition Data

| | IC50 (nM) | | | |
|---|---|---|---|---|
| | Class A | | Class B | Class C |
| Compound | TEM-1 | Imi | Ccr | AmpC |
| Example 1 | 10 | 160 | 350 | 1.4 |
| Example 2 | 18 | 180 | 250 | 2.4 |
| Example 3 | 5.6 | 22 | 74 | 3.2 |
| Example 4 | 6 | 90 | 900 | 2.1 |
| Example 5 | 1.4 | 72 | 240 | 2.1 |
| Example 6 | 2.5 | 210 | 350 | 1.2 |
| Example 7 | 2.6 | 106 | 103 | 1.1 |
| Example 8 | 2.4 | 15 | 450 | 1.4 |
| Example 9 | 3.5 | 3600 | 220 | 4.5 |
| Example 10 | 48 | 35 | 140 | 5.8 |
| Example 11 | 1.4 | 78 | 62 | 3.6 |
| Example 12 | 2.6 | 6.4 | 42 | 28 |
| Example 13 | 8.7 | 102 | 228 | 1.6 |
| Example 14 | 8.1 | 270 | 370 | 2.4 |
| Example 15 | 2.8 | 100 | 200 | 1.5 |
| Example 16 | 4.5 | 70 | 130 | 9.5 |
| Example 17 | ND | ND | ND | ND |
| Example 18 | ND | ND | ND | ND |
| Example 19 | 1.9 | 33 | 215 | 0.62 |
| Example 20 | ND | ND | ND | ND |
| Example 21 | 11 | 580 | 210 | 3.7 |
| Example 22 | ND | ND | ND | ND |
| Example 23 | ND | ND | ND | ND |
| Example 24 | ND | ND | ND | ND |
| Example 25 | ND | ND | ND | ND |
| Example 26 | 48 | 63 | 420 | 10 |
| Example 27 | 12 | 33 | 180 | 3 |
| Example 28 | 3.2 | 90 | 110 | 5.7 |
| Example 29 | 15 | 300 | 240 | 18 |
| Example 30 | 46 | 200 | 97 | 9.3 |
| Example 31 | 4.3 | 140 | 130 | 4 |
| Example 32 | 2.6 | 110 | 180 | 5.6 |
| Example 33 | 10 | 360 | 160 | 140 |

ND = NOT DETERMINED

Antimicrobial susceptibility testing. The in vitro activities of the antibiotics were determined by the microbroth dilution method as recommended by the National Committee for Clinical Laboratory Standards (NCCLS). (NCCLS. 2000. Methods for Dilution Antimicrobial Susceptibility Tests for Bacteria That Grow Aerobically; Approved Standards: M7-A5, vol. 19. National Committee for Clinical Laboratory Standards, Villanova, Pa.). Mueller-Hinton it broth (MHBII) (BBL Cockeysville, Md.), was used for the testing procedure. Microtiter plates containing 50 μl per well of two-fold serial dilutions of piperacillin combined with a constant amount (4 μg/ml) of a B-lactamase inhibitor (final concentration) were inoculated with 50 μl of inoculum to yield the appropriate density ($10^5$ CFU/ml) in 100 μl. The plates were incubated for 18-22 hours at 35° C. in ambient air. The minimal inhibitory concentration (MIC) for all isolates was defined as the lowest concentration of antimicrobial agent that completely inhibits the growth of the organism as detected by the unaided eye. The MIC data obtained by the above said procedure are listed in Table 2.

TABLE 2

Minimal Inhibitory Concentration (µg/ml) Data; Inc: 35° C. for 18 hours

| Example | E. Coli GC2844 | E. Coli GC2847 (TEM-1) | E. Coli GC2920 (IRT-2) | E. Coli GC2894 (Ampc) | E. Cloacae GC1477 (Ampc) | P. aeruginos GC1764 (Ampc) | S. Marcescens GC1781 Sme-1 + Ampc | E. Coli GC2203 | S. aureus GC2216 |
|---|---|---|---|---|---|---|---|---|---|
| 1 | 2 | 2 | 2 | 1 | 4 | 8 | 0.5 | 2 | <0.06 |
| 2 | 2 | 16 | 2 | 1 | 64 | 16 | 2 | 1 | <0.06 |
| 3 | 2 | 4 | 1 | 2 | 16 | 8 | 1 | 1 | <0.06 |
| 4 | 2 | 4 | 2 | 4 | 32 | 8 | 0.5 | 2 | <0.06 |
| 5 | 2 | 4 | 2 | 2 | 16 | 1 | 0.5 | 2 | <0.06 |
| 6 | 1 | 2 | 0.25 | 16 | 16 | 16 | 1 | 0.25 | <0.06 |
| 7 | 2 | 4 | 2 | 4 | 32 | 16 | 0.5 | 1 | <0.06 |
| 8 | 2 | 8 | 2 | 2 | 64 | 32 | 0.5 | 1 | <0.06 |
| 9 | 1 | 64 | 2 | >64 | >64 | >64 | 8 | 1 | 0.5 |
| 10 | 2 | >64 | 2 | 32 | >64 | 64 | 4 | 1 | <0.06 |
| 11 | 1 | 8 | 1 | 4 | 32 | 16 | 1 | 1 | <0.06 |
| 12 | 2 | 4 | 4 | 4 | 32 | 64 | 1 | 2 | <0.06 |
| 13 | 2 | 8 | 2 | 8 | 32 | 2 | 4 | 2 | ND |
| 14 | 2 | 8 | 2 | 8 | 32 | 4 | 2 | 2 | ND |
| 15 | 2 | 4 | 2 | 2 | 16 | 4 | 1 | 2 | 0.05 |
| 16 | 2 | 64 | 2 | 32 | >64 | 32 | 1 | 4 | 0.05 |
| 17 | 2 | 64 | 4 | >64 | >64 | 32 | 8 | 2 | ND |
| 18 | 2 | >64 | 4 | >64 | >64 | 64 | 4 | 4 | ND |
| 19 | 2 | 8 | 2 | 4 | 32 | 1 | 8 | 2 | .06 |
| 20 | 4 | >64 | 4 | 32 | >64 | 32 | 2 | 2 | ND |
| 21 | 2 | >64 | 4 | 32 | >64 | 64 | 2 | 2 | ND |
| 22 | 2 | 16 | 4 | 64 | >64 | 64 | 4 | 2 | ND |
| 23 | 2 | 64 | 2 | >64 | >64 | 64 | 4 | 2 | ND |
| 24 | 2 | 64 | 4 | >64 | >64 | 64 | 8 | 4 | ND |
| 25 | 2 | 64 | 4 | >64 | 64 | 64 | 8 | 4 | ND |
| 26 | 2 | 8 | 2 | 16 | 32 | 8 | 2 | 4 | ND |
| 27 | 2 | >64 | 4 | 64 | >64 | 64 | >64 | 2 | ND |
| 28 | 2 | 64 | 4 | 32 | >64 | 64 | 2 | 2 | ND |
| 29 | 2 | 64 | 4 | 32 | >64 | 64 | 2 | 64 | ND |
| 30 | 2 | 64 | 8 | 32 | >64 | 1 | 32 | 2 | ND |
| 31 | 2 | 32 | 2 | 16 | 64 | 32 | 2 | 4 | ND |
| 32 | 2 | 16 | 4 | 32 | 64 | 64 | 2 | 2 | .05 |
| 33 | 2 | 64 | 4 | 64 | >64 | >64 | 2 | 2 | ND |

ND = NOT DETERMINED

In Vivo Antibacterial Protection

Materials:

Animals:

Female mice strain CD-1, approximately 18-22 grams, were received from Charles River Laboratories and quarantined 7 days prior to use. In addition, mice may be rendered neutropenic using cytoxan for particular studies.

Infections:

Clinical isolates that have been adapted to cause infection in mice, are used in the experiment, including infections with strains of E. coli, K. pneumoniae, M. morganii, E. cloacae, S. marcescens, C. freundii, staphylococci, streptococci, P. aeruginosa and N. gonorrhoeae.

PREPARATION: Animals are housed five to a cage with free access to food and water, in accordance with NIH guidelines.

Experimental Protocol:

Mice are challenged by injecting 0.5 ml intraperitoneally or 0.05 ml intranasally of a predetermined bacterial inoculum suspended in broth, saline or hog gastric mucin (supplemented with dried bovine hemoglobin for N. gonorrhoeae). The bacterial inoculum is equivalent to 10-100 $LD_{50}$s of the specific infecting strain and will result in death of the non-treated control animals within 7 days: "Bacterial Virulence in Mice". Antibacterial doses (dose concentration prepared by two fold serial dilutions of the antibiotic) are dissolved or suspended in 0.2% aqueous agar or methocel, phosphate buffered saline or an adjuvant are administered orally, subcutaneously or intravenously in the following manner:

a) Orally or subcutaneously: Dose volume of 0.5 ml administered ½ hr after infection. A second dose may be administered 3 hr. after infection for treatment of infections with more virulent organisms.

b) Intravenously: Dose volume of 0.2 ml, administered ½ hr. after infection. For the treatment of infections with more virulent organisms, more doses, up to 48 hr may be administered. (Intravenous dosing will not exceed 3 doses/24 hr period.)

c) Oral pretreatment: Under special circumstances, the pH of the stomach needs to be adjusted in order to increase the gastric stability of the antibiotic. For this purpose, 0.5 ml of phosphate buffered saline (pH7.8, 0.06M) (or specific approved adjuvant) is administered orally ½ hr after infection, followed 5 minutes later by 0.5 ml of antibiotic (also orally) contained in phosphate buffered saline (pH7.8, 0.06M).

Animal Species

A detailed explanation as to the number of animals needed for the determination of in vivo efficacy follows:

A) Novel antibiotics are tested at 5 different dose levels with 5 mice per dose level at each of three routes of administration (oral, subcutaneous and intravenous). Initially the three routes of administration should be investigated so as to determine if the drug is orally absorbed and/or which is the most effective route. This would require 25 mice/route with 3 routes/antibiotic or 75 mice per novel compound tested. One to two novel antibiotics will be tested per experiment (75-150 mice)

B) The effectiveness of the new compound must be compared to that of a standard, or antibiotic of known effectiveness. Known or previously tested antibiotics are tested at 5 dose levels with 5 mice per dose level by a single route of administration, for a total of 25 mice/antibiotic. Usually 3-6 antibiotics will be tested per experiment. (75-150 mice).

C) Untreated controls—In each of the above tests, untreated animals are infected with 3 different concentrations of bacterial inoculum with 10 mice per concentration (30 mice total in each and every test). These untreated controls are used to determine and maintain the infection level between 10-100 LD50s as required for test to test comparison and validity.

Determination of Protective Effects of Antibacterial Agents:

The protective effects of the antibacterial agent(s) are measured by the survival of the infected untreated as compared to the treated animals. For this determination, animals are observed for 7 days after treatment. A census of survivors is taken twice daily and at that time dead as well as moribund animals are removed. The 7 day survival ratio from three separate tests are pooled for estimation of median effective dose (ED50) by computerized program for probit analysis (Cleeland, R. and E. Squires. 1991. Evaluation of New Antimicrobials in Vitro and in Experimental Animal Infections. In Antibiotics in Laboratory Medicine", 3rd. ed., edited by Victor Lorian. Willams and Wilkins Baltimore, Md. pp. 752-783). The test is performed three times on separate days to provide a statistically valid number of animals and to minimize variation in test results on a day to day and test to test basis.

TABLE 3

| Example | $ED_{50}$ mg/kg | Ratio of Piperacillin Inhibitor |
|---------|-----------------|--------------------------------|
| 1 | 32-64 | 2:1 |
| 2 | >64 | 2:1 |
| 3 | 32-64 | 4:1 |
| 4 | 32-64 | 2:1 |
| 5 | 19.5 | 4:1 |

TABLE 3-continued

| Example | $ED_{50}$ mg/kg | Ratio of Piperacillin Inhibitor |
|---------|-----------------|--------------------------------|
| 6 | NT | |
| 7 | 137 | 4:1 |
| 8 | 16-64 | 4:1 |
| 9 | NT | |
| 10 | 55.6 | 4:1 |
| 11 | NT | |
| 12 | 50 | 4:1 |
| 13 | ND | |
| 14 | >64 | |
| 15 | 25 | |
| 16 | ND | |
| 17 | ND | |
| 18 | ND | |
| 19 | 63 | |
| 20 | ND | |
| 21 | ND | |
| 22 | ND | |
| 23 | ND | |
| 24 | ND | |
| 25 | ND | |
| 26 | ND | |
| 27 | ND | |
| 28 | ND | |
| 29 | ND | |
| 30 | ND | |
| 31 | ND | |
| 32 | ND | |
| 33 | ND | |

Compounds of the general formula I can be prepared by a novel, mild and a facile way, by condensing an appropriately substituted aldehyde 4 with a 6-bromo-penem derivative of structure 1 (Scheme 1) in the presence of anhydrous $MgBr_2$ or $MgBr_2$:etherate and a base such as triethylamine, DMAP or DBU, preferably at −20° C. to −40° C. The intermediate aldol product 5 can be functionalized with acid chlorides or anhydrides to an acetate, triflate or a tosylate 6. Compound 6 can be smoothly converted to the desired product by a reductive elimination process using a metal such as activated zinc and phosphate buffer at 20° C. to 35° C. at a pH of 6.5 to 8.0. If the protecting group on the carboxylate oxygen is a para-nitrobenzyl substituent then the reductive elimination and deprotection can be achieved by a single step. However, if the protecting group is other than a para-nitrobenzyl substituent, a two step

SCHEME 1

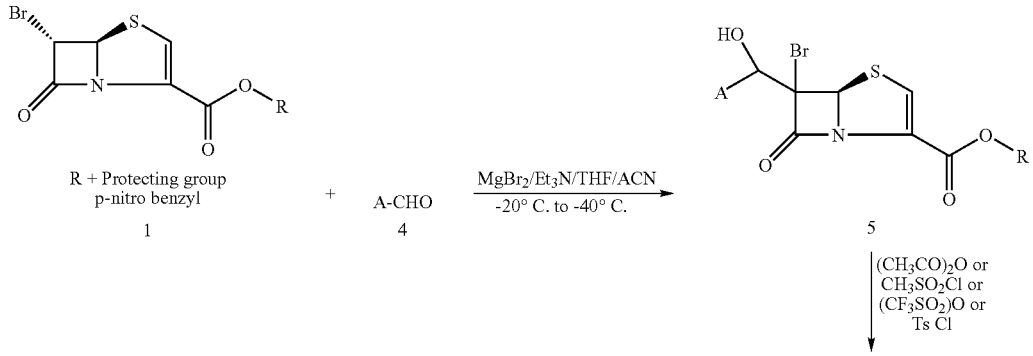

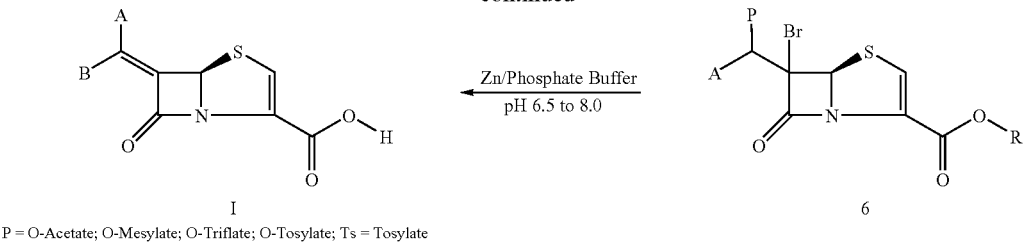

P = O-Acetate; O-Mesylate; O-Triflate; O-Tosylate; Ts = Tosylate procedure can be followed depending up on the nature of the protecting group. In an alternate procedure, the intermediate 6 can be hydrogenated at 40 Psi pressure in the presence of 10% Pd/C. The product can be isolated as a free acid or as an alkali metal salt. The above mentioned two step procedure can be carried out in one step by carrying out the entire process without isolating the intermediate 6. This is a very general, relatively simple and efficient procedure in terms of yield and economic feasibility. This procedure can be adopted to large scale synthesis and is amenable to a variety of aldehydes. The above mentioned aldol condensation reaction is very versatile and it can be applied to any bromopenem derivative, where the carboxy group is protected other than 4-nitrobenzyl moiety. Example of other protecting group include benzyl, para-methoxy benzyl derivative, benzyhydrol, trityl, alkyl and allyl derivatives. However, when the protecting group is other than 4-nitrobenzyl group, a separate deprotection step need to be carried out after the reductive elimination procedure. The chemistry involved in the deprotection step is well known to people who are skilled in that art.

The required aldehydes 4 for the above mentioned transformations can be prepared from their respective alcohol derivatives by MnO$_2$ oxidation or by Swern oxidation. In some cases the required aldehyde functionality can be introduced directly in the heterocyclic moiety by a Vilsmier Haack reaction using DMF/POCl$_3$. The aldehydes required for the present investigation may be prepared as depicted in Schemes 2 to 8. This procedure can be adopted to any system where there is an amino functionality adjacent to the —N=system. For example, the aldehyde required to synthesize compound in Example 12, was prepared starting from 2-aminophenyl acetonitrile (Scheme 6).

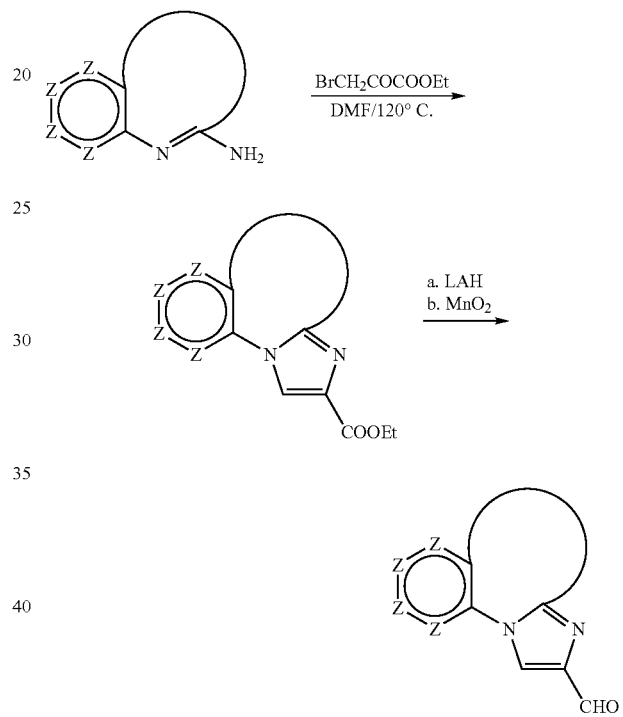

SCHEME 3

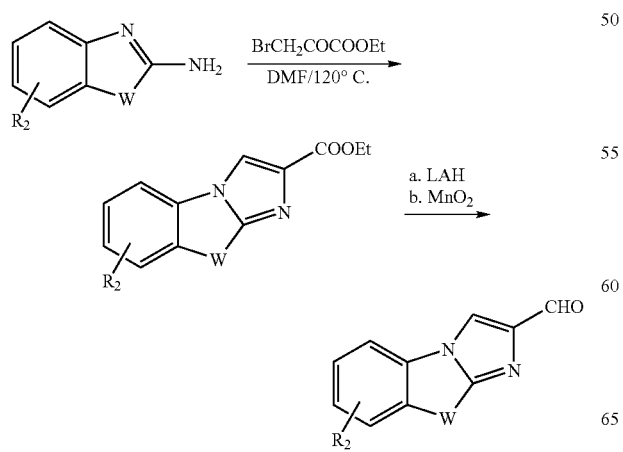

SCHEME 2

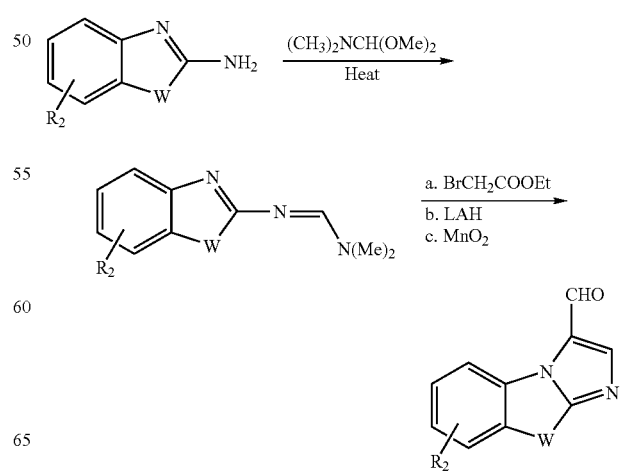

SCHEME 4

SCHEME 5

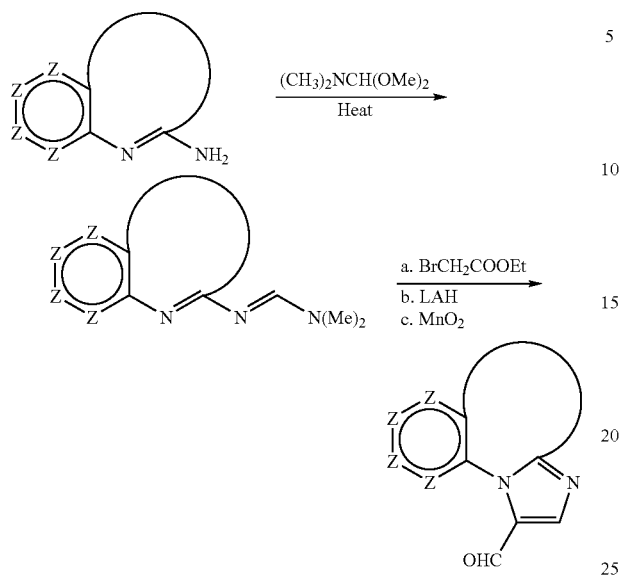

Scheme 6

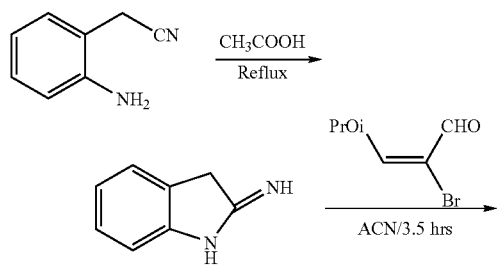

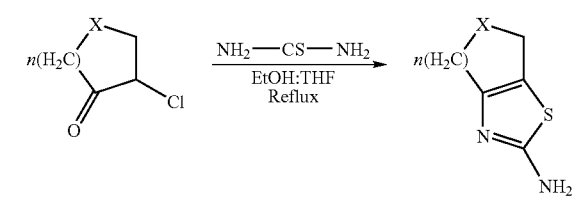

2-Amino-condensed thiazole ring systems (Exemplified with the preparation of ethyl 6,7-dihydro-5H-cyclopenta[d]imidazo[2,1-b]thiazole-2-carboxylate, Example 5) can be prepared by reacting cyclic α-halo ketones with thiourea. Scheme 7)

Scheme 7 n = 1 to 3
X = CH$_2$ or N—R$_1$ or O, S(O)$m$
m = 0 to 2

The aldehyde required to prepare example 10, can be synthesized by following the procedure outlined in Scheme 8. This procedure can be adopted to prepare a variety of condensed tricyclic imidazolo pyrimidine ring systems. The other examples that are enlisted here Examples 13 to 33 were prepared by the route enlisted in Schemes 9 to 16.

Scheme 8

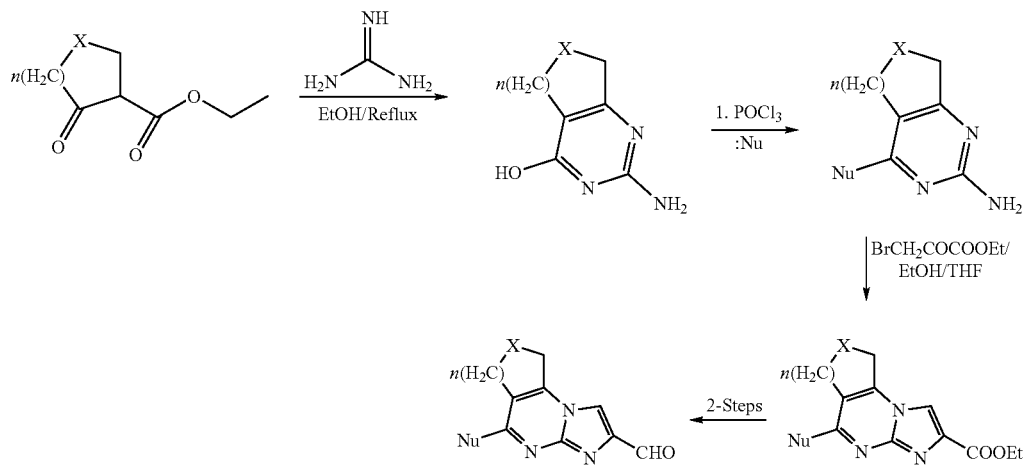

n = 1 to 3
X = CH$_2$ or N-R$_1$ or O, S(O)$m$
m = 0 to 2
:NU = nucleophile

Scheme 9
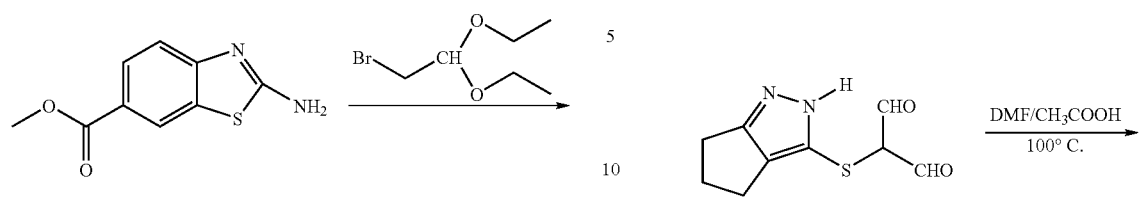
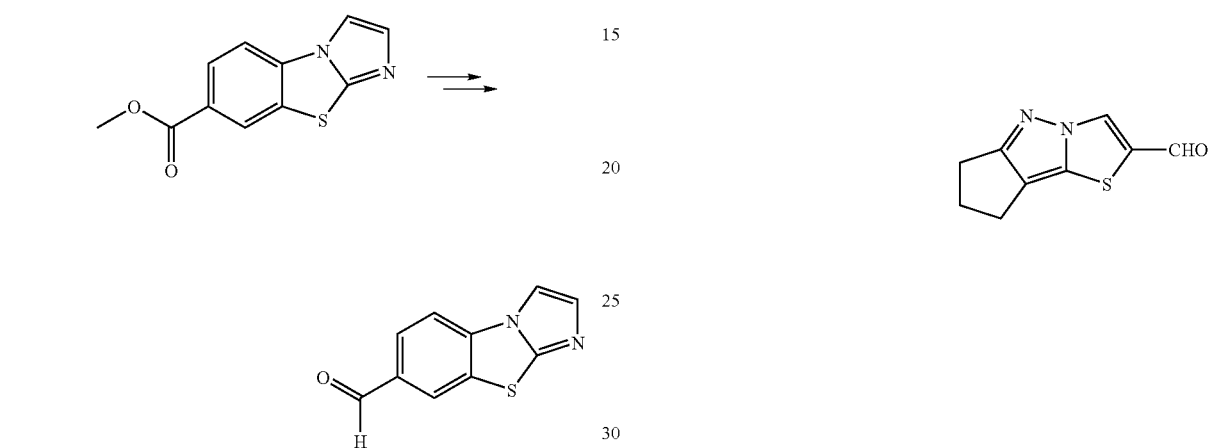
Scheme 10
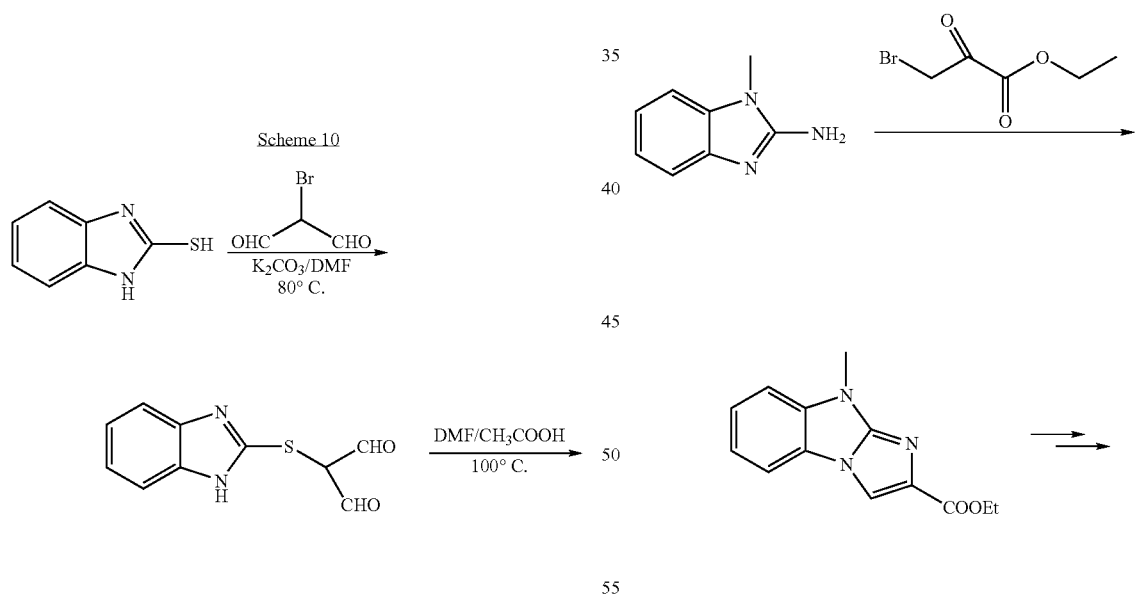
Scheme 11

Scheme 13
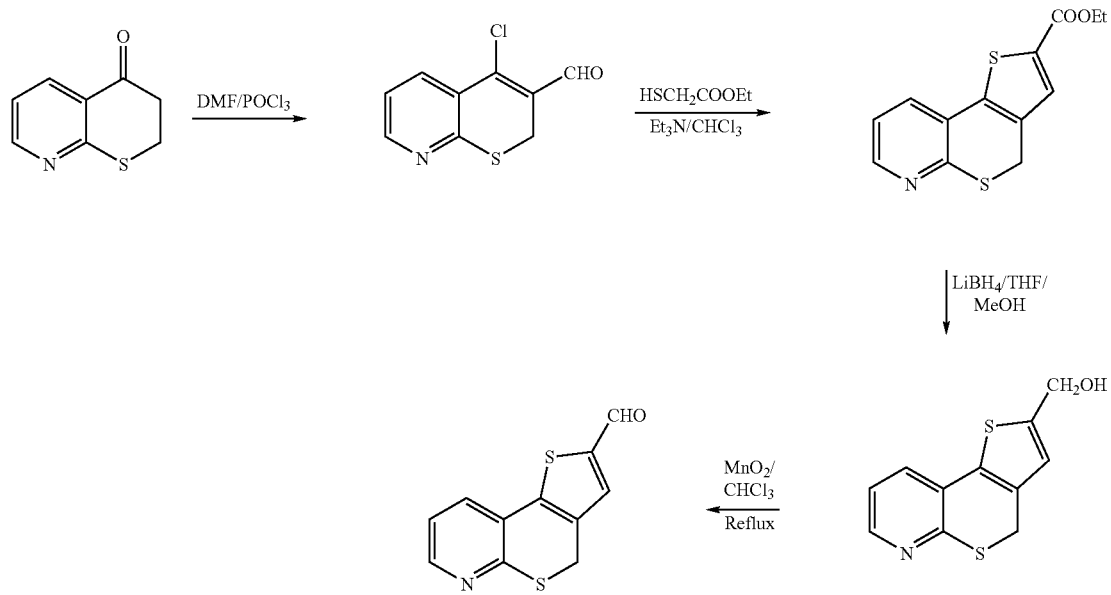
Scheme 14
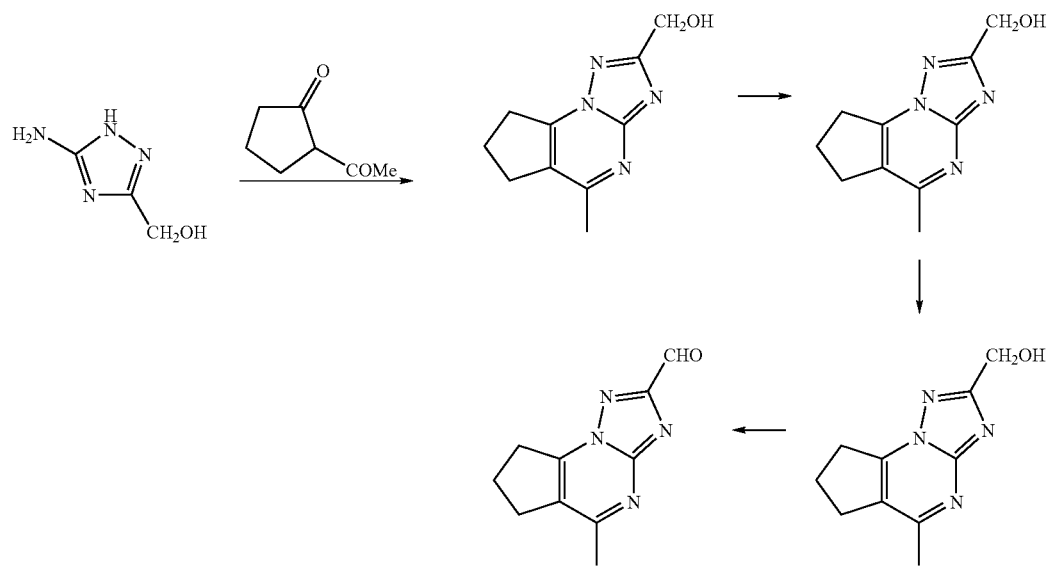
Scheme 15
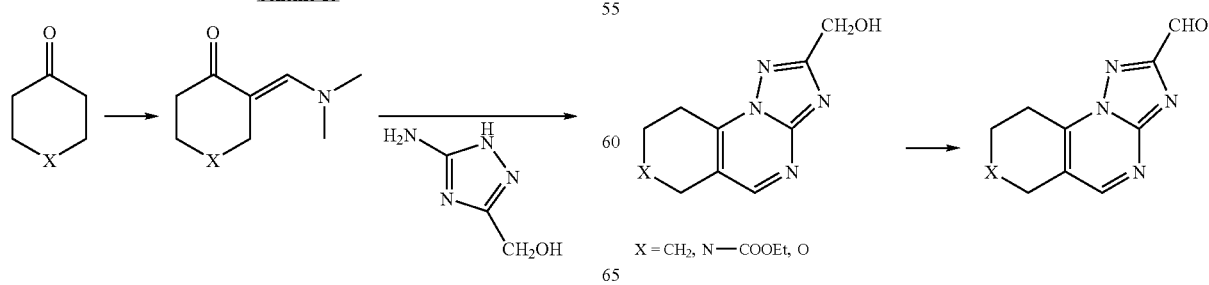
X = CH₂, N—COOEt, O Scheme 16

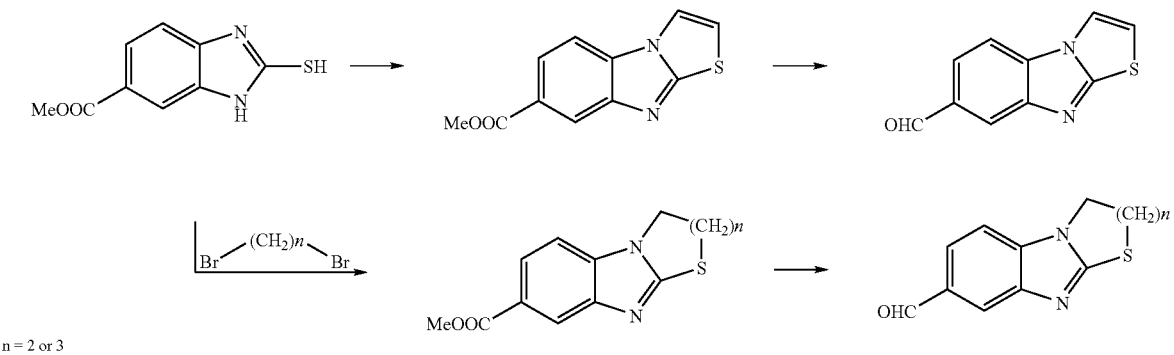

n = 2 or 3

EXPERIMENTALS

Example 1

Preparation of (5R,6Z)-6-(Imidazo[2,1-b][1,3]benzothiazol-2-ylmethylene)-7-oxo-4-thia-1-azabicyclo[3.2.0]hept-2-ene-2-carboxylic acid

Step 1: Ethyl imidazo[2,1-b]-benzthiazole-2-carboxylate

Ethyl bromopyruvate (9.8 g, 50 mmol) was added dropwise to a stirred solution of 2-aminobenzothiazole (7.5 g, 50 mmol) in DMF (100 ml) at room temperature. After the addition, the reaction mixture was heated to reflux for 6 h. The reaction mixture was cooled to room temperature and quenched with ice cold water. The aqueous layer was neutralized with NH$_4$OH and the separated solid was filtered. It was washed well with water and dried. The crude product obtained was taken to next step without purification.

Brown solid; Yield: 10 g, 81%; M+H 248. mp 97° C.

Step 2: Imidazo[2,1-b]-benzthiazole-2-methanol

To a stirred slurry of LiAlH$_4$ (2.0 g, excess) in dry THF, ethyl imidazo[2,1-b]-benzthiazole-2-carboxylate (4.9 g, 20 mmol) was slowly added in THF (100 ml) at 0° C. After the addition, the reaction mixture was stirred at room temperature for 1 h and quenched with saturated NH$_4$Cl/NH$_4$OH. The separated solid was diluted with Chloroform/MeOH (3:1) and filtered through a pad of celite. The organic layer was washed once with saturated NaCl and dried over anhydrous MgSO$_4$. It was filtered and concentrated. The brown solid obtained was taken to next step with out purification. Yield: 3.8 g, 93%; M+H 205; mp 131° C.

Step 3: 2-Formyl-Imidazo[2,1-b]-benzthiazole

To a stirred solution of imidazo[2,1-b]-benzthiazole-2-methanol (2.04 g, 10 mmol) in methylene chloride (200 ml), activated MnO$_2$ (15 g, excess) was added. The reaction mixture was stirred at room temperature for 24 h and filtered through a pad of celite. The reaction mixture was concentrated and the product was purified by silica gel column chromatography by eluting it with 75% ethyl acetate: hexane. Brown solid; Yield: 800 mg, 40%; M+H 203.

Step 4: 4-Nitrobenzyl-6-[(acetyloxy) (imidazo[2,1-b][1,3]benzothiazol-2-yl)methyl]-6-bromo-7-oxo-4-thia-1-azabicyclo[3.2.0]hept-2-ene-2-carboxylate 2-Formyl-Imidazo[2,1-b]-benzthiazole (444 mg, 2.2 mmol) and a dry THF solution (20 mL) of (5R,6S)-6-bromo-7-oxo-4-thia-1-aza-bicyclo[3.2.0]hept-2-ene-2-carboxylic acid 4-nitro-benzyl ester (772 mg, 2 mmol) were added successively to a dry acetonitrile (15 mL) solution of anhydrous MgBr$_2$:etherate (619 mg 2.4 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to a silica gel column, then the column was eluted with ethyl acetate:hexane (1:1). Collected fractions were concentrated under reduced pressure and the mixture of diastereo isomers were taken to the next step. Pale yellow amorphous solid; Yield: 850 mg, 67%; mp 69° C.; M+H 630

Step 5: (5R),(6Z)-6-(Imidazo[1,2-b][1,3]benzothiazol-2-ylmethylene)-7-oxo-4-thia-1-azabicyclo[3.2.0]hept-2-ene-2-carboxylic acid 4-Nitrobenzyl-6-[(acetyloxy) (imidazo[2,1-b][1,3]benzothiazol-2-yl)methyl]-6-bromo-7-oxo-4-thia-1-azabicyclo[3.2.0]hept-2-ene-2-carboxylate (500 mg, 0.79 mmol) was dissolved in THF (17 mL) and acetonitrile (36 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 1 N NaOH was added to adjust the pH to 8.5. The filtrate was washed with ethyl acetate and the aqueous layer was separated. The aqueous layer was concentrated under high vacuum at 35° C. to give a yellow precipitate. The precipitate was dissolved in acetonitrile and loaded on a HP-21 reverse phase column. It was eluted with deionized water (2 L) and latter eluted with 10% acetonitrile: water. Yield: 105 mg, 35%; as yellow crystals; mp 233° C.; M+H 356.

¹H NMR (DMSO-d₆) δ 6.51 (s, 1H), 6.53 (s, 1H), 7.09 (s, 1H), 7.47 (t, 1H, J=7.5 Hz), 7.54 (t, 1H, J=7.5 Hz), 8.06 (t, 1H), 8.62 (s, 1H).

Example 2

Preparation of (5R,6Z)-6-[(7-methoxyimidazo[2,1-b] [1,3]benzothiazol-2-ylmethylene)-7-oxo-4-thia-1-azabicyclo[3.2.0]hept-2-ene-2-carboxylic acid Step 1: Ethyl 7-methoxyimidazo[2,1-b]-benzthiazole-2-carboxylate Ethyl 7-methoxyimidazo[2,1-b]-benzthiazole-2-carboxylate was prepared according to the procedure as outlined in Example 1, (Step 1). Starting from 6-methoxy-2-amino benzothiazole (27 g, 0.15 mol) and ethyl bromopyruvate (39.9 g, 0.2 mol), 24 g (43% Yield) of ethyl 7-methoxyimidazo[2,1-b]-benzthiazole-2-carboxylate was isolated as a brown solid. (M+H) 277.

Step 2: 7-methoxy imidazo[2,1-b]-benzthiazole-2-methanol 7-methoxy imidazo[2,1-b]-benzthiazole-2-methanol was prepared according to the procedure outlined in Example 1, (Step 2). Starting from ethyl 7-methoxyimidazo[2,1-b]-benzthiazole-2-carboxylate (12.5 g, 43.5 mmol) and LiAlH₄ solution (43.5 ml, 0.5 M solution in THF), 4.0 g (40% yield) of the alcohol derivative was isolated as a brown solid. (M+H) 235.

Step 3: 2-Formyl-7-methoxyimidazo[2,1-b]-benzthiazole

2-Formyl-7-methoxyimidazo[2,1-b]-benzthiazole was prepared according to the procedure outlined in Example 1, (Step 3). Starting from 7-methoxy imidazo[2,1-b]-benzthiazole-2-methanol (4.0 g 17 mmol) in methylene chloride/DMF (300 mL: 50 mL) and active MnO₂ (12 g, excess), 822 mg (21% Yield) of the aldehyde derivative was isolated as brown solid. (M+H) 233.

Step 4: 4-Nitrobenzyl-6-[(acetyloxy) (7-methoxyimidazo[2,1-b][1,3]benzothiazol-2-yl)methyl]-6-bromo-7-oxo-4-thia-1-azabicyclo[3.2.0]hept-2-ene-2-carboxylate 2-Formyl-7-methoxyimidazo[2,1-b]-benzthiazole (822 mg, 3.5 mmol) and the dry THF solution (40 mL) of (5R,6S)-6-bromo-7-oxo-4-thia-1-aza-bicyclo[3.2.0]hept-2-ene-2-carboxylic acid 4-nitro-benzyl ester (1.364, 3.54 mmol) were added successively to the dry acetonitrile (15 mL) solution of anhydrous MgBr₂:etherate (1.3 g, 5 mmol) under an argon atmosphere at room temperature. After cooling to −20° C., Et₃N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO₄) and filtered through a pad of Celite. The pad was washed with ethyl acetate. The filtrate was concentrated under reduced pressure. The residue was applied to a silica gel column, then the column was eluted with ethyl acetate:hexane (1:1). Collected fractions were concentrated under reduced pressure and the mixture of diastereo isomers were taken to next step. Pale yellow amorphous solid; Yield: 2.24 g, 95%; M+H 660.

Step 5: (5R),(6Z)-6-[(7-methoxyimidazo[1,2-b][1,3] benzothiazol-2-ylmethylene]-7-oxo-4-thia-1-azabicyclo[3.2.0]hept-2-ene-2-carboxylic acid 4-Nitrobenzyl-6-[(acetyloxy) (7-methoxyimidazo[2,1-b] [1,3]benzothiazol-2-yl)methyl]-6-bromo-7-oxo-4-thia-1-azabicyclo[3.2.0]hept-2-ene-2-carboxylate (659 mg, 1.0 mmol) was dissolved in THF (17 mL) and acetonitrile (36 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 1 N NaOH was added to adjust pH to 8.5. The filtrate was washed with ethyl acetate and the aqueous layer was separated. The aqueous layer was concentrated under high vacuum at 35° C. to give yellow precipitate. The precipitate was filtered and washed with H₂O, MeCN, acetone to give the title compound. Yield: 68 mg, 23%; as yellow crystals; mp 284; M+H 386.

¹H NMR (DMSO-d₆) δ 3.89 (s, 3H), 6.58 (s, 1H), 6.64 (s, 1H), 7.14 (s, 1H), 7.2 (dd, 1H, J=6.0 Hz), 7.75 (d, 1H, J=3.0 Hz), 8.03 (d, J=6.0 Hz 1H), 8.62 (s, 1H).

Example 3

Preparation of (5R,6Z)-6-[(7-chloroimidazo[2,1-b] [1,3]benzothiazol-2-ylmethylene)-7-oxo-4-thia-1-azabicyclo[3.2.0]hept-2-ene-2-carboxylic acid Step 1: Ethyl 7-chloroimidazo[2,1-b]-benzthiazole-2-carboxylate Ethyl 7-chloroimidazo[2,1-b]-benzthiazole-2-carboxylate was prepared according to the procedure as outlined in Example 1, (Step 1). Starting from 6-chloro-2-amino benzothiazole (9.2 g, 50 mmol) and ethyl bromopyruvate (11.6 g, 60 mmol), 8.5 g (60% Yield) of ethyl 7-chloroimidazo[2,1-b]-benzthiazole-2-carboxylate was isolated as brown solid. (M+H) 281.

Step 2: 7-chloroimidazo[2,1-b]-benzthiazole-2-methanol 7-chloro imidazo[2,1-b]-benzthiazole-2-methanol was prepared according to the procedure outlined in Example 1, (Step 2). Starting from ethyl 7-chloroimidazo[2,1-b]-benzthiazole-2-carboxylate (9.0 g, 32.1 mmol) and LiAlH₄ (4.0 g, excess), 5.5 g (72% yield) of the alcohol derivative was isolated as brown solid. mp 166° C. (M+H) 239.

Step 3: 2-Formyl-7-chloroimidazo[2,1-b]-benzthiazole

2-Formyl-7-chloroimidazo[2,1-b]-benzthiazole was prepared according to the procedure outlined in Example 1, (Step 3). Starting from 7-chloroimidazo[2,1-b]-benzthiazole-2-methanol (4.0 g 16.8 mmol) in methylene chloride/MeOH (300 mL: 50 mL) and active MnO₂ (20 g, excess), 2.2 g (55% yield) of the aldehyde derivative was isolated as brown solid. (M+H) 236.

Step 4: 4-Nitrobenzyl-6-[(acetyloxy) (7-chloroimi-dazo[2,1-b][1,3]benzothiazol-2-yl)methyl]-6-bromo-7-oxo-4-thia-1-azabicyclo[3.2.0]hept-2-ene-2-carboxylate 2-Formyl-7-chloroimidazo[2,1-b]-benzthiazole (270 mg, 1.14 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (500 mg, 1.14 mmol) were added successively to the dry acetonitrile (15 mL) solution of anhydrous $MgBr_2:O(Et)_2$ (390 mg, 1.5 mmol) under an argon atmosphere at room temperature. After cooling to $-20°$ C., $Et_3N$ (2.0 mL) was added in one portion. The reaction vessel was covered with foil to exclude light. The reaction mixture was stirred for 2 h at $-20°$ C. and treated with acetic anhydride (1.04 mL) in one portion. The reaction mixture was warmed to $0°$ C. and stirred for 15 h at $0°$ C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 495 mg, 65%; M+H 665.

Step 5: (5R),(6Z)-6-[(7-chloroimidazo[1,2-b][1,3]benzothiazol-2-ylmethylene)]-7-oxo-4-thia-1-azabicyclo[3.2.0]hept-2-ene-2-carboxylic acid 4-Nitrobenzyl-6-[(acetyloxy)(7-chloroimidazo[2,1-b][1,3]benzothiazol-2-yl)methyl]-6-bromo-7-oxo-4-thia-1-azabicyclo[3.2.0]hept-2-ene-2-carboxylate (450 mg, 0.67 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to $3°$ C., and 0.1 N NaOH was added to adjust the pH to 8.5. The filtrate was washed with ethyl acetate and the aqueous layer was separated. The aqueous layer was concentrated under high vacuum at $35°$ C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 80 mg, 18%; as yellow crystals; mp $240°$ C.; (M+H+Na) 412.
$^1$H NMR (DMSO-$d_6$) δ 6.6 (s, 2H), 7.1 (s, 1H), 7.62 (dd, 1H), 8.11 (d, 1H), 8.2 (s, 1H), 8.6 (s, 1H).

Example 4

Preparation of (5R),(6Z)-6-Imidazo[1,2-a]quinolin-2-ylmethylene-7-oxo-4-thia-1-azabicyclo[3.2.0]hept-2-ene-2-carboxylic acid Imidazo[1,2-a]quinoline-2-carbaldehyde Imidazo[1,2-a]quinoline-2-carbaldehyde was prepared by the method of Westwood and co-workers (*J. Med. Chem.* 1988, 31, 1098-1115).

Step 1: (5R,6RS)-6-[(RS)-Acetoxyimidazo[1,2-a]quinolin-2-ylmethyl]-6-bromo-7-oxo-4-thia-1-azabicyclo[3.2.0]hept-2-ene-2-carboxylic acid 4-nitrobenzyl ester Imidazo[1,2-a]quinoline-2-carbaldehyde (1.09 g) and a dry THF solution (75.5 mL) of (5R,6S)-6-bromo-7-oxo-4-thia-1-aza-bicyclo[3.2.0]hept-2-ene-2-carboxylic acid 4-nitro-benzyl ester (2.22 g) were added successively to a dry acetonitrile (75.5 mL) solution of anhydrous $MgBr_2$ (2.5 g) under an argon atmosphere at room temperature. After cooling to $-20°$ C., $Et_3N$ (1.85 mL) was added in one portion. The reaction vessel was covered with foil to exclude light. The reaction mixture was stirred for 2 h at $-20°$ C. and treated with acetic anhydride (1.04 mL) in one portion. The reaction mixture was warmed to $0°$ C. and stirred for 15 h at $0°$ C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to a silica gel column, then the column was eluted with $CHCl_3$-acetone (1/0~95/5). Collected fractions were concentrated under reduced pressure followed by recrystallization from $CHCl_3$-$Et_2O$ to give the title compound as one isomer. (pale yellow crystals, yield: 1.3 g, 38%).
$^1$H NMR (CDCl$_3$) δ 2.37 (s, 3H), 5.29 (d, 1H, J=13.5 Hz), 5.45 (d, 1H, J=13.5 Hz), 6.22 (s, 1H), 7.14 (s, 1H), 7.46-7.52 (m, 3H), 7.56 (d, 1H, J=9.6 Hz), 7.62 (d, 2H, J=8.6 Hz), 7.64-7.69 (m, 1H), 7.83 (dd, 1H, J=1.1, 7.9 Hz), 7.93 (d, 1H, J=8.3 Hz), 7.99 (s, 1H), 8.25 (d, 2H, J=8.6 Hz).

Step 2: (5R),(6Z)-6-Imidazo[1,2-a]quinolin-2-ylmethylene-7-oxo-4-thia-1-azabicyclo[3.2.0]hept-2-ene-2-carboxylic acid (5R,6RS)-6-[(RS)-Acetoxyimidazo[1,2-a]quinolin-2-ylmethyl]-6-bromo-7-oxo-4-thia-1-azabicyclo[3.2.0]hept-2-ene-2-carboxylic acid 4-nitrobenzyl ester (1.3 g) was dissolved in THF (17 mL) and acetonitrile (36 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to $3°$ C., and 1 N NaOH was added to adjust the pH to 8.5. The filtrate was washed with ethyl acetate and the aqueous layer was separated. The aqueous layer was concentrated under high vacuum at $35°$ C. to give a yellow precipitate. The precipitate was filtered and washed with $H_2O$, acetonitrile, and acetone to give the title compound, yield 297 mg, 38%, as yellow crystals mp $205°$ C.
$^1$H NMR (D$_2$O) δ 6.19 (s, 1H), 6.36 (s, 1H), 6.87 (s, 1H), 6.96 (d, 1H, J=9.5 Hz), 7.32 (d, 1H, J=9.5 Hz), 7.33 (s, 1H), 7.44~7.57 m, 4H).

Example 5

Preparation of (5R),(6Z)-6-(6,7-dihydro-5H-cyclopenta[d]imidazo[2,1-b][1,3]thiazol-2-ylmethylene)-7-oxo-4-thia-1-azabicyclo[3.2.0]hept-2-ene-2-carboxylic acid Step 1: Preparation of ethyl 6,7-dihydro-5H-cyclopenta[d]imidazo[2,1-b][1,3]thiazole-2-carboxylate A mixture of 2-chlorocyclopentanone (11.8 g, 100 mmol) and thiourea (8.0 g 101 mmol) was refluxed in ethanol:THF (1:2) for 16 hrs. The reaction mixture was cooled to room temperature and the separated white solid was filtered. (9.0 g separated) This was dissolved in anhydrous ethanol (100 ml) and sodium methoxide (2.7 g, 51 mmol). To this ethyl bromopyruvate (10.0 g) was added and stirred at room temperature for 2 hrs. Then it was refluxed for 48 hrs. At the end reaction mixture was cooled to room temperature and concentrated. The residue was extracted with chloroform and washed well with water. The product was purified by silica-gel column chromatography by eluting it with 50% ethyl acetate:hexane. Red semi-solid; Yield: 3.0 g; M+H 237.

The ester was reduced with LiAlH$_4$ and the resultant alcohol was oxidized with active MnO$_2$. The aldehyde obtained was taken to next step.

Step 3: Preparation of 4-nitrobenzyl (5R)-6-[(acetyloxy)(6,7-dihydro-5H-cyclopenta[d]imidazo[2,1-b][1,3]thiazol-2-yl)-6-bromo-7-oxo-4-thia-1-azabicyclo[3.2.0]hept-2-ene-2-carboxylate 2-Formyl-6,7-dihydro-5H-cyclopenta[d]imidazo[2,1-b][1,3]thiazole (600 mg, 3.1 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (1.2 g, 3 mmol) were added successively to the dry acetonitrile (15 mL) solution of anhydrous MgBr$_2$:O(Et)$_2$ (1.2 g, 3.0 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 850 mg, 45%; M+H 620.

Step 4: Preparation of (5R),(6Z)-6-(6,7-dihydro-5H-cyclopenta[d]imidazo[2,1-b][1,3]thiazol-2-ylmethylene)-7-oxo-4-thia-1-azabicyclo[3.2.0]hept-2-ene-2-carboxylic acid 4-nitrobenzyl (5R)-6-[(acetyloxy)(6,7-dihydro-5H-cyclopenta[d]imidazo[2,1-b][1,3]thiazol-2-yl)-6-bromo-7-oxo-4-thia-1-azabicyclo[3.2.0]hept-2-ene-2-carboxylate (850 mg, 1.37 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 138 mg, 29%; as yellow crystals; mp 192° C.; (M+H+Na) 367. $^1$H NMR (DMSO-d$_6$) δ 2.51 (m, 4H), 3.01 (m, 2H), 8.2 (s, 1H), 7.1 (s, 1H), 6.55 (s, 1H), 6.4 (s, 1H).

Example 6

Preparation of (5R),(6Z)-6-(Imidazo[1,2-a]quinoxaline-2-ylmethylene)-7-oxo-4-thia-1-azabicyclo[3.2.0]hepto-2-ene-2-carboxylic acid, sodium salt Imidazo[1,2-a]quinoxaline-2-carboxaldehyde Imidazo[1,2-a]quinoxaline-2-carboxaldehyde was prepared by the method of Westwood and co-workers (*J. Med. Chem.* 1998, 31, 1098-1115).

Step 1: (5R,6RS)-6-((RS)-Acetoxy imidazo[1,2-a]quinoxalin-2-ylmethyl)-6-bromo-7-oxo-4-thia-1-azabicyclo[3.2.0]hept-2-ene-2-carboxylic acid p-nitrobenzyl ester A dry acetonitrile (33 mL) solution of imidazo[1,2-a]quinoxaline-2-carboxaldehyde (505 mg) was added to a dry acetonitrile (20 mL) solution of MgBr$_2$ (1.1 g) under an nitrogen atmosphere at room temperature, and the mixture was stirred for 10 min. After addition of the dry THF (25 mL) solution of (5R,6S)-6-bromo-7-oxo-4-thia-1-aza-bicyclo[3.2.0]hept-2-ene-2-carboxylic acid 4-nitro-benzyl ester (931 mg), the mixture was cooled to −20° C. then triethylamine (0.8 mL) was added in one portion. The reaction vessel was covered with foil to exclude light. The reaction mixture was stirred for 4 h at −20° C. and treated with 4,4-dimethylamino pyridine (58 mg) and acetic anhydride (0.44 mL) in one portion. The reaction mixture was warmed to 0° C. and stirred for 16 h at 0° C. 10% Citric acid aqueous solution (200 mL) was added to the reaction mixture and the aqueous layer was extracted with ethyl acetate (3×100 mL). The organic layer was washed with water, saturated sodium hydrogen carbonate and brine, dried (MgSO$_4$) and filtered. The filtrate was concentrated under reduced pressure. The residue was purified by silica gel column chromatography, eluted with CH$_2$Cl$_2$-acetone (50:1), and the title compound was obtained as a diastereomeric mixture (78:22, pale brown foamy amorphous, 1.0 g, 68.9%).

$^1$H NMR (CDCl$_3$) δ 2.07 (s, 0.66H), 2.38 (s, 2.34H), 5.30 (d, 1H, J=13.5 Hz), 5.45 (d, 0.78H, J=13.5 Hz), 5.48 (d, 0.22H, J=13.5 Hz), 6.24 (s, 0.78H), 6.46 (s, 0.22H), 6.63 (s, 0.22H), 7.18 (s, 0.78H), 7.50 (s, 0.78H), 7.52 (s, 0.22H), 7.61 (d, 1.56H, J=8.7 Hz), 7.63 (d, 0.44H, J=8.8 Hz), 7.64-7.67 (m, 1H), 7.68-7.73 (m, 1H), 7.92-7.95 (m, 1H), 8.08 (s, 0.78H), 8.13-8.16 (m, 1H), 8.24 (d, 1.56H, J=8.7 Hz), 8.25 (d, 0.44H, J=8.8 Hz), 8.33 (s, 0.22H), 9.05 (s, 0.78H), 9.09 (s, 0.22H).

Step 2: (5R),(6Z)-6-(Imidazo[1.2-a]quinoxaline-2-ylmethylene)-7-oxo-4-thia-1-azabicyclo[3.2.0]hepto-2-ene-2-carboxylic acid, sodium salt (5R,6RS)-6-((RS)-Acetoxy imidazo[1,2-a]quinoxalin-2-ylmethyl)-6-bromo-7-oxo-4-thia-1-azabicyclo [3.2.0]hept-2-ene-2-carboxylic acid p-nitrobenzyl ester (951 mg) and 10% Pd—C (50% wet, 477 mg) were added to a mixture of THF (48 mL) and 0.5 mol/L phosphate buffer (pH 6.5, 48 mL). The mixture was hydrogenated at 400 kPa at room temperature for 4 h. The reaction solution was filtered and Pd—C was washed with water and n-butanol. The reaction mixture was cooled to 0° C. and 1 N NaOH was added to adjust the ph to 8.5. The aqueous layer was separated and then the organic layer was extracted with water. The combined aqueous layer was concentrated to 57 g and applied to Diaion HP-21 resin (60 mL, Mitsubishi Kasei Co. Ltd.) column chromatography. After adsorbing, the column was eluted with water and then 5, 10, 15 and 20% acetonitrile:water solution (each 60 mL). The combined fractions were concentrated under high vacuum at 35° C. and lyophilized to give the title compound as a yellow amorphous solid, yield 148 mg (26.1%), mp 300° C. (dec.). $^1$H NMR (D$_2$O) δ 5.92 (s, 1H), 6.23 (s, 1H), 6.66 (s, 1H), 7.11-7.22 (m, 3H), 7.25 (d, 1H, J=7.9 Hz), 7.50 (s, 1H), 8.03 (s, 1H); IR (KBr) 3413, 1748, 1592, 1553 cm$^{-1}$; $I^{max}$ (H$_2$O) 340, 293, 237, 218 nm.

Example 7

Preparation of (5R,6Z)-6-[(7-methylimidazo[2,1-b] [1,3]benzothiazol-2-ylmethylene)-7-oxo-4-thia-1-azabicyclo[3.2.0]hept-2-ene-2-carboxylic acid Step 1: Ethyl 7-methylimidazo[2,1-b]-benzthiazole-2-carboxylate Ethyl 7-methylimidazo[2,1-b]-benzthiazole-2-carboxylate was prepared according to the procedure as outlined in Example 1, (Step 1). Starting from 6-methyl-2-amino benzothiazole (3.2 g, 20 mmol) and ethyl bromopyruvate (4.0 g, 20.4 mmol), 3.0 g (57% Yield) of ethyl 7-methylimidazo[2,1-b]-benzthiazole-2-carboxylate was isolated as brown solid. (M+H) 261.

Step 2: 2-Formyl-7-methylimidazo[2,1-b]-benzthiazole

To a stirred solution of Ethyl 7-methylimidazo[2,1-b]-benzthiazole-2-carboxylate (4.0 g, 15.38 mmol) in dry THF at −78° C., DIBAL (1M. solution in toluene) (16.0 ml, 16 mmol) was added. The reaction mixture was stirred at −78° C. and slowly elevated to room temperature. The reaction mixture was stirred at room temperature for 30 minutes and quenched with saturated NH$_4$Cl. The reaction mixture was extracted with chloroform and washed well with water. The organic layer was dried over anhydrous MgSO$_4$; filtered and concentrated. The residue was purified bt SiO$_2$ column chromatography by eluting it with chloroform:methanol (20:1). Brown solid; (M+H) 217; Yield: 800 mg (24%)

Step 3: 4-Nitrobenzyl-6-[(acetyloxy) (7-methylimidazo[2,1-b][1,3]benzothiazol-2-yl)methyl]-6-bromo-7-oxo-4-thia-1-azabicyclo[3.2.0]hept-2-ene-2-carboxylate 2-Formyl-7-methylimidazo[2,1-b]-benzthiazole (432 mg, 2.0 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (772 mg, 2.0 mmol) were added successively to the dry acetonitrile (15 mL) solution of anhydrous MgBr$_2$:O(Et)$_2$ (566 mg, 2.0 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 400 mg, 31%; M+H 645.

Step 4: (5R),(6Z)-6-[(7-methylimidazo[1,2-b][1,3]benzothiazol-2-ylmethylene)]-7-oxo-4-thia-1-azabicyclo[3.2.0]hept-2-ene-2-carboxylic acid 4-Nitrobenzyl-6-[(acetyloxy)(7-methylimidazo[2,1-b][1,3]benzothiazol-2-yl)methyl]-6-bromo-7-oxo-4-thia-1-azabicyclo[3.2.0]hept-2-ene-2-carboxylate (350 mg, 0.54 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 110 mg, 55%; as yellow crystals; mp 178° C. (Dec); (M+H+Na) 392.
$^1$H NMR (DMSO-d$_6$) δ 8.56 (s, 1H), 7.93 (d, 1H), 7.83 (s, 1H), 7.38 (d, 1H), 7.07 (s, 1H), 6.51 (s, 2H), 2.42 (s, 3H).

Step 4: (5R),(6Z)-6-[(7-methylimidazo[1,2-b][1,3]benzothiazol-2-ylmethylene)]-7-oxo-4-thia-1-azabicyclo[3.2.0]hept-2-ene-2-carboxylic acid: (Procedure B)

4-Nitrobenzyl-6-[(acetyloxy)(7-methylimidazo[2,1-b][1,3]benzothiazol-2-yl)methyl]-6-bromo-7-oxo-4-thia-1-azabicyclo[3.2.0]hept-2-ene-2-carboxylate (350 mg, 0.54 mmol) was dissolved in THF (40 mL) and 6.5 pH phosphate buffer (40 ml) and hydrogenated over Pd/C (10%, 200 mg) at 40 psi pressure for 3 hrs at room temperature. At the end, reaction mixture was filtered through a pad of celite and washed with acetonitrile. The reaction mixture was concentrated to 40 ml and cooled to 0° C. and pH was adjusted to 8.5 by adding 1N NaOH. The product was directly loaded over HP21 resin reverse phase column chromatography. Initially the column was eluted with deionized water (2 L) and latter with 10% acetonitrile:water. The fractions were concentrated and the yellow solid was washed with acetone, filtered and dried. Yield: 110 mg, 55% as yellow solid.

Example 8

Preparation of (5R), (6Z)-6-(4,5,6,7-tetrahydro-1,3a,3b,8-tetraaza-cyclopenta[a]indene-2-ylmethylene)-7-oxo-4-thia-1-aza-bicyclo[3.2.0]hept-2-ene-2-carboxylic acid sodium salt Step 1: 5,6,7,8-Tetrahydro-[1,2,4]triazolo[1,5-a]pyridin-2-ylamine The 12.7% solution of HCl in ethanol (5.35 mL) and 10% Pd—C (50% wet) (2.5 g) were added to the mixture of [1,2, 4]triazolo[1,5-a]pyridin-2-ylamine (2.5 g) in ethanol (72 mL). The reaction mixture was hydrogenated at 400 KPa of $H_2$ for 3 days at room temperature. The mixture was filtered and concentrated under reduced pressure. The residue was treated with saturated potassium carbonate solution and extracted with chloroform. The organic layer was dried ($Na_2SO_4$) and concentrated under reduced pressure. The title compound was obtained as a pale yellow solid (2.31 g, 90%). $^1$H-NMR (400 MHz, $CDCl_3$) δ 1.88-1.94 (m, 2H), 1.98-2.05 (m, 2H), 2.77 (t, 2H, J=6.2 Hz), 3.95 (t, 2H, J=6.2 Hz), 4.09 (brs, 2H).

Step 2: 4,5,6,7-Tetrahydro-1,3a,3b,8-tetraaza-cyclopenta[a]indene-2-carboxylic acid ethyl ester Ethyl bromopyruvate (10.23 g) was added to the mixture of 5,6,7,8-tetrahydro-[1,2,4]triazolo[1,5-a]pyridin-2-ylamine (5.8 g) in 1,2-dimethoxyethane (320 mL). The reaction mixture was stirred for 5 hours at room temperature and concentrated to 100 mL under reduced pressure. The precipitate was obtained by an addition of diethyl ether (200 mL), followed by filtration. The precipitate was dissolved in ethanol (175 mL) and stirred for 20 hours at 110° C. in shield tube. The reaction mixture was cooled to room temperature and concentrated under reduced pressure. The residue was treated with saturated potassium carbonate solution and extracted with chloroform. The organic layer was dried ($Na_2SO_4$) and concentrated under reduced pressure. The residue was applied to silica gel column chromatography, then eluted with ethyl acetate-methanol (1/1). The title compound was obtained as a pale yellow solid (7.56 g, 77%). $^1$H-NMR (400 MHz, $CDCl_3$) δ 1.42 (t, 3H, J=7.1 Hz), 2.14-2.25 (m, 4H), 3.11 (t, 2H, J=6.1 Hz), 4.37 (t, 2H, J=5.7 Hz), 4.41 (q, 2H, J=7.1 Hz), 7.57 (s, 1H).

Step 3: 4,5,6,7-Tetrahydro-1,3a,3b,8-tetraaza-cyclopenta[a]indene-2-carbaldehyde 1.01 M Diisobutylalminium hydride in toluene (1.06 mL) was added dropwise to the solution of 4,5,6,7-tetrahydro-1,3a,3b,8-tetraaza-cyclopenta[a]indene-2-carboxylic acid ethyl ester (100 mg) in dry THF (5 mL) at −78° C. under a nitrogen atmosphere. The reaction mixture was stirred for 30 minutes at −78° C. and treated with ethanol (ca. 1 mL). The mixture was warmed to 0° C. and stirred for 1 h at 0° C. The reaction solution was diluted with ethyl acetate (20 mL), treated with 0.5 mL saturated ammonium chloride solution, and sonicated for ca. 5 minutes (until a precipitate was deposited enough). The mixture was dried ($Na_2SO_4$) and filtered through a pad of Celite. The filtrate was concentrated under reduced pressure. The residue was crystallized from dichloromethane and diethyl ether to give the title compound (47.4 mg, 58%). $^1$H-NMR (400 MHz, $CDCl_3$) δ 2.16-2.27 (m, 4H), 3.14 (t, 2H, J=6.1 Hz), 4.39 (t, 2H, J=5.7 Hz), 7.53 (s, 1H), 10.01 (s, 1H).

Step 4: (5R,6RS)-6-{(RS)-Acetoxy-[4,5,6,7-tetrahydro-1,3a,3b,8-tetraaza-cyclopentar[a]indene-2-yl]-methyl}-6-bromo-7-oxo-4-thia-1-aza-bicyclo[3.2.0]hept-2-ene-2-carboxylic acid 4-nitro-benzyl ester 4,5,6,7-Tetrahydro-1,3a,3b,8-tetraaza-cyclopenta[a]indene-2-carbaldehyde (2.97 g) was added to the dry acetonitrile (110 mL) solution of anhydrous $MgBr_2$ (4.45 g) under a nitrogen atmosphere at room temperature. The dry THF solution (110 mL) of (5R,6S)-6-bromo-7-oxo-4-thia-1-aza-bicyclo[3.2.0]hept-2-ene-2-carboxylic acid 4-nitro-benzyl ester (2.97 g) was added to the reaction mixture, cooled to −20° C., and triethylamine (6.45 mL) was added in one portion. The reaction vessel was covered with foil to exclude light. After the mixture was stirred for 1.2 h at −20° C., acetic anhydride (2.9 mL) was added in one portion. The reaction mixture was warmed to 0° C. and stirred for 16.5 h at 0° C. The mixture was diluted with ethyl acetate and washed with $H_2O$ and brine. The organic layer was dried ($MgSO_4$) and filtered through a pad of Celite. The pad was washed with ethyl acetate. The filtrate was concentrated under reduced pressure. The residue was applied to silica gel column chromatography, eluted with ethyl acetate-n-hexane (3/1) and then with ethyl acetate-methanol (5/1). The title compound was obtained as a brown amorphous solid (651.6 mg, 13%). $^1$H-NMR (400 MHz, $CDCl_3$) δ 2.10-2.24 (m, 4H), 2.29 (s, 3H), 3.04-3.07 (m, 2H), 4.28-0.32 (m, 2H), 5.27 (d, 1H, J=13.7 Hz), 5.43 (d, 1H, J=13.7 Hz), 6.19 (s, 1H), 6.91 (s, 1H), 7.01 (s, 1H), 7.49 (s, 1H), 7.59-7.62 (m, 2H), 8.23-8.25 (m, 2H).

Step 5: (5R), (6Z)-6-(4,5,6,7-tetrahydro-1,3a,3b,8-tetraaza-cyclopenta[a]indene-2-ylmethylene)-7-oxo-4-thia-1-aza-bicyclo[3.2.0]hept-2-ene-2-carboxylic acid sodium salt (5R,6RS)-6-{(RS)-Acetoxy-[4,5,6,7-tetrahydro-1,3a,3b,8-tetraaza-cyclopenta[a] indene-2-yl]-methyl}-6-bromo-7-oxo-4-thia-1-aza-bicyclo[3.2.0]hept-2-ene-2-carboxylic acid 4-nitro-benzyl ester (643.6 mg) was dissolved in THF (9 mL) and acetonitrile (4.2 mL). Freshly activated Zn dust (2.57 g) and 0.5 M phosphate buffer (pH 6.4, 13.2 mL) were added to the reaction mixture. The reaction vessel was covered with foil to exclude light. The mixture was vigorously stirred for 2 h at room temperature. The mixture was cooled to 3° C., and 1 N NaOH aqueous solution was added to adjust pH to 7.5. The reaction solution was mixed with ethyl acetate and filtered through a pad of Celite. The pad was washed with water. The aqueous layer was concentrated to 20 mL under high vacuum at 35° C. The concentrate was applied to Diaion HP-21 (60 mL, Mitsubishi Kasei Co. Ltd.) resin column chromatography. After adsorbing, the column was eluted with water and then with 2.5-10% acetonitrile-water. The combined fractions was concentrated under high vacuum at 35° C. and lyophilized to give the title compound as a yellow amorphous solid (68 mg, 18%, pH 7.4). Mp 175° C. (dec); $^1$H-NMR (400 MHz, $D_2O$) δ 1.85-2.03 (m, 4H), 2.85-2.99 (m, 2H), 4.07-4.14 (m, 2H), 6.34 (s, 1H), 6.74 (s, 1H), 6.76 (s, 1H), 7.28 (s, 1H).

Example 9

Preparation of (5R,6E)-6-[(10-benzyl-ii-oxo-10,11-dihydrodibenzo[b,f][1,4]oxazepin-8-yl)methylene]-7-oxo-4-thia-1-azabicyclo[3.2.0]hept-2-ene-2-carboxylic Acid

Step 1: Preparation of 8-(hydroxymethyl)dibenzo[b, f][1,4]oxazepin-11(10H)-one Lithium aluminum hydride (11 mL, 11 mmole) was slowly added to the solution of 11-Oxo-10,11-dihydro-dibenzo[b,f] [1,4]oxazepine-8-carboxylic acid methyl ester (1.346 g, 5 mmole) in THF under $N_2$ at room temperature. The reaction mixture was stirred for 1 hour and 45 minutes then quenched with 2N of HCl until the pH value reaches 2-3. Removed all the THF by rotary evaporation, and extracted the reaction mixture with ethyl acetate for five times, dried the organic layer with sodium sulfate and filtered and concentrated. Obtained the desired compound (white solid) in 46% yield.

Step 2: Preparation of 11-oxo-10,11-dihydrodibenzo[b,f][1,4]oxazepine-8-carbaldehyde 8-(hydroxymethyl)dibenzo[b,f][1,4]oxazepin-11(10H)-one (0.241 g, 1 mmole) in acetonitrile was added to the molecular sieves (1 g) under $N_2$ at room temperature then 4-methylmorpholine N-oxide (0.175 g, 1.5 mmole) was also added into the reaction mixture. After stirring the mixture for 10 minutes, tetrapropylammonium perruthenate (0.0176 g, 0.05 mmole) was added and the reaction followed by t.l.c. until complete. Dilute the reaction mixture with 10 ml of ethyl acetate and flashed it through a small silica gel column. Collected all the ethyl acetate that contains desired material, extracted the organic layer with 1N HCl and also washed it with brine. Dried the organic layer over sodium sulfate and filtered and concentrated. Obtained the desired compound (white solid) in 83% yield.

Step 3: Preparation of 10-benzyl-11-oxo-10,11-dihydro-dibenzo[b,f][1,4]oxazepine-8-carbaldehyde Potassium carbonate anhydrous (0.207 g, 1.5 mmole) and benzyl bromide (0.205 g, 1.2 mmole) were added to a solution of the 11-oxo-10,11dihydrodibenzo[b,f][1,4]oxazepine-8-carbaldehyde (0.240 g, 1 mmole) in acetonitrile under $N_2$ at room temperature. The reaction mixture then was refluxed for 4 hours, and cooled to room temperature. Diluted the reaction mixture with ethyl acetate and filtered through a magnesol pad and concentrated. Purified with silica gel column and 50% ethyl acetate in hexane. Obtained the desired compound (light yellow oil) in 63% yield.

Step 4: Preparation of 6-[acetoxy-(10-benzyl-11-oxo-10,11-dihydro-dibenzo[b,f][1,4]oxazepin-8-yl)-methyl]-6-bromo-7oxo-4-thia-1-aza-bicyclo[3.2.0]hept-2-ene-2-carboxylic acid 4-nitro-benzyl ester 10-benzyl-11-oxo-10,11-dihydro-dibenzo[b,f][1,4]oxazepine-8-carbaldehyde (0.250 g, 0.759 mmole) in acetonitrile was added to magnesium bromide (0.419 g, 2.28 mmole) under $N_2$ at room temperature. The dry THF solution of (5R, 6S)-6-bromo-7-oxo-4-thia-1-azabicyclo[3.2.0]hept-2-ene-2-carboxylic acid 4-nitrobenzyl ester (0.292 g, 0.758 mmole) then was added to the mixture. After 15 minutes the reaction mixture was cooled to −20° C., and triethylamine (0.317 mL, 2.27 mmole) was added. The reaction flask was covered with foil to exclude light. After 4 hours at −20° C., treated with acetic anhydride (0.358 mL, 3.795 mmole) and DMAP (0.00927 g, 0.0759 mmole). Warmed up the reaction mixture to 0° C. and placed it in freezer overnight. Reaction solution was concentrated and dissolved with ethyl acetate and washed with 5% of citric acid aqueous solution, saturated $NaHCO_3$, water and brine. Organic layer was dried in sodium sulfate and filtered and concentrated. Purified with silica gel column and 1:15 ethyl acetate/$CH_2Cl_2$. Obtained the desired compound (light yellow oil) in 41% yield.

Step 5: Preparation of 6-(10-benzyl-11-oxo-10,11-dihydro-dibenzo[b,f][1,4]oxazepin-8-ylmethylene)-7-oxo-4-thia-1-aza-bicyclo[3.2.0]hept-2-ene-2-carboxylic acid, sodium salt A 0.5M phosphate buffer solution (pH 6.5) was added to a solution of 6-[acetoxy-(10-benzyl-11-oxo-10,11-dihydro-dibenzo[b,f][1,4]oxazepin-8-yl)-methyl]-6-bromo-7oxo-4-thia-1-aza-bicyclo[3.2.0]hept-2-ene-2-carboxylic acid 4-nitro-benzyl ester (0.210 g, 0.273 mmole) in THF, followed by 10% Pd—C (0.0546 g). The reaction mixture then was hydrogenated at 40 psi for three hours. Filtered through a celite pad and removed the THF by rotary evaporation, extracted the mixture with ethyl acetate and washed with water and brine. Dried the organic layer with sodium sulfate and filtered and concentrated. Dissolved the $NaHCO_3$ with minimal amount of distal water and added it to the reaction mixture along with a small amount of ethyl acetate until the pH value reaches 7-8, evaporated the ethyl acetate. Purified with reverse phase column (MCI Gel CHP20P) with varying amounts of acetonitrile (0%-20%) in water. Removed the acetonitrile and water by rotary evaporation, and freeze-dried the compound. Obtained the desired material (yellow solid) in 24% yield. Mp: 179° C. $^1$H NMR (DMSO) δ 1.755-1.825 (s, 1H), 2.497-2.506 (d, 2H), 5.243-5.434 (m, 2H), 6.516-6.770 (m, 1H), 7.039-7.792 (m, 11H).

Example 10

Preparation of 6-(5-ethoxy-7,8-dihydro-6H-3,4,8b-triaza-as-indacen-2-ylmethylene)-7-oxo-4-thia-1-aza-bicyclo[3.2.0]hept-2-ene-2-carboxylic acid

Step 1: Preparation of 4-ethoxy-6,7-dihydro-5H-cyclopentapyrimidin-2-ylamine (SM: Ross, L. O.; Goodman, L.; Baker, B. R. J. Am. Chem. Soc. 1959, 81, 3108)

5.1 grams of 4-chloro-6,7-dihydro-5H-cyclopentapyrimidin-2-ylamine was dissolved in 200 ml xylene and 30 ml absolute ethanol. Then 6.8 gram for sodium ethoxide was added and the mixture was refluxed for 3 hours. Then the solvent was removed in vacuo and 100 ml water was added to the residue. Filter and wash the cake with water (50 ml). The solid was further vacuumed to dry for several hours. The desired product weighed 5.3 gram (98% yield). Mp: 133.8~134.9° C.

H-NMR: (300 MHz, $CDCl_3$) δ. 6.23 (s, NH2), 4.28 (quartet, 2H, J=6.9 Hz), 2.6 (m, 2H), 1.93 (m, 2H), 1.27 (t, CH3, J=6.9 Hz); MS: 180.0 (M+H)

Step 2: Preparation of 5-Ethoxy-7,8-dihydro-6H-3,4,8b-triaza-as-indacene-2-carboxylic acid ethyl ester 5.2 gram (29 mmol) 4-ethoxy-6,7-dihydro-5H-cyclopentapyrimidin-2-ylamine was dissolved in 100 ml dry THF. Bromopyruvate (5.4 ml) was then added dropwise with in five minutes. The mixture was stirred at 23° C. for one hour. It was then filtered and washed with ether to give 8.7 gram of solid. This solid was then dissolved in 50 ml ethanol and refluxed for two hours. The reaction mixture was cooled to room temperature and partitioned between 350 ml chloroform and 200 ml saturated sodium bicarbonate. The organic layer was separated and dried over magnesium sulfate. Filter off the drying agent and concentrate to give 6.5 gram of product.

MP: 168.6~168.7° C.

H-NMR: (300 MHz, $CDCl_3$) δ. 7.69 (s, 1H), 4.50 (qartet, 2H, J=7.2 Hz), 4.40 (qartet, 2H, J=7.2 Hz), 3.11 (t, 2H, J=9.6 Hz), 2.88 (t, 2H, J=9.6 Hz), 2.88 (m, 2H), 1.43 (t, 2H, J=7.2 Hz); MS: 276.2 (M+H)

Step 3: Preparation of 5-ethoxy-7,8-dihydro-6H-3,4,8b-triaza-as-indacene-2-carbaldehyde 1.925 grams 5-ethoxy-7,8-dihydro-6H-3,4,8b-triaza-as-indacene-2-carboxylic acid ethyl ester was dissolved in 40 ml dichloromethane and then cooled to −78° C. DIBAL (1 M, 21 ml, 3 eq.) was then added within five minutes. The reaction media was then quenched with 2 ml ethanol and partitioned between 350 ml dichloromethane and 100 ml 1 N sodium hydroxide. The aqueous layer was washed with another 150 ml chloroform and the combined organic layer was dried over magnesium sulfate and filtered and concentrated to give the corresponding alcohol. The alcohol is then dissolved in 150 ml dichloromethane and 10 grams of manganese dioxide is then added. The mixture was stirred at 23° C. for two hours. The reaction mixture was then filtered through a pad of celite and concentrated to give 1.1 gram (68%) of the desired aldehyde.

MP: 237.2~237.3° C.

H-NMR: (300 MHz, CDCl$_3$) δ. 9.94 (s, 1H, CHO), 8.39 (s, 1H), 4.46 (quartet, 2H, J=7.2 Hz), 3.2 (m, 2H, CH2), 2.85 (m, 2H, CH2), 2.24 (m, 2H, CH2), 1.38 (t, 3H, CH3, J=7.2 Hz); MS: 232.1 (M+H)

Step 4: Preparation of 6-[acetoxy-(5-ethoxy-7,8-dihydro-6H-3,4,8b-triaza-as-indacen-2-yl)-methyl]-6-bromo-7-oxo-4-thia-1-aza-bicyclo[3.2.0]hept-2-ene-2-carboxylic acid 4-nitro-benzyl ester A 30 ml acetonitrile solution of 5-ethoxy-7,8-dihydro-6H-3,4,8b-triaza-as-indacene-2-carbaldehyde (693 mg, 3 mmol) was added 1.03 gram of magnesium bromide etherate. The mixture was stirred at 23° C. for half an hour. Then a 30 ml dry THF solution of the 6-Bromo-7-oxo-4-thia-1-aza-bicyclo [3.2.0]hept-2-ene-2-carboxylic acid 4-nitro-benzyl ester (1.155 gram, 1 eq.) was injected within a minute and the reaction mixture was then cooled to −20° C. Triethylamine (0.7 ml, eq.) was then injected and the reaction mixture was stirred for five hours at −20° C. Then acetic anhydride (0.377 ml, eq.) was injected and the reaction mixture was left at zero degree for 18 hours. The reaction media was then diluted with 400 ml ethyl acetate and washed with 100 ml 5% citric acid, 100 ml saturated sodium bicarbonate, and 100 ml brine. The organic layer was then dried over magnesium sulfate, filtered and concentrated. Flash column chromatography using 20% ethyl acetate in hexane gave 1.1 gram product.

MP: 118.7~119.1° C.

H-NMR: (300 MHz, CDCl$_3$) δ. 8.35 (d, 2H, J=11 Hz), 7.63 (m, 2H), 7.41 (d, 1H, J=6.9 Hz), 7.08 (d, 1H, J=1 Hz), 6.47 (s, 1H), 5.55 (4H, CH2), 4.54 (m, 2H), 3.09 (m, 2H), 2.93 (m, 2H), 2.32 (m, 2H), 1.41 (t, J=9.6 Hz); MS: 660.1 (M+H)

Step 5: Preparation of 6-(5-ethoxy-7,8-dihydro-6H-3,4,8b-triaza-as-indacen-2-ylmethylene)-7-oxo-4-thia-1-aza-bicyclo[3.2.0]hept-2-ene-2-carboxylic acid 6-[acetoxy-(5-ethoxy-7,8-dihydro-6H-3,4,8b-triaza-as-indacen-2-yl)-methyl]-6-bromo-7-oxo-4-thia-1-aza-bicyclo [3.2.0]hept-2-ene-2-carboxylic acid 4-nitro-benzyl ester (1.03 gram, 1.565 mmol) was suspended in 20 ml THF and 20 ml pH=6.5 aqueous phosphate buffer. The mixture was then subjected to 45 psi hydrogen for two hours. Then it was filtered through a pad of celite and concentrated in vacuo to remove most of the THF. The solution was then cooled to zero degree and basified to pH=8 with 1 N sodium hydroxide. Then it was purified via reverse phase HPLC using 1 liter of water followed by 5%~25% acetonitrile and water. Water was then removed through concentrate in vacuo and 100 mg of product was collected.

MP: >250° C.

H-NMR: (300 MHz, CDCl$_3$) δ. 7.52 (s, 1H), 6.95 (s, 1H), 6.54 (s, 1H), 4.73 (m, 2H), 3.06 (m, 2H), 2.84 (m, 2H), 2.27 (m, 2H), 1.43 (t, 3H); MS: 383.2 (M+H).

Example 11

(5R,6E&Z)-7-oxo-6-(4H,10H-pyrazolo[5,1-c][1,4]-benzoxazepin-2-ylmethylene)-4-thia-1-azabicyclo [3.2.0]hept-2-ene-2-carboxylic acid, sodium salt Step 1: Preparation of 1-(2-fluorobenzyl)-1H-pyrazole-3,5-dicarboxylate 2-fluorobenzyl bromide (2.0 ml, 16.58 mmol) was added to a mixture of diethyl 3,5-pyrazoledicarboxylate (3.01 g, 14.18 mmol), Cs$_2$CO$_3$ (5.57 g, 17.1 mmol), and acetonitrile (140 ml) under N$_2$. Heated to 60° C. for two hours and then cooled to room temperature. Filtered and concentrated the reaction solution. Added water (~200 mL) to the resulting residue and extracted with EtOAc. Washed organics with water and brine. Dried organics over sodium sulfate and filtered and concentrated. Obtained diethyl 1-(2-fluorobenzyl)-1H-pyrazole-3,5-dicarboxylate (light-yellow oil) in quantitative yield.

Step 2: Preparation of 1-(2-fluorobenzyl)-1H-pyrazole-3,5-methanediol

A 1M solution of DIBAL-H in THF (90 ml, 90 mmol) was added to a solution of diethyl 1-(2-fluorobenzyl)-1H-pyrazole-3,5-dicarboxylate (4.80 g, 14.99 mmol) in CH$_2$Cl$_2$ (90 ml) at 0° C. under N$_2$. After two hours quenched with NH$_4$Cl$_{(aq)}$ and suspension was formed. Filtered and extracted with EtOAc and washed with brine. Dried organics over sodium sulfate and filtered and concentrated. Purified with silica gel column and 5% MeOH in CH$_2$Cl$_2$. Obtained 3.4 g of the diol compound (clear oil) in 96% yield.

Step 3: Preparation of 4H,10H-pyrazolo[5,1-c][1,4] benzoxazepine-2-carbaldehyde

The diol compound (3.83 g, 16.21 mmol) in HMPA (24 ml) was added to a suspension of NaH (60%, 1.34 g, 33.5 mmol) in toluene (330 ml) under N$_2$. Rapidly heated to 95° C. for three hours and cooled to room temperature. Quenched with water and extracted with EtOAc. Washed organics with water and brine. Dried organics over sodium sulfate and filtered and concentrated. Purified with silica gel column and 2% MeOH in CH$_2$Cl$_2$. Obtained 4H,10H-pyrazolo[5,1-c][1,4]benzoxazepin-2-ylmethanol (white solid). Yield: 0.71 g 20%. 4H,10H-pyrazolo[5,1-c][1,4]benzoxazepin-2-ylmethanol (0.71 g, 3.28 mmol), 4-methylmorpholine N-oxide (1/198 g, 10.23 mmol), molecular sieves (powder, 4 angstroms) (3.32 g), and acetonitrile (0.07M) were placed together under N$_2$. Tetrapropylammoniumperruthenate (0.113 g, 0.322 mmol) was added and after three hours the reaction solution was filtered through celite and concentrated. Purified with silica gel column and 1:1 EtOAc/Hexane. Obtained 4H,10H-pyrazolo[5,1-c][1,4]benzoxazepine-2-carbaldehyde (white solid). Yield: 0.31 g 44%.

Step 4: Preparation of Preparation of 6-[acetoxy-(4H,10H-pyrazolo[5,1-c][1,4]benzoxazepine-8-yl)-methyl]-6-bromo-7oxo-4-thia-1-aza-bicyclo[3.2.0] hept-2-ene-2-carboxylic acid 4-nitro-benzyl ester 4H, 10H-pyrazolo[5,1-c][1,4]benzoxazepine-2-carbaldehyde (0.19 g, 0.887 mmol) in acetonitrile (14 ml) was added to MgBr$_2$ (0.49 g, 2.66 mmol) under N$_2$. After 25 minutes 6-Bromo-7-oxo-4-thia-1-aza-bicyclo[3.2.0]hept-2-ene-2-carboxylic acid 4-nitro-benzyl ester (0.342 g, 0.888 mmol.) in THF (14 ml) was added. After 15 minutes the reaction was cooled to −20° C. Ten minutes later added Et$_3$N (3 eq) and placed reaction in the dark. After 6.5 hours added Ac$_2$O (0.42 ml, 4.45 mmol) and DMAP (0.011 g, 0.0900 mmol). Warmed to 0° C. and placed in freezer overnight. Reaction solution was concentrated and resulting residue was taken up in EtOAc. Washed with 5% citric acid$_{(aq)}$ and saturated NaHCO$_{3(aq)}$. Further washed with water and brine. Dried organics over sodium sulfate and filtered and concentrated. Purified with silica gel prep plates and 1:2 EtOAc/Hexane. Obtained the condensation product (yellow gum/solid). Yield: 0.31 g, 54% yield.

Step 5: (5R,6E&Z)-7-oxo-6-(4H,10H-pyrazolo[5,1-c][1,4]benzoxazepin-2-ylmethylene)-4-thia-1-azabicyclo[3.2.0]hept-2-ene-2-carboxylic acid, sodium salt Step 6: A 0.5M phosphate buffer solution (pH 6.5) (18 mL) was added to a solution of the condensation product (5) (0.300 g, 0.468 mmol) in THF (18 mL). The Pd on Carbon (0.102 g) was added and the reaction mixture was hydrogenated at 40 psi for two hours. Filtered through celite and removed THF by rotary evaporation. Extracted with EtOAc. Dried organics over sodium sulfate and filtered and concentrated. NaHCO$_3$ (0.08 g, 0.952 mmol) was dissolved in a minimal amount of water and added to the concentrated organics along with a small amount of EtOAc. Filtered and removed EtOAc by rotary evaporation. Purified with reverse phase column (MCI Gel CHP20P) and varying amounts of acetonitrile (0% to 15%) in water. Removed the acetonitrile and most of the water from the collected fractions by rotary evaporation. Freeze-dried the rest to obtain 41 mg of (5R,6E)-7-oxo-6-(4H,10H-pyrazolo[5,1-c][1,4]benzoxazepin-2-ylmethylene)-4-thia-1-azabicyclo[3.2.0]hept-2-ene-2-carboxylic acid, sodium salt (6) (yellow solid) in 22% yield. HPLC found the purity to be 77% and the E/Z isomer ratio to be 3:2. $^1$H-NMR (δ, DMSO-d$_6$) 5.366 (m, 4H), 5.649 (m, 4H), 6.326 (t, 2H), 6.444 (s, 2H), 6.551 (s, 2H), 6.640 (s, 2H), 6.810 (s, 2H), 6.974 (m, 2H), 7.249 (m, 2H), 7.355 (m, 2H). m/z (M+H) 390.0

Example 12

(5R), (6Z)-6-(5H-Imidazo[2,1-a]isoindol-2-ylmethylene)-7-oxo-4-thia-1-aza-bicyclo[3.2.0]hept-2-ene-2-carboxylic acid sodium salt

Step 1: Preparation of 5H-Imidazo[2,1-a]isoindole-2-carbaldehyde

The solution of 2-bromo-3-isopropoxy-propenal (4.97 g) in dry acetonitrile (3 mL) was added to the mixture of 3-amino-1H-isoindole (3.4 g) in dry acetonitrile (100 mL). The reaction mixture was stirred for 3.25 h at room temperature. Then triethylamine (3.6 mL) was added to the mixture and heated to reflux for 2 h. The mixture was cooled to room temperature, diluted with ethyl acetate, and washed with 20% potassium hydrogen carbonate. After filtration through a pad of Celite, the organic layer was dried (MgSO$_4$) and concentrated under reduced pressure. The residue was applied to silica gel column chromatography, then eluted with ethyl acetate-hexane (3/1~4/1). The crude compound was crystallized from ethyl acetate and n-hexane to give the title compound (1.04 g, 22%). $^1$H NMR (400 MHz, CDCl$_3$) δ 5.01 (s, 2H), 7.28-7.52 (m, 3H), 7.90 (s, 1H), 7.91-7.93 (m, 1H), 9.92 (s, 1H).

Step 2: Preparation of (5R,6RS)-6-[(RS)-Acetoxy-(5H-imidazo[2,1-a]isoindol-2-yl)-methyl]-6-bromo-7-oxo-4-thia-1-aza-bicyclo[3.2.0]hept-2-ene-2-carboxylic acid 4-nitro-benzyl ester 5H-Imidazo[2,1-a]isoindole-2-carbaldehyde (736.8 mg) was added to the dry acetonitrile (50 mL) solution of anhydrous MgBr$_2$ (1.8 g) under a nitrogen atmosphere at room temperature. The dry THF solution (50 mL) of (5R,6S)-6-bromo-7-oxo-4-thia-1-aza-bicyclo[3.2.0]hept-2-ene-2-carboxylic acid 4-nitro-benzyl ester (1.55 g) was added to the reaction mixture, cooled to −20° C., and triethylamine (1.34 mL) was added in one portion. The reaction vessel was covered with foil to exclude light. The mixture was stirred for 2 h at −20° C. and treated with acetic anhydride (0.76 mL) in one portion. The reaction mixture was warmed to 0° C. and stirred for 18 h at 0° C. The mixture was diluted with ethyl acetate and washed with H$_2$O, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then eluted with ethyl acetate-hexane (2/3~1/1). The title compound was obtained as two diastereo mixture (5/1, a pale yellow amorphous solid, 1.8 g, 73%). $^1$H NMR (400 MHz, CDCl$_3$) δ 2.02 (s, 0.84×3H), 2.27 (s, 0.16×3H), 4.89-4.94 (m, 2H), 5.29 (d, 1H, J=13.6 Hz), 5.47 (d, 1H, J=13.6 Hz), 6.18 (s, 0.16×1H), 6.40 (s, 0.84×1H), 6.42 (s, 0.84×1H), 6.94 (d, 0.16×1H, J=0.9 Hz), 7.18 (d, 0.16×1H, J=0.7 Hz), 7.35-7.48 (m, 3H), 7.51 (s, 0.84×1H), 7.60-7.64 (m, 2H), 7.79-7.83 (m, 1H), 8.23-8.27 (m, 2H).

Step 3: (5R), (6Z)-6-(5H-Imidazo[2,1-a]isoindol-2-ylmethylene)-7-oxo-4-thia-1-aza-bicyclo[3.2.0]hept-2-ene-2-carboxylic acid sodium salt (5R,6RS)-6-[(RS)-Acetoxy-(5H-imidazo[2,1-a]isoindol-2-yl)-methyl]-6-bromo-7-oxo-4-thia-1-aza-bicyclo[3.2.0]hept-2-ene-2-carboxylic acid 4-nitro-benzyl ester (1.5 g) was dissolved in THF (21 mL) and acetonitrile (9.8 mL). Freshly activated Zn dust (6 g) and 0.5 M phosphate buffer (pH 6.4, 30.8 mL) were added to the reaction mixture. The reaction vessel was covered with foil to exclude light. The mixture was vigorously stirred for 2 h at room temperature. The mixture was cooled to 9° C., and 1 M NaOH aqueous solution was added to adjust pH to 7.5. The reaction solution was mixed with ethyl acetate and filtered through a pad of Celite. The pad was washed with water and the aqueous layer was separated. The aqueous layer was concentrated to 25 mL under high vacuum at 35° C. The concentrate was applied to Diaion HP-21 (100 mL, Mitsubishi Kasei Co. Ltd.) resin column chromatography. After adsorbing, the column was eluted with water and then with 5-15% acetonitrile-water. The combined fractions was concentrated under high vacuum at 35° C. and lyophilized to give the title compound as a yellow amorphous solid (527 mg, 58%). Mp 170° C. (dec); $^1$H NMR (400 MHz, D$_2$O) δ 4.62 (s, 2H), 6.27 (s, 1H), 6.56 (s, 1H), 6.78 (s, 1H), 7.22-7.31 (m, 4H), 7.52 (d, 1H, J=6.7 Hz).

Example 13

Preparation of (5R,6Z)-6-[(5-methylimidazo[2,1-b][1,3]benzothiazol-2-ylmethylene)-7-oxo-4-thia-1-azabicyclo[3.2.0]hept-2-ene-2-carboxylic acid

Step 1: Ethyl 5-methylimidazo[2,1-b]-benzthiazole-2-carboxylate

Ethyl 5-methylimidazo[2,1-b]-benzthiazole-2-carboxylate was prepared according to the procedure as outlined in Example 1, (Step 1). Starting from 4-methyl-2-amino benzothiazole (8.0 g, 48.7 m.mol) and ethyl bromopyruvate (14.0 g, 71.7 mmol), 6.0 g (45% Yield) of ethyl 5-methylimidazo[2,1-b]-benzthiazole-2-carboxylate was isolated as a brown solid. (M+H) 261.

Step 2: 5-methyl imidazo[2,1-b]-benzthiazole-2-methanol 5-methyl imidazo[2,1-b]-benzthiazole-2-methanol was prepared according to the procedure outlined in Example 1, (Step 2). Starting from ethyl 5-methylimidazo[2,1-b]-benzthiazole-2-carboxylate (5.2 g, 20 mmol) and LiAlH$_4$ solution (22 ml, 0.5 M solution in THF), 3 g (69% yield) of the alcohol derivative was isolated as a brown solid. (M+H) 219.

Step 3: 2-Formyl-5-methylimidazo[2,1-b]-benzthiazole

2-Formyl-5-methylimidazo[2,1-b]-benzthiazole was prepared according to the procedure outlined in Example 1, (Step 3). Starting from 5-methyl imidazo[2,1-b]-benzthiazole-2-methanol (2.0 g 9.1 mmol) in methylene chloride/DMF (300 mL: 50 mL) and active MnO$_2$ (12 g, excess), 700 mg (35% Yield) of the aldehyde derivative was isolated as brown solid. (M+H) 217.

Step 4: 4-Nitrobenzyl-6-[(acetyloxy) (5-methylimidazo[2,1-b][1,3]benzothiazol-2-yl)methyl]-6-bromo-7-oxo-4-thia-1-azabicyclo[3.2.0]hept-2-ene-2-carboxylate 2-Formyl-5-methylimidazo[2,1-b]-benzthiazole (432 mg, 2.0 mmol) and the dry THF solution (40 mL) of (5R,6S)-6-bromo-7-oxo-4-thia-1-aza-bicyclo[3.2.0]hept-2-ene-2-carboxylic acid 4-nitro-benzyl ester (770 mg, 2 mmol) were added successively to the dry acetonitrile (15 mL) solution of anhydrous MgBr$_2$:etherate (1.3 g, 5 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to a silica gel column, then the column was eluted with ethyl acetate:hexane (1:1). Collected fractions were concentrated under reduced pressure and the mixture of diastereo isomers were taken to next step. Pale yellow amorphous solid; Yield: 270 mg, 20%; M+H 644.

Step 5: (5R),(6Z)-6-[(5-methylimidazo[1,2-b][1,3]benzothiazol-2-ylmethylene)]-7-oxo-4-thia-1-azabicyclo[3.2.0]hept-2-ene-2-carboxylic acid 4-Nitrobenzyl-6-[(acetyloxy) (5-methylimidazo[2,1-b][1,3]benzothiazol-2-yl)methyl]-6-bromo-7-oxo-4-thia-1-azabicyclo[3.2.0]hept-2-ene-2-carboxylate (400 mg, 0.62 mmol) was dissolved in THF (17 mL) and acetonitrile (36 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 1 N NaOH was added to adjust pH to 8.5. The filtrate was washed with ethyl acetate and the aqueous layer was separated. The aqueous layer was concentrated under high vacuum at 35° C. to give yellow precipitate. The precipitate was filtered and washed with H$_2$, MeCN, acetone to give the title compound. Yield: 60 mg, 24%; as yellow crystals; mp 192; M+Na 392.

$^1$H NMR (DMSO-d$_6$) δ 2.1 (s, 3H), 6.53 (s, 2H), 7.1 (s, 1H), 7.34-7.36 (m, 2H), 7.85 (m, 1H), 8.58 (s, 1H).

Example 14

Preparation of (5R,6Z)-6-[(7-fluoroimidazo[2,1-b][1,3]benzothiazol-2-ylmethylene)-7-oxo-4-thia-1-azabicyclo[3.2.0]hept-2-ene-2-carboxylic acid

Step 1: Ethyl 7-fluoroimidazo[2,1-b]-benzthiazole-2-carboxylate

Ethyl 7-fluoro-imidazo[2,1-b]-benzthiazole-2-carboxylate was prepared according to the procedure as outlined in Example 1, (Step 1). Starting from 6-fluoro-2-amino benzothiazole (10.0 g, 59.5 m.mol) and ethyl bromopyruvate (17.4 g, 89.2 mmol), 3.0 g (19% Yield) of ethyl 7-fluoroimidazo[2,1-b]-benzthiazole-2-carboxylate was isolated as a brown semi-solid. (M+H) 265.

Step 2: 7-fluoro-imidazo[2,1-b]-benzthiazole-2-methanol

7-Fluoro-imidazo[2,1-b]-benzthiazole-2-methanol was prepared starting from Ethyl 7-fluoro-imidazo[2,1-b]-benzthiazole-2-carboxylate (2.64 g, 0.01 mol) and LiBH$_4$ (50 mg) in THF at refluxing temperature for 2 hrs. at the end, reaction mixture was quenched with ice cold water and acidified with 10 N. HCl. Reaction mixture was stirred for 1 hr and neutralized with K$_2$CO$_3$. The separated residue was extracted with chloroform:methanol (3:1) and dried over anhydrous MgSO$_4$. It was filtered and concentrated. The crude reaction mixture was found to be pure and taken to next step with out any purification. Yield: 1.5 g (68%) Semi solid; M+H 223.

Step 3: 2-Formyl-7-fluoro-imidazo[2,1-b]-benzthiazole

2-Formyl-7-fluoro-imidazo[2,1-b]-benzthiazole was prepared according to the procedure outlined in Example 1, (Step 3). Starting from 7-fluoro-imidazo[2,1-b]-benzthiazole-2-methanol (1.5 g 6.7 mmol) in methylene chloride/DMF (300 mL: 50 mL) and active MnO$_2$ (12 g, excess), 1.1 g (78% Yield) of the aldehyde derivative was isolated as brown solid. (M+H) 221.

Step 4: 4-Nitrobenzyl-6-[(acetyloxy) (7-fluoro-midazo[2,1-b][1,3]benzothiazol-2-yl)methyl]-6-bromo-7-oxo-4-thia-1-azabicyclo[3.2.0]hept-2-ene-2-carboxylate 2-Formyl-7-fluoro-imidazo[2,1-b]-benzthiazole (500 mg, 2.3 mmol) and the dry THF solution (40 mL) of (5R,6S)-6-bromo-7-oxo-4-thia-1-aza-bicyclo[3.2.0]hept-2-ene-2-carboxylic acid 4-nitro-benzyl ester (875 mg, 2.3 mmol) were added successively to the dry acetonitrile (15 mL) solution of anhydrous $MgBr_2$:etherate (1.3 g, 5 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to a silica gel column, then the column was eluted with ethyl acetate:hexane (1:1). Collected fractions were concentrated under reduced pressure and the mixture of diastereoisomers were taken to next step. Pale yellow amorphous solid; Yield: 330 mg, 22%; M+H 649.

Step 5: (5R),(6Z)-6-[(7-fluoro-imidazo[1,2-b][1,3]benzothiazol-2-ylmethylene)]-7-oxo-4-thia-1-azabicyclo[3.2.0]hept-2-ene-2-carboxylic acid 4-Nitrobenzyl-6-[(acetyloxy) (7-fluoro-imidazo[2,1-b][1,3]benzothiazol-2-yl)methyl]-6-bromo-7-oxo-4-thia-1-azabicyclo[3.2.0]hept-2-ene-2-carboxylate (710 mg, 1.07 mmol) was dissolved in THF (17 mL) and acetonitrile (36 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 1 N NaOH was added to adjust pH to 8.5. The filtrate was washed with ethyl acetate and the aqueous layer was separated. The aqueous layer was concentrated under high vacuum at 35° C. to give yellow precipitate. The precipitate was filtered and washed with $H_2O$, MeCN, acetone to give the title compound. Yield: 80 mg, 19%; as yellow crystals; mp 200 (dec); M+Na 396.

$^1$H NMR (DMSO-$d_6$) δ 6.53 (s, 1H), 6.63 (s, 1H), 7.1 (s, 1H), 7.45 (t, 1H), 8.04 (m, 1H), 8.13-8.10 (m, 1H), 8.61 (s, 1H).

Example 15

Preparation of (5R),(6Z)-6-(5,8-dihydro-6H-imidazo[2,1-b]pyrano[4,3-d][1,3]thiazol-2-ylmethylene)-7-oxo-4-thia-1-azabicyclo[3.2.0]hept-2-ene-2-carboxylic acid

Step 1: Preparation of ethyl 5,8-dihydro-6H-imidazo[2.1-b]pyrano[4,3-d][1,3]thiazole-2-carboxylate A mixture of tetrahydro-4H-pyran-4-one (5.0 g, 50 mmol) in $CCl_4$ (100 ml) at 0° C., $SO_2Cl_2$ (7.4 g, 55 mmol) was slowly added. After the addition, reaction mixture was stirred at room temperature for 4 hrs and carefully quenched with ice cold water. Recation mixture was washed well and dried over anhydrous $MgSO_4$. The organic layer was filtered and concentrated. The colourless oil obtained was dissolved in THF/EtOH containing thiourea (4.0 g, 52 mmol) and refluxed for 8 hrs. At the end, reaction mixture was cooled to room temperature and the separated, 6,7-dihydro-4H-pyrano[4,3-d][1,3]thiazol-2-amine hydrochloride white solid was filtered. Yield. 4.5 g (47%); M.Pt. 115° C., (M+H) 157.

To a stirred mixture of, 6,7-dihydro-4H-pyrano[4,3-d][1,3]thiazol-2-amine hydrochloride (4.0 g, 20.8 mmol) was dissolved in anhydrous ethanol (100 ml) and sodium methoxide (1.1 g, 21 mmol). This was stirred at room temperature for 30 minutes and to this ethyl bromopyruvate (10.0 g) was added and stirred at room temperature for 2 hrs. Then it was refluxed for 48 hrs. At the end reaction mixture was cooled to room temperature and concentrated. The residue was extracted with chloroform and washed well with water. The product was purified by silica-gel column chromatography by eluting it with 50% ethyl acetate:hexane. Red semi-solid; Yield: 3.1 g, (59%) M+H 253.

The ester was reduced with $LiBH_4$ and the resultant alcohol was oxidized with active $MnO_2$. The aldehyde obtained was taken to next step.

Step 3: Preparation of 4-nitrobenzyl (5R)-6-[(acetyloxy)(5,8-dihydro-6H-imidazo[2,1-b][1,3]pyrano[4,3-d][1,3]thiazol-2-yl)-6-bromo-7-oxo-4-thia-1-azabicyclo[3.2.0]hept-2-ene-2-carboxylate 2-Formyl-5,8-dihydro-6H-imidazo[2.1-b]pyrano[4,3-d][1,3]thiazole (208 mg, 1.0 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (400 mg, 1.1 mmol) were added successively to the dry acetonitrile (15 mL) solution of anhydrous $MgBr_2$:O(Et)$_2$ (1.2 g, 3.0 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 400 mg, 62%; M.Pt. 78° C.; M+H 636.

Step 4: Preparation of (5R),(6Z)-6-(5,8-dihydro-6H-imidazo[2,1-b]pyrano[4,3-d][1,3]thiazol-2-ylmethylene)-7-oxo-4-thia-1-azabicyclo[3.2.0]hept-2-ene-2-carboxylic acid 4-nitrobenzyl (5R)-6-[(acetyloxy)(5,8-dihydro-6H-imidazo[2,1-b][1,3]pyrano[4,3-d][1,3]thiazol-2-yl)-6-bromo-7-oxo-4-thia-1-azabicyclo[3.2.0]hept-2-ene-2-carboxylate (500 mg, 0.79 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 85 mg, 30%; as yellow crystals; mp 205° C.; (M+H+Na) 383. $^1$H NMR (DMSO-$d_6$) δ 2.8 (m, 2H), 4.0 (m, 2H), 4.6 (s, 2H), 6.4 (s, 1H), 6.5 (s, 1H), 7.0 (s, 1H), 8.1 (s, 1H).

Example 16

Preparation of (5R),(6Z)-6-(imidazo[2,1-b]beb-zothiazol-7-ylmethylene)-7-oxo-4-thia-1-azabicyclo [3.2.0]hept-2-ene-2-carboxylic acid Step 1: Preparation of imidazo[2,1-b][1,3]benzothiazol-7-ylmethanol A solution of ethyl imidazo[2,1-b][1,3]benzothizole-7-carboxylate (1.1 g, 4.5 mmol) in THF (50 ml) was slowly added to a stirred solution of LiBH$_4$ (1 g) in THF (100 ml) at 0° C. The reaction mixture was refluxed for 2 hrs and cooled to room temperature. It was quenched with ice cold water and carefully neutralized with Con. HCl. The solution was stirred at room temperature for 2 hrs and basified with K$_2$CO$_3$ (solid). At the end, reaction mixture was extracted with chloform:methanol (3:1) and dried over anhydrous MgSO$_4$. It was filtered and concentrated. The product was pure enough and taken to next step with out purification. Brown solid. M.t. 75° C.; (M+H) 205. Yield; 800 mg, (87%).

Step 2: Preparation of 7-formyl-imidazo[2,1-b][1,3]benzothiazol

Imidazo[2,1-b][1,3]benzothiazol-7-ylmethanol (700 mg, 3.4 mmol) obtained by the above mentioned process was oxidized with active MnO$_2$ (2 g) in CH$_2$Cl$_2$= under refluxing condition. The reaction mixture was stirred for 6 hrs and cooled to room temperature. It was filtered and through celite and concentrated. The separated brown color solid was triturated with diethyl ether and filtered. It was found to be pure enough and taken to next step with out purification. Yield. 400 mg (58%); (M+H) 203.

Step 3: 4-Nitrobenzyl-6-[(acetyloxy) (imidazo[2,1-b] [1,3]benzothiazol-7-yl)methyl]-6-bromo-7-oxo-4-thia-1-azabicyclo[3.2.0]hept-2-ene-2-carboxylate 7-formyl-imidazo[2,1-b][1,3]benzothiazol (260 mg, 1.3 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (500 mg, 1.14 mmol) were added successively to the dry acetonitrile (15 mL) solution of anhydrous MgBr$_2$:O(Et)$_2$ (390 mg, 1.5 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 750 mg, 91%; M.pt. 82° C.; M+H 630.

Step 5: 5R),(6Z)-6-(imidazo[2,1-b]bebzothiazol-7-ylmethylene)-7-oxo-4-thia-1-azabicyclo[3.2.0]hept-2-ene-2-carboxylic acid 4-Nitrobenzyl-6-[(acetyloxy) (imidazo[2,1-b][1,3]benzothiazol-7-yl)methyl]-6-bromo-7-oxo-4-thia-1-azabicyclo [3.2.0]hept-2-ene-2-carboxylate (900 mg, 1.4 mmol) was dissolved in THF (20 mL) and acetonitrile (20 mL) and 0.5 M phosphate buffer (pH 6.5, 20 mL) and hydrogenated over Pd/C (10%) at 40 psi pressure for 6 hrs. The reaction vessel was covered with foil to exclude light. The reaction mixture was filtered, cooled to 3° C., and 0.1 N NaOH was added to adjust the pH to 8.5. The filtrate was concentrated and the aqueous layer was washed with ethyl acetate. The aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 180 mg, 36%; as yellow crystals; mp 235° C.; (M+H+Na) 378.
$^1$H NMR (DMSO-$d_6$) δ 6.3 (s, 1H), 6.6 (s, 1H), 7.1 (s, 1H), 7.52 (s, 1H), 8.1-8.5 (m, 3H), 8.7 (s, 1H).

Example 17

Preparation of (5R),(6Z)-7-oxo-6-([1,3]thiazolo[3,2-a]benzimidazol-2-ylmethylene)-4-thia-1-azabicyclo [3.2.0]hept-2-ene-2-carboxylic acid Step 1: Preparation of benzo[4,5]imidazo[2,1-b]thazole-2-carbaldehyde To a stirred solution of 2-mercapto benzimidazole (5.0 g, 33.3 mmol) and K$_2$CO$_3$ (4.59 g, 33.3 mmol) in anhydrous DMF (100 mL) bromomalonaldehyde (4.99 g, 33.3) was added and heated for 8 hrs at 80° C. At the end, reaction mixture was concentrated to dryness and ice cold water was added and neutralized with 1N HCl. The product was extracted with chloroform and washed with water and dried over anhydrous MgSO$_4$. It was filtered and concentrated. The residue was taken in DMF/acetic acid mixture (1:1) (100 ml) and heated at 120° C. for 6 hrs. The reaction mixture was concentrated and extracted with chloroform; washed well with water and dried over anhydrous MgSO$_4$. It was filtered and concentrated. The separated solid was triturated with diethyl ether and filtered. Yield: 4.2 g (62%); (M+H) 203.

Step 2: 4-Nitrobenzyl (5R)-6-[(acetyloxy)([1,3]thiazolo[3,2-a]benzimidazol-2-yl)methyl]-6-bromo-7-oxo-4-thia-1-azabicyclo[3.2.0]hept-2-ene-2-carboxylate Benzo[4,5]imidazo[2,1-b]thazole-2-carbaldehyde (404 mg, 2 mmol) and the dry THF solution (20 mL) of (5R,6S)-6-bromo-7-oxo-4-thia-1-aza-bicyclo[3.2.0]hept-2-ene-2- carboxylic acid 4-nitro-benzyl ester (772 mg, 2 mmol) were added successively to the dry acetonitrile (15 mL) solution of anhydrous MgBr$_2$:O(Et)$_2$ (1.65 g, excess) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 800 mg 63%; M.pt. 78° C.; (M+H) 630.

Step 3: (5R),(6Z)-7-oxo-6-([1,3]thiazolo[3,2-a]benz-imidazol-2-ylmethylene0-4-thia-1-azabicyclo[3.2.0]hept-2-ene-2-carboxylic acid Nitrobenzyl (5R)-6-[(acetyloxy) ([1,3]thiazolo[3,2-a]benzimidazol-2-yl)methyl]-6-bromo-7-oxo-4-thia-1-azabicyclo[3.2.0]hept-2-ene-2-carboxylate: (630 mg, 1.0 mmol) was dissolved in THF (20 mL) and acetonitrile (20 mL) and 0.5 M phosphate buffer (pH 6.5, 20 mL) and hydrogenated over Pd/C (10%) at 40 psi pressure for 6 hrs. The reaction vessel was covered with foil to exclude light. The reaction mixture was filtered, cooled to 3° C., and 0.1 N NaOH was added to adjust the pH to 8.5. The filtrate was concentrated and the aqueous layer was washed with ethyl acetate. The aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 190 mg, 50%; as yellow crystals; mp 240° C. (Dec); (M+H+Na) 378.

$^1$H NMR (DMSO-d$_6$) δ 6.3 (s, 1H), 6.4 (s, 1H), 6.6 (d, 2H), 7.29-7.39 (m, 2H), 7.69-7.73 (t, 1H), 8.1-8.19 (m, 1H), 8.84 (s, 1H).

Example 18

Preparation of (5R),(6Z)-6-(7,8-dihydro-6H-cyclopenta[3,4]pyrazolo[5,1-b][1,3]thiazol-2-ylmethylene)-7-oxo-64-thia-1-azabicyclo[3.2.0]hept-2-ene-2-carboxylic acid Step 1: Preparation of 7,9-dihydro-6H-cyclopenta[3,4]pyrazolo[5,1-b][1,3]thiazole-2-carbaldehyde To a stirred solution of 1,4,5,6-tetrahydrocyclopenta[c]pyrazole-3(H)-thione [Prepared by the procedure of T. takeshima, N. Oskada, E. Okabe and F. mineshima, J. Chem. Soc. Perkin. Trans. I, 1277-1279, (1975)] (5.3 g, 37.85 mmol) and K$_2$CO$_3$ (10.4 g, 75 mmol) in anhydrous DMF (100 mL) bromomalonaldehyde (5.7 g, 37.85) was added and heated for 8 hrs at 80° C. At the end, reaction mixture was concentrated to dryness and ice cold water was added and neutralized with 1N HCl. The product was extracted with chloroform and washed with water and dried over anhydrous MgSO$_4$. It was filtered and concentrated. The residue was taken in DMF/acetic acid mixture (1:1) (100 ml) and heated at 120° C. for 6 hrs. The reaction mixture was concentrated and extracted with chloroform; washed well with water and dried over anhydrous MgSO$_4$. It was filtered and concentrated. The product was purified by SiO$_2$ column chromatography by eluting it with 75% ethyl acetate:hexane. Yield: 2.2 g (30%); M.Pt. 112° C.; (M+H) 193.

Step 2: 4-Nitrobenzyl-(5R)-6-[(acetyloxy) (7,8-dihydro-8H-cyclopenta[3,4]pyrazolo[5,1-b][1,3]thiazol-2-yl)methyl]-6-bromo-7-oxo-4-thia-1-azabicyclo[3.2.0]hept-2-ene-2-carboxylate 7,9-dihydro-6H-cyclopenta[3,4]pyrazolo[5,1-b][1,3]thiazole-2-carbaldehyde (576 mg, 3 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (1.16 g, 3 mmol) were added successively to the dry acetonitrile (15 mL) solution of anhydrous MgBr$_2$:O(Et)$_2$ (1.65 g, excess) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 1.5 g, 83%; M.pt. 69° C.; (M+H) 620.

Step 3: (5R),(6Z)-6-(7,8-dihydro-6H-cyclopenta[3,4]pyrazolo[5,1-b][1,3]thiazol-2-ylmethylene)-7-oxo-4-thia-1-azabicyclo[3.2.0]hept-2-ene-2-carboxylic acid 4-Nitrobenzyl-(5R)-6-[(acetyloxy) (7,8-dihydro-8H-cyclopenta[3,4]pyrazolo[5,1-b][1,3]thiazol-2-yl)methyl]-6-bromo-7-oxo-4-thia-1-azabicyclo[3.2.0]hept-2-ene-2-carboxylate (1.2 g, 1.9 mmol) was dissolved in THF (30 mL) and acetonitrile (30 mL) and 0.5 M phosphate buffer (pH 6.5, 30 mL) and hydrogenated over Pd/C (10%) at 40 psi pressure for 6 hrs. The reaction vessel was covered with foil to exclude light. The reaction mixture was filtered, cooled to 3° C., and 0.1 N NaOH was added to adjust the pH to 8.5. The filtrate was concentrated and the aqueous layer was washed with ethyl acetate. The aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 420 mg, 38%; as yellow crystals; mp 190° C. (Dec); (M+H+Na) 368.

$^1$H NMR (DMSO-d$_6$) $^1$H NMR (DMSO-d$_6$) δ 2.38-2.42 (m, 2H), 2.69-2.89 (m, 4H), 6.57 (s, 1H), 6.58 (s, 1H), 7.36 (s, 1H), 8.53 (s, 1H).

Example 19

Preparation of (5R),(6Z)-7-oxo-6-(5,6,7,8-tetrahydroimidazo[2,1-b][1,3]benzothiazol-2-ylmethylene)-4-thia-1-azabicyclo[3.2.0]hept-2-ene-2-carboxylic acid

Step 1: Preparation of ethyl 5,6,7,8-tetrahydroimidazo[2,1-b][1,3]benzothiazole-2-carboxylate A mixture of 2-chlorocyclohexanone (13.2 g, 100 mmol) and thiourea (8.0 g 101 mmol) was refluxed in ethanol:THF (1:2) for 16 hrs. The reaction mixture was cooled to room temperature and the separated white solid was filtered. (12.0 g separated) This was dissolved in anhydrous ethanol (100 ml) and sodium methoxide (3.3 g, 63 mmol). To this ethyl bromopyruvate (15.0 g) was added and stirred at room temperature for 2 hrs. Then it was refluxed for 48 hrs. At the end reaction mixture was cooled to room temperature and concentrated. The residue was extracted with chloroform and washed well with water. The product was purified by silica-gel column chromatography by eluting it with 50% ethyl acetate:hexane. Red semi-solid; Yield: 6.2 g (39%); M+H 251.

The ester was reduced with $LiBH_4$ and the resultant alcohol was oxidized with active $MnO_2$. The aldehyde obtained was taken to next step.

Step 3: Preparation of 4-nitrobenzyl (5R)-6-[(acetyloxy)(5,6,7,8-tetrahydroimidazo[2,1-b][1,3]benzothiazol-2-yl)methyl]-6-bromo-7-oxo-4-thia-1-azabicyclo[3.2.0]hept-2-ene-2-carboxylate 5,6,7,8-tetrahydroimidazo[2,1-b][1,3]benzothiazole-2-carbaldehyde (412 mg, 2.0 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (770 mg, 2 mmol) were added successively to the dry acetonitrile (15 mL) solution of anhydrous $MgBr_2$:O(Et)$_2$ (1.2 g, 3.0 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 980 mg, 77%; M+H 634.

Step 4: Preparation of (5R),(6Z)-7-oxo-6-(5,6,7,8-tetrahydroimidazo[2,1-b][1,3]benzothiazol-2-ylmethylene)-4-thia-1-azabicyclo[3.2.0]hept-2-ene-2-carboxylic acid 4-nitrobenzyl (5R)-6-[(acetyloxy)(5,6,7,8-tetrahydroimidazo[2,1-b][1,3]benzothiazol-2-yl)methyl]-6-bromo-7-oxo-4-thia-1-azabicyclo[3.2.0]hept-2-ene-2-carboxylate (980 mg, 1.55 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 120 mg, 20%; as yellow crystals; mp 250° C. (Dec); (M+H+Na) 382. $^1$H NMR (DMSO-d$_6$) δ 1.9 (m, 2H), 2.5 (m, 2H), 3.2-3.4 (m, 4H), 6.6 (s, 1H), 7.1 (s, 1H), 7.5 (s, 1H), 8.1 (s, 1H).

Example 20

Preparation of (5R),(6Z)-8-[(9-methyl-9H-imidazo[1,2-a]benzimidazol-2-yl)methylene]-7-oxo-4-thia-1-azabicyclo[3.2.0]hept-2-ene-2-carboxylic acid

Step 1: Preparation of 9-methyl-9H-imidazo[1,2-a]benzimidazole-2-carbaldehyde To stirred solution of LiBH$_4$ (1.79 g, 82 mmol) in THF at 0° C., ethyl 9-methyl-9H-imidazo[1,2-a]benzimidazole-2-carboxylate (2.5 g, 10.3 mmol) was added drop wise. The reaction mixture was refluxed for 2 hrs and cooled to room temperature. Ti was carefully quenched with ice cold water and acidified with Con. HCl to pH 4. The reaction mixture was stirred at room temperature for 1 hr and basified with K$_2$CO$_3$. The residue was extracted with chloroform:methanol (3:1) and dried over anhydrous MgSO$_4$. It was filtered and concentrated. Yield. 1.3 g (65%). (M+H) 202. The residue (1.3 g, 6.4 mmol) was oxidised with MnO$_2$ (5.0 g) in CH$_2$Cl$_2$ under refluxing condition. After the completion, reaction mixture was filtered and concentrated. It was purified by SiO$_2$ column chromatography by eluting it with 1:1 ethyl acetate:hexane. Brown solid. Yield. 330 mg (25%); (M+H) 200.

Step 2: Preparation of 4-nitrobenzyl (5R)-6-[(acetyloxy)(9-methyl-9H-imidazo[1,2-a]benzimidazole-2-)methyl]-6-bromo-7-oxo-4-thia-1-azabicyclo[3.2.0]hept-2-ene-2-carboxylate 9-methyl-9H-imidazo[1,2-a]benzimidazole-2-carbaldehyde. (330 mg, 1.65 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (770 mg, 2 mmol) were added successively to the dry acetonitrile (15 mL) solution of anhydrous MgBr$_2$:O(Et)$_2$ (1.2 g, 3.0 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:

hexane (1:1). Collected fractions were concentrated under reduced pressure and the mixture of diastereomers were taken to the next step. Pale yellow amorphous solid; Yield: 330 mg, 31%; (M+H) 628.

Step 3: Preparation of (5R),(6Z)-8-[(9-methyl-9H-imidazo[1,2-a]benzimidazol-2-yl)methylene]-7-oxo-4-thia-1-azabicyclo[3.2.0]hept-2-ene-2-carboxylic acid 4-nitrobenzyl (5R)-6-[(acetyloxy)(9-methyl-9H-imidazo[1,2-a]benzimidazole-2-)methyl]-6-bromo-7-oxo-4-thia-1-azabicyclo[3.2.0]hept-2-ene-2-carboxylate (1 g, 1.6 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 140 mg, 23%; as yellow crystals; mp 220° C. (Dec); (M+H+Na) 375. $^1$H NMR (DMSO-$d_6$) δ 3.4 (s, 3H), 6.54 (s, 1H), 6.56 (s, 1H), 7.01 (s, 1H), 7.21 (t, 1H), 7.3 (t, 1H), 7.56 (d, 1H), 7.85 (d, 1H), 8.1 (s, 1H).

Example 21

Preparation of (5R,6Z)-7-oxo-6-(4H-thieno[2',3':45]thiopyrano[2,3-b]pyridin-2-ylmethylene)-4-thia-1-azabicyclo[3.2.0]hept-2-ene-2-carboxylic acid (Sodium salt)

Step 1: 2,3 dihydro-4H-thiopyrano[2,3-b]pyridin-4-one

A solution of 14 g. (61.6 mmol) 3-(3-Carboxy-2-pyridylthio)propionic Acid [prepared as described in lit.: *J. Heterocyclic Chem.*, 37, 379 (2000)] and 15 g. (185 mmol, 3 eqs) of anhydrous sodium acetate, in 200 mL. of acetic anhydride was refluxed (160° C.) under stirring, $N_2$ atm, dry conditions, for 2 hours. Cooled, diluted with 300 mL of water, basified with 30% ammonium hydroxide solution to pH 8-9, extracted with 3×200 mL chloroform. Combined organics washed with 2×60 mL Sodium bicarbonate (satn.sol), water, dried, evaporated, gave 2.8 g. (27%) of the title compound, reddish solid, m.p. 66-8° C., (M+H)$^+$=166.2.

Step 2: 4-chloro-2H-thiopyrano[2,3b]pyridine-3-carbaldehyde

A solution of 6.6 g. (43 mmol, 1 eq) of phosphorous oxychloride in 30 mL methylene chloride was dropwise added to 3.95 g (43 mmol, 1.25 eqs) of anhydrous dimethylformamide (0° C., stirring, $N_2$ atm, dry conditions) with such a rate to maintain temperature between 0-5° C.; RM was stirred at RT for 2 hours, cooled to 0° C., and a solution of 8.9 g. (54 mmol, 1.25 eqs.) of 2,3 dihydro-4H-thiopyrano[2,3-b]pyridin-4-one in 30 mL of methylene chloride was dropwise added over a 20 min. period. RM stirred at RT for 2 hours, poured over crushed ice:sodium acetate 4:1 mixture, extracted with 4×150 mL methylene chloride, combined organics washed with water, dried, evaporated, gave 7.76 g. (68%) of the title compound, brownish solid, m.p. 56-8° C., (M+H)$^+$=212.6.

Step 3: Ethyl 4H-thieno[2'3':4,5]thiopyrano[2,3b]pyridine-2 carboxylate

To a solution of 7.5 g. (35 mmol, 1 eq.) of 4-chloro-2H-thiopyrano[2,3b]pyridine-3-carbaldehyde in 250 mL of methylene chloride were added (under stirring, $N_2$ atm, dry conditions): 4.7 g. (39 mmol, 1.1 eqs) of ethyl mercaptoacetate, and 7.2 g. (71 mmol, 2 eqs) of triethylamine in 30 mL of methylene chloride. RM was refluxed for 2 hours, quenched with 100 mL of water, organics separated, waters extracted with 4×150 mL of methylene chloride, combined organics dried, evaporated. Residue purified on a silicagel column, using hexane:ethyl acetate 3:1 as a solvent, gave 7.6 g. (78%) of the title compound, yellow crystals, m.p. 113-5° C., (M+H)$^+$=278.3.

Step 4: 4H-thieno[2',3':4,5]thiopyrano[2,3b]pyridin-2-ylmethanol

To a cold solution of 7.5 g. (27 mmol) of Ethyl 4H-thieno[2'3':4,5]thiopyrano[2,3b]pyridine-2 carboxylate in 300 mL of dry tetrahydrofuran (0° C., $N_2$ atm, dry condition) was dropwise added 60 mL (60 mmol, 2.1 eqs) of 1 M cold solution of Lithium Aluminum Hydride in tetrahydrofuran, and RM stirred at RT until the SM disappeared (monitored by TLC/MS). Cooled to 0° C., RM was quenched with aqueous 2N formic acid solution to neutral pH=8, and stirred at RT for 2 hours, filtered, filtrate extracted 4×200 mL methylene chloride, combined organics dried, evaporated gave 6.0 g. (94%) of the desired compound, yellow crystals, m.p. 112-4° C., (M+H)$^+$=236.4.

Step 5: 4H-thieno[2',3':4,5]thiopyrano[2,3b]pyridin-2-carbaldehyde

To a solution of 3.0 g. (12.8 mmol) of 4H-thieno[2',3':4,5]thiopyrano[2,3b]pyridin-2-ylmethanol in 200 mL of chloroform, was added 9.0 g. (80 mmol, 7 eqs) of activated manganese(IV) oxide, and RM refluxed under stirring, $N_2$ atm., for 12 hours. Filtered trough a celite pad, filtrate evaporated, and residue purified on a silicagel column, gave 2.5 g. (86%) of the title compound, yellow crystals, m.p. 93-5° C., (M+H)$^+$=234.4.

Step 6: 4-nitrobenzyl(5R)-6-[(acetyloxy)(4H-thieno[2',3':4,5]thiopyrano[2,3b]pyridin-2-yl)methyl]-6-bromo-7-oxo-4-thia-1-azabicyclo[3.2.0.]hept-ene-2carboxylate In a sealed dry r.b. flask, flushed with $N_2$, were added: 4H-thieno[2',3':4,5]thiopyrano[2,3b]-pyridin-2-carbaldehyde 0.6 g. (2.57 mmol, 1 eq), anhydrous THF (15 mL), anhydrous ACN (15 mL), 0.520 g. (2.8 mmol, 1.1 eqs) anhydrous $MgBr_2$, and RM stirred at RT for 30 min. To the RM was added 2.5 mL (14 mmol, 5.4 eqs) of anhydrous triethylamine, 10 mL of anhydrous THF, RM cooled at (−20° C.), and 0.95 g. (2.5 mmol, 1 eq) of bromopenam was added. RM stirred at (−20° C.) for 6 hours. At the same temperature, 3 mL (3 mmol, 1.15 eqs) of acetic anhydride was added, RM stirred for 15 min and kept at 0° C. for 12 hours, evaporated to dryness, residue extracted with 5×80 mL ethyl acetate.

Organic solvent evaporated, and residue purified an a silicagel column (solvent hexane:ethyl acetate 4:1), gave 0.880 g. (52%) of the title compound, yellowish crystals, m.p. 141-3° C., (M+H)+=661.6.

Step 7: (5R,6Z)-7-oxo-6-(4H-thieno[2',3':4,5]thiopyrano[2,3-b]pyridin-2-ylmethylene)-4-thia-1-azabicyclo[3.2.0]hept-2-ene-2-carboxylic acid (Sodium salt)

A solution of 4-nitrobenzyl(5R)-6-[(acetyloxy)(4H-thieno[2', 3':4,5]thiopyrano[2,3b]pyridin-2-yl)methyl]-6-bromo-7-oxo-4-thia-1-azabicyclo[3.2.0.]hept-ene-2carboxylate 0.8 g. (1.21 mmol, 1 eq) in 40 mL THF and 40 mL phosphate buffer solution (pH=6.36) was hydrogenated at 40 psi for 3 hours in the presence of 0.4 g. Palladium on Carbon 10% catalyst. RM filtrated trough celite pad, filtrate adjusted to pH=8.0, concentrated in vacuo, residue purified on a reverse-phase column (amberlite), using 5% . . . 10% ACN/water mixture as solvent, gave 0.103 g. (21%) of the title compound, reddish crystals, m.p. 362.4° C., (M+H)+=409.5. $^1$H NMR: (DMSO-$d_6$) δ 4.12 (s, 2H), 6.49 (s, 1H), 6.53 (s, 1H); 7.22 (d, 1H); 7.34 (s, 1H); 7.41 9s, 1H), 7.76 (t, 1H); 8.28 (d, 1H).

Example 22

Preparation of (5R,6Z)-6-[(5-methyl-7,8-dihydro-6H-cyclopenta[e][1,2,4]triazolo[1,5-a]pyrimidin-2-yl)methylene]-7-oxo-4-thia-1-azabicyclo[3.2.0]hept-2-ene-2-carboxylic acid, sodium salt Step 1: Preparation of (8-Methyl-6,7-dihydro-5H-cyclopenta[d][1,2,4]triazolo[1,5-a]pyrimidin-2-yl)-methanol To a round bottomed flask was loaded 3.78 grams of 2-acetylcyclopentanone, 3.52 grams of (5-Amino-1H-[1,2,4]triazol-3-yl)-methanol and 50 ml 2-methoxyethanol. The mixture was refluxed for 18 hours. Then it was cooled down to 23° C. and concentrated to 5 ml. Then 50 ml ethyl ether was added and the precipitate was filtered and vacuum dried to yielded 2.0 grams of product. This compound was used directly for the next step. MS: 205.2 (M+H). H-NMR (DMSO): δ 5.55 (t, 1H, OH, J=6.2 Hz), 4.63 (d, 2H, J=6.2 Hz), 3.28 (m, 2H), 3.02 (t, 2H, CH2, J=6.8 Hz), 2.51 (s, 3H, CH3), 2.27 (m, 2H, CH2).

Step 2: Preparation of 8-Methyl-6,7-dihydro-5H-cyclopenta[d][1,2,4]triazolo[1,5-a]pyrimidine-2-carbaldehyde To a round bottomed flask was loaded 0.17 ml of DMSO and 1 ml dichloromethane. The mixture was cooled to −50~−60° C. Then a mixture of 0.1 ml oxalyl chloride and 2 ml dichloromethane was injected in into the flask all at once. The mixture was stirred at the same temperature for another 5 minutes. Then 0.174 grams of (8-Methyl-6,7-dihydro-5H-cyclopenta[d][1,2,4]triazolo[1,5-a]pyrimidin-2-yl)-methanol in 2 ml dichloromethane was added within 2 minutes. The mixture was stirred at −50~−60° C. for fifteen minutes and 0.7 ml triethylamine was next added. After another five minutes the reaction media was warmed up to 23° C. and a mixture of 20 ml water and 200 ml dichloromethane was added. The organic layer was dried over magnesium sulfate. Filter off the drying agent and concentrate the filtrate yielded 0.153 grams of product (89%). MS: 203.1 (M+H). H-NMR (CDCl$_3$): δ 10.24 (s, 1H), 3.49 (m, 2H), 3.15 (m, 2H), 2.67 (s, 3H, CH$_3$), 2.44 (m, 2H, CH$_2$).

Step 3: Preparation of 4-nitrobenzyl (5R)-6-[(acetyloxy)(5-methyl-7,8-dihydro-6H-cyclopenta[e][1,2,4]triazolo[1,5-a]pyrimidin-2-yl)methyl]-6-bromo-7-oxo-4-thia-1-azabicyclo[3.2.0]hept-2-ene-2-carboxylate 8-Methyl-6,7-dihydro-5H-cyclopenta[d][1,2,4]triazolo[1,5-a]pyrimidine-2-carbaldehyde (153 mg, 0.75 mmol) and the dry THF solution (20 mL) of (5R,6S)-6-bromo-7-oxo-4-thia-1-aza-bicyclo[3.2.0]hept-2-ene-2-carboxylic acid 4-nitrobenzyl ester (385 mg, 1 mmol) were added successively to the dry acetonitrile (15 mL) solution of anhydrous MgBr$_2$:O(Et)$_2$ (1.2 g, 3.0 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 200 mg, 42%; (M+H) 631.

Step 4: Preparation of (5R,6Z)-6-[(5-methyl-7,8-dihydro-6H-cyclopenta[e][1,2,4]triazolo[1,5-a]pyrimidin-2-yl)methylene]-7-oxo-4-thia-1-azabicyclo[3.2.0]hept-2-ene-2-carboxylic acid 4-nitrobenzyl (5R)-6-[(acetyloxy)(5-methyl-7,8-dihydro-6H-cyclopenta[e][1,2,4]triazolo[1,5-a]pyrimidin-2-yl)methyl]-6-bromo-7-oxo-4-thia-1-azabicyclo[3.2.0]hept-2-ene-2-carboxylate (200 mg, 0.31 mmol) was dissolved in THF (20 mL) and acetonitrile (20 mL) and phosphate buffer (6.5 pH) (20 ml) and hydrogenated over Pd/C (10%) (200 mg) under 40 psi pressure. At the end, reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 15 mg, 13%; as yellow crystals; mp 250° C. (Dec); (M+H+Na) 378. $^1$H NMR (DMSO-d$_6$) δ 6.80 (s, 1H), 6.76 (s, 1H), 6.25 (s, 1H), 3.24 (m, 2H), 2.96 (m, 2H), 2.49 (s, 3H), 2.25 (m, 2H).

Example 23

Preparation of (5R,6Z)-6-{[7-(ethoxycarbonyl)-6,7,8,9-tetrahydropyrido[3,4-e][1,2,4]triazolo[1,5-a]pyrimidin-2-yl]methylene}-7-oxo-4-thia-1-azabicyclo[3.2.0]hept-2-ene-2-carboxylic acid, sodium salt

Step 1: Preparation of 2-Hydroxymethyl-8,9-dihydro-6H-1,3,4,7,9b-pentaaza-cyclopenta[a]naphthalene-7-carboxylic acid ethyl ester To a round bottomed flask was loaded 8.56 grams of 4-oxo-piperidine-1-carboxylic acid ethyl ester, 10.3 ml of dimethylformamide dimethylacetal, and the mixture was refluxed at 90° C. for two hours. Then it was poured into 75 ml water and extracted with 2×250 ml dichloromethane. The combined organic layers was washed with 50 ml brine and dried over magnesium sulfate. Filter off the drying agent and concentrate gave 28 grams of 3-Dimethylaminomethylene-4-oxo-piperidine-1-carboxylic acid ethyl ester. This material (12.8 grams) was then loaded into a round bottomed flask along with 3.42 grams of (5-Amino-1H-[1,2,4]triazol-3-yl)-methanol and 100 ml 2-methoxyethanol. The mixture was refluxed for 18 hours. Then it was cooled down to 23° C. and concentrated to 5 ml. Then 50 ml ethyl ether was added and the precipitate was filtered and vacuum dried to yielded 1.5 grams of product. MS: 278.1 (M+H). H-NMR (CDCL3): δ 8.60 (s, 1H), 4.98 (s, 2H), 4.78 (s, 2H, CH2), 4.22 (q, 2H, J=4.8 Hz), 3.75 (t, 2H, CH2, J=4 Hz), 3.51 (t, 2H, J=4 Hz), 1.32 (m, 3H, CH3, J=4.8 Hz).

Step 2: Preparation of 2-Formyl-8,9-dihydro-6H-1,3,4,7,9b-pentaaza-yclopenta[a]naphthalene-7-carboxylic acid ethyl ester 2-Hydroxymethyl-8,9-dihydro-6H-1,3,4,7,9b-pentaaza-cyclopenta[a]naphthalene-7-carboxylic acid ethyl ester (831 mg, 3 mmol) was converted to 2-formyl-8,9-dihydro-6H-1,3,4,7,9b-pentaaza-yclopenta[a]naphthalene-7-carboxylic acid ethyl ester (690 mg, 89% Yield) by the procedure outlined in example 22, (step 2).

MS: 276.1 (M+H). H-NMR (CDCl3): δ 10.24 (s, 1H), 8.76 (s, 1H), 4.86 (s, 2H), 4.23 (q, 2H, CH2, J=7.2 Hz), 4.13 (t, 2H, CH2, J=7.2 Hz) 3.39 (t, 2H, CH2, J=5.7 Hz), 1.34 (t, 3H, CH3, J=7.2 Hz).

Step 3: ethyl 2-[(acetyloxy)((5R)-6-bromo-2-{[(4-nitrobenzyl)oxy]carbonyl}-7-oxo-4-thia-1-azabicyclo[3.2.0]hept-2-en-6-yl)methyl]-8,9-dihydropyrido[3,4-e][1,2,4]triazolo[1,5-a]pyrimidine-7(6H)-carboxylate 2-formyl-8,9-dihydro-6H-1,3,4,7,9b-pentaaza-yclopenta[a]naphthalene-7-carboxylic acid ethyl ester (550 mg, 2 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (770 mg, 2 mmol) were added successively to the dry acetonitrile (15 mL) solution of anhydrous $MgBr_2$:$O(Et)_2$ (1.2 g, 3.0 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 220 mg, 15%; (M+H) 703.

Step 4: Preparation of (5R,6Z)-6-{[7-(ethoxycarbonyl)-6,7,8,9-tetrahydropyrido[3,4-e][1,2,4]triazolo[1,5-a]pyrimidin-2-yl]methylene}-7-oxo-4-thia-1-azabicyclo[3.2.0]hept-2-ene-2-carboxylic acid ethyl 2-[(acetyloxy)((5R)-6-bromo-2-{[(4-nitrobenzyl)oxy]carbonyl}-7-oxo-4-thia-1-azabicyclo[3.2.0]hept-2-en-6-yl)methyl]-8,9-dihydropyrido[3,4-e][1,2,4]triazolo[1,5-a]pyrimidine-7(6H)-carboxylate (220 mg, 0.28 mmol) was dissolved in THF (20 mL) and acetonitrile (20 mL) and phosphate buffer (6.5 pH) (20 ml) and hydrogenated over Pd/C (10%) (200 mg) under 40 psi pressure. At the end, reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 15 mg, 2%; Yellow crystals; mp>250° C. (Dec); (M+H+Na) 449. $^1$H NMR (DMSO-$d_6$) δ 8.61 (s, 1H), 7.01 (s, 1H), 6.90 (s, 1H), 6.44 (s, 1H), 4.74 (m, 2H, CH2), 4.13 (q, 2H, J=5.4 Hz), 3.84 (s, m, 2H, CH2), 1.22 (t, 3H, CH3, J=5.7 Hz).

Example 24

Preparation of (5R,6Z)-6-(8',9'-dihydro-6'H-spiro[1,3-dioxolane-2,7'-[1,2,4]triazolo[1,5-a]quinazolin]-2'-ylmethylene)-7-oxo-4-thia-1-azabicyclo[3.2.0]hept-2-ene-2-carboxylic acid, sodium salt

Step 1: Preparation of 2-Hydroxymethyl-8,9-dihydro-6H-[1,2,4]triazolo[1,5-a]quinazolin-7-ethylene ketal To a round bottomed flask was loaded 15.6 g of 1,4-cyclohexadione mono-ethylene ketal, 11.9 g of dimethylformamide dimethylacetal, and the mixture was refluxed at 90° C. for two hours. Then it was poured into 75 ml water and extracted with 2×250 ml dichloromethane. The combined organic layers was washed with 50 ml brine and dried over magnesium sulfate. Filter off the drying agent and concentrate gave 28 grams of 3-Dimethylaminomethylene-4-oxo-cyclohexane. The crude product was then loaded into a round bottomed flask along with 11.9 grams of (5-Amino-1H-[1,2,4]triazol-3-yl)-methanol and 100 ml 2-methoxyethanol. The mixture was refluxed for 18 hours. Then it was cooled down to 23° C. and concentrated to 5 ml. Then 50 ml ethyl ether was added and the precipitate was filtered and vacuum dried to yielded 2.0 grams (8% Yield) of product. MS: 263 (M+H). H-NMR (CDCL3): δ 8.51 (s, 1H), 5.17 (s, 2H, $CH_2$), 4.08 (s, 4H, OCH2CH2O), 3.42 (t, 2H, CH2, J=5.1 Hz), 3.07 (s, 2H, CH2), 2.15 (t, 3H, CH3, J=5.1 Hz).

Step 2: Preparation of 7-ethylene ketal-6,7,8,9-tetrahydro[1,2,4]triazolo[1,5-a]quinazoline-2-carbaldehyde To a round bottomed flask was loaded 5 ml of DMSO and 5 ml dichloromethane. The mixture was cooled to −50∼−60° C. Then a mixture of 1 ml oxallyl chloride and 5 ml dichloromethane was injected in into the flask all at once. The mixture was stirred at the same temperature for another 5 minutes. 2-Hydroxymethyl-8,9-dihydro-6H-[1,2,4]triazolo[1,5-a]quinazolin-7-ethylene ketal (1.31 g, 5 mmol) in 20 ml dichloromethane was added within 2 minutes. The mixture was stirred at −50∼−60° C. for fifteen minutes and 0.7 ml triethylamine was next added. After another five minutes the reaction media was warmed up to 23° C. and a mixture of 20 ml water and 200 ml dichloromethane was added. The organic layer was dried over magnesium sulfate. Filter off the drying agent and concentrate the filtrate yielded 910 mg of product (70%). MS: 261 (M+H). H-NMR (CDCl3): δ 10.26 (s, 1H), 8.66 (s, 1H), 4.08 (s, 4H, OCH2CH2O), 3.49 (t, 2H, J=6.9 Hz), 3.11 (s, 2H), 2.18 (t, 3H, CH3, J=6.9 Hz), 2.44 (m, 2H, CH2).

Step 3: Preparation of 4-nitrobenzyl (5R)-6-[(acetyloxy)(8',9'-dihydro-6'H-spiro[1,3-dioxolane-2,7'-[1,2,4]triazolo[1,5-a]quinazolin]-2'-yl)methyl]-6-bromo-7-oxo-4-thia-1-azabicyclo[3.2.0]hept-2-ene-2-carboxylate 7-Ethyleneketal-6,7,8,9-tetrahydro-[1,2,4]triazolo[1,5-a]quinazoline-2-carbaldehyde (780 mg, 3 mmol) and the dry THF solution (20 mL) of (5R,6S)-6-bromo-7-oxo-4-thia-1-aza-bicyclo[3.2.0]hept-2-ene-carboxylic acid 4-nitro-benzyl ester (1.15 g g, 3 mmol) were added successively to the dry acetonitrile (15 mL) solution of anhydrous MgBr$_2$:O(Et)$_2$ (1.2 g, 3.0 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 300 mg, 15%; (M+H) 688.8.

Step 4: Preparation of Preparation of (5R,6-6-(8',9'-dihydro-6'H-spiro[1,3-dioxolane-2,7'-[1,2,4]triazolo[1,5-a]quinazolin]-2'-ylmethylene)-7-oxo-4-thia-1-azabicyclo[3.2.0]hept-2-ene-2-carboxylic acid 4-nitrobenzyl (5R)-6-[(acetyloxy)(8',9'-dihydro-6'H-spiro[1,3-dioxolane-2,7'-[1,2,4]triazolo[1,5-a]quinazolin]-2'-yl)methyl]-6-bromo-7-oxo-4-thia-1-azabicyclo[3.2.0]hept-2-ene-2-carboxylate (300 mg, 0.43 mmol) was dissolved in THF (20 mL) and acetonitrile (20 mL) and phosphate buffer (6.5 pH) (20 ml) and hydrogenated over Pd/C (10%) (200 mg) under 40 psi pressure. At the end, reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 15 mg, 9%; Yellow crystals; mp>250° C. (Dec); (M+H+Na) 435.9. $^1$H NMR (DMSO-d$_6$) δ 8.50 (s, 1H), 6.97 (s, 1H), 6.85 (s, 1H), 6.38 (s, 1H), 4.05 (s, 4H, OCH2CH2O), 3.28 (m, 2H), 3.07 (s, 2H), 2.13 (t, 3H, CH3, J=4.8 Hz).

Example 25

Preparation of (5R,6Z)-6-[(5-methyl-6,7,8,9-tetrahydro[1,2,4]triazolo[1,5-a]quinazolin-2-yl)methylene]-7-oxo-4-thia-1-azabicyclo[3.2.0]hept-2-ene-2-carboxylic acid, sodium salt

Step 1: Preparation of (5-Methyl-6,7,8,9-tetrahydro-[1,2,4]triazolo[1,5-a]quinazolin-2-yl)-methanol To a round bottomed flask was loaded 4.2 grams of 2-acetylcyclohexanone, 3.52 grams of (5-Amino-1H-[1,2,4]triazol-3-yl)-methanol and 50 ml 2-methoxyethanol. The mixture was refluxed for 18 hours. Then it was cooled down to 23° C. and concentrated to 5 ml. Then 50 ml ethyl ether was added and the precipitate was filtered and vacuum dried to yielded 3.32 grams of product Yield. 49%. This compound was used directly for the next step. MS: 219.2 (M+H). H-NMR (DMSO): δ 5.49 (t, 1H, OH, J=6 Hz), 4.61 (d, 2H, J=6 Hz), 3.24 (m, 2H), 2.93 (m, 2H), 2.69 (s, 3H), 2.52 (s, 2H), 1.84 (m, 4H).

Step 2: Preparation of 5-Methyl-6,7,8,9-tetrahydro-[1,2,4]triazolo[1,5-a]quinazoline-2-carbaldehyde To a round bottomed flask was loaded 1 ml of DMSO and 5 ml dichloromethane. The mixture was cooled to −50∼−60° C. Then a mixture of 1 ml oxallyl chloride and 2 ml dichloromethane was injected in into the flask all at once. The mixture was stirred at the same temperature for another 5 minutes. Then 0.218 grams of (5-Methyl-6,7,8,9-tetrahydro-[1,2,4]triazolo[1,5-a]quinazolin-2-yl)-methanol in 2 ml dichloromethane was added within 2 minutes. The mixture was stirred at −50∼−60° C. for fifteen minutes and 0.7 ml triethylamine was next added. After another five minutes the reaction media was warmed up to 23° C. and a mixture of 20 ml water and 200 ml dichloromethane was added. The organic layer was dried over magnesium sulfate. Filter off the drying agent and concentrate the filtrate yielded 0.216 grams of product (99%). MS: 217.1 (M+H). H-NMR (CDCl3): δ 10.20 (s, 1H), 3.23 (m, 2H), 2.78 (m, 2H) 2.63 (s, 3H, CH3), 2.00 (m, 4H),

Step 3: Preparation of 4-nitrobenzyl (5R)-6-[(acetyloxy)(5-methyl-6,7,8,9-tetrahydro[1,2,4]triazolo[1,5-a]quinazolin-2-yl)methyl]-6-bromo-7-oxo-4-thia-1-azabicyclo[3.2.0]hept-2-ene-2-carboxylate 5-Methyl-6,7,8,9-tetrahydro-[1,2,4]triazolo[1,5-a]quinazoline-2-carbaldehyde (432 mg, 2 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (770 mg, 2 mmol) were added successively to the dry acetonitrile (15 mL) solution of anhydrous $MgBr_2:O(Et)_2$ (1.2 g, 3.0 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereomers were taken to the next step. Pale yellow amorphous solid; Yield: 600 mg, 47%; (M+H) 644.7.

Step 4: Preparation of Preparation of (5R,6Z)-6-[(5-methyl-6,7,8,9-tetrahydro[1,2,4]triazolo[1,5-a]quinazolin-2-yl)methylene]-7-oxo-4-thia-1-azabicyclo[3.2.0]hept-2-ene-2-carboxylic acid 4-nitrobenzyl (5R)-6-[(acetyloxy)(5-methyl-6,7,8,9-tetrahydro[1,2,4]triazolo[1,5-a]quinazolin-2-yl)methyl]-6-bromo-7-oxo-4-thia-1-azabicyclo[3.2.0]hept-2-ene-2-carboxylate (600 mg, 0.93 mmol) was dissolved in THF (20 mL) and acetonitrile (20 mL) and phosphate buffer (6.5 pH) (20 ml) and hydrogenated over Pd/C (10%) (200 mg) under 40 psi pressure. At the end, reaction mixture was filtered, cooled to 3° C., and 0.1 N NaOH was added to adjust the pH to 8.5. The filtrate was washed with ethyl acetate and the aqueous layer was separated. The aqueous layer was concentrated under high vacuum at 35° C. to give a yellow precipitate. The product was purified by HP21 resin reverse phase column chromatography. Initially the column was eluted with deionized water (2 L) and latter with 10% acetonitrile:water. The fractions containing the product were collected and concentrated under reduced pressure at room temperature. The yellow solid was washed with acetone, filtered and dried. Yield: 37 mg, 11%; as yellow crystals; mp 250° C. (Dec); (M+H+ Na) 392. $^1$H NMR (DMSO-$d_6$) δ 6.90 (s, 1H), 6.85 (s, 1H), 6.28 (s, 1H), 2.98 (m, 2H), 2.77 (m, 2H), 2.55 (m, 3H), 1.78 (m, 4H).

Example 26

Preparation of (5R,6Z)-6-[(5-methoxy-7,8-dihydro-6H-cyclopenta[e]imidazo[1,2-a]pyrimidin-2-yl)methylene]-7-oxo-4-thia-1-azabicyclo[3.2.0]hept-2-ene-2-carboxylic acid, sodium salt, Step 1: Preparation of 4-methoxy-6,7-dihydro-5H-cyclopentapyrimidin-2-ylamine (SM: Ross, L. O.; Goodman, L.; Baker, B. R. J. Am. Chem. Soc. 1959, 81, 3108)
5.3 grams of 4-chloro-6,7-dihydro-5H-cyclopentapyrimidin-2-ylamine was dissolved in 200 ml xylene and 30 ml absolute methanol. Then 5.4 gram for sodium methoxide was added and the mixture was refluxed for 3 hours. Then the solvent was removed in vacuo and 100 ml water was added to the residue. Filter and wash the cake with water (50 ml). The solid was further vacuumed to dry for several hours. The desired product weighed 4.8 gram (98% yield). Mp: 133.8-134.9° C.; MS: 166.2.0 (M+H)

Step 2: Preparation of 5-methoxy-7,8-dihydro-6H-3,4,8b-triaza-as-indacene-2-carboxylic acid ethyl ester 4.8 gram (29 mmol) 4-ethoxy-6,7-dihydro-5H-cyclopentapyrimidin-2-ylamine was dissolved in 100 ml dry THF. Bromopyruvate (5.4 ml) was then added dropwise with in five minutes. The mixture was stirred at 23° C. for one hour. It was then filtered and washed with ether to give 8.7 gram of solid. This solid was then dissolved in 50 ml ethanol and refluxed for two hours. The reaction mixture was cooled to room temperature and partitioned between 350 ml chloroform and 200 ml saturated sodium bicarbonate. The organic layer was separated and dried over magnesium sulfate. Filter off the drying agent and concentrate to give 5.3 gram of product (70% Yield). MP: 105-106° C. (M+H) 262.

Step 3: Preparation of 5-methoxy-7,8-dihydro-6H-3,4,8b-triaza-as-indacene-2-carbaldehyde 5.2 grams (19.8 mmol) 5-methoxy-7,8-dihydro-6H-3,4,8b-triaza-as-indacene-2-carboxylic acid ethyl ester was dissolved in 40 ml dichloromethane and then cooled to −78° C. DIBAL (1 M, 30 ml, 1.5 eq.) was then added within five minutes. The reaction media was then quenched with 2 ml ethanol and partitioned between 350 ml dichloromethane and 100 ml 1 N sodium hydroxide. The aqueous layer was washed with another 150 ml chloroform and the combined organic layer was dried over magnesium sulfate and filtered and concentrated to give the corresponding alcohol. The alcohol is then dissolved in 150 ml dichloromethane and 10 grams of manganese dioxide is then added. The mixture was stirred at 23° C. for two hours. The reaction mixture was then filtered through a pad of celite and concentrated to give 1.1 gram (68%) of the desired aldehyde. MP: 235.2~236.3° C.; MS: 218.1 (M+H)

Step 4: Preparation of 6-[acetoxy-(5-methoxy-7,8-dihydro-6H-3,4,8b-triaza-as-indacen-2-yl)-methyl]-6-bromo-7-oxo-4-thia-1-aza-bicyclo[3.2.0]hept-2-ene-2-carboxylic acid 4-nitro-benzyl ester A 30 ml acetonitrile solution of 5-methoxy-7,8-dihydro-6H-3,4,8b-triaza-as-indacene-2-carbaldehyde (660 mg, 3 mmol) was added 1.03 gram of magnesium bromide etherate. The mixture was stirred at 23° C. for half an hour. Then a 30 ml dry THF solution of the 6-Bromo-7-oxo-4-thia-1-azabicyclo[3.2.0]hept-2-ene-2-carboxylic acid 4-nitro-benzyl ester (1.155 gram, 1 eq.) was injected within a minute and the reaction mixture was then cooled to −20° C. Triethylamine (0.7 ml, eq.) was then injected and the reaction mixture was stirred for five hours at −20° C. Then acetic anhydride (0.377 ml, eq.) was injected and the reaction mixture was left at zero degree for 18 hours. The reaction media was then diluted with 400 ml ethyl acetate and washed with 100 ml 5% citric acid, 100 ml saturated sodium bicarbonate, and 100 ml brine. The organic layer was then dried over magnesium sulfate, filtered and concentrated. Flash column chromatography using 20% ethyl acetate in hexane gave 1.8 gram product. (93% Yield); MP: 118.7~119.1° C.; MS: 645.9 (M+H)

Step 5: Preparation of 6-(5-methoxy-7,8-dihydro-6H-3,4,8b-triaza-as-indacen-2-ylmethylene)-7-oxo-4-thia-1-aza-bicyclo[3.2.0]hept-2-ene-2-carboxylic acid 6-[acetoxy-(5-methoxy-7,8-dihydro-6H-3,4,8b-triaza-as-indacen-2-yl)-methyl]-6-bromo-7-oxo-4-thia-1-aza-bicyclo[3.2.0]hept-2-ene-2-carboxylic acid 4-nitro-benzyl ester (966 mg, 1.4 mmol) was suspended in 20 ml THF and 20 ml pH=6.5 aqueous phosphate buffer. The mixture was then subjected to 45 psi hydrogen for two hours. Then it was filtered through a pad of celite and concentrated in vacuo to remove most of the THF. The solution was then cooled to zero degree and basified to pH=8 with 1 N sodium hydroxide. Then it was purified via reverse phase HPLC using 1 liter of water followed by 5%-25% acetonitrile and water. Water was then removed through concentrate in vacuo and 100 mg of product was collected. MP: >250° C.

H-NMR: (300 MHz, $D_2O$) δ 10.12 (s, 1H), 9.29 (s, 1H), 8.81 (s, 1H), 8.78 (s, 1H), 6.19 (s, 3H), 5.36 (m, 2H), 5.05 (m, 2H), 4.43 (m, 2H); MS: 371.2 (M+H).

Example 27

Preparation of (5R,6Z)-6-(5-[2-(benzyloxy)ethoxy]-7,8-dihydro-6H-cyclopenta[e]imidazo[1,2-a]pyrimidin-2-ylmethylene)-7-oxo-4-thia-1-azabicyclo[3.2.0]hept-2-ene-2-carboxylic acid, sodium salt Step 1: Preparation of 4-benzyloxyethoxy-6,7-dihydro-5H-cyclopentapyrimidin-2-ylamine (SM: Ross, L. O.; Goodman, L.; Baker, B. R. J. Am. Chem. Soc. 1959, 81, 3108)

To stirred suspension of NaH (60% 552 mg) in THF 2-benzyloxyethanol (3.38 g, 20 mmol) was slowly added at room temperature. After the addition, 3.28 grams (19.4 mmol) of 4-chloro-6,7-dihydro-5H-cyclopentapyrimidin-2-ylamine was dissolved in 200 ml THF and added to it and the mixture was refluxed for 3 hours. Then the solvent was removed in vacuo and 100 ml water was added to the residue. The product was extracted with chloroform; washed well with water and dried over anhydrous $MgSO_4$. It was filtered and concentrated. Low melting solid; Yield: 4.2 gram (73%); (M+H) 286.1

Step 2: Preparation of 5-benzyloxyethoxy-7,8-dihydro-6H-3,4,8b-triaza-as-indacene-2-carboxylic acid ethyl ester 6.0 gram (21 mmol) of 4-benzyloxyethoxy-6,7-dihydro-5H-cyclopentapyrimidin-2-ylamine was dissolved in 100 ml dry THF. Bromopyruvate (8 ml) was then added dropwise with in five minutes. The mixture was stirred at 23° C. for one hour. It was then filtered and washed with ether to give a solid. This solid was then dissolved in 50 ml ethanol and refluxed for two hours. The reaction mixture was cooled to room temperature and partitioned between 350 ml chloroform and 200 ml saturated sodium bicarbonate. The organic layer was separated and dried over magnesium sulfate. Filter off the drying agent and concentrate to give 5.36 gram of product (67% Yield). (M+H) 382.1

Step 3: Preparation of 5-benzyloxyethoxy-7,8-dihydro-6H-3,4,8b-triaza-as-indacene-2-carbaldehyde 3.81 grams (10 mmol) 5-benzyloxyethoxy-7,8-dihydro-6H-3,4,8b-triaza-as-indacene-2-carboxylic acid ethyl ester was dissolved in 40 ml dichloromethane and then cooled to −78° C. DIBAL (1 M, 30 ml, 1.5 eq.) was then added within five minutes. The reaction media was then quenched with 2 ml ethanol and partitioned between 350 ml dichloromethane and 100 ml 1 N sodium hydroxide. The aqueous layer was washed with another 150 ml chloroform and the combined organic layer was dried over magnesium sulfate and filtered and concentrated to give the corresponding alcohol. The alcohol is then dissolved in 150 ml dichloromethane and 10 grams of manganese dioxide is then added. The mixture was stirred at 23° C. for two hours. The reaction mixture was then filtered through a pad of celite and concentrated to give 2.25 gram (67%) of the desired aldehyde. MS: 338 (M+H)

Step 4: Preparation of 6-[acetoxy-(5-[2-(benzyloxy)emethoxy-7,8-dihydro-6H-3,4,8b-triaza-as-indacen-2-yl)-methyl]-6-bromo-7-oxo-4-thia-1-aza-bicyclo[3.2.0]hept-2-ene-2-carboxylic acid 4-nitro-benzyl ester A 30 ml acetonitrile solution of 5-benzyloxyethoxy-7,8-dihydro-6H-3,4,8b-triaza-as-indacene-2-carbaldehyde (676 mg, 2 mmol) was added 1.03 gram of magnesium bromide etherate. The mixture was stirred at 23° C. for half an hour. Then a 30 ml dry THF solution of the 6-Bromo-7-oxo-4-thia-1-aza-bicyclo[3.2.0]hept-2-ene-2-carboxylic acid 4-nitro-benzyl ester (770 mg, 2 mmol) was injected within a minute and the reaction mixture was then cooled to −20° C. Triethylamine (0.7 ml, eq.) was then injected and the reaction mixture was stirred for five hours at −20° C. Then acetic anhydride (0.377 ml, eq.) was injected and the reaction mixture was left at zero degree for 18 hours. The reaction media was then diluted with 400 ml ethyl acetate and washed with 100 ml 5% citric acid, 100 ml saturated sodium bicarbonate, and 100 ml brine. The organic layer was then dried over magnesium sulfate, filtered and concentrated. Flash column chromatography using 20% ethyl acetate in hexane gave 1.05 gram product. (68% Yield); MS: 765.8 (M+H)

Step 5: Preparation of Preparation of (5R,6Z)-6-({5-[2-(benzyloxy)ethoxy]-7,8-dihydro-6H-cyclopenta[e]imidazo[1,2-a]pyrimidin-2-yl}methylene)-7-oxo-4-thia-azabicyclo[3.2.0]hept-2-ene-2-carboxylic acid 6-[acetoxy-(5-[2-(benzyloxy)emethoxy-7,8-dihydro-6H-3,4,8b-triaza-as-indacen-2-yl)-methyl]-6-bromo-7-oxo-4-thia-1-aza-bicyclo[3.2.0]hept-2-ene-2-carboxylic acid 4-nitro-benzyl ester (966 mg, 1.2 mmol) was suspended in 20 ml THF and 20 ml pH=6.5 aqueous phosphate buffer. The mixture was then subjected to 45 psi hydrogen for two hours. Then it was filtered through a pad of celite and concentrated in vacuo to remove most of the THF. The solution was then cooled to zero degree and basified to pH=8 with 1 N sodium hydroxide. Then it was purified via reverse phase HPLC using 1 liter of water followed by 5%-25% acetonitrile and water. Water was then removed through concentrate in vacuo and 100 mg of product was collected. MP: >250° C.; H-NMR (DMSO): ☐ 7.66 (s, 1H), 7.36 (s, 1H), 7.08 (m, 5H), 6.87 (s, 1H), 6.85 (s, 1H), 4.37 (m, 2H), 4.29 (m, 2H, CH2), 3.65 (m, 2H, CH2), 2.73 (m, 2H, CH2), 2.46 (m, 2H, CH2), 2.02 (m, 2H, CH2).

MS: 491.1 (M+H).

Example 28

Preparation of (5R,6Z)-6-(2,3-dihydro[1,3]thiazolo[3,2-a]benzimidazol-6-ylmethylene)-7-oxo-4-thia-1-azabicyclo[3.2.0]hept-2-ene-2-carboxylic acid, sodium salt Step 1: Preparation of (2,3-Dihydro-benzo[4,5]imidazo[2,1-b]thiazol-7-yl)-methanol To a round bottomed flask was added 2.83 grams of 2-Thioxo-2,3-dihydro-1H-benzoimidazole-5-carboxylic acid methyl ester, 2.55 grams of dibromoethane and 50 ml DMF and 50 ml ethanol. The mixture was refluxed for 10 hours. Then it was concentrated to dry on a rotary evaporator. The solid was next dissolved in 100 ml THF and 20 ml of 1 M LiAlH$_4$ (in THF) was next injected within five minutes. The reaction media was stirred at room temperature for one hour. Ethanol was next added (~10 ml), followed by 50 ml 2N HCl. The aqueous layer was adjusted to basic Ph=14 with 10N sodium hydroxide. The aqueous was extracted with 2×500 ml ethyl acetate. The combined organic layers was dried over magnesium sulfate. Filter off the drying agent and concentrate yielded 2.04 grams (60%) product. MS: 207.0 (M+H). H-NMR (DMSO): □ 7.34 (m, 2H), 7.08 (m, 1H), 5.15 (m, 1H, OH), 4.53 (m, 2H, CH2), 4.34 (m, 2H, CH2), 4.00 (m, 2H, CH2).

Step 2: Preparation of 2,3-Dihydro-benzo[4,5]imidazo[2,1-b]thiazole-7-carbaldehyde To a pre-cooled (−50~−60° C.) mixture of 1.7 ml DMSO and 5 ml dichloromethane was injected a 20 ml dichloromethane solution of 1 ml oxallyl chloride within five minutes. The mixture was stirred for another five minutes at the same temperature. Then 1.9 grams of 2,3-Dihydro-benzo[4,5]imidazo[2,1-b]thiazol-7-yl)-methanol in a mixture of 20 ml dichloromethane and 20 ml THF was injected within 2 minutes. The mixture was kept stirred at −50~−60° C. for 15 minutes. Then 7 ml triethylamine was injected all at once and after another 5 minutes the cooling bath was removed and the reaction was warmed up to room temperature by itself. Water (100 ml) was next added and the reaction media was extracted with 2×200 ml ethyl acetate. The combined organic layers was dried over magnesium sulfate. Filter off the drying agent and concentrate gave 1.2 grams product (64%). MS: 205.0 (M+H). H-NMR (CDCl3): □ 9.98 (m, 1H), 7.67 (m, 2H), 7.17 (m, 1H), 4.33 (m, 2H), 3.99 (m, 2H, CH2).

Step 3: Preparation of 6-[Acetoxy-(2,3-dihydro-benzo[4,5]imidazo[2,1-b]thiazol-6-yl)-methyl]-6-bromo-7-oxo-4-thia-1-aza-bicyclo[3.2.0]hept-2-ene-2-carboxylic acid 4-nitro-benzyl ester A 30 ml acetonitrile solution of 2,3-Dihydro-benzo[4,5]imidazo[2,1-b]thiazole-7-carbaldehyde (610 mg, 2 mmol) was added 1.03 gram of magnesium bromide etherate. The mixture was stirred at 23° C. for half an hour. Then a 30 ml dry THF solution of the 6-Bromo-7-oxo-4-thia-1-aza-bicyclo[3.2.0]hept-2-ene-2-carboxylic acid 4-nitro-benzyl ester (770 mg, 2 mmol) was injected within a minute and the reaction mixture was then cooled to −20° C. Triethylamine (0.7 ml, eq.) was then injected and the reaction mixture was stirred for five hours at −20° C. Then acetic anhydride (0.377 ml, eq.) was injected and the reaction mixture was left at zero degree for 18 hours. The reaction media was then diluted with 400 ml ethyl acetate and washed with 100 ml 5% citric acid, 100 ml saturated sodium bicarbonate, and 100 ml brine. The organic layer was then dried over magnesium sulfate, filtered and concentrated. Flash column chromatography using 20% ethyl acetate in hexane gave 690 mg product. (54% Yield); MS: 630.8 (M+H)

Step 4: Preparation of (5R,6Z)-6-(2,3-dihydro[1,3]thiazolo[3,2-a]benzimidazol-6-ylmethylene)-7-oxo-4-thia-1-azabicyclo[3.2.0]hept-2-ene-2-carboxylic acid 6-[Acetoxy-(2,3-dihydro-benzo[4,5]imidazo[2,1-b]thiazol-6-yl)-methyl]-6-bromo-7-oxo-4-thia-1-aza-bicyclo[3.2.0]hept-2-ene-2-carboxylic acid 4-nitro-benzyl ester (690 mg, 1.1 mmol) was suspended in 20 ml THF and 20 ml pH=6.5 aqueous phosphate buffer. The mixture was then subjected to 45 psi hydrogen for two hours. Then it was filtered through a pad of celite and concentrated in vacuo to remove most of the THF. The solution was then cooled to zero degree and basified to pH=8 with 1 N sodium hydroxide. Then it was purified via reverse phase HPLC using 1 liter of water followed by 5%-25% acetonitrile and water. Water was then removed through concentrate in vacuo and 32 mg of product (Yield 3%) was collected. MP: >250° C.; H-NMR (D$_2$O): □ 7.08 (m, 6H), 7.36 (s, 1H), 4.05 (m, 2H), 3.90 (b, 1H); MS: 358.3 (M+H).

Example 29

Preparation of (5R,6Z)-6-(3,4-dihydro-2H-[1,3]thiazino[3,2-a]benzimidazol-7-ylmethylene)-7-oxo-4-thia-1-azabicyclo[3.2.0]hept-2-ene-2-carboxylic acid, sodium salt Step 1: Preparation of (3,4-Dihydro-2H-1-thia-4a,9-diaza-fluoren-6-yl)-methanol To a round bottomed flask was added 4.06 grams of 2-Thioxo-2,3-dihydro-1H-benzoimidazole-5-carboxylic acid methyl ester, 4.04 grams of 1,3-dibromopropane and 50 ml DMF and 50 ml ethanol. The mixture was refluxed for 10 hours. Then it was concentrated to dry on a rotary evaporator. The solid was next dissolved in 100 ml THF and 20 ml of 1M LiAlH$_4$ (in THF) was next injected within five minutes. The reaction media was stirred at room temperature for one hour. Ethanol was next added (~10 ml), followed by 50 ml 2N HCl. The aqueous layer was adjusted to basic Ph=14 with 10N sodium hydroxide. The aqueous was extracted with 2×500 ml ethyl acetate. The combined organic layers was dried over magnesium sulfate. Filter off the drying agent and concentrate yielded 3 grams (68%) product. NMR (DMSO): δ 7.91 (m, 3H), 4.13 (m, 2H), 3.93 (s, 1H), 3.23 (m, 2H, CH2), 2.48 (m, 2H, CH2). MS: 221.0 (M+H).

Step 2: Preparation of 3,4-Dihydro-2H-1-thia-4a,9-diaza-fluorene-6-carbaldehyde

To a round bottomed flask was loaded 1.1 grams of (3,4-Dihydro-2H-1-thia-4a,9-diaza-fluoren-6-yl)-methanol, 6 grams of manganese dioxide and 250 ml chloroform. The mixture was stirred for one hour at room temperature and then filtered through a pad of celite. This yielded 0.67 grams of product (61%). MS: 219.0 (M+H). H-NMR (CDCl3): δ 10.04 (s, 1H), 7.67 (m, 3H), 4.25 (m, 2H), 3.27 (m, 2H), 2.50 (m, 2H).

Step 3: Preparation of 4-nitrobenzyl (5R)-6-[(acetyloxy)(3,4-dihydro-2H-[1,3]thiazino[3,2-a]benzimidazol-7-yl)methyl]-6-bromo-7-oxo-4-thia-1-azabicyclo[3.2.0]hept-2-ene-2-carboxylate A 30 ml acetonitrile solution of 3,4-Dihydro-2H-1-thia-4a,9-diaza-fluorene-6-carbaldehyde (660 mg, 3 mmol) was added 1.03 gram of magnesium bromide etherate. The mixture was stirred at 23° C. for half an hour. Then a 30 ml dry THF solution of the 6-Bromo-7-oxo-4-thia-1-aza-bicyclo[3.2.0]hept-2-ene-2-carboxylic acid 4-nitro-benzyl ester (1.15 g, 3 mmol) was injected within a minute and the reaction mixture was then cooled to −20° C. Triethylamine (0.7 ml, eq.) was then injected and the reaction mixture was stirred for five hours at −20° C. Then acetic anhydride (0.377 ml, eq.) was injected and the reaction mixture was left at zero degree for 18 hours. The reaction media was then diluted with 400 ml ethyl acetate and washed with 100 ml 5% citric acid, 100 ml saturated sodium bicarbonate, and 100 ml brine. The organic layer was then dried over magnesium sulfate, filtered and concentrated. Flash column chromatography using 20% ethyl acetate in hexane gave 690 mg product. (36% Yield); MS: 644.9 (M+H)

Step 4: Preparation of (5R,6Z)-6-(3,4-dihydro-2H-[1,3]thiazino[3,2-a]benzimidazol-7-ylmethylene)-7-oxo-4-thia-1-azabicyclo[3.2.0]hept-2-ene-2-carboxylic acid 4-nitrobenzyl (5R)-6-[(acetyloxy)(3,4-dihydro-2H-[1,3]thiazino[3,2-a]benzimidazol-7-yl)methyl]-6-bromo-7-oxo-4-thia-1-azabicyclo[3.2.0]hept-2-ene-2-carboxylate (700 mg, 1.1 mmol) was suspended in 20 ml THF and 20 ml pH=6.5 aqueous phosphate buffer. The mixture was then subjected to 45 psi hydrogen for two hours. Then it was filtered through a pad of celite and concentrated in vacuo to remove most of the THF. The solution was then cooled to zero degree and basified to pH=8 with 1 N sodium hydroxide. Then it was purified via reverse phase HPLC using 1 liter of water followed by 5%-25% acetonitrile and water. Water was then removed through concentrate in vacuo and 75 mg of product (Yield 18%) was collected. MP: >250° C., H-NMR ($D_2O$): δ 7.08 (m, 6H), 3.70 (m, 2H), 4.05 (m, 2H), 3.13 (m, 2H), 2.22 (m, 2H); MS: 372.1 (M+H).

Example 30

Preparation of (5R,6Z)-7-oxo-6-([1,3]thiazolo[3,2-a]benzimidazol-6-ylmethylene)-4-thia-1-azabicyclo[3.2.0]hept-2-ene-2-carboxylic acid, sodium salt

Step 1: Preparation of Benzo[4,5]imidazo[2,1-b]thiazole-6-carboxylic acid methyl ester To a round bottomed flask was loaded with 3.3 grams of 2-Thioxo-2,3-dihydro-1H-benzoimidazole-5-carboxylic acid methyl ester, 4.5 ml alpha-bromodiethylacetal, 50 ml DMF. The mixture was refluxed for 10 hours. Then is was poured into 10% sat. sodium bicarbonate (100 ml) and extracted with 2×100 ml ethyl acetate. The combined organic layers were dried over magnesium sulfate. Filter off the drying agent, concentrate to dry, flash column chromatography using 10-30% ethyl acetate/hexane yielded 1.16 grams (32%) crude product. MS: 233.1 (M+H). H-NMR (DMSO): δ 7.78 (m, 5H), 2.04 (s, 3H, CH3).

Step 2: Preparation of Benzo[4,5]imidazo[2,1-b]thiazole-6-carbaldehyde

To a round bottomed flask was loaded 1.16 grams of (3,4-Dihydro-2H-1-thia-4a,9-diaza-fluoren-6-yl)-methanol, 25 grams of manganese dioxide and 250 ml chloroform. The mixture was stirred for one hour at room temperature and then filtered through a pad of celite. This yielded 0.42 grams of product (42%). MS: 203.0 (M+H). H-NMR ($CDCl_3$): δ 10.10 (ss, 1H), 8.24 (ss, 1H), 7.85 (m, 3H), 6.96 (m, 1H).

Step 3: Preparation of 4-nitrobenzyl (5R)-6-[(acetyloxy)([1,3]thiazolo[3,2-a]benzimidazol-6-yl)methyl]-6-bromo-7-oxo-4-thia-1-azabicyclo[3.2.0]hept-2-ene-2-carboxylate A 30 ml acetonitrile solution of benzo[4,5]imidazo[2,1-b]thiazole-6-carbaldehyde (404 mg, 2 mmol) was added 1.03 gram of magnesium bromide etherate. The mixture was stirred at 23° C. for half an hour. Then a 30 ml dry THF solution of the 6-Bromo-7-oxo-4-thia-1-aza-bicyclo[3.2.0]hept-2-ene-2-carboxylic acid 4-nitro-benzyl ester (770 mg, 2 mmol) was injected within a minute and the reaction mixture was then cooled to −20° C. Triethylamine (0.7 ml, eq.) was then injected and the reaction mixture was stirred for five hours at −20° C. Then acetic anhydride (0.377 ml, eq.) was injected and the reaction mixture was left at zero degree for 18 hours. The reaction media was then diluted with 400 ml ethyl acetate and washed with 100 ml 5% citric acid, 100 ml saturated sodium bicarbonate, and 100 ml brine. The organic layer was then dried over magnesium sulfate, filtered and concentrated. Flash column chromatography using 20% ethyl acetate in hexane gave 630 mg product. (50% Yield); MS: 631.9 (M+H)

Step 4: Preparation of (5R,6Z)-7-oxo-6-([1,3]thiazolo[3,2-a]benzimidazol-6-ylmethylene)-4-thia-1-azabicyclo[3.2.0]hept-2-ene-2-carboxylic acid 4-nitrobenzyl (5R)-6-[(acetyloxy)([1,3]thiazolo[3,2-a]benzimidazol-6-yl)methyl]-6-bromo-7-oxo-4-thia-1-azabicyclo[3.2.0]hept-2-ene-2-carboxylate (630 mg, 1 mmol) was suspended in 20 ml THF and 20 ml pH=6.5 aqueous phosphate buffer. The mixture was then subjected to 45 psi hydrogen for two hours. Then it was filtered through a pad of celite and concentrated in vacuo to remove most of the THF. The solution was then cooled to zero degree and basified to pH=8 with 1 N sodium hydroxide. Then it was purified via reverse phase HPLC using 1 liter of water followed by 5%-25% acetonitrile and water. Water was then removed through concentrate in vacuo and 33 mg of product (Yield 8%) was collected. MP: >250° C.; H-NMR ($D_2O$): ε 6.89 (m, 8H), 5.22 (s, 2H), 5.02 (s, 2H), 4.81 (s, 2H). MS: 378.1 (M+H+Na).

Example 31

Preparation of (5R,6Z)-6-(7,8-dihydro-5H-pyrano[4,3-d]pyrazolo[5,1-b][1,3]oxazol-2-ylmethylene)-7-oxo-4-thia-1-azabicyclo[3.2.0]hept-2-ene-2-carboxylic acid, sodium salt

Step 1: Preparation of ethyl-5-[(4-oxotetrahydro-2H-pyran-3-yl)oxy]-1H-pyrazole-3-carboxylate To the stirred suspension of ethyl 5-hydroxy-1H-pyrazole-3-carboxylate (7.0 g, 45 mmol) and 24.9 g g of potassium carbonate in 500 ml of acetonitrile was added 8.0 g of 3-bromo-tetrahydro-pyran-4-one, and refluxed for 16 hours. The reaction mixture was allowed to cool to room temperature, then filtered, the solid was washed with acetonitrile. The filtrate was concentrated to an oil. The residue was dissolved in ethyl acetate and extracted with water. The organic phase was dried over $MgSO_4$ and evaporated to dryness. 9.0 g (78%) of the desired product was obtained as a white solid. M.Pt. 121-123° C.; (M+H) 255.

Step 2: Preparation of ethyl 7,8-dihydro-5H-pyrano[4,3-d]pyrazolo[5,1-b][1,3]oxazole-2-carboxylate A mixture of ethyl-5-[(4-oxotetrahydro-2H-pyran-3-yl)oxy]-1H-pyrazole-3-carboxylate (254 mg, 1 mmol) and methane sulfonic acid (192 mg) in 7 ml of acetic acid and toluene (50 ml) was refluxed for 18 hours using a Dean-Stark trap to remove water. The reaction mixture was allowed to cool to room temperature. The reaction mixture was filtered. The filtrate was concentrated to an oil. The residue was dissolved in ethyl acetate aqueous bicarbonate solution. The organic layer was washed with water and dried over $MgSO_4$. After removal of the ethyl acetate, the residue was purified by silica gel chromatography eluting with ethyl acetate/hexane to give 120 mg (51%) of the desired product as white solid. Mp; 116-118° C.; Electrospray-MS m/z 237.0 $(M+H)^+$

Step 3: Preparation of 7,8-dihydro-5H-pyrano[4,3-d]pyrazolo[5,1-b][1,3]oxazol-2-ylmethanol To the stirred solution of 7,8-dihydro-5H-pyrano[4,3-d]pyrazolo[5,1-b][1,3]oxazole-2-carboxylate (1.5 g, 6.3 mmol) of in 100 ml of THF was added 1.05 g of lithium borohydride and 1.54 g of methanol. The solution was heated at 40 C for 2.5 hour. The reaction was quenched by 1 N HCl, and adjusted to pH 1.3 and stirred at room temperature for 1 hour. The reaction mixture was adjusted pH to 8 with $k_2CO_3$. The reaction mixture was extracted with ethyl acetate. The organic layer was dried over $MgSO_4$, and concentrated to an oil and column chromatographed to give 0.74 g of the desired product (60%). (M+H) 196.

Step 4: Preparation of 7,8-dihydro-5H-pyrano[4,3-d]pyrazolo[5,1-b][1,3]oxazol-2-carbaldehyde To the stirred solution of 7,8-dihydro-5H-pyrano[4,3-d]pyrazolo[5,1-b][1,3]oxazol-2-ylmethanol (1.0 g, 5.1 mmol) in 60 ml of $CHCl_3$ was added 8 g of $MnO_2$. Th suspension was refluxed for 1.5 hour under a nitrogen atmosphere. The reaction mixture was filtered through a pad of Celite. The filtrate was concentrated to give yellow oil. The product was purified by chromatography. 0.79 g of the product was obtained (80%); (M+H) 193

Step 5: 4-Nitrobenzy(5R)-6-[(acetyloxy)(7,8-dihydro-5H-pyrano[4,3]pyrazolo[5,1-b][1,3]oxazol-2-yl)methyl]-6-bromo-7-oxo-4-thia-1-azabicyclo[3.2.0]hept-2-ene-2-carboxylate 7,8-dihydro-5H-pyrano[4,3-d]pyrazolo[5,1-b][1,3]oxazol-2-carbaldehyde (600 mg, 3.1 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (1.54 g, 4.6 mmol) were added successively to the dry acetonitrile (15 mL) solution of anhydrous $MgBr_2:O(Et)_2$ (2.21 g, 8.5 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 1.35 g, 70%; (M+H) 619.

Step 6: Preparation of (5R,6Z)-6-(7,8-dihydro-5H-pyrano[4,3-d]pyrazolo[5,1-b][1,3]oxazol-2-ylmethylene)-7-oxo-4-thia-1-azabicyclo[3.2.0]hept-2-ene-2-carboxylic acid, sodium salt & (5R,6E)-6-(7,8-dihydro-5H-pyrano[4,3-d]pyrazolo[5,1-b][1,3]oxazol-2-ylmethylene)-7-oxo-4-thia-1-azabicyclo[3.2.0]hept-2-ene-2-carboxylic acid, sodium salt 4-Nitrobenzy(5R)-6-[(acetyloxy)(7,8-dihydro-5H-pyrano[4,3]pyrazolo[5,1-b][1,3]oxazol-2-yl)methyl]-6-bromo-7-oxo-4-thia-1-azabicyclo[3.2.0]hept-2-ene-2-carboxylate (1.2 g, 1.9 mmol) was dissolved in THF (20 mL), acetonitrile (10 mL) and 0.5 M phosphate buffer (pH 6.5, 28 mL) and hydrogenated over 10% Pd/C at 40 psi pressure. After 4 hrs the reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% acetonitrile: Water. The fractions containing the product were collected and concentrated at reduced pressure at room temperature. The yellow solid was washed with acetone and filtered. In this reaction both E and Z isomers were formed and they were separated by prep. HPLC. (5R,6Z)-6-(7,8-dihydro-5H-pyrano[4,3-d]pyrazolo[5,1-b][1,3]oxazol-2-ylmethylene)-7-oxo-4-thia-1-azabicyclo[3.2.0]hept-2-ene-2-carboxylic acid, sodium salt: Yield 87 mg, (25%); Yellow solid; (M+H+Na) 368.2.

H-NMR ($D_2O$): 7.04 (1H, s), 7.01 (1H, s), 6.45 (1H, s), 6.09 (1H, s), 4.76 (2H, m), 4.12 (2H, m), 2.96 (2H, m). (5R,6E)-6-(7,8-dihydro-5H-pyrano[4,3-d]pyrazolo[5,1-b][1,3]oxazol-2-ylmethylene)7-oxo-4-thia-1-azabicyclo[3.2.0]hept-2-ene-2-carboxylic acid, sodium salt: Yield 75 mg, (21%); Yellow solid; (M+H+Na) 368.2.

H-NMR ($D_2O$): 7.08 (1H, s), 6.81 (1H, s), 6.71 (1H, s), 6.40 (1H, s), 4.68 (2H, m), 4.03 (2H, m), 2.87 (2H, m).

Example 32

Preparation of (5R,6Z)-7-oxo-6-(5,6,7,8-tetrahydro-pyrazolo[5,1-b][1,3]benzoxazol-2-ylmethylene)-4-thia-1-1-azabicyclo[3.2.0]hept-2-ene-2-carboxylic acid, sodium salt

Step 1: Preparation of ethyl-5-[(2-oxocyclohexyl)oxy]-1H-pyrazole-3-carboxylate To the stirred suspension of ethyl 5-hydroxy-1H-pyrazole-3-carboxylate (6.25 g, 40 mmol) and 22.1 g of potassium carbonate in 500 ml of acetonitrile was added 6.35 g of 2-chlorocyclohexanone, and refluxed for 16 hours. The reaction mixture was allowed to cool to room temperature, then filtered, the solid was washed with acetonitrile. The filtrate was concentrated to an oil. The residue was dissolved in ethyl acetate and extracted with water. The organic phase was dried over $MgSO_4$ and evaporated to dryness. The product was purified by silics-gel column chromatography by eluting it with 1:1 ethyl acetaet;hexane. 4.92 g (49%) of the desired product was obtained as a white solid. M.Pt. 122-124° C.; (M+H) 253.

Step 2: Preparation of ethyl 5,6,7,8-tetrahydropyrazolo[5,1-b][1,3]benzoxazole-2-carboxylate A mixture of ethyl-5-[(2-oxocyclohexyl)oxy]-1H-pyrazole-3-carboxylate (127.6 mg, 0.5 mmol) and methane sulfonic acid (95 mg) in 5 ml of acetic acid and toluene (50 ml) was refluxed for 18 hours using a Dean-Stark trap to remove water. The reaction mixture was allowed to cool to room temperature. The reaction mixture was filtered. The filtrate was concentrated to an oil. The residue was dissolved in ethyl acetate and aqueous bicarbonate solution. The organic layer was washed with water and dried over $MgSO_4$. After removal of the ethyl acetate, the residue was purified by silica gel chromatography eluting with 1:1 ethyl acetate/hexane to give 69.7 mg (59%) of the desired product as white solid. Mp; 55-57° C.; Electrospray-MS m/z 235.0 $(M+H)^+$

Step 3: Preparation of 5,6,7,8-tetraihydropyrazolo[5,1-b][1,3]benzoxazol-2-ylmethanol To the stirred solution of ethyl 5,6,7,8-tetrahydropyrazolo[5,1-b][1,3]benzoxazole-2-carboxylate (3.84 g, 16.4 mmol) of in 100 ml of THF was added 3.05 g of lithium borohydride and 3 ml of methanol. The solution was heated at 40 C for 2.5 hour. The reaction was quenched by 1N HCl, and adjusted to pH 1.3 and stirred at room temperature for 1 hour. The reaction mixture was adjusted pH to 8 with $k_2CO_3$. The reaction mixture was extracted with ethyl acetate. The organic layer was dried over $MgSO_4$, and concentrated to an oil and column chromatographed to give 2.62 g of the desired product (83%). Mpt. 82-84° C.; (M+H) 193.

Step 4: Preparation of 5,6,7,8-tetrahydropyrazolo[5,1-b][1,3]benzoxazole-2-carbaldehyde To the stirred solution of 5,6,7,8-tetraihydropyrazolo[5,1-b][1,3]benzoxazol-2-ylmethanol (2.30 g, 11.97 mmol) in 60 ml of $CHCl_3$ was added 10 g of $MnO_2$. Th suspension was refluxed for 1.5 hour under a nitrogen atmosphere. The reaction mixture was filtered through a pad of Celite. The filtrate was concentrated to give yellow solid. The product was purified by chromatography. 1.95 g of the product was obtained (85.5%); (M+H) 191

Step 5: 4-Nitrobenzy (5R)-6-[(acetyloxy)(5,67,8-tetrahydropyrazolo[5,1-b][1,3]benzoxazol-2-yl)methyl-6-bromo-7-oxo-4-thia-1-azabicyclo[3.2.0]hept-2-ene-2-carboxylate 5,6,7,8-tetrahydropyrazolo[5,1-b][1,3]benzoxazole-2-carbaldehyde (589 mg, 3.1 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (1.54 g, 4.6 mmol) were added successively to the dry acetonitrile (15 mL) solution of anhydrous $MgBr_2$:$O(Et)_2$ (2.21 g, 8.5 mmol) under an argon atmosphere at room temperature, After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 792 mg, 42%; M.pt. 160-162° C.; (M+H) 618.

Step 6: Preparation of (5R,6Z)-7-oxo-6-(5,6,7,8-tetrahydropyrazolo[5,1-b][1,3]benzoxazol-2-ylmethylene)-4-thia-1-1-azabicyclo[3.2.0]hept-2-ene-2-carboxylic acid, sodium salt 4-Nitrobenzy (5R)-6-[(acetyloxy)(5,67,8-tetrahydropyrazolo[5,1-b][1,3]benzoxazol-2-yl)methyl-6-bromo-7-oxo-4-thia-1-azabicyclo[3.2.0]hept-2-ene-2-carboxylate (318 mg, 0.5 mmol) was dissolved in THF (20 mL), acetonitrile (10 mL) and 0.5 M phosphate buffer (pH 6.5, 28 mL) and hydrogenated over 10% Pd/C (100 mg) at 40 psi pressure. After 4 hrs the reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% acetonitrile: Water. The fractions containing the product were collected and concentrated at reduced pressure at room temperature. The yellow solid was washed with acetone and filtered. Yield 150 mg, (76%); Yellow solid; (M+H+Na) 365.2.

H-NMR ($D_2O$): δ 6.92 (1H, s), 6.91 (1H, s), 6.32 (1H, s), 5.85 (1H, s), 2.59 (4H, m), 1.80 (4H, m).

Example 33

Preparation of (5R,6Z)-6-{[6-(ethoxycarbonyl)-5,6,7,8-tetrahydropyrazolo[5',1':2,3][1,3]oxazolo[5,4-c]pyridin-2-yl]methylene}-7-oxo-4-thia-1-1-azabicyclo[3.2.0]hept-2-ene-2-carboxylic acid, sodium salt

Step 1: Preparation of ethyl 3-{[3-ethoxycarbonyl)-1H-pyrazol-5-yl]oxy}-4-oxopiperidine-1-carboxylate To the stirred suspension of ethyl 5-hydroxy-1H-pyrazole-3-carboxylate (19.5 g, 127 mmol) and 50.0 g of potassium carbonate in 500 ml of acetonitrile was added 3-bromo-4-oxo-piperidine-1-carboxylic acid ethyl ester (37.45 g, 149 mmol), and refluxed for 16 hours. The reaction mixture was allowed to cool to room temperature, then filtered, the solid was washed with acetonitrile. The filtrate was concentrated to an oil. The residue was dissolved in ethyl acetate and extracted with water. The organic phase was dried over $MgSO_4$ and evaporated to dryness. The product was purified by silics-gel column chromatography by eluting it with 1:1 ethyl acetaet;hexane. 8.5 g (19%) of the desired product was obtained as an yellow oil. (M+H) 326.

Step 2: Preparation of diethyl 7,8-tetrahydropyrazolo[5', 1':2,3][1,3]oxazolo[5,4-c]pyridine-2,6(5H)-dicarboxylate A mixture of ethyl 3-{[3-ethoxycarbonyl)-1H-pyrazol-5-yl]oxy}-4-oxopiperidine-1-carboxylate (325 mg, 1 mmol) and methane sulfonic acid (95 mg) in 5 ml of acetic acid and toluene (50 ml) was refluxed for 18 hours using a Dean-Stark trap to remove water. The reaction mixture was allowed to cool to room temperature. The reaction mixture was filtered.

The filtrate was concentrated to an oil. The residue was dissolved in ethyl acetate and aqueous bicarbonate solution. The organic layer was washed with water and dried over $MgSO_4$. After removal of the ethyl acetate, the residue was purified by silica gel chromatography eluting with 1:1 ethyl acetate/hexane to give 175 mg (57%) of the desired product as an yellow oil Electrospray-MS m/z 308.0 $(M+H)^+$ Step 3: Preparation of ethyl 2-(hydroxymethyl)-7,8-dihydropyrazolo[5',1':2,3][1,3][1,3]oxazolo[5,4-c]pyridine-6(5H)-carboxylate To the stirred solution of diethyl 7,8-tetrahydropyrazolo[5',1':2,3][1,3]oxazolo[5,4-c]pyridine-2,6(5H)-dicarboxylate (307 mg, 1 mmol) of in 40 ml of THF was added 305 mg of lithium borohydride and 1 ml of methanol. The solution was heated at 40 C for 2.5 hour. The reaction was quenched by 1 N HCl, and adjusted to pH 1.3 and stirred at room temperature for 1 hour. The reaction mixture was adjusted pH to 8 with $k_2CO_3$. The reaction mixture was extracted with ethyl acetate. The organic layer was dried over $MgSO_4$, and concentrated to an oil and column chromatographed to give 172 mg of the desired product (65%); (M+H) 266.

Step 4: Preparation of ethyl 2-formyl-7,8-dihydropyrazolo[5',1':2,3][1,3]oxazolo[5,4-c]pyridine-6(5H)-carboxylate To the stirred solution of ethyl 2-(hydroxymethyl)-7,8-dihydropyrazolo[5',1':2,3][1,3]oxazolo[5,4-c]pyridine-6 (5H)-carboxylate (1.76 g, 6.6 mmol) in 60 ml of $CHCl_3$ was added 10 g of $MnO_2$. Th suspension was refluxed for 1.5 hour under a nitrogen atmosphere. The reaction mixture was filtered through a pad of Celite. The filtrate was concentrated to give yellow solid. The product was purified by chromatography. 1.43 g of the product was obtained (82%); M.pt: 97-99° C. (M+H) 264.

Step 5: Preparation of ethyl 2-[(acetyloxy)(5R)-6-bromo-2-Z{[(4-nitrobenzyl)oxy]carbonyl}-7-oxo-4-thia-1-azabicyclo[3.2.0]hept-2-en-6-yl)methyl]-7,8-dihydropyrazolo[5',1':2,3][1,3]oxazolo[5,4-c]pyridine-6(5H)-carboxylate Ethyl 2-formyl-7,8-dihydropyrazolo[5',1':2,3][1,3]oxazolo[5,4-c]pyridine-6(5H)-carboxylate (790 mg, 3.0 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (1.54 g, 4.6 mmol) were added successively to the dry acetonitrile (15 mL) solution of anhydrous $MgBr_2$:$O(Et)_2$ (2.21 g, 8.5 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 1.67 g, 81%; (M+H) 690.

Step 6: Preparation of (5R,6Z)-6-{[6-(ethoxycarbonyl)-5,6,7,8-tetrahydropyrazolo[5',1':2,3][1,3]oxazolo[5,4-c]pyridin-2-yl]methylene}-7-oxo-4-thia-1-azabicyclo[3.2.0]hept-2-ene-2-carboxylic acid, sodium salt Ethyl 2-[(acetyloxy)(5R)-6-bromo-2-Z{[(4-nitrobenzyl)oxy]carbonyl}-7-oxo-4-thia-1-azabicyclo[3.2.0]hept-2-en-6-yl)methyl]-7,8-dihydropyrazolo[5', 1':2,3][1,3]oxazolo[5,4-c]pyridine-6(5H)-carboxylate (828 mg, 0.5 mmol) was dissolved in THF (20 mL), acetonitrile (10 mL) and 0.5 M phosphate buffer (pH 6.5, 28 mL) and hydrogenated over 10% Pd/C (200 mg) at 40 psi pressure. After 4 hrs the reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% acetonitrile: Water. The fractions containing the product were collected and concentrated at reduced pressure at room temperature. The yellow solid was washed with acetone and filtered. Yield 375 mg, (71%); Yellow solid; (M+H+Na) 438.4.

H-NMR ($D_2O$): δ 6.96 (1H, s), 6.94 (1H, s), 6.41 (1H, s), 6.00 (1H, s), 4.53 (2H, m), 4.13 (2H, q), 3.78 (2H, m), 2.78 (2H, m), 1.21 (3H, t).

What is claimed is:
1. A compound of formula I

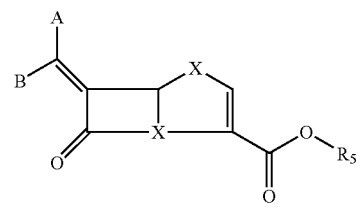

wherein:
one of A and B denotes hydrogen and the other an optionally substituted fused tricyclic heteroaryl group;
X is O;
$R_5$ is H, C1-C6 alkyl, C5-C6 cycloalkyl, or $CHR_3OCOC1$-C6alkyl; and
$R_3$ is hydrogen, C1-C6 alkyl, C5-C6 cycloalkyl, optionally substituted aryl, or optionally substituted heteroaryl;
or a pharmaceutically acceptable salt or in vivo hydrolysable ester thereof.

2. The compound according to claim 1 wherein the tricyclic heteroarylgroup has the formula

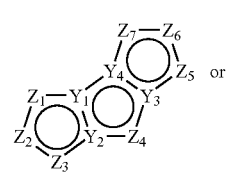

or

-continued

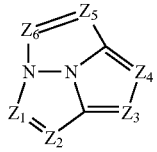

1-B wherein formula 1-A, $Z_1$, $Z_2$, $Z_3$, $Z_4$, $Z_5$, $Z_6$ and $Z_7$ are independently $CR_2$, N, O, S or N—$R_1$ and in formula 1-B, $Z_1$, $Z_2$, $Z_3$, $Z_4$, $Z_5$, $Z_6$ and $Z_7$ are independently $CR_2$ or N, except one of $Z_1$-$Z_7$ is a carbon atom to which the remainder of the molecule is attached;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system optionally having, in addition to said N, one or two heteroatoms selected from N—$R_1$, O, and $S(O)_n$, wherein n=0-2; and $Y_1$, $Y_2$, $Y_3$ and $Y_4$ may independently be C or N.

3. The compound according to claim 1 wherein the tricyclic heteroaryl group is

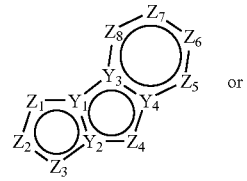

2-A

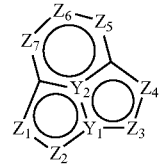

2-B wherein $Z_1$, $Z_2$, $Z_3$, and $Z_4$ are independently $CR_2$, N, O, S or N—$R_1$; $Z_5$, $Z_6$, $Z_7$, and are independently $CR_2$ or N; except one of the $Z_1$-$Z_8$ is a carbon atom to which the remainder of the molecule is attached;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached to form a 3-7 membered saturated ring system having one or two heteroatoms selected from N—$R_1$, O, and $S(O)_n$, wherein n=0-2; and $Y_1$ and $Y_2$ are independently C or N; $Y_3$ and $Y_4$ are C; provided that in formula 2-B, is C.

4. The compound according to claim 1 wherein the tricyclic heteroaryl group is

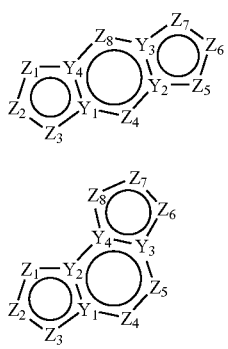

3-A

3-B wherein in formula 3-A, $Z_1$, $Z_2$, $Z_3$, $Z_5$, $Z_6$ and $Z_7$ are independently CR$_2$, N, O, S or N—R$_1$; and in formula 3-A, $Z_4$ and $Z_8$ are independently CR$_2$ or N; and in formula 3-B, $Z_1$, $Z_2$, $Z_3$, $Z_6$, $Z_7$ and $Z_8$ are independently CR$_2$, N, O, S or N—R$_1$ and $Z_4$ and $Z_5$ are independently CR$_2$ or N; except one of $Z_1$-$Z_8$ is a carbon atom to which the remainder of the molecule is attached;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C═Oheteroaryl, optionally substituted —C═Oaryl, optionally substituted —C═Oalkyl, optionally substituted —C═Ocycloalkyl, optionally substituted —C═O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and $Y_1, Y_2, Y_3$ and $Y_4$ are C.

5. The compound according to claim 1 wherein the tricyclic heteroaryl group is

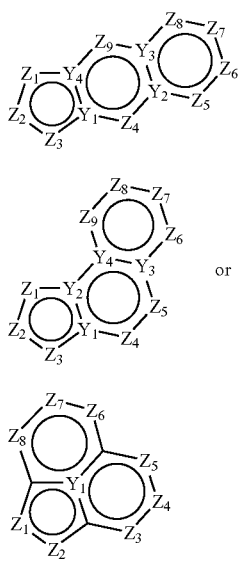

4-A

4-B or

4-C wherein $Z_1$, $Z_2$ and $Z_3$ are independently $CR_2$, N, O, S or N—$R_1$; and $Z_4$, $Z_5$, $Z_6$, $Z_7$, $Z_8$ and $Z_9$ are independently $CR_2$ or N; except one of the $Z_1$-$Z_9$ is a carbon atom to which the remainder of the molecule is attached; provided that in formula 4-C, $Z_3$ cannot be O, S or N—$R_1$;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, $S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkylaryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and $Y_1, Y_2, Y_3$ and $Y_4$ are C.

6. The compound according to claim 1 wherein the tricyclic heteroaryl group is

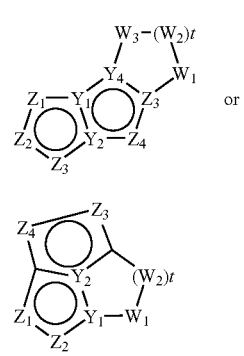

5-A or

5-B wherein $Z_1$, $Z_2$, $Z_3$ and $Z_4$ are independently $CR_2$, N, O, S or N—$R_1$ except one of $Z_1$-$Z_4$ is a carbon atom to which the remainder of the molecule is attached;

$Y_1, Y_2, Y_3$ and $Y_4$ are independently C or N; provided that $Y_1$ and $Y_2$ are C in formula 5-B;

$W_1$, $W_2$ and $W_3$ are independently $CR_4R_4$, $S(O)r$ (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryioxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and t=1 to 3.

7. The compound according to claim 1 wherein the tricyclic heteroaryl group is

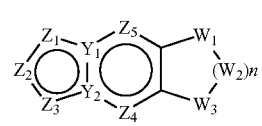

6-A

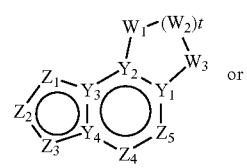 or

6-B

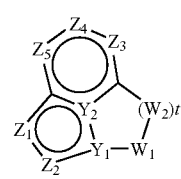

6-C wherein $Z_1$, $Z_2$; and $Z_3$ are independently $CR_2$, N, O, S or N—$R_1$; $Z_4$ and $Z_5$ are $CR_2$ or N; except one of $Z_1$-$Z_5$ is a carbon atom to which the remainder of the molecule is attached; provided that in formula 6-C, $Z_3$ cannot be O, S or N—$R_1$;

$Y_1$ is selected from C and N; provided that in formula 6-A and 6-B, $Y_1$ is C;

$Y_2$, $Y_3$ and $Y_4$ are C;

$W_1$, $W_2$ and $W_3$ are independently $CR_4R_4$, $S(O)r$ (r=0-2), O, or N—$R_1$ with the proviso that no S—S, S—O or O—O bond formation can occur to form a saturated ring; $R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

R$_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

R$_4$ is H, optionally substituted C1-C6 alkyl, OH (provided both R$_4$ are not OH), C1-C6 alkoxy, —S—C1-C6 alkyl, COOR$_6$, —NR$_6$R$_7$, —CONR$_6$R$_7$; or R$_4$R$_4$ may together be =O or R$_4$R$_4$ together with the carbon to which they are attached may form a spiro system of five to eight members with or without the presence of heteroatoms selected N, O, S(O)n (where n=0 to 2), N—R$_1$;

R$_6$ and R$_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or R$_6$ and R$_7$ together with the N to which they are attached form a 3-7 membered saturated ring system having one or two heteroatoms selected from N—R$_1$, O, and S(O)$_n$, wherein n=0-2; and t=1 to 3.

8. The compound according to claim 1 wherein the tricyclic heteroaryl group is

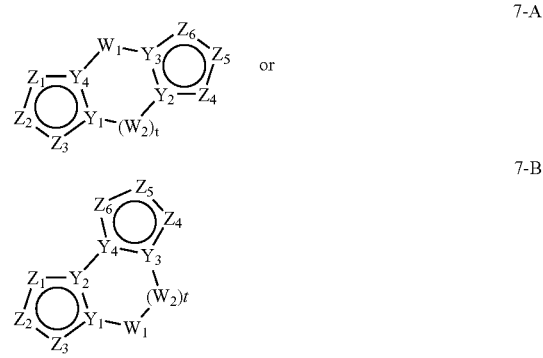

$Z_1$, $Z_2$, $Z_3$, $Z_4$, $Z_5$ and $Z_6$ are independently CR$_2$, N, O, S, and N—R$_1$; except one of $Z_1$-$Z_6$ is a carbon atom to which the remainder of the molecule is attached;

$Y_1$, $Y_2$, $Y_3$ and $Y_4$ are independently C or N;

$W_1$ and $W_2$ are independently CR$_4$R$_4$, S(O)r (r=0-2), O, N—R$_1$ with the proviso that no S—S, S—O or O—O bond formation can occur to form a saturated ring; R$_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

R$_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

R$_4$ is H, optionally substituted C1-C6 alkyl, OH (provided both R$_4$ are not OH), C1-C6 alkoxy, —S—C1-C6 alkyl, COOR$_6$, —NR$_6$R$_7$, —CONR$_6$R$_7$; or R$_4$R$_4$ may together be =O or R$_4$R$_4$ together with the carbon to which they are attached may form a spiro system of five to eight members with or without the presence of heteroatoms selected N, O, S(O)n (where n=0 to 2), N—R$_1$;

R$_6$ and R$_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or R$_6$ and R$_7$ together with the N to which they are attached form a 3-7 membered saturated ring system having one or two heteroatoms selected from N—R$_1$, O, and S(O)$_n$, wherein n=0-2; and t=1 to 3.

9. The compound according to claim 1 wherein the tricyclic heteroaryl group is

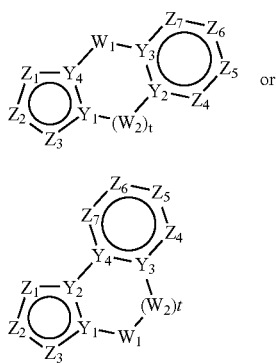

8-A

8-B wherein Z$_1$, Z$_2$, and Z$_3$ are independently CR$_2$, N, O, S or N—R$_1$; Z$_4$, Z$_5$, Z$_6$ and Z7 are independently CR$_2$ or N; exceptone of the Z$_1$-Z$_7$ is a carbon atom to which the remainder of the molecule is attached;

Y$_1$ and Y$_4$ are independently C or N; Y$_2$ and Y$_3$ are C; provided that Y$_4$ is C in formula 8-B;

W$_1$ and W$_2$ are independently CR$_4$R$_4$, S(O)r (r=0-2), O, or N—R$_1$ with the proviso that no S—S, S—O or O—O bond formation can occur to form a saturated ring; R$_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

R$_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl , S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

R$_4$ is H, optionally substituted C1-C6 alkyl, OH (provided both R$_4$ are not OH), C1-C6 alkoxy, —S—C1-C6 alkyl, COOR$_6$, —NR$_6$R$_7$, —CONR$_6$R$_7$; or R$_4$R$_4$ may together be =O or R$_4$R$_4$ together with the carbon to which they are attached may form a spiro system of five to eight members with or without the presence of heteroatoms selected N, O, S(O)n (where n=0 to 2), N—R$_1$;

R$_6$ and R$_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2; and t=0-3.

10. The compound according to claim 1 wherein the tricyclic heteroaryl group is

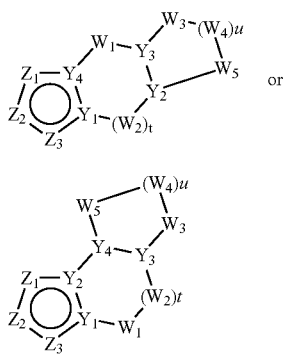

9-A or

9-B wherein $Z_1$, $Z_2$ and $Z_3$ are independently $CR_2$, N, O, S or N—$R_1$ except one of $Z_1$-$Z_3$ is a carbon atom to which the remainder of the molecule is attached;

$Y_1$ is selected from C and N;

$Y_3$ are independently is selected from CH and N;

$Y_2$ and $Y_4$ are independently C, CH or N; provided that in formula 9-A, $Y_2$ cannot be C nor can $Y_4$ be CH; and provided that in formula 9-B, $Y_2$ cannot be CH nor can $Y_4$ be C;

$W_1$, $W_2$ $W_3$, $W_4$ and $W_5$ are independently $CR_4R_4$, S(O)r (r=0-2), O, or N—$R_1$ with the proviso that no S—S, S—O or O—O bond formation can occur to form a saturated ring; $R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C=Oheteroaryl, optionally substituted —C=Oaryl, optionally substituted —C=Oalkyl, optionally substituted —C=Ocycioalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxycarbonyl;

$R_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C1-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, COOR$_6$, —NR$_6$R$_7$, —CONR$_6$R$_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two hetero atoms selected from N—$R_1$, O, and S(O)$_n$, wherein n=0-2;

t=0 to 2; and u=1 to 3.

11. The compound according to claim 1 wherein the tricyclic heteroaryl group is

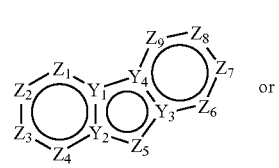

10-A or

-continued

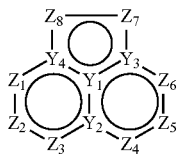

10-B wherein $Z_1$, $Z_2$, $Z_3$, $Z_4$, $Z_5$, $Z_6$, $Z_7$, $Z_8$ and $Z_9$ are independently $CR_2$, N, O, S or N—$R_1$ except one of the $Z_1$-$Z_9$ is a carbon atom to which the remainder of the molecule is attached; provided that $Z_1$, $Z_2$, $Z_3$, $Z_4$, $Z_5$, $Z_6$, $Z_7$, $Z_8$ and $Z_9$ are not O, S, or N—$R_1$ in formula 10-A and provided that $Z_4$-$Z_8$ are not O, S or N—$R_1$ in formula 10-B;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C═Oheteroaryl, optionally substituted —C═Oaryl, optionally substituted —C═Oalkyl, optionally substituted —C═Ocycloalkyl, optionally substituted —C═O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2; and $Y_1$, $Y_2$, $Y_3$ and $Y_4$ are C.

12. The compound according to claim 1 wherein the tricyclic heteroaryl group is

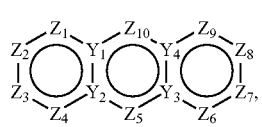

11-A

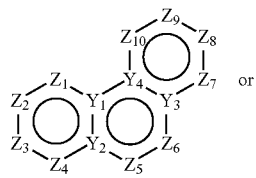

11-B or

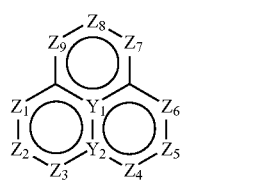

11-C wherein $Z_1$, $Z_2$, $Z_3$, $Z_4$, $Z_5$, $Z_6$, $Z_7$, $Z_8$, $Z_9$ and $Z_{10}$ are independently $CR_2$ or N except one of $Z_1$-$Z_{10}$ is a carbon atom to which the remainder of the molecule is attached;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C═Oheteroaryl, optionally substituted —C═Oaryl, optionally substituted —C═Oalkyl, optionally substituted —C═Ocycloalkyl, optionally substituted —C═O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 car bon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and $Y_1, Y_2, Y_3$ and $Y_4$ are C.

13. The compound according to claim 1 wherein the tricyclic heteroaryl group is

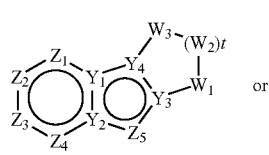

12-A or

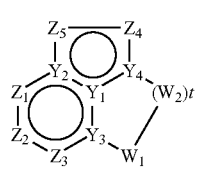

12-B wherein $Z_1, Z_2$, and $Z_3$, are independently $CR_2$ or N; $Z_4$ and $Z_5$ are independently $CR_2$, N, O, S or N—$R_1$ except that one of $Z_1$-$Z_5$ is a carbon atom to which the remainder of the molecule is attached; provided that in formula 12-A, $Z_4$ is not O, S or N—$R_1$;

$Y_1$ and $Y_2$ are C; $Y_3$ and $Y_4$ are independently C or N; provided that in formula 12-B, $Y_3$ is C;

$W_1, W_2, W_3$ are independently $CR_4R_4$, O, N—$R_1$, or $S(O)_r$ (r=0-2) with the proviso that no S—S, S—O or O—O bond formation can occur to form a saturated ring; $R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perifluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and t=1-4.

14. The compound according to claim 1 wherein the tricyclic heteroaryl group is

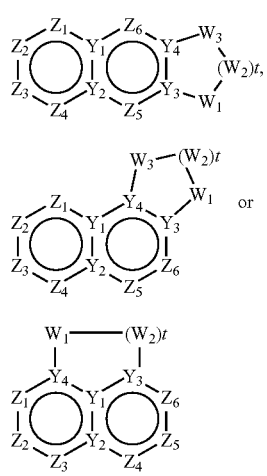

wherein $Z_1$, $Z_2$, $Z_3$, $Z_4$, $Z_5$ and $Z_6$ are independently $CR_2$ or N except one of $Z_1$-$Z_6$ is a carbon atom to which the remainder of the molecule is attached;

$Y_1$, $Y_2$, $Y_3$ and $Y_4$ are C;

$W_1$, $W_2$ and $W_3$ are independently $CR_4R_4$, S(O)r (r=0-2), O, or N—$R_1$ with the proviso that no S—S, S—O or O—O bond formation can occur to form a saturated ring; $R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally sub stituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and t=1 to 3.

15. The compound according to claim 1 wherein the tricyclic heteroaryl group is

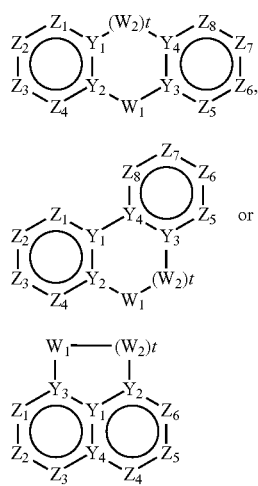

14-A

14-B

14-C wherein $Z_1, Z_2, Z_3, Z_4, Z_5, Z_6, Z_7$ and $Z_8$ are independently $CR_2$ or N except one of $Z_8$ is a carbon atom to which the remainder of the molecule is attached;

$Y_1, Y_2, Y_3$ and $Y_4$ are C;

$W_1$ and $W_2$ are independently $CR_4R_4$, $S(O)r$ ($r=0-2$), O, or N—$R_1$ with the proviso that no S—S, S—O or O—O bond formation can occur to form a saturated ring; $R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=Omono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1—C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and t=1 to 2.

16. The compound according to claim 1 wherein the tricyclic heteroaryl group is

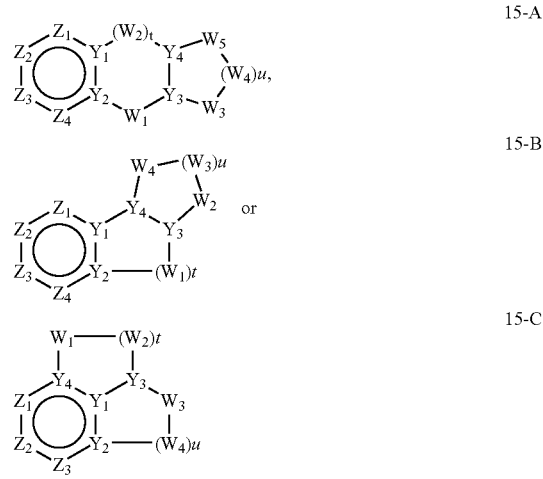

15-A

15-B

15-C wherein $Z_1$, $Z_2$, $Z_3$ and $Z_4$ are independently $CR_2$ or N except one of $Z_1$-$Z_4$ is a carbon atom to which the remainder of the molecule is attached;

$Y_1$ and $Y_2$ are C; $Y_3$ and $Y_4$ are independently C$\underline{H}$ or N; provided that in formula 15-C, $Y_4$ is C;

$W_1$, $W_2$, $W_3$, $W_4$ and $W_5$ are independently $CR_4R_4$, S(O)r (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C═Oheteroaryl, optionally substituted —C═Oaryl, optionally substituted —C═Oalkyl, optionally substituted —C═Ocycloalkyl, optionally substituted —C═O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NRR$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, COOR$_6$, —NR$_6R_7$, —CONR$_6R_7$; or $R_4R_4$ may together be ═O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2;

t=1 to 3; and u=1 to 3.

17. A method for the treatment of bacterial infection or disease in a patient in need thereof which comprises providing to said patient an effective amount of a compound of formula I:

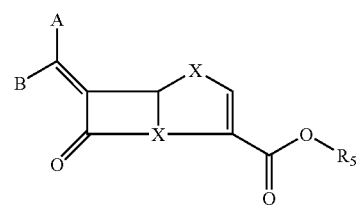

I wherein:

one of A and B denotes hydrogen and the other an optionally substituted fused tricyclic heteroaryl group;

X is O;

$R_5$ is H, C1-C6 alkyl, C5-C6 cycloalkyl, or CHR$_3$OCOC1-C6alkyl; and $R_3$ is hydrogen, C1-C6 alkyl, C5-C6 cycloalkyl, optionally substituted aryl, or optionally substituted heteroaryl;

or a pharmaceutically acceptable salt or in vivo hydrolysable ester thereof.

18. The method according to claim 17 wherein the compound is co-administered with a betalactam antibiotic.

19. The method according to claim 18 wherein the ratio of β-lactam antibiotic to the compound is in a range from about 1:1 to 100:1.

20. The method according to claim 19 wherein the ratio of the β-lactam antibiotic to the compound is less than 10:1.

21. The method according to claim 17 wherein the tricyclic heteroaryl group has the formula

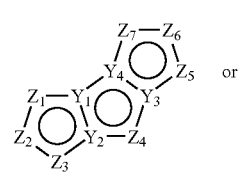

1-A

-continued

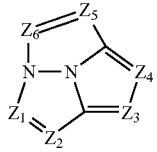
1-B wherein formula 1-A, $Z_1$, $Z_2$, $Z_3$, $Z_4$, $Z_5$, $Z_6$ and $Z_7$ are independently $CR_2$, N, O, S or N—$R_1$ and in formula 1B, $Z_1$, $Z_2$, $Z_3$, $Z_4$, $Z_5$, $Z_6$ and $Z_7$ are independently $CR_2$ or N; except one of $Z_1$-$Z_7$ is a carbon atom to which the remainder of the molecule is attached;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C=Oheteroaryl, optionally substituted —C=±0aryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$ optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system optionally having, in addition to said N, one or two heteroatoms selected from N—$R_1$, O, and S(O)$_n$, wherein n=0-2; and $Y_1, Y_2, Y_3$ and $Y_4$ may independently be C or N.

22. The method according to claim 17 wherein the tricyclic heteroaryl group is

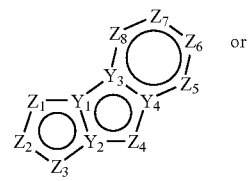
2-A

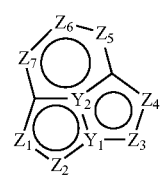
2-B wherein $Z_1$, $Z_2$, $Z_3$, and $Z_4$ are independently $CR_2$, N, O, S or N—$R_1$; $Z_5$, $Z_6$, $Z_7$, and $Z_8$ are independently $CR_2$ or N; except one of the $Z_1$-$Z_8$ is a carbon atom to which the remainder of the molecule is attached;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2; and $Y_1$ and $Y_2$ are independently C or N; $Y_3$ and $Y_4$ are C; provided that in formula 2-B, is C.

23. The method according to claim 17 wherein the tricyclic heteroaryl group is

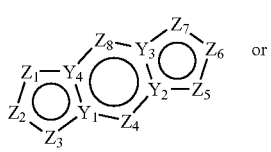

3-A or

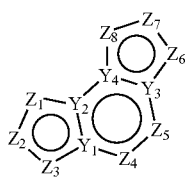

3-B wherein in formula 3-A, $Z_1$, $Z_2$, $Z_3$, $Z_5$, $Z_6$ and $Z_7$ are independently CR$_2$, N, O, S or N—$R_1$; and in formula 3-A, $Z_4$ and $Z_8$ are independently CR$_2$ or N; and in formula 3-B, $Z_1$, $Z_2$, $Z_3$, $Z_6$, $Z_7$ and $Z_8$ are independently CR$_2$, N, O, S or N—$R_1$ and $Z_4$ and $Z_5$ are independently CR$_2$ or N; except one of $Z_1$-$Z_8$ is a carbon atom to which the remainder of the molecule is attached;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C═Oheteroaryl, optionally substituted —C═Oaryl, optionally substituted —C═Oalkyl, optionally substituted —C═Ocycloalkyl, optionally substituted —C═O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6R_7$, —SO$_2$NR$_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or R₆ and R₇ together with the N to which they are attached form a 3-7 membered saturated ring system having one or two heteroatoms selected from N—R₁, O, and S(O)ₙ, wherein n=0-2; and Y₁, Y₂, Y₃ and Y₄ are C.

24. The method according to claim 17 wherein the tricyclic heteroaryl group is

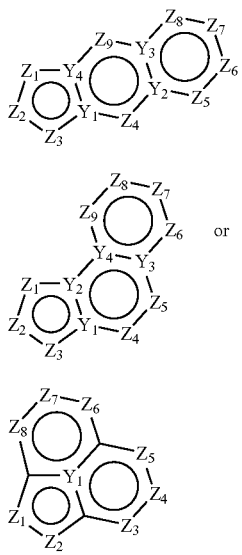

wherein Z₁, Z₂ and Z₃ are independently CR₂, N, O, S or N—R₁; and Z₄, Z₅, Z₆, Z₇, Z₈ and Z₉ are independently CR₂ or N; except one of the Z₁-Z₉ is a carbon atom to which the remainder of the molecule is attached; provided that in formula 4-C, Z₃ cannot be O, S or N—R₁;

R₁ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)ₚ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR₆R₇, —SO₂NR₆R₇, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

R₂ is hydrogen, optionally substituted C1-C6 alkyl, optionally substituted C2-C6 alkenyl, optionally substituted C2-C6 alkynyl, halogen, cyano, N—R₆R₇, optionally substituted C1-C6 alkoxy, hydroxy; optionally substituted aryl, optionally substituted heteroaryl, COOR₆, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)_q— optionally substituted C1-C6 alkyl, S(O)_q— optionally substituted aryl where q is 0, 1 or 2, CONR₆R₇, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO₂NR₆R₇, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

R₆ and R₇ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or R₆ and R₇ together with the N to which they are attached form a 3-7 membered saturated ring system having one or two heteroatoms selected from N—R₁, O, and S(O)ₙ, wherein n=0-2; and Y₁, Y₂, Y₃ and Y₄ are C.

25. The method according to claim 17 wherein the tricyclic heteroaryl group is

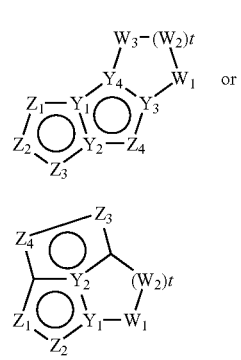

wherein Z₁, Z₂, Z₃ and Z₄ are independently CR₂, N, O, S or N—R₁ except one of Z₁-Z₄ is a carbon atom to which the remainder of the molecule is attached;

Y₁, Y₂, Y₃ and Y₄ are independently C or N; provided that Y₁ and Y₂ are C in formula 5-B;

$W_1$, $W_2$ and $W_3$ are independently $CR_4R_4$, $S(O)r$ (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, $COOR_6$, —$NR_6R_7$, —$CONR_6R_7$ or $R_4R_4$ may together be or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and t=1 to 3.

26. The method according to claim 17 wherein the tricyclic heteroaryl group is

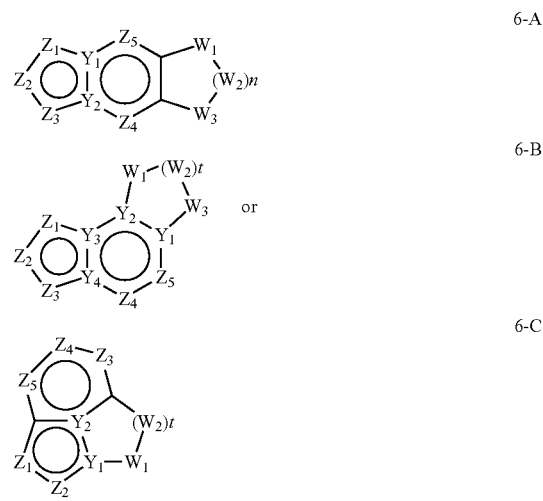

wherein $Z_1$, $Z_2$ and $Z_3$ are independently $CR_2$, N, O, S or N—$R_1$; $Z_4$ and $Z_5$ are $CR_2$ or N; except one of $Z_1$-$Z_5$ is a carbon atom to which the remainder of the molecule is attached; provided that in formula 6-C, $Z_3$ cannot be O, S or $Y_1$ is selected from C and N; provided that in formula 6-A and 6-B, $Y_1$ is C;

$Y_2$, $Y_3$ and $Y_4$ are C;

$W_1$, $W_2$ and $W_3$ are independently $CR_4R_4$, $S(O)r$ (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

R$_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

R$_4$ is H, optionally substituted C1-C6 alkyl, OH (provided both R$_1$ are not OH), C1-C6 alkoxy, —S—C1-C6 alkyl, COOR$_6$, —NR$_6$R$_7$, —CONR$_6$R$_7$; or R$_4$R$_4$ may together be =O or R$_4$R$_4$ together with the carbon to which they are attached may form a spiro system of five to eight members with or without the presence of heteroatoms selected N, O, S(O)n (where n=0 to 2), N—R$_1$;

R$_6$ and R$_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or R$_6$ and R$_7$ together with the N to which they are attached form a 3-7 membered saturated ring system having one or two heteroatoms selected from N—R$_1$, O, and S(O)$_n$, wherein n=0-2; and t=1 to 3.

27. The method according to claim 17 wherein the tricyclic heteroaryl group is

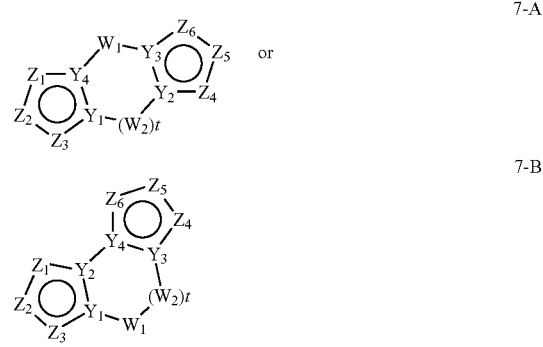

wherein Z$_1$, Z$_2$, Z$_3$, Z$_4$, Z$_5$ and Z$_6$ are independently CR$_2$, N, O, S, and N—R$_1$; except one of Z$_1$-Z$_6$ is a carbon atom to which the remainder of the molecule is attached;

Y$_1$, Y$_2$, Y$_3$ and Y$_4$ are independently C or N;

W$_1$ and W$_2$ are independently CR$_4$R$_4$, S(O)r (r=0-2), O, N—R$_1$ with the proviso that no S—S, S—O or O—O bond formation can occur to form a saturated ring;

R$_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

R$_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and t=1 to 3.

28. The method according to claim 17 wherein the tricyclic heteroaryl group is

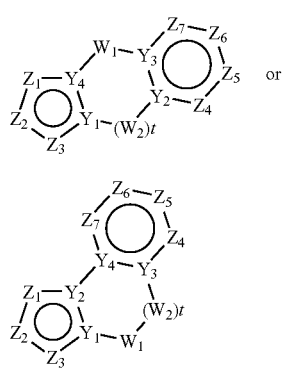

wherein $Z_1$, $Z_2$, and $Z_3$ are independently $CR_2$, N, O, S or N—$R_1$; $Z_4$, $Z_5$, $Z_6$ and $Z_7$ are independently $CR_2$ or N; except one of the $Z_1$-$Z_7$ is a carbon atom to which the remainder of the molecule is attached;

$Y_1$ and $Y_4$ are independently C or N; $Y_2$ and $Y_3$ are C; provided that $Y_4$ is C in formula 8-B;

$W_1$ and $W_2$ are independently $CR_4R_4$, $S(O)_r$ (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2; and t=0-3.

29. The method according to claim 17 wherein the tricyclic heteroaryl group is

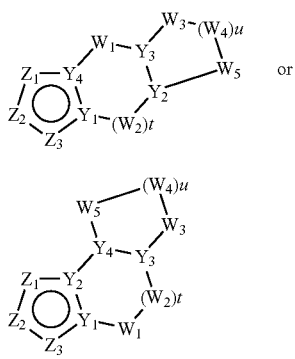

9-A

9-B wherein $Z_1$, $Z_2$ and $Z_3$ are independently $CR_2$, N, O, S or N—$R_1$ except one of $Z_1$-$Z_3$ is a carbon atom to which the remainder of the molecule is attached;

$Y_1$ is selected from C and N;

$Y_3$ is selected from CH and N;

$Y_2$ and $Y_4$ are independently C, CH or N; provided that in formula 9-A, $Y_2$ cannot be C nor can $Y_4$ be CH; and provided that in formula 9-B, $Y_2$ cannot be CH nor can $Y_4$ be C;

$W_1$, $W_2$, $W_3$, $W_4$ and $W_5$ are independently $CR_4R_4$, S(O)r (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C═Oheteroaryl, optionally substituted —C═Oaryl, optionally substituted —C═Oalkyl, optionally substituted —C═Ocycloalkyl, optionally substituted —C═O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, COOR$_6$, —NR$_6$R$_7$, —CONR$_6$R$_7$; or $R_4R_4$ may together be ═O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2;

t=0 to 2; and u=1 to 3.

30. The method according to claim 17 wherein the tricyclic heteroaryl group is

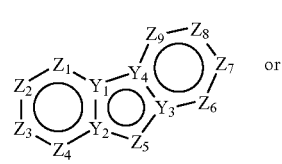

10-A

-continued

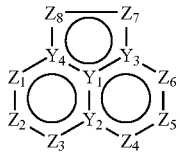

10-B wherein $Z_1, Z_2, Z_3, Z_4, Z_5, Z_6, Z_7, Z_8$ and $Z_9$ are independently $CR_2$, N, O, S or N—$R_1$ except one of the $Z_1$-$Z_9$ is a carbon atom to which the remainder of the molecule is attached; provided that $Z_1, Z_2, Z_3, Z_4, Z_5, Z_6, Z_7, Z_8$ and $Z_9$ are not O, S, or N—$R_1$ in formula 10-A and provided that $Z_4$-$Z_8$ are not O, S or N—$R_1$ in formula 10-B;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryl optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and $Y_1, Y_2, Y_3$ and $Y_4$ are C.

31. The method according to claim 17 wherein the tricyclic heteroaryl group is

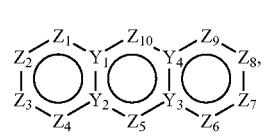

11-A

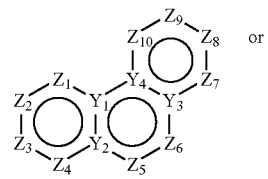

11-B

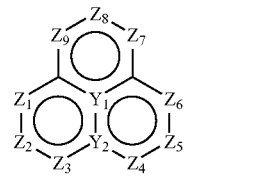

11-C wherein $Z_1, Z_2, Z_3, Z_4, Z_5, Z_6, Z_7, Z_8, Z_9$ and $Z_{10}$ are independently $CR_2$ or N except one of $Z_1$-$Z_{10}$ is a carbon atom to which the remainder of the molecule is attached;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and $S(O)_n$, wherein n=0-2; and $Y_1$, $Y_2$, $Y_3$ and $Y_4$ are C.

32. The method according to claim 17 wherein the tricyclic heteroaryl group is

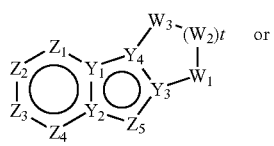

12-A

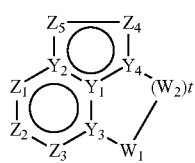

12-B wherein $Z_1$, $Z_2$ and $Z_3$, are independently CR$_2$ or N; $Z_4$ and $Z_5$ are independently CR$_2$, N, O, S or N—$R_1$ except that one of $Z_1$-$Z_5$ is a carbon atom to which the remainder of the molecule is attached; provided that in formula 12-A, $Z_4$ is not O, S or N—$R_1$;

$Y_1$ and $Y_2$ are C; $Y_3$ and $Y_4$ are independently C and N; provided that in formula 12-B, $Y_3$ is C;

$W_1$, $W_2$, $W_3$ are independently CR$_4$R$_4$O, N—$R_1$, or $S(O)_r$ (r=0-2) with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —$S(O)_p$ optionally substituted alkyl or aryl where p is 0-2, optionally substituted —C=Oheteroaryl, optionally substituted —C=Oaryl, optionally substituted —C=Oalkyl, optionally substituted —C=O cycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, $COOR_6$, —$NR_6R_7$, —$CONR_6R_7$; or $R_4R_1$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2; and t=1-4.

33. The method according to claim 17 wherein the tricyclic heteroaryl group is

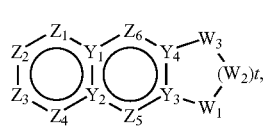

13-A

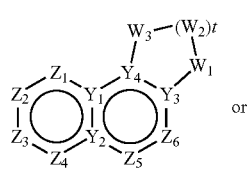

13-B or

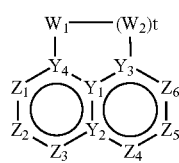

13-C wherein $Z_1$, $Z_2$, $Z_3$, $Z_4$, $Z_5$ and $Z_6$ are independently $CR_2$ or N except one of $Z_1$-$Z_6$ is a carbon atom to which the remainder of the molecule is attached;

$Y_1$, $Y_2$, $Y_3$ and $Y_4$ are C;

$W_1$, $W_2$ and $W_3$ are independently $CR_4R_4$, S(O)r (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, $CONR_6R_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_1$ are not OH), C1-C6 alkoxy, —S—C1-C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2; and t=1 to 3.

34. The method according to claim 17 wherein the tricyclic heteroaryl group is

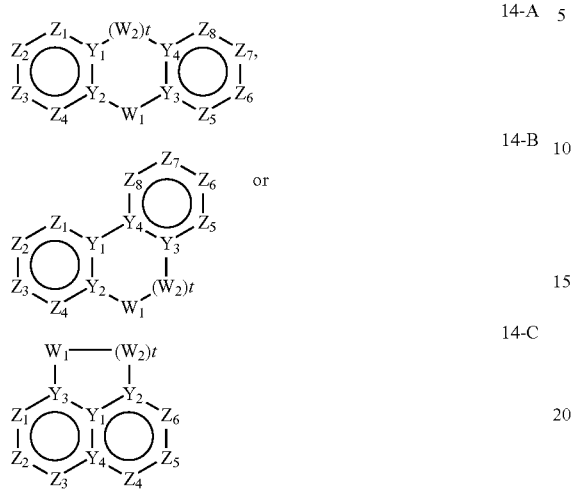

wherein $Z_1$, $Z_2$, $Z_3$, $Z_4$, $Z_5$, $Z_6$, $Z_7$ and $Z_8$ are independently $CR_2$ or N except one of $Z_8$ is a carbon atom to which the remainder of the molecule is attached;

$Y_1$, $Y_2$, $Y_3$ and $Y_4$ are C;

$W_1$, and $W_2$ are independently $CR_4R_4$, S(O)r (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—R$_6$R$_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylaminoC1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, COOR$_6$, —NR$_6$R$_7$, —CONR$_6$R$_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2; and t=1 to 2.

35. The method according to claim 17 wherein the tricyclic heteroaryl group is

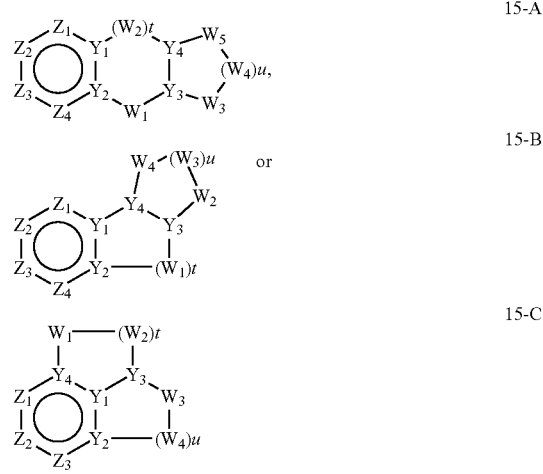

wherein $Z_1$, $Z_2$, $Z_3$ and $Z_4$ are independently $CR_2$ or N except one of $Z_1$-$Z_4$ is a carbon atom to which the remainder of the molecule is attached;

$Y_1$ and $Y_2$ are C; $Y_3$ and $Y_4$ are independently CH or N; provided that in formula 15-C, $Y_4$ is C;

$W_1$, $W_2$, $W_3$, $W_4$ and $W_5$ are independently $CR_4R_4$, S(O)r (r=0-2), O, or N—$R_1$ with the proviso that no S—S, S—O or O—O bond formation can occur to form a saturated ring;

$R_1$ is H, optionally substituted alkyl, optionally substituted aryl, optionally substituted heteroaryl or mono or bicyclic saturated heterocycles, optionally substituted cycloalkyl, optionally substituted alkenyl, optionally substituted alkynyl with the proviso that neither the double bond nor the triple bond should be present at the carbon atom which is directly linked to N; optionally substituted perfluoroalkyl, —S(O)$_p$ optionally substituted alkyl or aryl where p is 0-2, optionally substituted —C=Oheteroaryl, optionally substituted —C=Oaryl, optionally substituted —C=Oalkyl, optionally substituted —C=Ocycloalkyl, optionally substituted —C=O mono or bicyclic saturated heterocycles, optionally substituted C1-C6 alkylaryl, optionally substituted C1-C6 alkylheteroaryl, optionally substituted aryl-C1-C6alkyl, optionally substituted heteroaryl-C1-C6alkyl, optionally substituted C1-C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkylaryloxyalkylamines, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, N—$R_6R_7$, optionally substituted C1-C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylenedioxy, optionally substituted aryloxy-C1-C6 alkyl amine, C1-C6 perfluoro alkyl, S(O)$_q$— optionally substituted C1-C6 alkyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1-C6 alkyl, OH (provided both $R_4$ are not OH), C1-C6 alkoxy, —S—C1-C6 alkyl, COOR$_6$, —NR$_6$R$_7$, —CONR$_6$R$_7$; or $R_4R_4$ may together be =O or $R_4R_4$ together with the carbon to which they are attached may form a spiro system of five to eight members with or without the presence of heteroatoms selected N, O, S(O)n (where n=0 to 2), N—$R_1$;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, or $R_6$ and $R_7$ together with the N to which they are attached form a 3-7 membered saturated ring system having one or two heteroatoms selected from N—$R_1$, O, and S(O)$_n$, wherein n=0-2;

t=1 to 3; and u=1 to 3.

36. A pharmaceutical composition which comprises a pharmaceutically acceptable carrier and an effective amount of a compound as defined in claim 1 or a pharmaceutically acceptable salt or in vivo hydrolysabie ester thereof.

\* \* \* \* \*